US012806438B2

(12) United States Patent
Lang et al.

(10) Patent No.: US 12,806,438 B2
(45) Date of Patent: Nov. 24, 2026

(54) LIGHTING DEVICE TO PROMOTE CIRCADIAN HEALTH

(71) Applicant: Children's Hospital Medical Center, Cincinnati, OH (US)

(72) Inventors: Richard Lang, Cincinnati, OH (US); James Greenberg, Cincinnati, OH (US); Robert Soler, San Marcos, CA (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 727 days.

(21) Appl. No.: 17/799,485

(22) PCT Filed: Feb. 11, 2021

(86) PCT No.: PCT/US2021/017681
§ 371 (c)(1),
(2) Date: Aug. 12, 2022

(87) PCT Pub. No.: WO2021/163343
PCT Pub. Date: Aug. 19, 2021

(65) Prior Publication Data

US 2023/0122476 A1 Apr. 20, 2023

Related U.S. Application Data

(60) Provisional application No. 63/085,234, filed on Sep. 30, 2020, provisional application No. 62/975,357, filed on Feb. 12, 2020.

(51) Int. Cl.
*A61M 21/00* (2006.01)
*A61N 5/06* (2006.01)
(Continued)

(52) U.S. Cl.
CPC .... *A61N 5/0613* (2013.01); *A61N 2005/0652* (2013.01); *A61N 2005/0661* (2013.01); *A61N 2005/0663* (2013.01)

(58) Field of Classification Search
CPC .......... A61N 5/0613; A61N 2005/0652; A61N 2005/0661; A61N 2005/0663;
(Continued)

(56) References Cited

U.S. PATENT DOCUMENTS 5,589,741 A 12/1996 Terman et al.
6,554,439 B1 4/2003 Teicher et al.
(Continued)

FOREIGN PATENT DOCUMENTS

CN 103442765 A 12/2013
EP 3561798 A1 10/2019
(Continued)

OTHER PUBLICATIONS

Nguyen et al.; "An opsin 5-dopamine pathway mediates light-dependent vascular development in the eye"; Nature Cell Biology; vol. 21; Apr. 2019; p. 420-429.
(Continued)

*Primary Examiner* — Brian T Gedeon
(74) *Attorney, Agent, or Firm* — BakerHostetler

(57) ABSTRACT

A method, system and computer-readable medium of utilizing artificial lighting regulate a circadian clock of a human. By utilizing light emitting diodes (LEDs) that emit wavelengths associated with human opsin absorption spectra, a device may stimulate opsins in the human. For example, the device may replicate normal sunlight (e.g., based on season or time of day) by emitting light that changes in rhythmic intensity or spectral modulation.

22 Claims, 75 Drawing Sheets

Specification includes a Sequence Listing.

(51) Int. Cl.
*H05B 45/20* (2020.01)
*H05B 47/155* (2020.01)

(58) Field of Classification Search
CPC .... A61N 2005/0626; A61N 2005/0636; A61N 2005/0651; A61N 5/0618; Y02B 20/40; H05B 45/20; H05B 47/105; H05B 45/10; H05B 47/155; H05B 47/165; A61M 21/00; A61M 2021/0044; H10H 20/855; H10H 29/142
See application file for complete search history.

(56) References Cited

U.S. PATENT DOCUMENTS

| | | | | |
|---|---|---|---|---|
| 8,436,556 | B2 | 5/2013 | Eisele et al. | |
| 8,469,547 | B2 | 6/2013 | Paolini | |
| 9,289,622 | B2 | 3/2016 | Feng et al. | |
| 9,462,661 | B2 | 10/2016 | Barroso et al. | |
| 9,635,732 | B2 | 4/2017 | Herremans et al. | |
| 9,642,209 | B2 | 5/2017 | Eisele et al. | |
| 9,782,605 | B2 | 10/2017 | Feather et al. | |
| 9,844,116 | B2 | 12/2017 | Soler et al. | |
| 9,949,339 | B2 | 4/2018 | Akcasu et al. | |
| 10,339,591 | B2 | 7/2019 | Paolini et al. | |
| 10,420,184 | B1 * | 9/2019 | Soler | H05B 45/24 |
| 10,471,231 | B2 | 11/2019 | Moore-Ede et al. | |
| 10,595,376 | B2 | 3/2020 | Soler et al. | |
| 10,631,385 | B2 | 4/2020 | Paulsen et al. | |
| 10,805,998 | B2 | 10/2020 | Petluri et al. | |
| 10,827,579 | B2 | 11/2020 | Soler et al. | |
| 11,662,067 | B2 | 5/2023 | David et al. | |
| 11,950,343 | B2 | 4/2024 | Yadav et al. | |
| 2010/0197996 | A1 | 8/2010 | Cornel | |
| 2017/0105265 | A1 | 4/2017 | Sadwick | |
| 2017/0208673 | A1 | 7/2017 | Schlangen et al. | |
| 2017/0231058 | A1 | 8/2017 | Sadwick | |
| 2017/0259079 | A1 * | 9/2017 | Grajcar | A01G 7/045 |
| 2018/0073712 | A1 | 3/2018 | Baaijens et al. | |
| 2018/0077767 | A1 | 3/2018 | Soler et al. | |
| 2018/0318602 | A1 * | 11/2018 | Ciccarelli | A61M 21/02 |
| 2018/0339158 | A1 | 11/2018 | Taylor | |
| 2019/0129204 | A1 | 5/2019 | Tsubota et al. | |
| 2019/0209806 | A1 | 7/2019 | Allen et al. | |
| 2019/0209858 | A1 | 7/2019 | Slaughter et al. | |
| 2019/0297704 | A1 | 9/2019 | Van De Ven et al. | |
| 2019/0336789 | A1 | 11/2019 | Garner et al. | |
| 2020/0016365 | A1 | 1/2020 | Soler | |
| 2020/0108272 | A1 | 4/2020 | Bahmani et al. | |
| 2020/0368550 | A1 | 11/2020 | Moore-Ede et al. | |
| 2022/0353972 | A1 | 11/2022 | Heerink | |
| 2023/0077872 | A1 | 3/2023 | Buschbeck et al. | |

FOREIGN PATENT DOCUMENTS

| | | | | |
|---|---|---|---|---|
| JP | 2007504925 * | 7/2007 | A61N 5/06 |
| JP | 2020-058802 A | 4/2020 | |
| JP | 2020-106857 A | 7/2020 | |
| WO | WO 2016/145064 A1 | 9/2016 | |
| WO | WO 2018/039433 A1 | 3/2018 | |
| WO | WO 2020/014688 A1 | 1/2020 | |
| WO | WO 2020/097580 A1 | 5/2020 | |
| WO | WO 2020/148913 A1 | 7/2020 | |

OTHER PUBLICATIONS

Buhr et al.; "Neuropsin (OPN5) Mediates Local Light-Dependent Induction of Circadian Clock Genes and Circadian Photoentrainment in Exposed Murine Skin"; Current Biology; vol. 29; Oct. 2019; p. 3478-3487.

Zhang et al.; "Violet-light suppression of thermogenesis by Opsin 5 hypothalamic neurons"; Nature; vol. 585(7825); Sep. 2020; p. 420-425.

Nayak et al.; "Adaptive Thermogenesis in Mice Is Enhanced by Opsin 3-Dependent Adipocyte Light Sensing"; Cell Reports; vol. 30; Jan. 2020; p. 672-686.

Rao et al.; "A direct and melanopsin-dependent fetal light response regulates mouse eye development"; Nature; vol. 494; Feb. 2013; p. 243-246.

Ozdeslik et al.; "Human nonvisual opsin 3 regulates pigmentation of epidermal melanocytes through functional interaction with melanocortin 1 receptor"; PNAS; vol. 116; Jun. 2019; p. 11508-11517.

International Patent Application No. PCT/US2021/017681; Int'l Search Report and the Written Opinion; dated; Aug. 25, 2021; 16 pages.

International Patent Application No. PCT/US2021/017681; Int'l Preliminary Report on Patentability; dated Aug. 25, 2022; 12 pages.

Kojima et al.; "UV-Sensitive Photoreceptor Protein OPN5 in Humans and Mice"; PLos One; vol. 6 Issue 10; Oct. 2011; 12 pages.

LEDs Magazine; Technology and Applications of Light Emitting Diodes; Feb. 2017; 86 pages.

Anadi Martel; "Light Therapies—A Complete Guide to the Healing Power of Light"; Healing Art Press; © 2018; 387 pages.

Vemaraju et al.; "An adipocyte light—Opsin 3 pathway regulates the circadian clock and 5 energy balance"; bioRxiv; Jul. 2018; 29 pages.

L. Schlangen; "The Effect of Light on Our Sleep/Wake Cycle"; Philips; White Paper; © 2014; 12 pages.

Adams et al.; "An Investigation of the Operational and Design Characteristics of Circadian Lighting Systems—Report"; University of Nebraska; UCARA Research Products; 2020; 36 pages.

Engwall et al.; "Lighting, sleep and circadian rhythm: An intervention study in the intensive care unit"; Intensive and Critical Care Nursing; vol. 31; Dec. 2015; p. 325-335.

Schlangen et al.; "Lighting for Health and Well-Being in Education, Work Places, Nursing Homes, Domestic Applications, and Smart Cities"; Innovation for Europe; SSL-erate Consortium; © 2014; p. 5, 6, 7, 8, 39-48.

Buhr et al.; "Neuropsin (OPN5)-mediated photoentrainment of local circadian oscillators in mammalian retina and cornea"; PNAS; vol. 112 No. 42; Oct. 2015; p. 13093-13098.

Diaz et al.; "Wounding Induces Facultative Opn5-Dependent Circadian Photoreception in the Murine Cornea"; Invest Opthalmol Vis Sci; vol. 61 No. 6; Jun. 2020; 11 pages.

* cited by examiner

Light engine LED emission spectra

Hughes et al., *Plant, Cell and Environment*, 1984

Spectral composition during summer and winter days at 57 degrees latitude

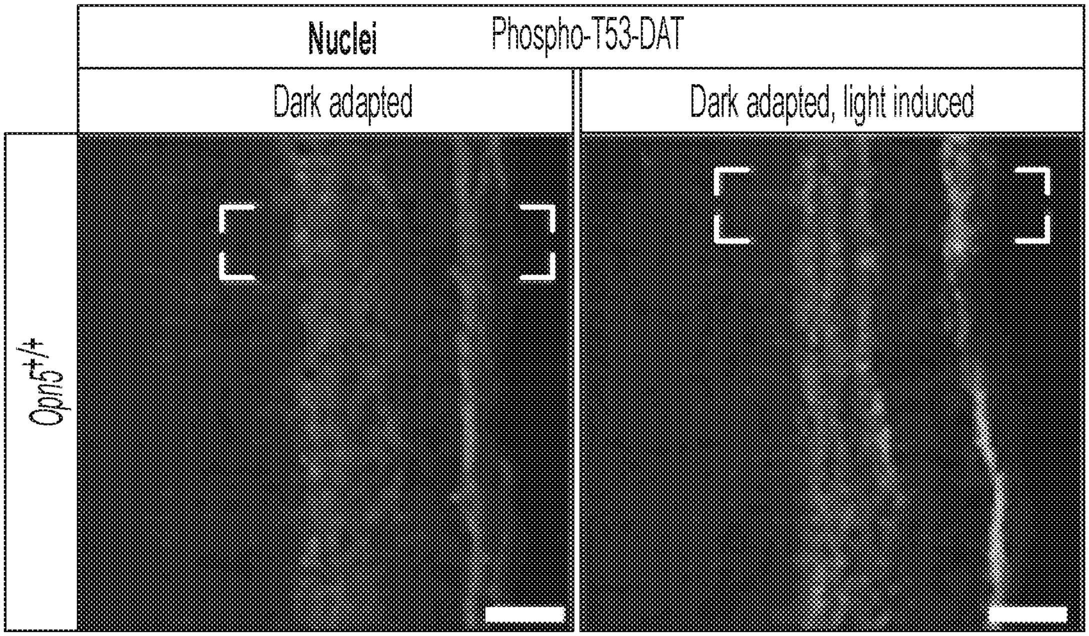
FIG. 23A
FIG. 23B
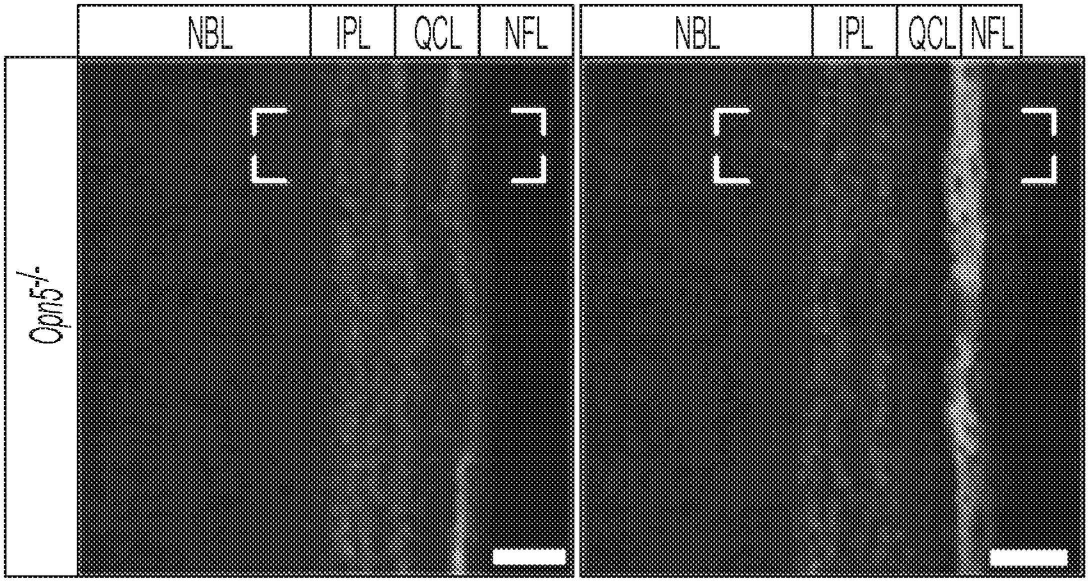
FIG. 23C
FIG. 23D

LIGHTING DEVICE TO PROMOTE CIRCADIAN HEALTH

CROSS REFERENCE TO RELATED APPLICATIONS

This application is a 371 National Stage Application of PCT/US2021/017681 filed Feb. 11, 2021, which claims priority to U.S. Provisional Application Ser. No. 63/085,234 filed Sep. 30, 2020, the entire disclosure of which is incorporated herein by reference (including color figures), and [. This application also claims priority] to U.S. Provisional Application Ser. No. 62/975,357 filed Feb. 12, 2020, the entire disclosure of which is incorporated herein by reference (including color figures).

GOVERNMENT RIGHTS

This invention was made with government support under Grant No. EY027077 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 19, 2021, is named 027324_023021_SL.txt and is 11,901 bytes in size.

TECHNICAL FIELD

The present disclosure relates generally to artificial lighting systems and methods for promoting circadian health and more particularly to systems and methods for using artificial lighting to stimulate encephalopsin (OPN3), melanopsin (OPN4) and neuropsin (OPN5) in humans.

BACKGROUND

Human physiology is regulated by the light-dark cycle. The consequence of living on a rotating planet orbiting a yellow dwarf star is a rhythmic cycle of light and dark. In response, humans have evolved systems that detect and exploit light for adaptive advantage. For example, the human visual system decodes patterns of photons that bounce off objects. Equally important is the entrainment of circadian clocks by light. The circadian clock or circadian oscillator, is a biochemical oscillator that cycles with a stable phase and is synchronized by the light-dark cycle.

One light detection protein important for circadian function is an opsin called melanopsin. This is responsive to blue light in the 490 nm range. Based on more recent work, it is clear that other wavelengths (380 nm, violet light) and other opsins (encephalopsin and neuropsin) are also involved in regulating circadian clocks and acute light response physiology.

In the last 100 years, research examining the function of circadian clocks has shown that they have a crucial action in almost all aspects of human physiology. More recently, it has been shown that acute light response pathways also regulate our physiology. Acute light responses and circadian clock oscillation entrained by light stimulation, combine to generate a rhythmic systemic physiology that means humans are well adapted to time-of-day dependent activities. For example, these light response pathways enhance our alertness during the day and promote sleep at night. They also control our metabolic system so that we generate high energy levels during the day and low levels at night. Disruption of this rhythmic physiology can have serious consequences. The sleepiness and foggy mind of jet lag is one example, but also, we know that shift workers, who are subject to chronic circadian disruption, are more susceptible to metabolic disease and certain types of cancers. These findings are all good reasons to maintain rhythmic physiology via acute and circadian clock-dependent light responses.

Artificial lighting systems within building interiors typically do not provide the spectral composition, intensity or rhythm of light that matches natural sunlight. This means that the typical building lighting system does not satisfy the needs of human circadian physiology. Accordingly, there is a need for special lighting systems to rectify this deficiency by satisfying the requirements of circadian health. Moreover, because a hospital serves many different constituents (e.g., patients, care teams and shift workers) there is a need for a lighting system that is flexible enough to serve varied patients and workers within a hospital.

SUMMARY

The present disclosure discloses devices, methods, and computer program products for promoting circadian health (e.g., treating a patient or preventing disease) in a human by emitting light that stimulates one or more opsins in the human.

In some embodiments, light is emitted by a device (e.g., in a commercial heath care facility). The device may include a plurality of light emitting diodes (LEDs) (e.g., disposed around an interior perimeter of a room) or a display (e.g., associated with an electronic device). In some embodiments, the device may include a controller which may control each of the LEDs or the display. For example, the controller may control a rhythmic intensity or spectral modulation of light emitted from an interior lighting device or a display of an electronic device.

In some embodiments, one or more of the LEDs may have wavelengths selected to target human opsins absorption spectra. For example, the LEDs may have wavelengths of 380 nm, 430 nm, 480 nm, 530 nm, 580 nm, or 630 nm and may target stimulation of human opsins, such as OPSIN 3, 4, or 5. In some embodiments, the device may regulate an acute light response and the circadian clock of a human (e.g., a patient or a hospital worker) based on the stimulation of the opsin(s). For example, the device may simulate normal sunlight by reproducing dusk and dawn, or replicating spectral composition changes that occur in different seasons.

In some embodiments, a device may include an illumination source, e.g., light emitting diodes (LEDs), emitting violet light within a range of 360-420 nm (e.g., 380-410 nm), memory storing computer instructions, and one or more processors coupled with the memory and configured to execute the computer instructions stored in the memory. In some embodiments, the computer instructions may include steps for controlling a selective activation of the illumination source to stimulate neuropsin (OPN5) in a human based at least in part upon a circadian clock of the human. For example, the selective activation of the illumination source (e.g., LEDs) may include controlling a rhythmic intensity of the violet light emitted by the illumination source (e.g., based on a first transition associated with dawn and a second transition associated with dusk). In another example, the selective activation of the illumination source (e.g., LEDs) may be based on one or more spectral composition changes associated with one or more seasons.

According to some embodiments, the device may include an illumination source (e.g., LEDs) emitting blue light within a range of 400-525 nm (e.g., 450-500 nm). In some embodiments, the computer instructions may include steps for controlling the selective activation of the illumination source (e.g., LEDs) to stimulate melanopsin (OPN4) in the human based at least in part upon the circadian clock of the human. In some embodiments, the computer instructions may include steps for controlling the selective activation of the illumination source (e.g., LEDs) to stimulate melanopsin (OPN3) in the human based at least in part upon the circadian clock of the human.

According to some embodiments, the computer instructions may include steps for controlling the selective activation of the illumination source (e.g., LEDs) to stimulate an OPN5/OPN4 ratio in the human. For example, the computer instructions may include steps for controlling the selective activation of the illumination source (e.g., LEDs) to stimulate an OPN5/OPN4 ratio less than 0.4 in the human at a midpoint in a daytime schedule and to stimulate an OPN5/OPN4 ratio greater than 0.4 at a beginning and an end of the daytime schedule. According to some embodiments, the computer instructions may include steps for controlling the selective activation of the LEDs to stimulate an OPN5/OPN3 ratio in the human.

According to some embodiments, the device may include a display and the illumination source (e.g., LEDs) may be incorporated as micro-LEDs in the display. According to some embodiments, the device may include an optical element (e.g., a lens, window, enclosure or cover for the device) associated with the illumination source (e.g., LEDs) that is ultraviolet transmissive.

According to some embodiments, the device may include an interface (e.g., a graphical user interface) configured to receive information pertaining to a geographical location. For example, the selective activation of the illumination source (e.g., LEDs) may be based on transitions associated with the geographical location. According to some embodiments, the selective activation of the illumination source (e.g., LEDs) may be further based upon one or more additional conditions, including time of year, atmospheric conditions, weather conditions, genetic factors, age and health conditions, etc.

According to some embodiments, the interface may be configured to receive information pertaining to two or more of factors associated with a child (e.g., genetic makeup, conception location, birth location, birth time, gestational age, and sex) and the selective activation of the illumination source (e.g., LEDs) may be based on transitions associated with the received factors associated with the child. For example, the device may include one or more interior lighting devices disposed in a child-care facility.

According to some embodiments, a method for treating myopia in children may include providing a first illumination source emitting violet light within a range of 360-420 nm (e.g., 380-410 nm) in an area occupied by a child, providing a second illumination source emitting blue light within a range of 400-525 nm (e.g., 450-500 nm) in the area, and selectively activating the first illumination source to stimulate neuropsin (OPN5) in the child based at least in part upon a circadian clock of the child and selectively activating the second illumination source to stimulate neuropsin (OPN4) in the child based at least in part upon a circadian clock of the child (e.g., based on one or more spectral composition changes associated with one or more seasons). According to some embodiments, the method may control a rhythmic intensity of the violet light emitted by the first illumination source, e.g., based on a first transition associated with dawn and a second transition associated with dusk. For example, the selective activation steps may selectively activate the first and second illumination sources to stimulate an OPN5/OPN4 ratio less than 0.4 in the child at a midpoint in a daytime schedule and to stimulate an OPN5/OPN4 ratio greater than 0.4 at a beginning or an end of the daytime schedule.

According to some embodiments, selectively activating the first illumination source may be based on transitions associated information pertaining to a geographical location of the area. According to some embodiments, selectively activating the first illumination source may be based upon one or more additional condition, including time of year, atmospheric conditions, weather conditions, genetic factors, age and health conditions, etc. According to some embodiments, selectively activating the first illumination source may be based upon transitions associated with one or more received factors associated with a child (e.g., genetic makeup, conception location, birth location, birth time, gestational age, and sex).

In accordance with some examples, a computer readable storage medium has stored therein instructions that are computer executable to perform or cause performance of any of the methods described herein. In accordance with some examples, a device includes one or more processors, a memory, and one or more programs; the one or more programs are stored in the memory and configured to be executed by the one or more processors and the one or more programs include instructions for performing or causing performance of any of the methods described herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

Reference will now be made to the accompanying drawings, which are not necessarily drawn to scale.

Figure 1:
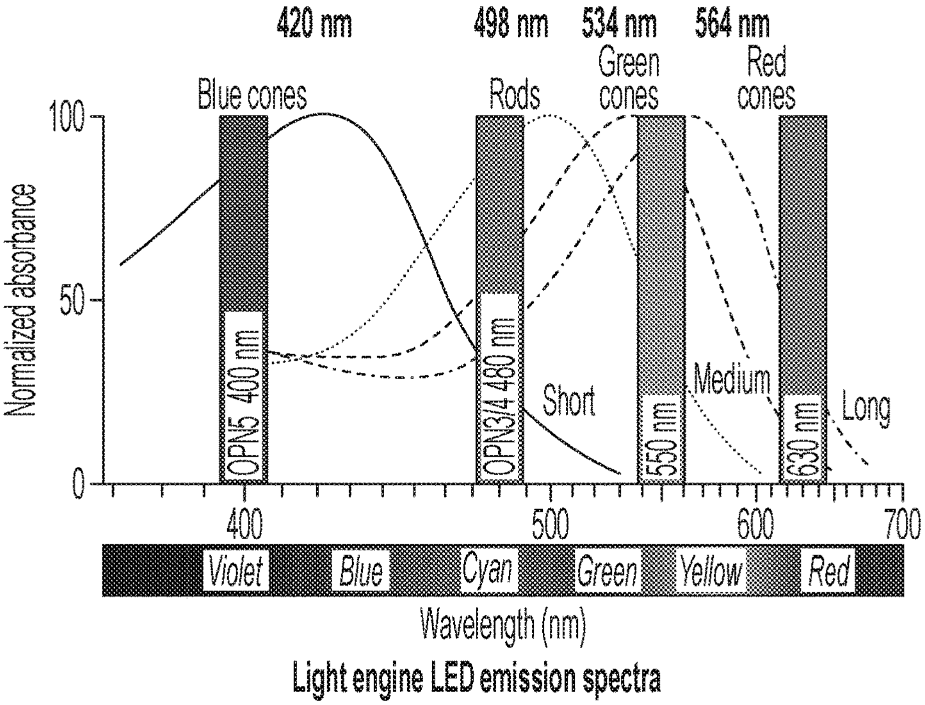
FIG. 1 illustrates an exemplary light engine LED emission spectra.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

The disclosed subject matter provides methods and lighting systems for lighting interior spaces and satisfy the need to activate OPNs 3, 4 and 5. In some examples, the lighting system may also take into account other possible light-decoding mechanisms and may be aesthetically pleasing, e.g., a physiologically beneficial system for commercial and residential installation.

The circadian clock is required to regulate some aspects of our rhythmic physiology including, for example, the sleep-wake cycle. In addition to circadian clock-based physiology, newly discovered light response pathways (that are the subject of this application) are required for acute regulation of physiology. For example, these newly discovered pathways regulate eye development and metabolism.

The light-detecting G-Protein Coupled Receptor (GPCR) Opsin 5 (OPN5) has an important role in regulating development of the eye in mice. OPN5 is a visual violet light (380 nm λ max) responsive opsin that regulates the levels of dopamine in the eye. Both violet light and dopamine suppress myopia, thus it is clear that OPN5 likely has a role in refractive development 1.

Myopia is the most common cause of visual impairment affecting 1.5 billion people and costing $268 billion annually worldwide. Myopia has no known cause or way to prevent its onset. Myopia, or nearsightedness, is a visual impairment in which people can see near objects but objects at distance are blurred. Myopia occurs if the eyeball is too long or the cornea is too curved. This change in structure causes incoming light to be focused in the front of the retina rather than on the retina as seen in emmetropic (normal sighted) patients. Myopia often manifests in school-age children and progresses through the late teens to early twenties as the eye continues to grow. High levels of myopia can lead to very serious ocular complications such as choroidal neovascularization, cataracts, glaucoma, retinal detachment, myopic retinopathy and myopic macular degeneration.

Those affected with myopia vary in age, race, ethnicity, urbanization, education level, and occupation. However, the prevalence differs between geographic location and environment. For example, a recent clinical trial in Taiwan randomized 693 school children for either additional outside time (up to 11 hrs/week) versus a control group of no change in outdoor time. The intervention group showed significantly less myopic shift and axial elongation along with a 54% lower risk of rapid myopia progression compared to the control group after 1 year. These findings suggest that when children spend time outside, they are much less likely to develop myopic refractive error. This is consistent with the hypothesis that a violet light-OPN5 pathway promotes normal refractive development because natural sunlight contains violet light while artificial light inside does not. Also consistent with this hypothesis is recent work showing that mice with germ line or retina conditional deletion of the OPN5 gene show changes in refractive development and in form-deprivation induced refractive changes.

As an example, one of the likely reasons children develop myopia is that they spend too much time using electronic devices inside, and are no longer exposed to the natural light cycle. Moreover, this creates a unique opportunity because any electronic device with a display, regardless of whether it is a phone, tablet, computer, or television, could be used to deliver the 380 nm light required to stimulate normal refractive development, reduce myopic shift and lower the risk of rapid myopia progression.

There are several key features of an electronic device that was designed to promote normal refractive development:

1. The display illumination technology or interior lighting source must be capable of producing 380 nm light as well as the 480 nm (blue) light that they currently produce.

2. The production of 380 nm and 480 nm light by the device must mimic a natural light cycle in timing. This will require an application that functions in the background of the electronic device to deliver a natural light cycle. This will include relative intensities of 380/480 nm light that mimics dawn and dusk transitions and no 380/480 nm light at night. The application should be synchronized to local time but might include the option to extend the daylight time to better match user behavior. The latter feature might be especially important during short winter days when user behavior is out of sync with the sunlight cycle.

In some embodiments, interior lighting may be provided that activates the neurological, visual, and metabolic development pathways for Opsins 3, 4 and 5. For example, OPN4 (melanopsin) has a central role in regulation of the circadian clock and is important for many aspects of human physiology and therefore a blue light (480 nm) cycle of light is important for normal physiological function, e.g., circadian clock entrainment. Moreover, two additional opsins, OPN3 (encephalopsin) and OPNS (neuropsin) also have important functions. For example, OPN3, a blue light sensitive opsin, has a crucial role in development of neural structures. Furthermore, OPN5, a violet light sensitive opsin, is required for normal development of the eye refractive and vascular systems. Both OPN3 and OPNS are also required for normal development and homeostasis of the metabolic system.

Current indoor lighting technology (including smartphone, tablet and computer screens) do not produce the violet light wavelengths (380 nm) that stimulate OPNS. This means that the indoor, electronics-intensive lifestyle of the developed world results in under-stimulation of this pathway. Accordingly, this deficiency may be part of the explanation for the prevalence of diseases like myopia and metabolic syndrome. OPN3 is activated by the same blue photons that activate OPN4. Thus, embodiments that produces both blue and violet light can satisfy all three pathways.

In some examples, the lighting system may have the following characteristics:

A light engine consisting of six single peak LEDs that can be combined to mimic full spectrum lighting.

The LEDs could produce peaks of light at 380 nm, 430 nm, 480 nm, 530 nm, 580 nm, and 630 nm. These wavelengths are targeted at human opsins absorption spectra (see schematic).

The output of each LED may be regulated by software that allows the independent control of intensity over time. The lighting system can thus produce dawn and dusk transitions that mimic normal sunlight. It can also mimic the spectral composition changes that occur in different seasons.

The lighting system may be configured as a horizontally mounted luminaire strip of discrete dimensions that can be mounted on the wall of a room around the complete perimeter. LED light will be directed onto the wall both above and below the lighting strip to produce indirect lighting of the room.

The LEDs may be configured within the lighting strip so that the color separations typical of dawn and dusk can be reproduced.

The lighting strip perimeter may be calibrated for North, South, East and West and operated in segments so that in the Northern hemisphere, dawn lighting is produced in the East, daytime lighting throughout and dusk lighting in the West.

In some embodiments, the lighting system may be designed to offer the health benefits that emerge from stimulation of Opsins 3, 4 and 5 at all stages of development and adulthood as well as the aesthetic characteristics that make it an appealing lighting option. For example, the lighting system may be very well suited to commercial health care facilities, commercial buildings in general and when produced in inexpensive form, for residential installation.

In some embodiments, the lighting system may utilize a light engine. For example, the light engine may employ at least four LEDs, e.g., each respective LED may emit photons with lambda maxes at 400 nm, 480 nm, 550 nm and 630 nm. In some embodiments, this distribution may target the circadian opsins OPN5 (at 400 nm), OPN3, and OPN4 (both at 480 nm) but may also satisfy low light vision and color rendering requirements given overlap with the absorption spectra of rod and cone photoreceptors. According to some embodiments, FIG. 1 shows how LED emission spectra may be distributed relative to the absorption spectra of both circadian and canonical opsins.

Figure 2:
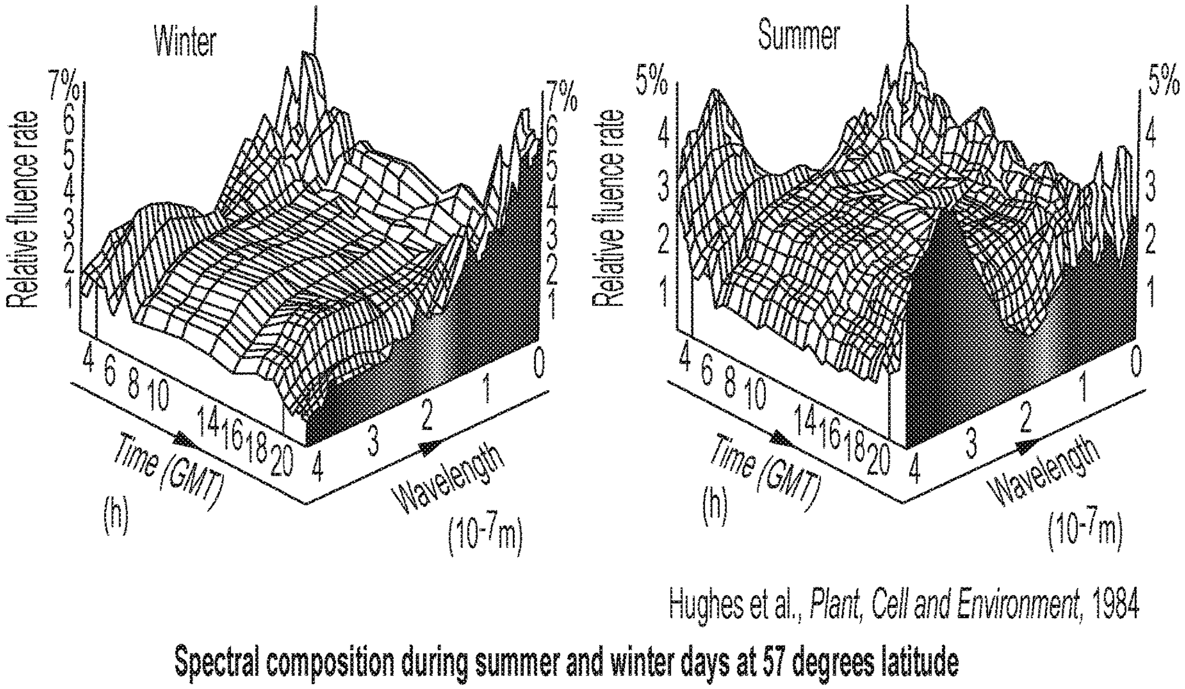
FIG. 2 illustrates an exemplary spectral composition during summer and winter days.

In some embodiments, a controller provides the ability to control, e.g., with complete temporal flexibility, the intensity of each individual LED within the light engine. For example, the controller may be configured to produce interior lighting that has the rhythmic intensity and spectral modulation to mimic a normal day. As an example of flexibility provided by the controller (e.g., flexibility required of the light engine, FIG. 2 shows a spectral composition during winter and summer days in Loughborough, UK, 53 degrees latitude. As illustrated in FIG. 2, in contrast to a winter day, summer dawn and dusk are accompanied by a peak of violet and blue light. Thus, in some embodiments, the light engine provides the flexibility to reproduce this kind of spectral modulation.

In some embodiments, the controller may provide coordinated control of sets of light engines within functional domains. For example, patient rooms may mimic normal sunlight, e.g., light during the day and dark at night. In some embodiments, the controller may also incorporate seasonal transition of wavelength composition (e.g., FIG. 2). However, in some embodiments, interior winter days may be stretched to promote normal hospital function. For example, 9.5 hours of daylight during winter in Cincinnati, Ohio may not be long enough for efficient hospital function. Thus, the controller may stretch the interior winter day to accommodate for short winter days by making any changes relatively subtle so patients and employees alike can easily adapt.

In some embodiments, the controller may provide hospital care team stations and access corridors with daytime lighting identical to patient rooms. However, night lighting programming may include deviations from the patient rooms to accommodate for hospital shift work (e.g., nighttime shifts).

Figure 3:
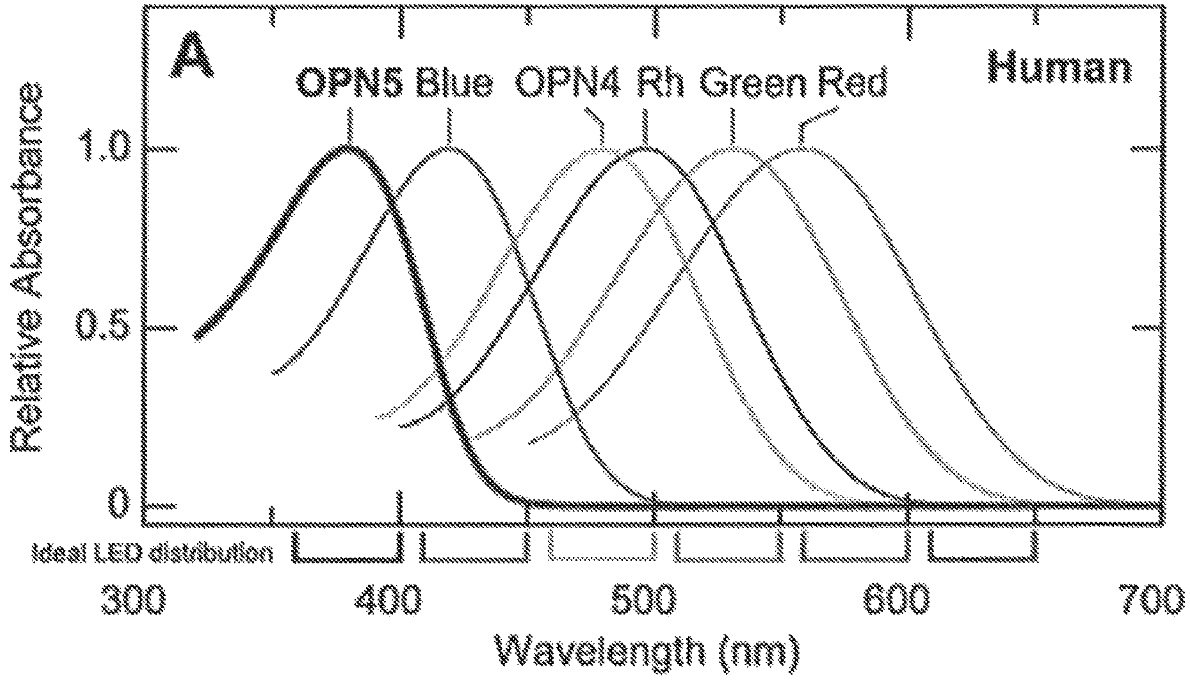
FIG. 3 illustrates an exemplary absorption spectra for human opsins and an exemplary distribution of emission spectrum from LEDs making up a lighting system.

According to some embodiments, FIG. 3 illustrates the absorption spectra for human opsins and an ideal distribution of emission spectrum from LEDs making up a lighting system.

Violet-Light Suppression of Thermogenesis by Opsin 5 Hypothalamic Neurons

The opsin family of G-protein coupled receptors are employed as light detectors in animals. Opsin 5 (neuropsin, OPN5) is a highly conserved, violet light (380 nm $\lambda_{max}$) sensitive opsin. In mice, OPN5 is a photoreceptor in retina and skin but is also expressed in the hypothalamic preoptic area (POA), e.g., a light-sensing pathway in which OPN5 expressing POA neurons regulate brown adipose tissue (BAT) thermogenesis. For example, OPN5 expression may include glutamatergic warm-sensing POA neurons that receive synaptic input from multiple thermoregulatory nuclei. Moreover, OPN5 POA neurons project to BAT and decrease its activity under chemogenetic stimulation. OPN5 null mice show overactive BAT, elevated body temperature, and exaggerated thermogenesis when cold challenged. Moreover, violet photostimulation during cold exposure acutely suppresses BAT temperature in wild-type, but not in OPN5 null mice. Direct measurements of intracellular cAMP ex vivo reveal that OPN5 POA neurons increase cAMP when stimulated with violet light. Thus, embodiments may include identification of a violet light sensitive deep brain photoreceptor that normally suppresses BAT thermogenesis.

The availability of photons emanating from our sun has been exploited for adaptive advantage by almost all living systems. For example, the visual sense of animals relies on detection of radiant photons for object identification. Plants and animals also anticipate the daily light-dark cycle using non-visual pathways to entrain circadian clocks. In animals, both visual and non-visual pathways employ the eyes for photic input, but extraocular light detection has been well-described in non-mammalian species. For example, in the fruit fly and in zebrafish, light can entrain the circadian clock in organs directly, without the need for input from the eyes. Though it had been thought that mammals do not employ extraocular light detection, this view has recently changed.

In animals, most light response pathways employ a member of the opsin family of G-protein coupled receptors as a light detector. Of the non-visual opsins, melanopsin (OPN4), a blue light sensitive (480 nm $\lambda_{max}$) opsin, has been most extensively studied in mice: ocular melanopsin has a role in circadian entrainment, the pupillary light reflex, eye development as well as mood and learning. There is evidence of the involvement of the visual violet light sensitive (380 nm $\lambda_{max}$)[1,2] neuropsin (OPN5) and blue light sensitive encephalopsin (OPN3) in extraocular light response pathways. In birds, OPN5 expression in the brain is implicated in the regulation of seasonal breeding behavior and in mice is necessary and sufficient for direct photoentrainment of retinal, corneal, and skin circadian clocks. OPN3 may be expressed in adipocytes where it promotes lipolysis in a blue light-dependent manner.

In the mouse and primate hypothalamus, OPN5 is expressed in the preoptic area (POA) and this raised the possibility that, as in birds, OPN5 might function as a deep brain photosensor. The POA is a thermoregulatory region that in mouse modulates the heat-generating capacity of brown adipose tissue (BAT) via sympathetic nervous system activity (SNS). Homeotherms rely on this system to defend core body temperature against ever-changing environments. According to some embodiments, the thermoregulatory apparatus of mice is violet light responsive in an OPN5-dependent manner. Moreover, according to some embodiments, the crucial light sensitive cells are neurons that reside in the preoptic area of the hypothalamus.

Opsin 5 in POA Thermoregulatory Neurons

Figures 4A, 4B, 4C, 4D, 4E:
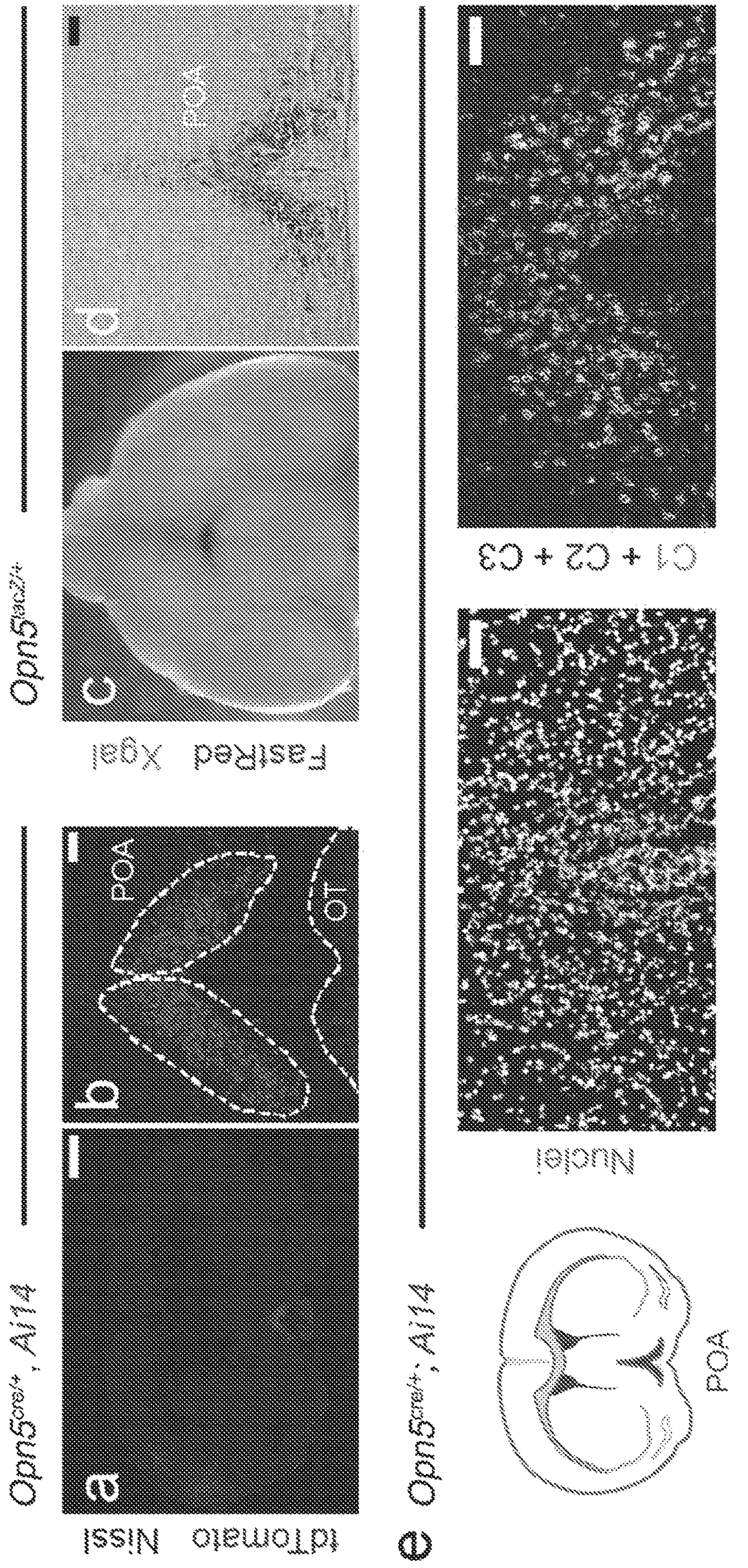
FIG. 4 illustrates an exemplary expression of OPN5 in a population of hypothalamic poa neurons that receive input from thermoregulatory nuclei.

According to some embodiments, using an OPN5 knock-in allele to activate the tdTomato reporter Ai14 ($OPN5^{cre/+}$; Ai14 mice), OPN5 expression is identified in the preoptic area (POA) of the hypothalamus in postnatal day (P)21 mice (FIG. 4*a, b*). According to some embodiments, this region was actively transcribing OPN5 using Xgal labeling in brain tissue from P10 $OPN5^{lacz/+}$ mice (FIG. 4*c, d*). Ai14+ neurons were also found in the raphe pallidus but were Xgal negative in P12 $OPN5^{lacz/+}$ cryosections, suggesting $OPN5^{cre/+}$; Ai14 lineage marking from an earlier developmental stage. A comprehensive lineage survey outside the CNS revealed no OPN5 expression in brown and white adipose tissue, thyroid, liver, heart, adrenal, and pancreas.

Figures 4F, 4G, 4H, 4I, 4J, 4K:
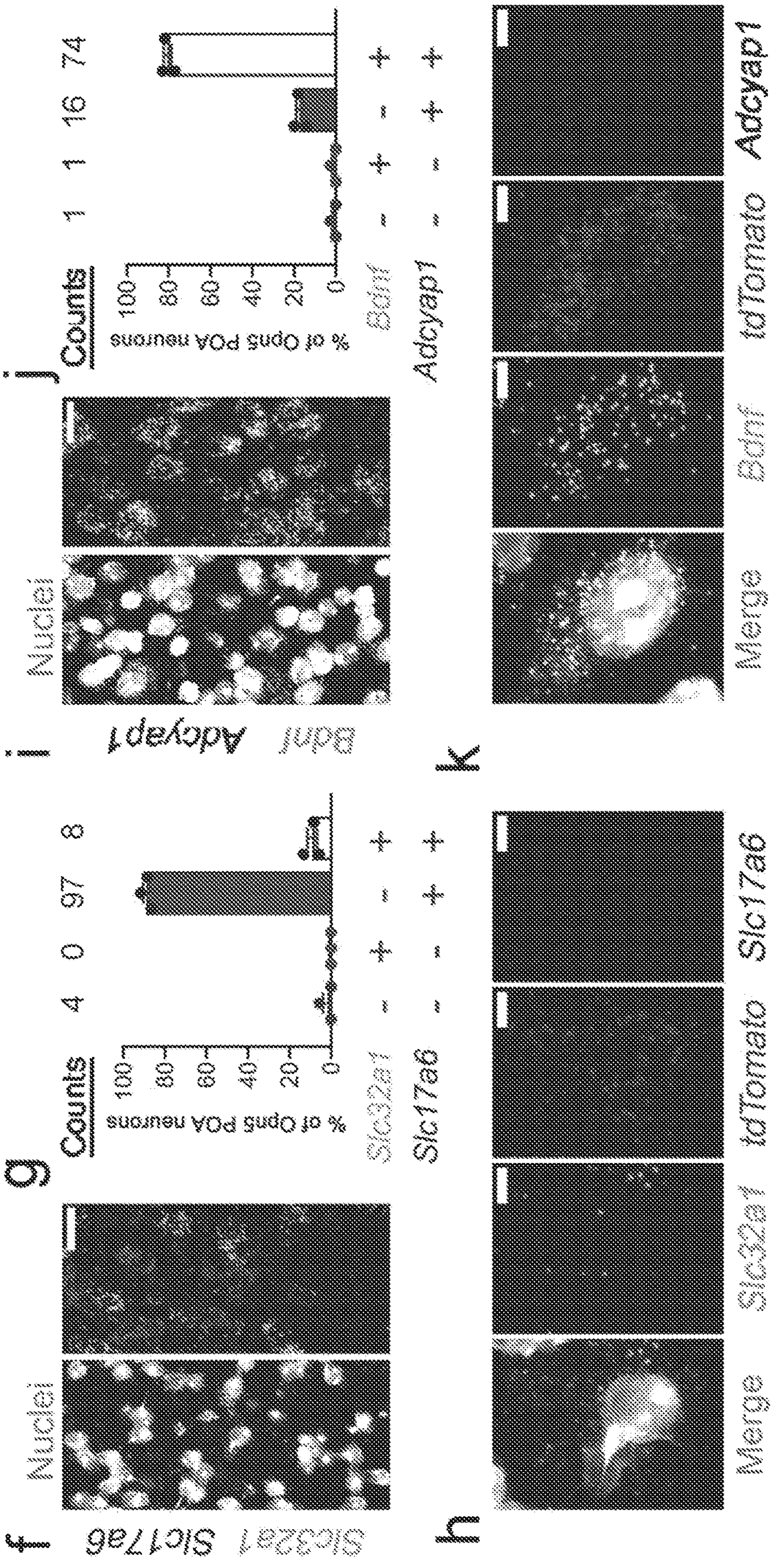

The POA contains several discrete neuronal subtypes associated with homeostatic control. Multiplex fluorescence in situ hybridization (M-FISH) were used to label distinct subpopulations in the POA of P21 $OPN5^{cre/+}$; Ai14 mice (FIG. 4*e*): the majority of OPN5 POA neurons expressed Slc17a6 (vesicular glutamate transporter 2, VGLUT2) and thus were glutamatergic, while only a small fraction colabeled with Slc32a1 (vesicular GABA transporter, VGAT) (FIG. 4*f*-*h*). The POA also contains temperature-sensitive neurons that co-express the neuropeptides PACAP (Adcyap1) and BDNF (Bdnf)[18] and use TRPM2 as a heat sensor[19]. Using M-FISH, it may be found that nearly all OPN5 POA neurons colabeled for Adcyap1 and Bdnf (FIG. 4*i*-*k*) and approximately half co-express Trpm2. Thus, OPN5 POA neurons are BDNF+/PACAP+ warm-sensitive glutamatergic neurons.

Figures 4L, 4M:
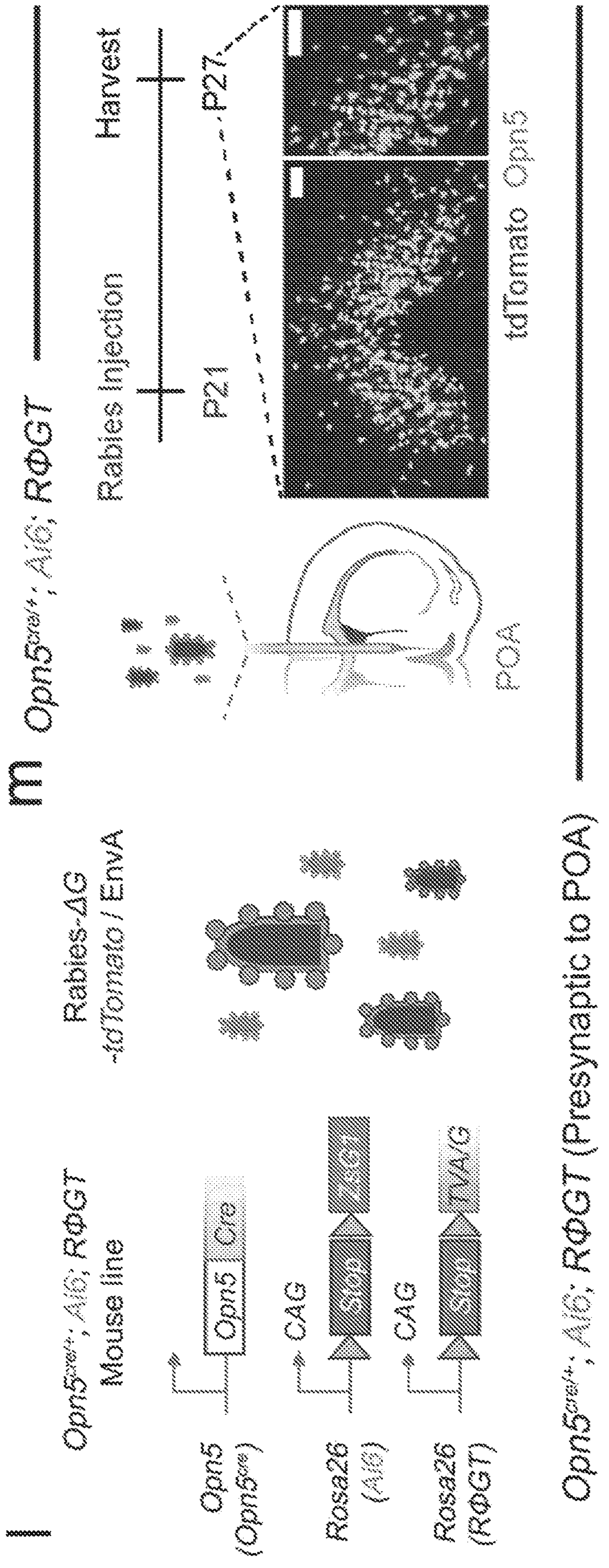
Figures 4N, 4O, 4P, 4Q, 4R, 4S, 4T, 4U, 4V, 4W, 4X:
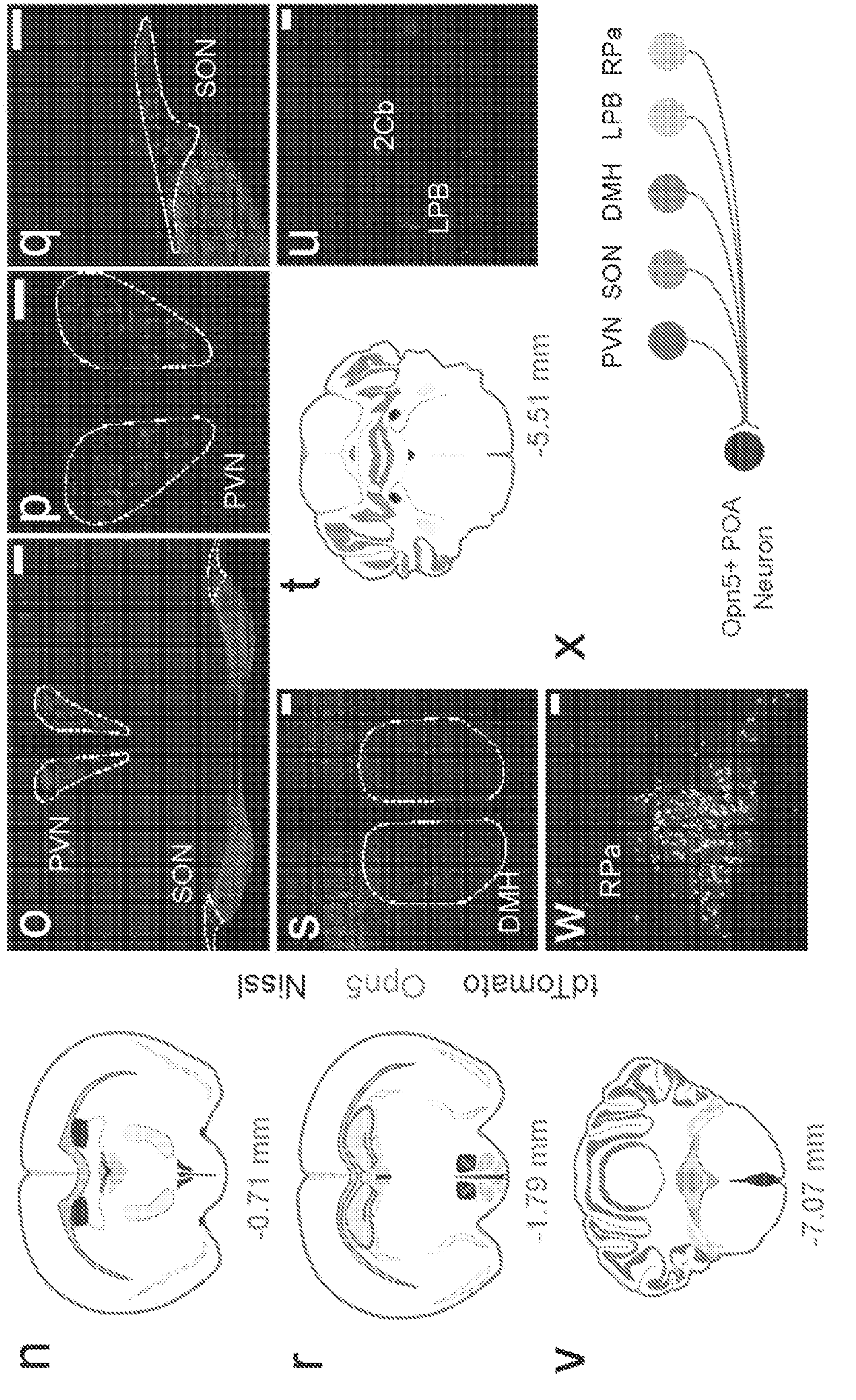

To map presynaptic inputs to OPN5 POA neurons, a tracing rabies virus was injected into the POA of P21 $OPN5^{cre/+}$; Ai6; RΦGT[20] mice (FIG. 4*l, m*). Six days post-injection, tdTomato-positive neurons were identified in the paraventricular nucleus (PVN, FIG. 4*n*-*p*), the supraoptic nucleus (SON, FIG. 4*n,o,q*), the dorsomedial hypothalamus (DMH, FIG. 4*r,s*), the lateral parabrachial nucleus (LPB, FIG. 4*t, u*), and raphe pallidus (RPa, FIG. 4*v,w*). These regions all have a role in thermoregulation (FIG. 4*x*), with the DMH, LPB, and RPa directly implicated in the cutaneous thermosensory circuit that controls brown adipose tissue (BAT) activity. Taken together, these results indicate that OPN5 POA neurons are an excitatory, warm-sensitive population synaptically connected to thermoregulatory nuclei.

OPN5 POA Neurons Regulate BAT Activity

Figures 5A, 5B, 5C, 5D, 5E, 5F, 5G:
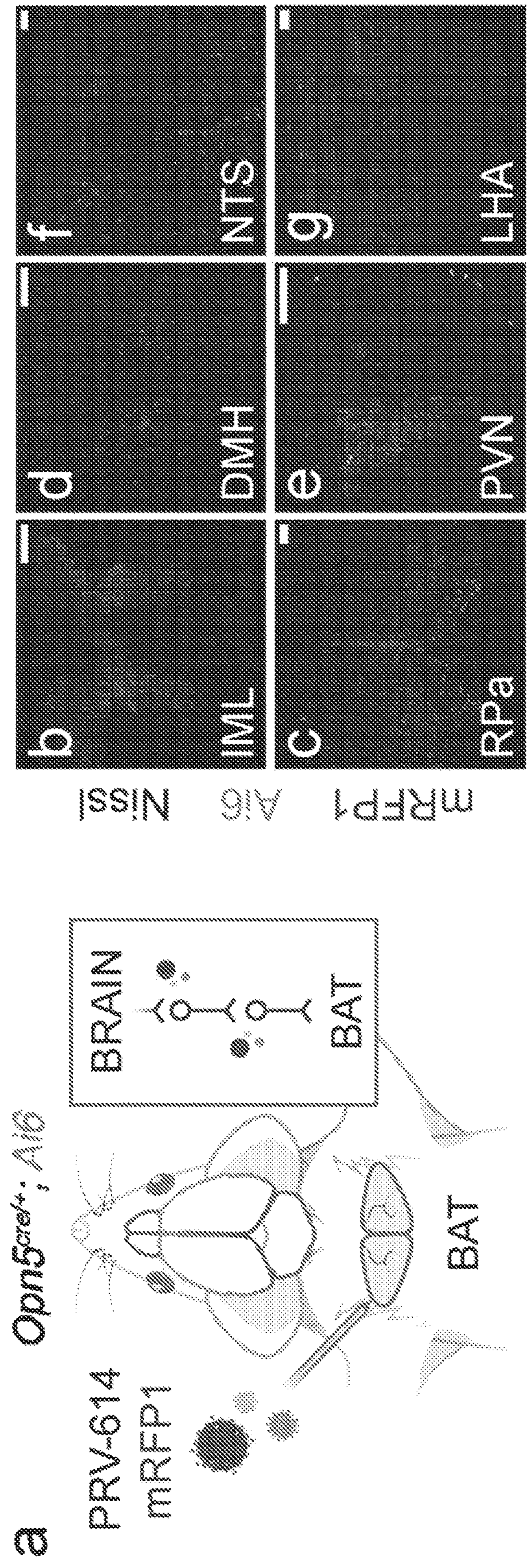
FIG. 5 illustrates that, according to some embodiments, OPN5 poa neurons regulate bat thermogenesis.
Figures 5H, 5I:
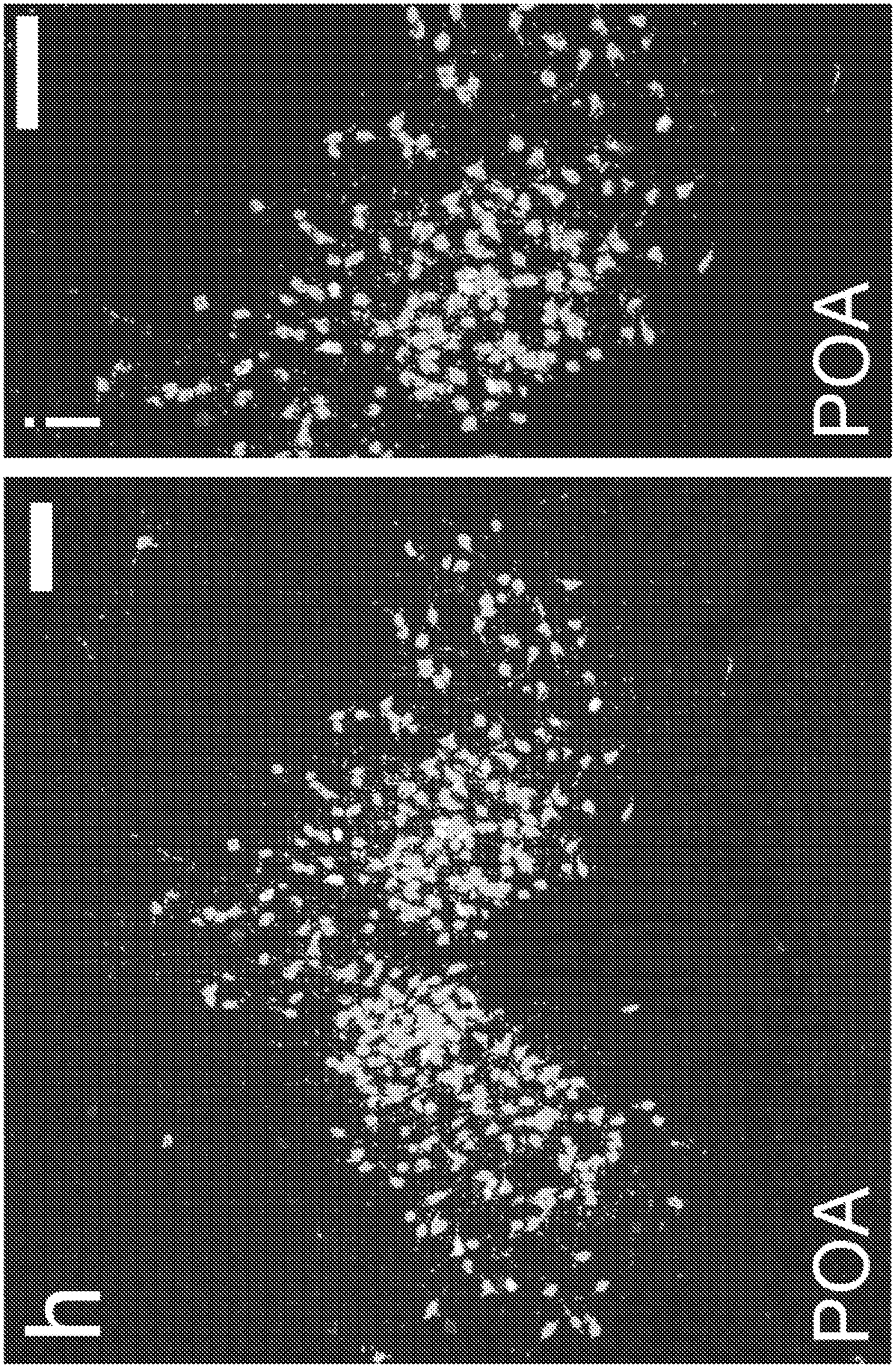
Figures 5J, 5K, 5L:
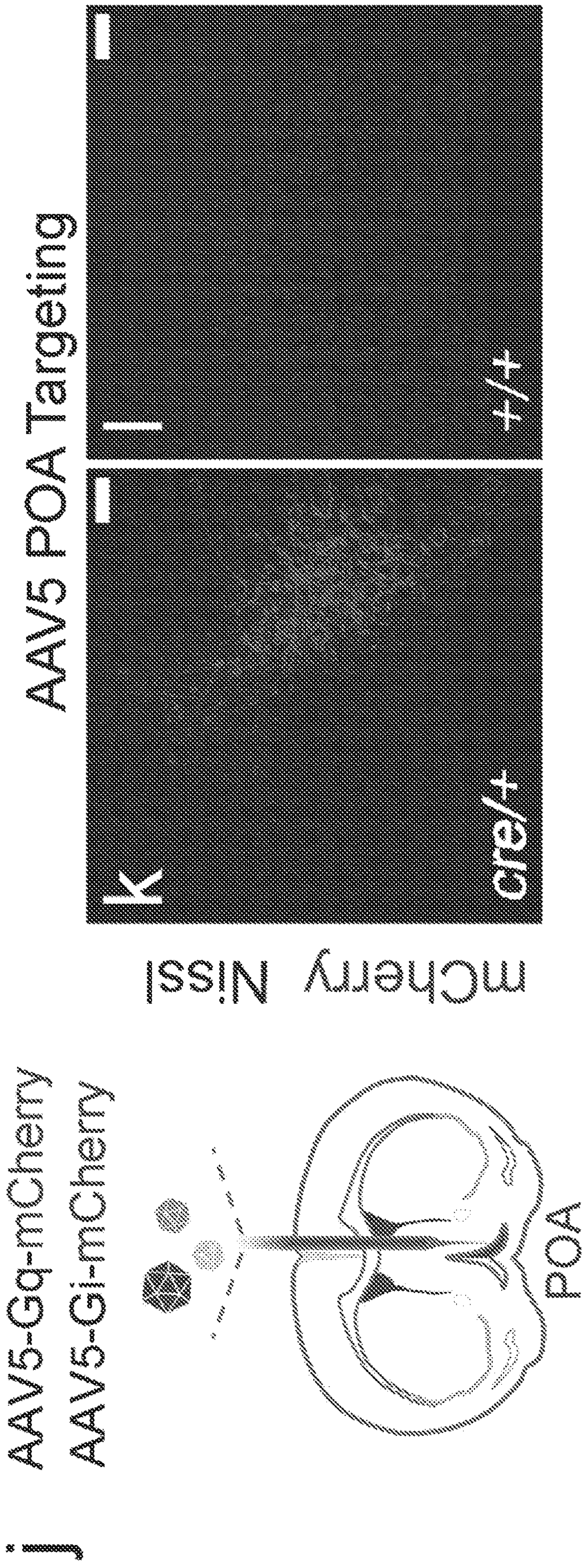

According to some embodiments, OPN5 POA neurons communicate with BAT. A transneuronal retrograde pseudorabies virus (PRV) expressing mRFP1 was injected into the BAT of P60 $OPN5^{cre/+}$; Ai6 mice (FIG. 5*a*). Five days post-injection, mRFP1-positive neurons were identified in the intermediolateral nucleus (IML) of the spinal cord, RPa, DMH, PVN, the nucleus tractus solitarius (NTS), and the lateral hypothalamic area (LHA)(FIG. 5*b*-*g*), all regions implicated in BAT thermogenesis. Importantly, we identified mRFP1-positive neurons in the POA that colabeled with Ai6 (FIG. 5*h, i*), demonstrating that a direct polysynaptic pathway exists between OPN5 POA neurons and the BAT.

Figure 5M:
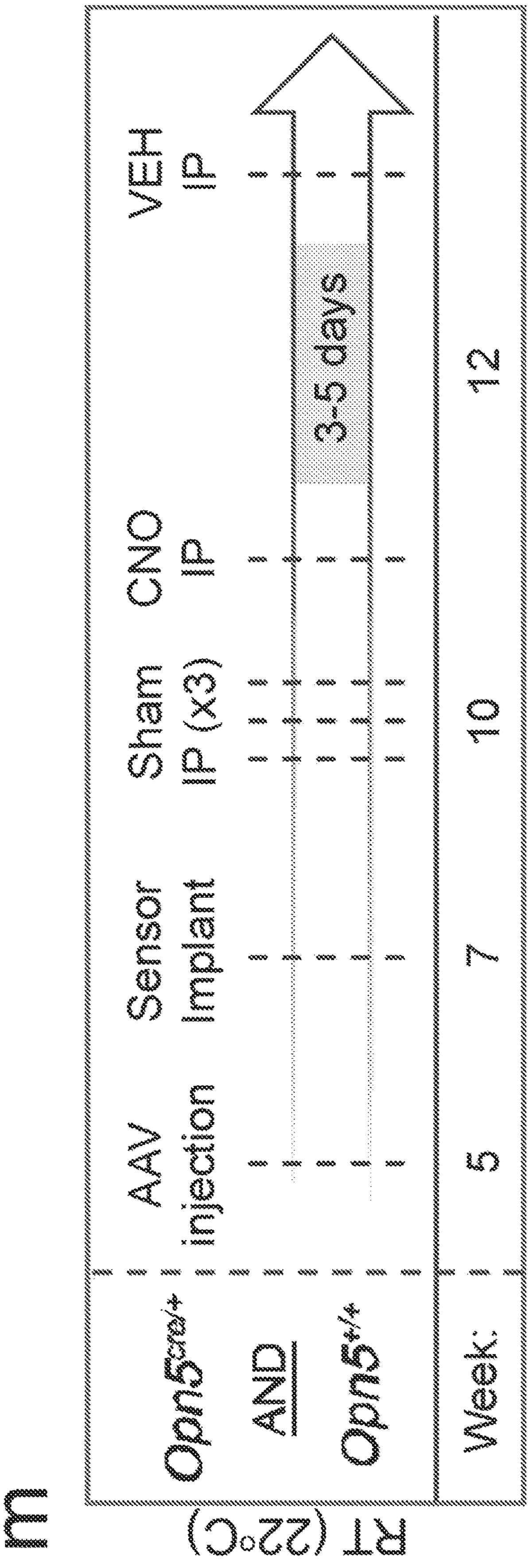
Figures 5N, 5O, 5P, 5Q:
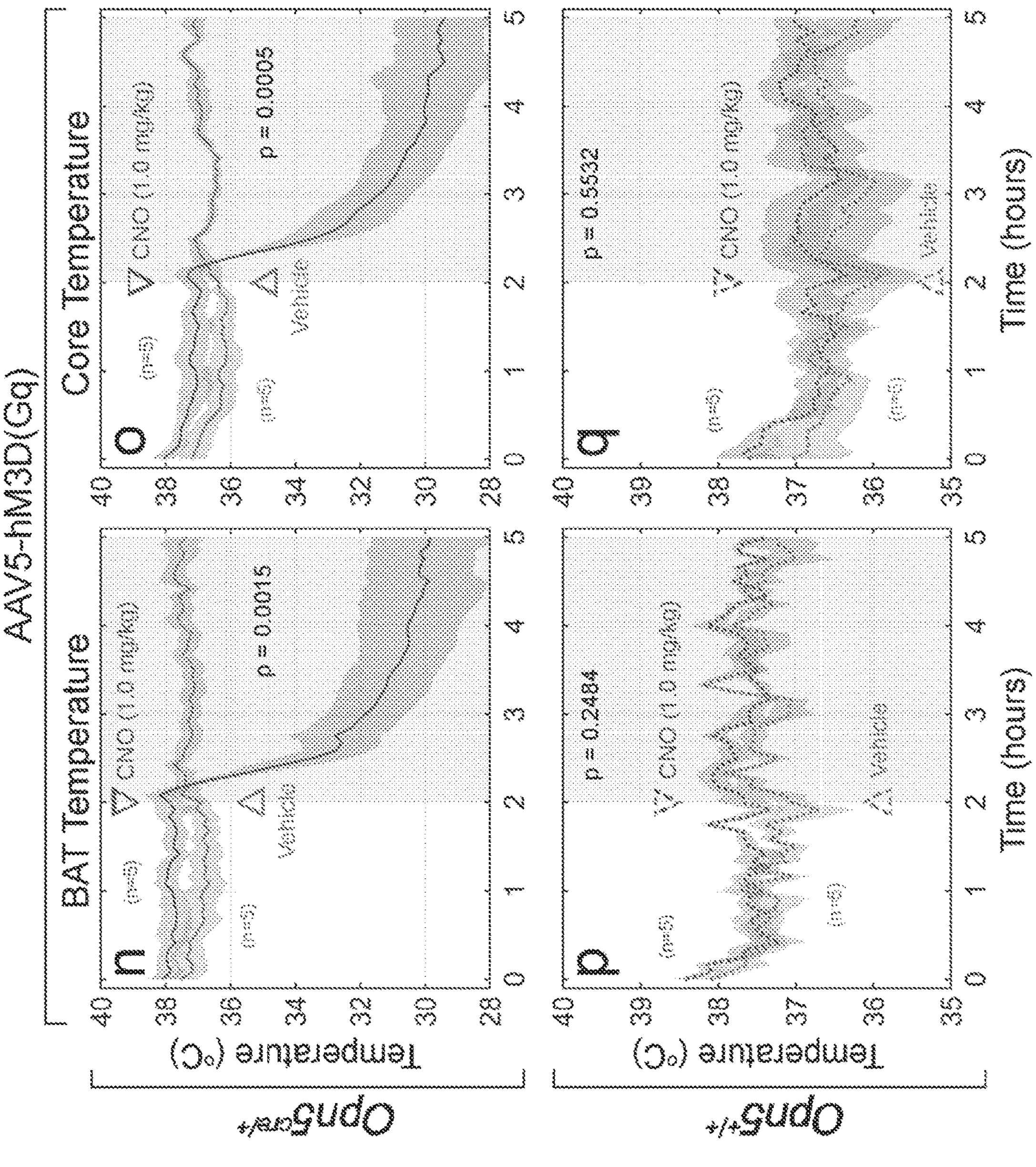
Figures 5R, 5S, 5T, 5U:
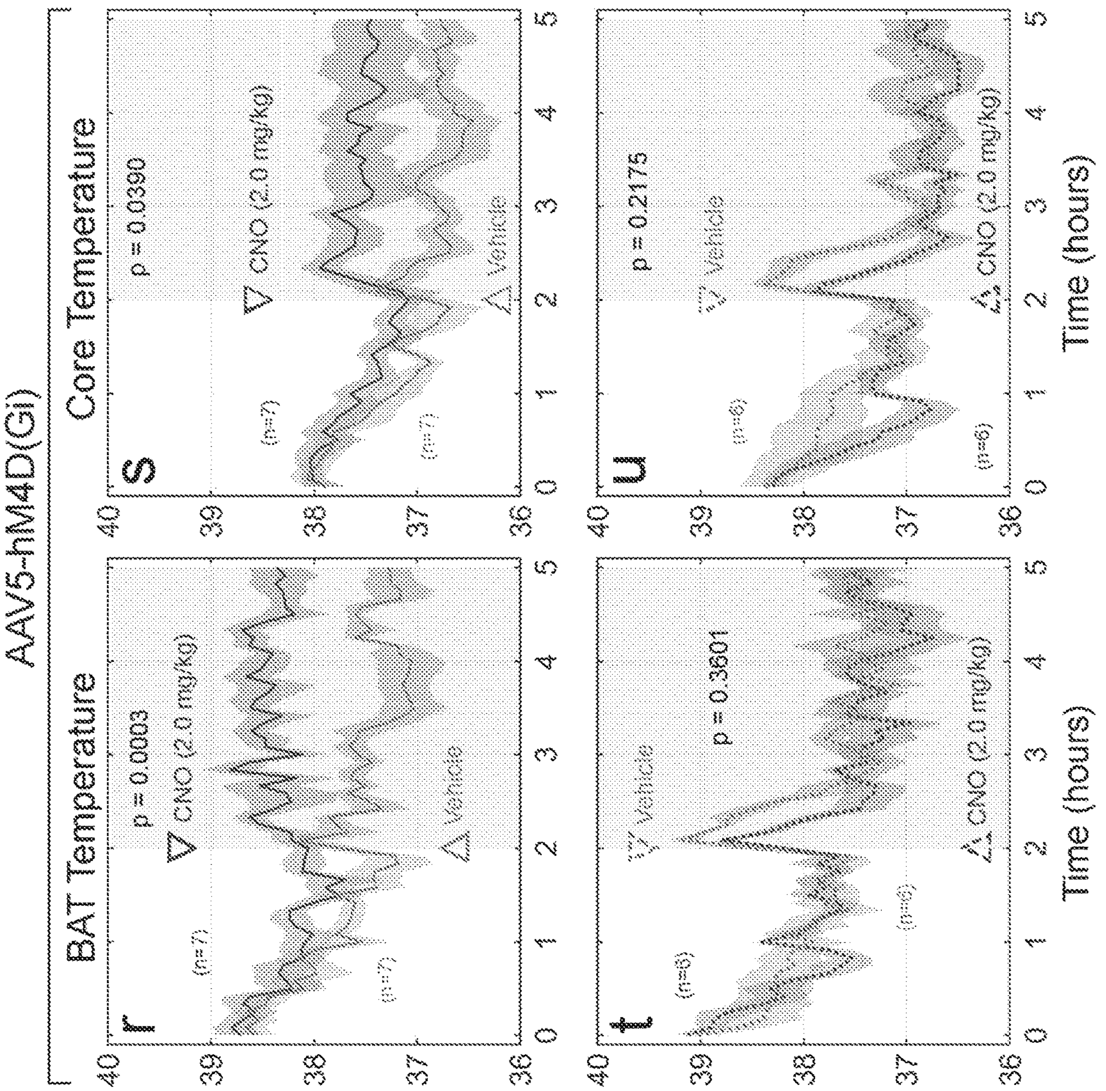

To determine whether OPN5 POA neurons can control BAT activity, chemogenetics were used to activate or inhibit these neurons while monitoring BAT and core temperature. Stimulatory hM3Dq or inhibitory hM4Di DREADDs (Designer Receptors Exclusively Activated by Designer Drugs) were targeted to OPN5 POA neurons by injecting a cre-dependent AAV5 (Adeno Associated Virus) vector into $OPN5^{cre/+}$ mice ($OPN5^{+/+}$ mice were used as a control) (FIG. 5*j*-*m*). Animals were implanted with a telemetric sensor to monitor BAT and core temperature and each received an injection of the DREADD ligand clozapine N-oxide (CNO) for experimental and control studies (FIG. 5*m*). Animals were then sacrificed, and the BAT harvested for molecular profiling of thermogenic gene expression. Chemogenetic activation of OPN5 POA neurons significantly suppressed BAT and core temperature (FIG. 5*n, o*). Cre-negative $OPN5^{+/+}$ animals administered either vehicle or CNO failed to show a similar effect (FIG. 5*p, q*). By contrast, chemogenetic inhibition of OPN5 POA neurons augmented BAT and core temperature (FIG. 5*r, s*), with this effect absent in cre-negative controls (FIG. 5*t, u*). Subsequent studies performed on $OPN5^{cre/-}$ (loss of OPN5 function) animals and animals under 4° C. cold exposure showed that heterozygous OPN5 loss of function does not change baseline BAT or core temperature and that neither loss of OPN5 nor temperature sensing alters the chemogenetic effects of OPN5 POA neurons on BAT activity. Overall, these results demonstrate that OPN5 POA neurons can robustly and bidirectionally regulate BAT activity.

Elevated Thermogenesis in OPN5 Null Mice

To study the function of OPN5 in thermogenesis, a germ-line OPN5 null mouse ($OPN5^{-/-}$) was used. Immunodetection in $OPN5^{-/-}$ BAT showed elevated levels of uncoupling protein UCP1 and tyrosine hydroxylase (TH), a marker for SNS innervation. Cold exposure revealed that that $OPN5^{-/-}$ animals were better at defending their body temperature and showed elevated thermogenesis pathway genes. Telemetry sensor recording further indicted that core and BAT temperature were elevated in OPN5 null mice even at 24° C. ambient, and that these differences were not due to a dysregulated circadian rhythm. By infrared thermography, cold exposed P8 and P90 $OPN5^{-/-}$ were warmer than controls. Surface temperatures in the Interscapular adipose (iAT) region of P90 $OPN5^{-/-}$ animals were quantifiably warmer, whereas tail temperatures were indistinguishable. In aggregate, these data suggested that mice lacking OPN5 exhibit increased BAT thermogenesis.

The exaggerated thermogenesis of $OPN5^{-/-}$ mice does not lead to changes in body weight and composition or locomotor activity but does result in elevated energy expenditure. Lack of body composition differences may be explained by the increased food and water consumption of $OPN5^{-/-}$ mice. Serum lipids are lower in the OPN5 null, but serum thyroxine (T4) and thyrotropin-releasing hormone (TRH) are unchanged, suggesting that facultative and not obligatory thermogenesis is primarily affected. Major white adipose depots are smaller in $OPN5^{-/-}$ mice, and show decreased adipocyte size and increased UCP1. Systolic and diastolic blood pressure, mean arterial pressure (MAP), and pulse rate are not different between $OPN5^{-/-}$ and $OPN5^{+/+}$ mice. However, $OPN5^{-/-}$ mice show an augmented response to the β3-adrenergic agonist CL-316,243. These results indicate that the exaggerated BAT thermogenesis of $OPN5^{-/-}$ animals cannot be attributed to differences in thyroid hormone or cardiovascular activity, but rather, is explained by adaptive changes in adrenergic BAT sensitivity and lipid mobilization. A POA-specific OPN5 deletion was generated using $Lepr^{cre}$. The previous analyses were repeated on control ($OPN5^{fl/fl}$) and conditional mutant mice ($Lepr^{cre/+}$; $OPN5^{fl/fl}$) and found that mutant mice largely phenocopied the global OPN5 loss-of-function model. These data provide strong support for a BAT thermogenic-suppressive role of preoptic OPN5.

Violet Light Suppresses BAT Activity

Figures 6A, 6B, 6C, 6D:
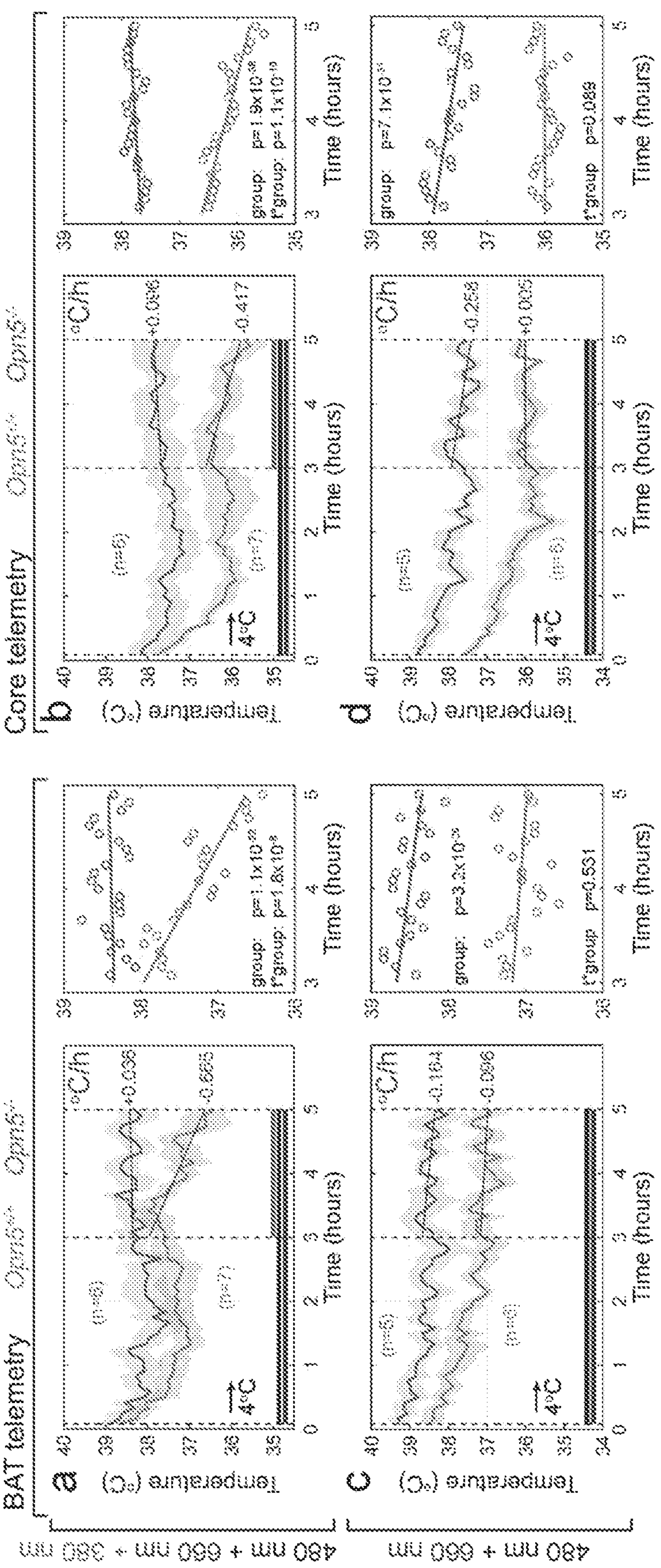
FIG. 6 illustrates that, according to some embodiments, violet light acutely suppresses bat thermogenesis.

The observation that $OPN5^{-/-}$ mice show an exaggerated thermogenic response suggested that OPN5 normally inhibits thermogenesis. To assess whether this suppressive role depends on the light-sensing function of OPN5, BAT and core temperature were monitored in cold-exposed P90-120 $OPN5^{+/+}$ and $OPN5^{-/-}$ animals while providing acute 380 nm violet light stimulation. In $OPN5^{+/+}$ mice, violet photostimulation decreased BAT and core temperatures, whereas $OPN5^{-/-}$ mice failed to respond (FIG. 6*a, b*). When violet light was not supplemented, there was no longer any divergence in BAT and core temperature between $OPN5^{+/+}$ and OPN5$^{-/-}$ mice (FIG. 6*c, d*). To assess the possibility that the addition of violet light might invoke a differential behavioral response in OPN5$^{+/+}$ and OPN5$^{-/-}$ animals, locomotor activity was recorded and revealed no differences in average speed or distance traveled.

Figures 6E, 6F, 6G, 6H:
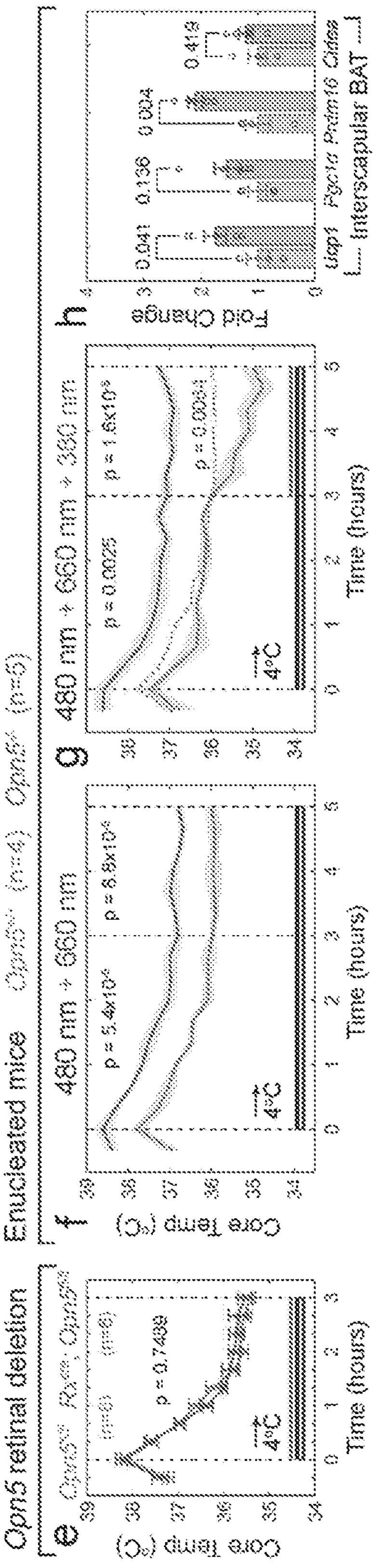

OPN5 is expressed in retinal ganglion cells and can photoentrain a retinal circadian clock. Two approaches were utilized to assess the possibility that retinal OPN5 might contribute to changes in BAT thermogenesis. First, OPN5$^{fl}$ was conditionally deleted from retinal progenitors using Rx$^{cre}$, and no differences were found in core temperature between cold exposed wild-type (OPN5$^{fl/fl}$) and retinal OPN5 conditional (Rx$^{cre}$; OPN5$^{fl/fl}$) animals (FIG. 6*e*). Second, P90-120 OPN5$^{+/+}$ and OPN5$^{-/-}$ mice were enucleated and subjected to the same cold-exposure photostimulation assay as sighted mice. Enculeated OPN5$^{+/+}$ mice decreased their core temperature in response to violet light while enucleated OPN5$^{-/-}$ showed no such response (FIG. 6*f, g*). Molecular profiling of dissected BAT from enucleated OPN5$^{+/+}$ and OPN5$^{-/-}$ animals showed differences in thermogenic gene induction (FIG. 6*h*) that resembled changes observed in sighted mice. These data show that the inhibitory role of OPN5 on BAT thermogenesis does not require retinal OPN5.

Violet Light Absence Enhances BAT Activity

As an extension of the acute response analysis, it was determined whether chronic elimination of violet photons would mimic OPN5 loss-of-function in wild-type mice. Male and female wild-type mice on a C57BL6/J background were raised under "full spectrum" (380 nm+480 nm+660 nm) or "minus violet" (480 nm+660 nm) lighting from embryonic day (E)16.5 to P70 under a standard 12L:12D light cycle. Analysis at P70 revealed that minus violet mice showed a milder version of the exaggerated thermogenesis phenotype characteristic of the OPN5 null.

Since the aggregated data suggested that OPN5 POA neurons might be directly light responsive, it was assessed whether the POA received sufficient photon flux for opsin activation. Using a custom-designed optic fiber probe, intratissue radiometry was performed at various depths in the brain of anesthetized mice. At the $\lambda_{max}$ of the OPN5 action spectrum, approximately 2.5 log-fold intensity attenuation was measured relative to the cranial surface at the depth of the POA. When extrapolating for normal sunlight intensities, a maximum violet flux of $9.0\times10^{12}$ photons $cm^{-2}s^{-1}$ can reach the POA. This is above the activation threshold for other mammalian nonvisual opsins.

OPN5 POA Neurons Respond to Violet Light

Figures 7A, 7B, 7C, 7D, 7E:
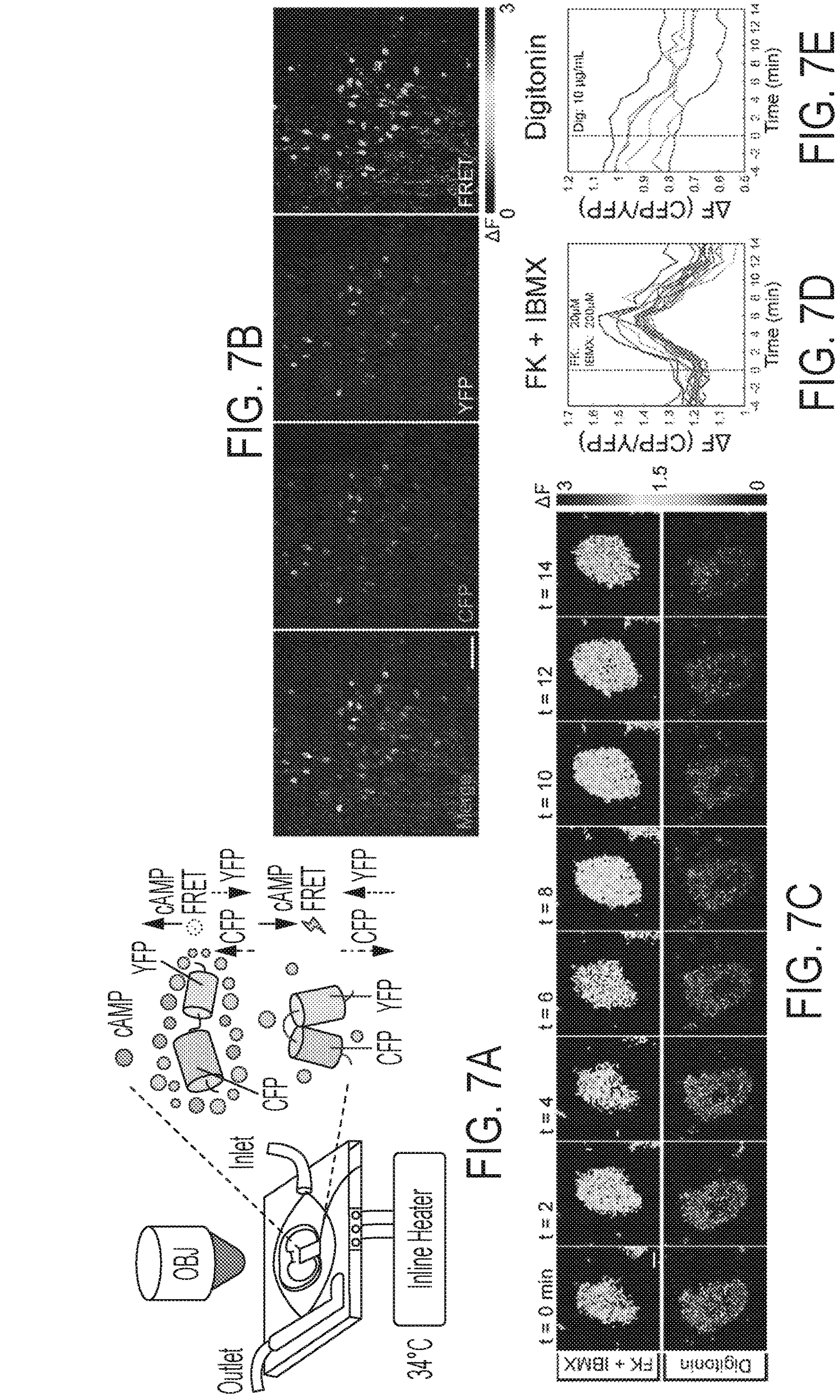
FIG. 7 illustrates that, according to some embodiments, OPN5 poa neurons respond to violet light ex vivo.
Figure 7F:
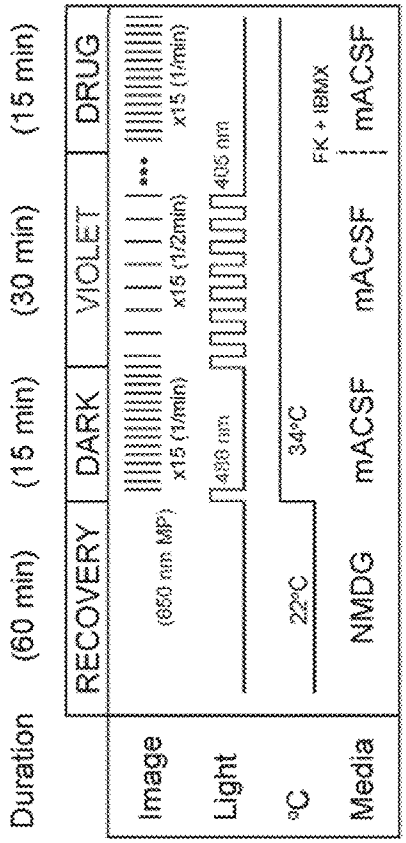
Figure 7G:
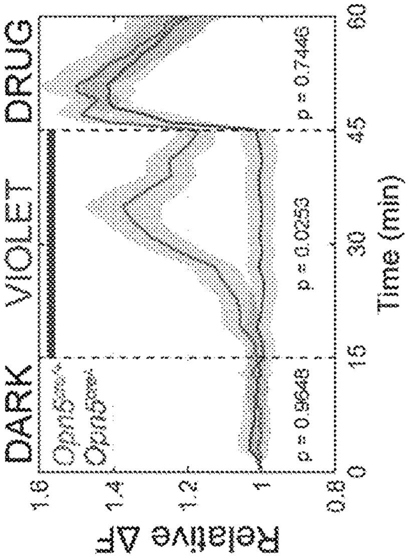
Figure 7H:
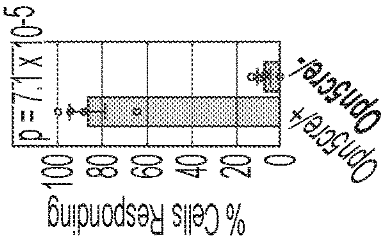
Figure 7I:
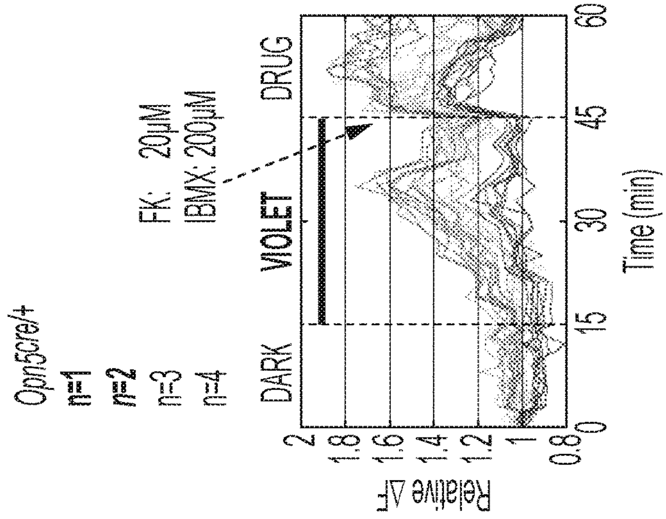
Figure 7J:
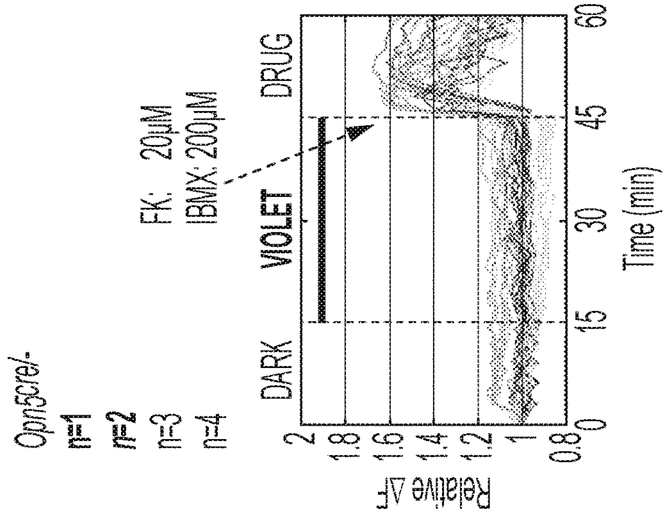
Figure 7K:
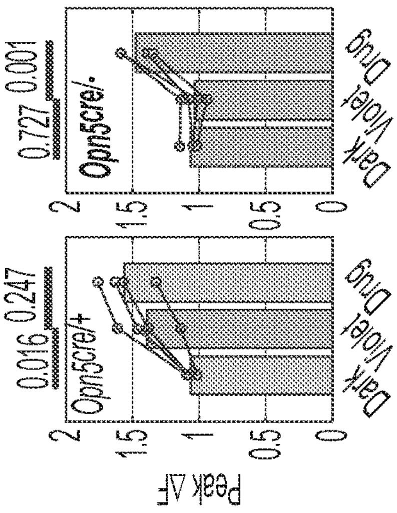

Thus, the crucial question of how OPN5 POA neurons signal in response to violet light was raised. To gain insight into these mechanisms, real-time intracellular cyclic AMP (cAMP) was monitored using a genetically encoding a TEpacVV cAMP sensor activated transcriptionally with OPN5$^{cre}$ TEpacVV reports cAMP binding by changes in fluorescence resonance energy transfer (FRET) between an mTurquoise donor (CFP) and a Venus acceptor ($^{cp173}$Venus-Venus, YFP)[23] that can be imaged using two-photon microscopy (FIG. 7*a, b*). Neurons that experience an elevation in intracellular cAMP, such as the response to forskolin (FK) and 3-isobutyl-1-methylxanthine (IBMX), will have an increase in the ratio of CFP to YFP (ΔF), while depleting cAMP by permeabilizing the cell with digitonin will decrease ΔF (FIG. 7*c-e*). A 1 hour experimental protocol was designed where 15 minutes of FRET measurements in darkness were followed by 30 minutes of 50% duty cycle violet photostimulation with measurements taken in between, ending with 15 minutes of dark measurements following the application of FK+IBMX (FIG. 7*f*). POA slices from P21 OPN5$^{cre/+}$ animals showed a dramatic increase in relative ΔF in response to violet photostimulation whereas slices from P21 OPN5$^{cre/-}$ animals featured little to no elevation in ΔF and was indistinguishable from dark conditions (FIG. 7*g-k*). These data argue that OPN5 POA neurons are directly sensitive to violet photostimulation ex vivo and in response, increase intracellular cAMP.

Discussion

Accordingly, evidence is presented in mice of a violet light-sensitive thermoefferent pathway from POA to BAT that employs OPN5 (Neuropsin) as a light sensor. Acting as a deep brain photoreceptor with a peak sensitivity of 380 nm, OPN5 inhibits BAT thermogenesis through a direct light response that raises intracellular cAMP.

Deep brain photoreceptors have been extensively documented in teleost and avian species, where nonvisual opsins regulate a host of behavioral and reproductive responses. By contrast, evidence of extraocular light sensing in mammals and the precise signaling mechanisms have not yet been fully determined. According to some embodiments, it is demonstrated that adipocyte OPN3 (a blue-light sensitive opsin) increases lipolysis through promoting cAMP-dependent phosphorylation of hormone sensitive lipase and thus enhances adaptive thermogenesis in mice. According to some embodiments, neuroanatomical and loss-of-function studies were used to establish preoptic area OPN5 in an inhibitory role for BAT thermogenesis. Chemogenetic stimulation of OPN5 POA neurons immediately decreases BAT temperature, whereas mice lacking OPN5 show profound elevations in adaptive thermogenesis and BAT activity. These opposing activities of OPN3 and OPN5 on thermogenesis raise the interesting hypothesis that nonvisual photoreceptive pathways decode light information to help calibrate time-of-day appropriate BAT activity. The precise mechanisms that integrate OPN3 and OPN5 activities in thermogenesis pathways may require further study.

By studying BDNF+/PACAP+, leptin receptor, TRPM2, and prostaglandin EP3 receptor expressing POA neurons, evidence may be uncovered that glutamatergic, and not GABAergic populations, directly regulate body temperature. Such data challenges prior models suggesting that BAT-projecting thermoregulatory POA neurons are GABAergic. According to some embodiments, the present analysis identified OPN5 POA neurons to be glutamatergic BDNF/PACAP double positive and showed robust decreases in BAT and core temperature under chemogenetic stimulation. It may be suggested that an excitatory subpopulation of warm-sensitive POA neurons is capable of integrating signaling from leptin, prostanglandin E2, and violet light. The most compelling evidence of this comes from a tandem scRNA-seq:MERFISH (single cell RNA-seq Multiplexed Error-Robust FISH) cell atlas of the POA, in which excitatory subcluster e13 is enriched for co-expression ofAdcyap1 (encoding PACAP), Bdnf, Slc17a6 (encoding VGLUT2), Ptger3 (encoding the prostanglandin E2 receptor), Lepr, and OPN5[27]. It will be crucial to investigate whether this population represents a bona fide nexus for signal integration for all these pathways.

According to some embodiments, an unexpected light-responsive POA-BAT neuraxis is revealed in mice that requires OPN5 as a deep brain photosensor. Thus, there is a possibility that normal thermogenesis in humans requires light input via extraocular pathways. This possibility is supported by the conservation of OPN3 expression in human adipocytes, OPN5 expression in the POA of primates, and many metabolic diseases showing a season-of-birth dependent risk, suggesting involvement of light response pathways. It is speculated that insufficient stimulation of OPN3 and OPN5 in these tissues may contribute to the growing epidemic of metabolic disease in the developed world, where artificial lighting has become the norm.

The following are shown in FIG. 4, e.g., OPN5 is expressed in a population of hypothalamic POA neurons that receive input from thermoregulatory nuclei:

a, b, Coronal brain section (P21 $OPN5^{cre/+}$; Ai14) showing OPN5 (tdTomato, red) restricted to the preoptic area (POA). Nissl labeling is blue. Red labeling in optic tracts (OT) are axons from OPN5 retinal ganglion cells. c, d, Xgal labeling (P10 $OPN5^{lacz/+}$) in (c) whole brain, ventral view and (d) coronal section through POA. e, M-FISH (see Methods) region schematic and low magnification images of nuclear (DAPI, greyscale) and three-colour probe labeling. f, g, Representative images of POA neurons (f) probed for tdTomato ($OPN5^{cre}$; Ai14, red), Slc32a1 (Vgat, green), and Slc17a6 (Vglut2, blue) with (g) quantification of overlap (n=3, 109 cells). h, Representative tdTomato+ cell from (f). i, j, As in (f, g) but for tdTomato ($OPN5^{cre}$; Ai14, red), Bdnf (green), and Adcyap1 (encoding PACAP, blue) with (j) quantification (n=3; 92 cells). k, Representative tdTomato+ cell from (i). l, Schematic of the mouse genetics used for rabies viral tracing. m, Experimental timeline for POA-tracing, and primary infected neurons (yellow). n-w, Traced neurons (red) located in the paraventricular nucleus; PVN (o, p), supraoptic nucleus; SON (o, q), dorsomedial hypothalamus; DMH (r, s), lateral parabrachial; LBP (t, u), and raphe pallidus; RPa (v, w). Green regions in (o, q) are optic tracts with axons from OPN5 retinal ganglion cells. x, Schematic representation of nuclei presynaptic to OPN5 POA neurons. Scale bars, 5 μm (h, k), 20 μm (f, i), 75 μm (e, m), 100 μm (b, p, q, s, w), 200 μm (o, u), 1 mm (a). 2Cb, lobule 2 of cerebellar vermis. Data in g, i are mean±s.e.m.

The following are shown in FIG. 5, e.g., OPN5 POA neurons regulate BAT thermogenesis:

a, Pseudorabies virus (PRV-mRFP1) injection into the BAT of P60 $OPN5^{cre/+}$; Ai6 mice. b-i, Representative images of PRV-infected (red) regions including the intermediolateral nucleus (IML) of the spinal cord (b), RPa (c), DMH (d), PVN (e), nucleus tractus solitarius (NST) (f), lateral hypothalamic area (LHA) (g), and OPN5; Ai6 (green) POA neurons (h, i). j, Schematic of DREADD virus delivery into the POA of $OPN5^{cre/+}$ or $OPN5^{+/+}$ animals. k, l, IF showing AAV-infected POA neurons in $OPN5^{cre/+}$ (k) and lack thereof in $OPN5^{+/+}$ (l). m, Experimental timeline. n-u, Chemogenetic manipulation of OPN5 POA neurons. CNO or vehicle (saline) injected at hour 2 (open arrowhead). CNO-mediated activation of OPN5 POA neurons with Gq DREADD decreases BAT and core temperature in $OPN5^{cre/+}$ animals (n, o) but not in $OPN5^{+/+}$ controls (p, q). CNO-mediated inhibition of OPN5 POA neurons with Gi DREADD increases BAT and core temperature in $OPN5^{cre/+}$ animals (r, s) but not in controls (t, u). Scale bars, 100 m. Data in n-u are mean s.e.m. All p values represent 1-way repeated measures ANOVA.

The following are shown in FIG. 6, e.g., Violet light acutely suppresses BAT thermogenesis:

a-d, BAT and core telemetry recordings during 5 hour 4° C. exposure with lighting wavelength modulation. All mice received 480 nm and 660 nm light exposure (see Methods). At the 3 hour mark (dotted line), $OPN5^{+/+}$ or $OPN5^{-/-}$ animals were either supplemented with 380 nm light (a, b) or remained in 480 nm+660 nm (c, d). BAT and core temperature trajectories during light modulation (hours 3-5) were calculated via linear regression and the rate of temperature change reported as ° C./h. e, Core temperature assessment (rectal) of $OPN5^{fl/fl}$ and $Rx^{cre}$; $OPN5^{fl/fl}$ mice during 3 h cold challenge in 380 nm+480 nm+660 nm lighting. f, g, Core temperature assessment in enucleated $OPN5^{+/+}$ (n=4) and $OPN5^{-/-}$ (n=5) mice under 480 nm+660 nm illumination (f) or supplemented with 380 nm violet light (g) at hour 3 (dotted line). Dotted trace in (g) represents wild-type average trace from (f). h, iBAT QPCR of thermogenesis genes (Ucp1, Pgc1α, Prdm16, Cidea) following 5 h cold exposure in mice from (g). Data are mean±s.e.m. p values are from (a-d) 1-way ANCOVA with time as covariate, (e-g) 1-way repeated measures ANOVA, (h) ANOVA with Tukey post-hoc analysis.

The following are shown in FIG. 7, e.g., OPN5 POA neurons respond to violet light ex vivo:

a, Schematic depicting two-photon assessment of cAMP biosensor FRET activity in POA slices from $OPN5^{cre}$; CAMPER mice. b, CFP, YFP, and FRET images (expressed as ΔF=CFP/YFP ratio). c, Time course ΔF images following response to forskolin (FK, 20 μM) and IBMX (200 μM) (top row) or digitonin (10 μg/mL) (bottom row). d, e, Individual traces from FK+IBMX (d, n=15 cells) or digitonin (e, n=6 cells) treated slices. f, Experimental timeline for testing violet responses of OPN5 neurons in POA slices as described in Methods. g, Relative ΔF plots for $OPN5^{cre/+}$ (gray trace, n=4) and $OPN5^{cre/-}$ (blue trace, n=4) animals. h, Percent of cells responding to violet light (average relative ΔF>1.1 between t=15 and t=45) for both groups. i, j, Individual traces from each biological replicate (n=6-8 cells per animal, 4 animals per genotype) from experiments in (g). k, Peak ΔF from dark, violet stimulation, and drug phases between $OPN5^{cre/+}$ and $OPN5^{cre/-}$ animals. Data in g, h, k are presented as mean s.e.m. p values are from (g) 1-way repeated measures ANOVA, (h, k) two-tailed Student's t-test. Scale bars, 10 μm (c), 100 μm (b).

Methods

Where appropriate, statistical methods were used to predetermine sample size. With the exception of imaging analysis, investigators were not blinded to allocation during experiments and outcome assessment.

Mice

Animals were housed in a pathogen-free vivarium maintained at an ambient temperature of 22° C. and a relative humidity of 30-70%. All pharmacological and surgical procedures were conducted in accordance with protocols approved by the Institutional Animal Care and Use Committee at Cincinnati Children's Hospital Medical Center (Protocol Number 2018-0046). This study is compliant with all relevant ethical regulations regarding animal research. Genetically modified mice used in this study include: Rx-cre, Ai14 (Jax stock 007914), Ai6 (Jax stock 007906), ROGT (Jax stock 024708), CAMPER (Rapgef3 Jax Stock 032205), Lepr-cre (ObRb-cre, Jax stock 008320), and $OPN5^{tm1a(KPMP)Wtsi}$ that were generated from C57BL/6N embryonic stem cells obtained from KOMP (embryonic stem clone ID: KOMP-HTGRS6008_A_B12-OPN5-ampicillin) as previously described. Briefly, the embryonic stem cells harbor a genetic modification in which a LacZ-Neomycin cassette is flanked by FRT sites, between exon 3 and exon 4, and a loxp site separates LacZ from the neomycin coding region. Loxp sites also flank exon 4 of OPN5, allowing multiple mouse lines that can serve as reporter nulls, conditional floxed and null mice. The $OPN5^{fl}$ allele was created by crossing the $OPN5^{tm1a(KOMP)Wtsi}$ mice to FLPeR (Jax stock 003946) to remove the LacZ cassette. The $OPN5^{-/-}$ line was created by crossing the OPN5 mice to E2a-cre (Jax stock 003724). The $OPN5^{-/-}$ line was propagated under a mixed background (C57/129/CD1/FVB). Littermate control animals were used for all experiments with the exception of C57BL/6J mice, which were reared under different lighting conditions. The $OPN5^{cre}$ mice were generated in-house using CRISPR (clustered regularly interspaced short palindromic repeats)-Cas9 (CRISPR-associated protein 9) technology as previously described.

Mice were placed on a normal chow diet (29% protein, 13% fat and 58% carbohydrate kcal; LAB Diet 5010) ad libitum with free access to water. Littermate controls were used for genetic crosses and both male and female mice were included in the study unless otherwise stated. Ages of mice used include postnatal day (P)8, P16, P21, P35, P60, P70, P90, and P120 and are indicated in the relevant experiments.

Lighting Conditions

Animals were housed in standard vivarium fluorescent lighting (photon flux $1.62\times10^{15}$ photons $cm^{-2}s^{-1}$) on a 12L:12D cycle except where noted. For generation of 'minus violet' animals, animals were housed in lighting chambers tuned to deliver full spectrum lighting or violet restricted lighting. For full spectrum lighting (above), light-emitting diodes (LEDs) were used to yield a comparable total photon flux of $1.642\times10^{15}$ photons $cm^{-2}s^{-1}$. Spectral and photon flux information for full spectrum LED lighting: near violet ($\lambda_{max}$=395 nm, $4.904\times10^{14}$ photons $cm^{-2}s^{-1}$ in the 375-435 nm range), blue ($\lambda_{max}$=470 nm, $4.035\times10^{14}$ photons $cm^{-2}s^{-1}$ in the 435-540 nm range), and red ($\lambda_{max}$=660 nm, $7.411\times10^{14}$ photons $cm^{-2}s^{-1}$ in the 600-700 nm range). Spectral and photon flux information for minus violet LED lighting: blue ($\lambda_{max}$=470 nm, $7.509\times10^{14}$ photons $cm^{-2}s^{-1}$ in the 435-540 nm range), and red ($\lambda_{max}$=630 nm, 9.705x1014 photons $cm^{-2}s^{-1}$ in the 600-700 nm range), yielding a total of $1.736\times10^{15}$ photons $cm^{-2}s^{-1}$. Photon fluxes were measured at approximately 24" from source and through an empty standard mouse cage. For wavelength restricted experiments, C57BL/6J animals were housed in a 12L:12D cycle starting in late gestation (embryonic day E16.5) either in full spectrum or in minus violet. These mice are referred to in the experiments as 'full spectrum' and 'minus violet' respectively.

Viral Vectors

All viruses used in these studies were obtained from the Center for Neuroanatomy with Neurotropic Viruses (CNNV), through its partner institutions at Princeton University, University of Pittsburgh, and Thomas Jefferson University. For monosynaptic tracing of OPN5 POA neurons, the CVS-N2cΔG/EnvA-tdTomato rabies virus was used, derived from the deletion mutant CVS-N2c rabies strain produced in Neuro2A neuroblastoma cells. For BAT projection mapping, PRV614-mRFP1 was used, which is an attenuated laboratory pseudorabies strain expressing red fluorescent protein mRFP1 under CMV promoter control. For chemogenetic studies, AAV5-hSyn-DIO-hM3D(Gq)-mCherry and AAV5-hSyn-DIO-hM4D(Gi)-mCherry viruses were used. The CVS-N2cΔG rabies virus was kindly provided by M. J. Schnell at Thomas Jefferson University. The PRV614-mRFP1 virus was kindly provided by L. W. Enquist at Princeton University. The AAV5-hSyn-DIO-hM3D(Gq)-mCherry and AAV5-hSyn-DIO-hM4D(Gi)-mCherry viruses were obtained through Addgene (Plasmid #44361 and #44362 respectively).

Stereotaxic Surgery

Mice were anesthetized with ventilated isoflurane (induction: 4%, maintenance: 1%-2%), and affixed to a stereotaxic frame (Stoelting Co.). To trace preoptic OPN5 neurons, P21 $OPN5^{cre}$; $R26^{R\Phi GT/Ai6}$ mice were injected with 0.5 μL of the CVS-N2c rabies virus (titer: $1.0\times10^{9}$ PFU/mL) into the POA (coordinates relative to bregma: +0.40 mm AP, +0.20 mm ML, −4.00 mm DV). Six days post injection, mice (P27) were sacrificed and perfused with PBS and 4% paraformaldehyde. For BAT projection mapping, P60 $OPN5^{cre}$; $R26^{Ai6/Ai6}$ mice were dissected to expose the interscapular adipose region. Six 50 nL nanoinjections of the PRV614-mRFP1 virus (titer: $4.9\times10^{9}$ PFU/mL) were made bilaterally into the interscapular brown adipose tissue. Mice were then sacrificed and perfused with PBS and 4% paraformaldehyde five days post-injection. For chemogenetic studies, 4 week old male $OPN5^{cre/+}$, $OPN5^{cre/-}$ (OPN5 reporter null), and $OPN5^{+/+}$ (cre-negative control) mice were injected with 1.0 μL AAV5-hSyn-DIO-hM3D(Gq)-mCherry or AAV5-hSyn-DIO-hM4D(Gi)-mCherry virus (titer: $7\times10^{12}$ vg/mL) into the POA (coordinates relative to bregma: +0.40 mm AP, +0.20 mm ML, −4.00 mm DV). All AAV-injected mice were given a recovery period of at least 2 weeks prior to further experimentation.

Chemogenetic Manipulation Experiments

Implanted mice were transferred to the lighting chamber that was situated in either cold (4° C.) or room temperature (22° C.) conditions for chemogenetic inhibitory hM4D(Gi) experiments, or just room temperature (22° C.) for chemogenetic stimulatory hM3D(Gq) experiments. BAT and core temperature recordings were collected every 5 minutes for a total of 5 hours, from 10 AM-3 PM. Lighting conditions were maintained with red (660 nm), blue (480 nm) and violet (380 nm) for the entire 5 hours. At hour 2, either CNO (1.0 mg/kg Gq DREADD, 2.0 mg/kg for Gi DREADD or vehicle (saline) was administered intraperitoneally to animals. All animals received both CNO and vehicle in separate experiments, and once telemetric recordings were complete, animals were administered CNO and sacrificed 6 hours later, with relevant tissues harvested and the telemetric sensor explanted.

Thermoregulation and Cold Exposure Assays

Core body temperature assessment upon acute cold exposure was performed as previously described[7] on OPN5 null ($OPN5^{-/-}$) and littermate controls ($OPN5^{+/+}$). Mice with OPN5 conditionally deleted from the retinal progenitors ($OPN5^{fl/fl}$ and Rx-cre; $OPN5^{fl/fl}$), and OPN5 conditionally deleted from Lepr-expressing neurons in the POA ($OPN5^{fl/fl}$ and Lepr-cre; $OPN5^{fl/fl}$) were also subjected to this assay. Furthermore, enucleated $OPN5^{+/+}$ and $OPN5^{-/-}$ mice, and 'full spectrum' and 'minus violet' reared C57BL/6J animals were also cold exposed.

P60 adult male and female littermates were separated from their home cage and individually housed in a home-built lighting chamber situated in an electronically monitored 4° C. cold room for 3 or 5 hours depending on the assay. While the mouse was conscious, core body temperature was measured with a RET-3 microprobe rectal thermometer (Kent Scientific Corporation, Torrington, Conn.) every 20 minutes for the duration of the assay. Food and water were available ad libitum. The thermometer probe operator was blinded to mouse genotype and prior temperature measurements throughout the experiment. At the end of the cold exposure, mice were euthanized and relevant tissues (BAT, inWAT, pgWAT) were dissected, weighed, and snap frozen for downstream molecular profiling.

For all 3 hour cold exposure assays, animals were subjected to a red (660 nm), blue (480 nm), and violet (380 nm) LED combination (RBV). For 5 hour cold exposure assays, animals were initially subjected to only red (660 nm) and blue (480 nm) lighting (RB) for the first three hours. After the initial 3 hours, violet light (380 nm) was then supplemented during hours 4 and 5. All 3 hour cold exposure assays were performed during the animals' subjective day from 11 AM-2 PM. The 5 hour assays were all performed from 10 AM-3 PM.

Telemetric Temperature Monitoring

P60 adult male OPN5 null mice ($OPN5^{-/-}$) and wild type littermate controls ($OPN5^{+/+}$), and OPN5cre; AAV5-hM3D (Gq) or AAV5-hM4D(Gi) injected mice were implanted with indwelling telemetric sensors and subjected to a 5 hour cold (4° C.) or ambient (22° C.) temperature exposure assay. $OPN5^{cre}$; AA V5-hM3D(Gq) animals did not undergo a cold exposure assay. In brief, animals were moved to individual housing and acclimated to a soft diet (DietGel® 76A, and DietGel® Recovery+1 mg/2 oz carprofen) 3 days prior to the implantation surgery. On the day of the surgery, animals were anesthetized and maintained with ventilated isoflurane, and a telemetric sensor (TTA-XS, Stellar Telemetry, TSE Systems) was subcutaneously implanted in the dorsal cavity. The sensor wirelessly communicates with an external antenna, and features two external thermistor leads, one advanced underneath the iAT (BAT temperature), and one advanced through the peritoneum to rest in the visceral cavity of the mouse (core temperature). Telemetric data was acquired using BIOPAC AcqKnowledge 5.0 software. Implanted mice were returned to individual housing and monitored for at least two weeks prior to experiments.

Acute Violet Light Stimulation Experiments

Implanted mice were transferred to a home-built lighting chamber that was situated either in the cold (4° C.) or in room temperature (22° C.). BAT and core temperature readings were collected every 5 minutes for a total of 5 hours, from 10 AM-3 PM. Lighting conditions were either maintained with red (660 nm) and blue (480 nm) for the entire 5 hours, or with violet (380 nm) light supplemented for hours 4 and 5. Following the experiment, mice were either returned to light-controlled housing, or sacrificed and perfused with 4% paraformaldehyde, with relevant tissues harvested and the telemetric sensor explanted.

Imaging Intracellular cAMP Dynamics

Two-photon imaging of intracellular cAMP dynamics ex vivo in acute brain slices was performed as follows.

Acute Brain Slice Preparation

P30-P60 $OPN5^{cre/+}$; CAMPER or $OPN5^{cre/+}$; CAMPER male and female mice were dark adapted for four hours prior to tissue harvest. Ice-cold modified artificial cerebrospinal fluid (mACSF, 92 mM NaCl, 2.5 mM KCl, 1.25 mM $NaH_2PO_4$, 30 mM $NaHCO_3$, 25 mM glucose, 20 mM HEPES, 5 mM Na-ascorbate, 3 mM Na-pyruvate, 2 mM thiourea, 10 mM $MgSO_4.7H_2O$, 0.5 mM $CaCl_2.2H_2O$, titrated to pH=7.22 by NaOH) was equilibrated with 95% oxygen and 5% carbon dioxide. Under dim red light, mice were anesthetized with isoflurane, thoracotamized, and transcardially perfused with oxygenated ice-cold mACSF. Brains were rapidly dissected and placed in oxygenated ice-cold mACSF. Coronal 300 μm sections were cut with a vibratome (Leica® VT1000 S) and placed in a foil-covered bubbled room-temperature N-methyl-D-glucamine recovery solution (NMDG, 92 mM N-methyl-D-glucamine, 2.5 mM KCl, 1.25 mM $NaH_2PO_4$, 30 mM $NaHCO_3$, 25 mM glucose, 20 mM HEPES, 5 mM Na-ascorbate, 3 mM Na-pyruvate, 2 mM thiourea, 10 mM $MgSO_4.7H_2O$, 0.5 mM $CaCl_2.2H_2O$, 92 mM N-methyl-D-glucamine, titrated to pH=7.25 by HCl) for 30 minutes. To record intracellular cAMP dynamics, slices were transferred to a recording chamber (RC-26G, Werner Instruments) and continuously perfused with 30-34° C. oxygenated mACSF at a rate of 2.1 mL/min. To isolate responses intrinsic to hypothalamic neurons, the perfused mACSF was supplemented with 1 μM tetrodotoxin citrate (HB1035, Hello Bio) during imaging.

Brain Slice Imaging

Two-photon imaging of FRET was performed on a Nikon A1R upright confocal microscope using the NIS Elements Confocal software package v5.20.02. Images were acquired through a 16× dipping objective (CF175 LWD 16X W, Nikon). mTurquoise (FRET donor) was excited by tuning a TiSapphire IR laser to 850 nm for two-photon imaging, with 470-500 nm (mTurquoise; FRET donor, CFP channel) and 525-575 nm ($^{cp173}$Venus-Venus; FRET acceptor, YFP channel) bandpass emission filtration. To visually locate Rapgef3-expressing cells, the POA was briefly exposed to blue epifluorescence of 488 nm for less than a minute. For dark-treated and drug-treated cells, images were taken every minute. For 405 nm-laser illuminated cells, images were taken every other minute, with one minute of continuous 405 nm photostimulation in between. Drugs were bath-applied at the 45 minute mark of the experiment. 20 μM forskolin NKH477 (344281, EMD Millipore), 200 μM IBMX (02195262-CF, MP Biomedicals), and 10 μg/mL digitonin (D141, Sigma Aldrich) were applied according to experimental timepoints. ΔF (change in FRET) is presented as the ratio of donor emission to acceptor emission (CFP/YFP). Images were processed and quantified using NIS Elements AR v5.20.00, ImageJ Ratio Plus plugin, and MATLAB 2018a.

Indirect Calorimetry

Male and female $OPN5^{+/+}$ and $OPN5^{-/-}$ mice aged P90-P120 were acclimated in metabolic chambers (PhenoMaster®, TSE Systems GmbH, Germany) for 3 days before the start of the study. Mice were continuously recorded for a total of 16 days with the following measurements taken every 15 minutes: gas exchange (02 and C02), food intake, water intake, and spontaneous locomotor activity (in the XY plane). Ambient temperature was adjusted via climate-controlled chambers that housed the metabolic chambers. $VO_2$, $VCO_2$, and energy expenditure (EE) were calculated according to the manufacturer's guidelines (PhenoMaster® Software, TSE Systems GmbH, Germany), with EE estimated via the abbreviated Weir formula. The respiratory exchange ratio (RER) was calculated by the ratio $VCO_2/VO_2$. Mass-dependent variables ($VO_2$, $VCO_2$, EE) were not normalized to body weight. Food and water intake were measured by top-fixed load cell sensors, from which food and water containers were suspended into the sealed cage environment. For food consumption, mice demonstrating excessive food grinding behavior were excluded from statistical analyses. After 8 days of continuous recording, cages were replaced with clean ones and sealed, and gas exchange re-equilibration completed all within 4 hours. Body mass composition (fat and lean mass) were measured using nuclear magnetic resonance and expressed as grams of fat and lean tissue, and as a percentage of total body mass.

For CL-316,243 experiments, mice aged P90-P120 were acclimated in metabolic chambers (Promethion, Sable Systems International) for 3 days prior to the start of the study. Male and female $OPN5^{+/+}$, $OPN5^{-/-}$, full spectrum, and minus violet mice were included for these studies. Oxygen consumption ($VO_2$), carbon dioxide production ($CO_2$), energy expenditure (EE), respiratory exchange ratio (RER), and locomotor activity (cm/s) were recorded every 5 minutes using Sable Systems International Metascreen software v2.3.15.11. Food and water were available ad libitum. 1.0 mg/kg CL316,243 or vehicle (saline) was intraperitoneally injected at hour 1 of a six-hour measurement window between 11 AM-5 PM. All animals received both CL316,243 and vehicle injections in randomized order. Data was exported using Sable Systems International ExpeData software v1.9.27.

Infrared Thermography (FLIR)

For whole-body infrared thermographic imaging, adult (P90) and neonatal (P8) $OPN5^{+/+}$ and $OPN5^{-/-}$ mice were individually housed and placed in a home-built lighting chamber situated in 4° C. for 30 minutes. IR thermographic images were taken with a FLIR T530 infrared camera (FLIR® Systems, Wilsonville, Oreg.) every minute for a total of 30 images per P90 adult or pair of P8 pups. To quantify interscapular region temperature, a pixel average from a region of interest drawn over the iAT was taken per image per mouse using FLIR Tools Desktop software v5.13.18031.2002. The size of the selected region of interest did not change. For the comparative IR images, P90 adult mice were briefly anesthetized after the 30 minute cold exposure and laid side by side. To quantify surface tail temperature of adult $OPN5^{+/+}$ and $OPN5^{-/-}$ mice, animals were placed in a tubular mouse restraint (Kent Scientific Corporation, Torrington, Conn.). These restraints permitted respiration through a slotted nose cone but immobilized the animal while exposing its tail through a rear port. Tail temperatures were quantified by describing a pixel-averaged circular region of interest of consistent size and rostrocaudal distance from the base of the tail, per minute, per mouse.

Video Tracking

P60 male $OPN5^{+/+}$ and $OPN5^{-/-}$ mice were placed in custom built cylindrical open-top acrylic enclosures with paper bedding and enrichment situated in an electronically monitored 4° C. cold room. A recording camera (Fujifilm XT-10, with Samyang 12 mm f/2.0 lens) was affixed approximately 24" above the cages and recorded video at 24 frames per second for a total of 140 minutes. Ambient 480 nm and 660 nm LEDs provided red and blue illumination, and at the 80 minute mark, 380 nm violet LEDs were switched on. The video was re-encoded at 2.4 frames per second and analyzed by centroid-based motion tracking in NIS Elements Ar v5.20.00.

Noninvasive Blood Pressure Measurements

Animals were acclimated to a tubular mouse restraint (Kent Scientific Corporation) situated on a heated stage for 2-3 days prior to the study. On the day of the experiment, animals were placed inside the restraint on a heated stage and connected to a tail occlusion cuff and a volume pressure recording (VPR) cuff that communicated with the CODA™ High Throughput Noninvasive Blood Pressure System (Kent Scientific Corporation). 30 trials of tail occlusion and VPR recordings were automatically and sequentially gathered per animal, and systolic/diastolic blood pressure, mean arterial pressure, and pulse rate calculated by the CODA™ Data Acquisition Software v4.1.

Intra-Adipose Tissue Radiometry

Fabrication of the Holt-Sweeney microprobe was performed as previously described[30]. The termination of one end of a 100 μm silica core fiber optic patch cable (Ocean Optics, Dunedin, Fla., USA) was removed. The fiber's furcation tubing and jacketing was stripped, and the fiber's polyimide buffer was removed 5 cm from the fiber's end using a butane torch. A 10 g weight was attached to the end of the fiber and then pulled upon heating with the butane torch, narrowing the diameter. The narrowed region of the fiber was then cut using carborundum paper, to yield a flat fiber end with a diameter of 30-50 μm. The sides of the narrowed fiber were painted with a film opaquing pen to prevent stray light from entering, while leaving a small transparent opening at the fiber tip. For structural support, this bare, tapered fiber was then secured in the tip of a pulled glass Pasteur pipette using a drop of cyanoacrylate glue, leaving only 6-9 mm of bare optical fiber protruding. A small light-scattering ball was added to the end of the tapered optical fiber for spectral scalar irradiance measurements. To do this, titanium dioxide was thoroughly mixed with a high-viscosity UV-curable resin, DELO-PHOTOBOND, GB368 (DELO Industrie Klebstoffe, Windach, Germany). The tip of a pulled fiber was quickly inserted and removed from a droplet of the resin and titanium dioxide mixture, resulting in a sphere with a diameter of approximately twice that of the tapered fiber. As all measurements from a given probe were normalized to the signal from the same probe in a gelatin blank, small variations in the probe diameter have no effect on our results. The sphere was cured for 12 h using a Thorlabs fiber coupled LED light source (M375F2, Thorlabs Inc, Newton, N.J., USA).

For intra-tissue radiometric measurements in mice, animals were anesthetized under ventilated isoflurane and placed in a mouse stereotaxic frame (Stoelting Co, Wood Dale, Ill., USA). Hair over the scalp was shaved and the skin incised rostrocaudally to expose the skull surface. The skull was breached with a small 0.5 mm diameter micromotor drill 0.4 mm anterior and 0.2 mm lateral to bregma. Following, the Holt-Sweeney microprobe was affixed to the stereotaxic frame, positioned over AP +0.40 mm, ML +0.20 mm, and lowered to DL −4.00 mm in 0.50 mm increments. While the probe is in position, the scalp skin was repositioned to cover as much of the incision site as possible without obstructing probe descent. For broadband light illumination, a Thorlabs plasma light source (HPLS345, Thorlabs Inc, Newton, N.J., USA) was positioned above and in front of the mouse stereotaxic frame. The light was delivered to the animal via a 5 mm liquid light guide connected to a 2 in. collimating lens secured in a vice. The distance from the collimating lens to the animal was approximately 2 ft.

Scalar irradiance measurements as a function of wavelength were obtained at the surface of the cortex and at probe depth increments of 0.50 mm up to 4.00 mm. Spectral irradiance data was collected using an Ocean Optics 200-850 nm spectrometer (JAZ Series, Ocean Optics, Dunedin. Fla., USA) and recorded using Ocean Optics OceanView v1.6.5 software.

Tissue Processing, Sectioning, and Immunohistochemistry

Animals were anesthetized under isoflurane and transcardially perfused with 4% paraformaldehyde solution. For immunofluorescence, brains were dissected and post-fixed in cold 4% paraformaldehyde overnight at 4° C. After washing in PBS, brains were cryoprotected in sucrose solution and embedded for sectioning in a cryostat (Leica® CM3050 S). 30 μm sections were obtained and subsequently processed for immunofluorescence (IF). For immunohistochemistry, iAT and inWAT tissues were dissected and post-fixed in 4% paraformaldehyde overnight at room temperature. After washing in PBS, tissues were processed (Leica® ASP300S) and embedded (Tissue-Tek® TECm 6). Embedded tissue blocks were cut using a microtome (Leica® RM2255) at a thickness of 4.5 μm. Slides were incubated overnight at 4° C. in primary, rinsed, and then incubated in secondary for 1 hour at room temperature. Slides were then rinsed and mounted with VectaShield® HardSet™ antifade mounting medium with DAPI.

Antibodies used for IF include NeuroTracem 435/455 blue fluorescent Nissl stain (ThermoFisher Scientific, N21479, 1:100 dilution), anti-Isolectin IB4 antibody (ThermoFisher Scientific, 121411, 1:300 dilution), anti-Tyrosine Hydroxylase antibody (Abcam, ab113, 1:500 dilution), and anti-insulin antibody (Dako, A0564, 1:500 dilution). Antibodies used for IHC include anti-UCP1 antibody (Abcam, ab10983, 1:500 dilution).

Xgal Staining

For Xgal labelling, P10 OPN5$^{lacz}$ and P16 Lepr-cre; Ai14; OPN5$^{lacz}$ animals were anesthetized and transcardially perfused with Xgal fixative (1% formaldehyde, 0.2% glutaraldehyde, 2 mM $MgCl_2$, 5 mM EGTA, and 0.01% Nonidet P-40). Brains were dissected and post-fixed in cold Xgal fixative overnight at 4° C. Brains were then washed and cryoprotected as described above and then labeled with Xgal enzyme. The reaction was monitored closely and stopped when background started to appear in control (lacZ negative) tissues. Following four washes in PBS, 30 μm cryosections from OPN5$^{lacz}$ animals were briefly post-fixed in 4% paraformaldehyde, counterstained with Nuclear Fast Red, dehydrated, and then imaged under standard transmitted brightfield using Zeiss AxioVision v4.9.1 SP2 software. For Lepr-cre; Ai14; OPN5$^{lacz}$ cryosections, the Nuclear Fast Red counterstain was not applied.

Cell Size Quantification (inWAT)

Hematoxylin stained paraffin sectioned inWAT samples were imaged under 594 nm excitation through a rhodamine filter. Monochrome images were thresholded and adipocyte cell boundaries automatically detected using NIS Elements Advanced Research v5.20.00 software (Nikon Instruments Inc.). Individual cells were demarcated as separate objects in a binary layer, filtered for circularity and size, and their area measured in μm2. Approximately 500-1000 cells were measured per field, with at least 20 fields per animal analyzed, for a total of 10,000-20,000 cells per animal. Cell areas were binned into 100 μm2 intervals and the frequency of total cells (%) charted for each interval.

Multiplex Fluorescence In Situ Hybridization (M-FISH)

M-FISH experiments were performed with fresh-frozen brain tissue. Briefly, P21 male and female OPN5$^{cre/+}$; Ai14 mice were sacrificed and their brains rapidly dissected into cryo-embedding medium. Embedded brains were snap-frozen in liquid nitrogen, and 14 μm cryosections of the POA were obtained and processed for M-FISH using the RNAscope® Fluorescent Multiplex Reagent Kit V1 (ACDBio). Probes against the following mRNAs were used: Slc32a1 (Vgat), Slc17a6 (Vglut2), Adcyap1 (PACAP), Bdnf (BDNF), and tdTomato. In situ hybridization was performed as per the manufacturer's protocol for fresh frozen tissue. Briefly, POA sections were pretreated by serial immersion of the slides in 1×PBS, nuclease-free water, and 100% EtOH at room temperature for two minutes each. Probe hybridization was achieved by incubating sections in 40 μL of mRNA target probes for 2 hours at 40° C., followed by signal amplification using manufacturer-provided Amp1, Amp2, Amp3, and Amp4 reagents for 30, 15, 30, and 15 minutes respectively at 40° C. Each incubation step was followed by two 2-min washes of manufacturer-provided wash buffer. Slides were mounted using Tris-buffered Fluoro-Gel mounting medium (Electron Microscopy Sciences).

M-FISH Quantification

60× fields were acquired from OPN5$^{cre/+}$; Ai14 POA regions from n=3 animals. Prior to cell counting, negative control regions of interest (ROI) were acquired. Single cell images (715 $\mu m^2$ ROIs) of ependymal cells or dural cells were acquired to calculate background labeling for all 3 channels, which varied across experiments and probes. Using the nuclear marker channel (DAPI) and tdTomato (C2) probe, several 715 $\mu m^2$ ROIs were acquired representing cells of interest. Then, puncta from C1 (Slc32a1 or Bdnf) and C3 (Slc17a6 or Adcyap1) for each ROI was calculated and the cell was assessed to be positive or negative for a marker. Cells were considered positive if the number of puncta was 1.5× above background for that section. Total of 109 cells from n=3 animals were used for Slc32a1 and Slc17a6 assessment, and a total of 97 cells from n=3 animals were used for Bdnf and Adcyap1 assessment.

Serum Lipids and Thyroid Hormones

Serum from P90-P120 OPN5$^{+/+}$ and OPN5$^{-/-}$ male and female mice were harvested and snap frozen. Lipid profiles (TG, PL, CHOL, NEFA) were obtained via standard colorimetric methods performed at the University of Cincinnati Mouse Metabolic Phenotyping Center (NIH 2U2C-DK059630-16). Briefly, triglyceride quantification was performed by the GPO-PAP method (Randox), phospholipids by the choline oxidase-DAOS method (Wako Diagnostics), cholesterol by the Infinity™ cholesterol liquid stable reagent method (Thermo Scientific), and NEFAs by the ACS-ACOD method (Wako Diagnostics). Colorimetric measurements were obtained using a Synergy HT (BioTek) with Gen5 software. Serum measurements of free thyroxine (T4) and thyrotropin releasing hormone (TRH) were made using competitive ELISA and performed at the University of Massachusetts MMPC (NIH 5U2C-DK093000-07).

Western Blotting

Western blots were performed using standard protocols. BAT from animals were dissected into 400 μL of modified RIPA lysis buffer and homogenized (Tissue Lyser II, Qiagen) using zirconium oxide beads (2.0 mm). After centrifugation and protein quantification (Pierce™ BCA Protein Assay Kit), 10 μg protein were loaded onto a 16% Novex Tris-Glycine protein gel and transferred to a PVDF (polyvinylidene difluoride) membrane, where bands were visualized by chemiluminescence. Antibodies used for western blotting include anti-UCP1 (Abcam, ab10983, 1:5000 dilution) and anti-alpha tubulin (Abcam, ab4074, 1:5000 dilution).

Quantitative RT-PCR

Intrascapular adipose depots were harvested immediately following cold exposure assays. Snap frozen tissue was homogenized in TRI Reagent (Invitrogen) using RNase-free zirconium oxide beads (2.0 mm) in a TissueLyser II sample disrupter (Qiagen). Phase separation was accomplished via chloroform and RNA in the aqueous phase was precipitated with ethanol and column-purified via the GeneJET RNA purification kit (ThermoFisher Scientific #K0732). Purified RNA was subsequently treated with RNase-free DNase I (ThermoFisher Scientific #EN0521) and cDNA was synthesized using a Verso cDNA synthesis kit (ThermoFisher Scientific AB1453/B). Quantitative RT-PCR was performed with Radiant™ SYBR Green Lo-ROX qPCR mix (Alkali Scientific Inc.) in a ThermoFisher QuantStudio 6 & 7 Flex Real-Time PCR system. Relative expression was calculated by the ΔΔCT method using Tbp (TATA binding protein) as the normalizing gene. Statistical significance was calculated by a two-way ANOVA followed by Tukey post-hoc analysis, using a p-value cutoff of 0.05.

Statistics and Reproducibility

Statistical and image analyses were performed with MATLAB 2018a, NIS Elements Ar v.5.20.00, and ImageJ. Sample sizes for each experiment are reported in the manuscript or in the figures. The numbers of experimental repetitions were as follows: FIG. 4*a, b,* 12 times; FIG. 4*c, d,* 3 times; FIG. 4*e-k,* 3 times; FIG. 4*l-x,* 7 times; FIG. 5*a-i,* 5 times; FIG. 5*j-u,* 4 times; FIG. 6*a-d,* 5 times; FIG. 6*e,* twice; FIG. 6*f-h,* twice; FIG. 7*a-k,* 4 times.

Adaptive Thermogenesis in Mice is Enhanced by Opsin 3-Dependent Adipocyte Light Sensing According to some embodiments, white adipocytes activate the lipolysis pathway to produce the free fatty acids that are used as heating fuel by brown adipose tissue. Opsin 3 is required for blue-light-enhanced activation of the lipolysis pathway, e.g., this explains the low body temperature of OPN3 mutant mice. Is discussed in further detail, adipocytes express encephalopsin (OPN3), a 480 nm blue-light-sensitive opsin, mice lacking OPN3 or blue light have diminished thermogenesis during cold exposure, loss of OPN3 reduces oxygen consumption and energy expenditure, and white adipocyte OPN3 promotes lipolysis during cold exposure.

Almost all life forms can detect and decode light information for adaptive advantage. Examples include the visual system, in which photoreceptor signals are processed into virtual images, and the circadian system, in which light entrains a physiological clock. According to some embodiments, a light response pathway in mice employs encephalopsin (OPN3, a 480 nm, blue-light-responsive opsin) to regulate the function of adipocytes. Germline null and adipocyte-specific conditional null mice show a light- and OPN3-dependent deficit in thermogenesis and become hypothermic upon cold exposure. Stimulating mouse adipocytes with blue light enhances the lipolysis response and, in particular, phosphorylation of hormone-sensitive lipase. This response is OPN3 dependent. These data establish a key mechanism in which light-dependent, local regulation of the lipolysis response in white adipocytes regulates energy metabolism.

The detection of photons by animals has been exploited for adaptive advantage in many ways. The visual sense—irradiance detection by photoreceptors in the retina and formation of virtual images in the brain—is the most obvious example, because it is a component of conscious existence. However, functioning in parallel in many types of animals are various non-visual ocular photoreceptors. In mammals, the best characterized are the retinal ganglion cells expressing melanopsin (Opsin 4 [OPN4]) and neuropsin (OPN5) that function in negative phototaxis, circadian clock entrainment, the pupillary light reflex, and eye development.

Photoreceptors that function outside the eye are found throughout the animal kingdom. They exist as chromatophores in the skin of frogs, within the pineal organs that produce melatonin, and as deep brain photoreceptors that regulate seasonal breeding responses in avian species. Extraocular photoreceptors were assumed to be absent from mammals until expression domains outside the eye were defined for OPN3, OPN4, and OPN5. However, according to some embodiments, OPN5 photoentrains the circadian clock in skin and OPN4 can acutely regulate blood vessel dilation. Adipocyte function might be modulated by light stimulation of OPN4. Although attempts to express mammalian OPN3 have proven difficult, studies on its vertebrate ortholog from pufferfish suggest that it may function as a photosensitive opsin. Accumulating evidence points to extraocular photoreception via OPN3 in both mouse and human.

Mammals employ three types of adipocytes. White adipose tissue (WAT) consists primarily of white adipocytes and is the major energy storage site. Brown adipose tissue (BAT) is made up exclusively of brown adipocytes, which generate heat via non-shivering thermogenesis (NST). Under conditions of cold exposure, WAT can differentiate into "brite" adipocytes that have functional UCP1, although its capacity is at most a third of that of BAT. The process of lipolysis releases free fatty acids (FFAs) and glycerol from WAT for systemic use. BAT then uses FFAs for the generation of heat by oxidative uncoupling via UCP1. Thus, WAT and BAT both have important functions in the regulation of energy balance. Though it was originally believed that only newborn humans had significant depots of brown fat, it is now understood to be present in the adult. Gathering evidence suggests that activation of BAT might be valuable in protecting against metabolic syndrome.

According to embodiments, an extraocular function for OPN3 in the light-dependent regulation of adipocyte function is described. When cold challenged, mice with an adipocyte-specific deletion of OPN3 fail to defend their body temperature normally, show an attenuated induction of cold-induced genes in BAT, and use less fat mass when fasted. Many of these phenotypes are reproduced in mice that are raised without the blue light wavelengths that normally stimulate OPN3. Furthermore, according to some embodiments, blue light has an adipocyte-specific, acute stimulatory effect on thermogenesis. These metabolic perturbations appear to be explained by the OPN3 and blue light dependence of the lipolysis response, a pathway that normally provides fatty acid fuel for thermogenesis. These data identify an unanticipated mechanism for light information decoding for energy homeostasis.

OPN3 is Expressed in Adipocytes

Figures 8A, 8B, 8C, 8D, 8E, 8F, 8G, 8H, 8I, 8J, 8K:
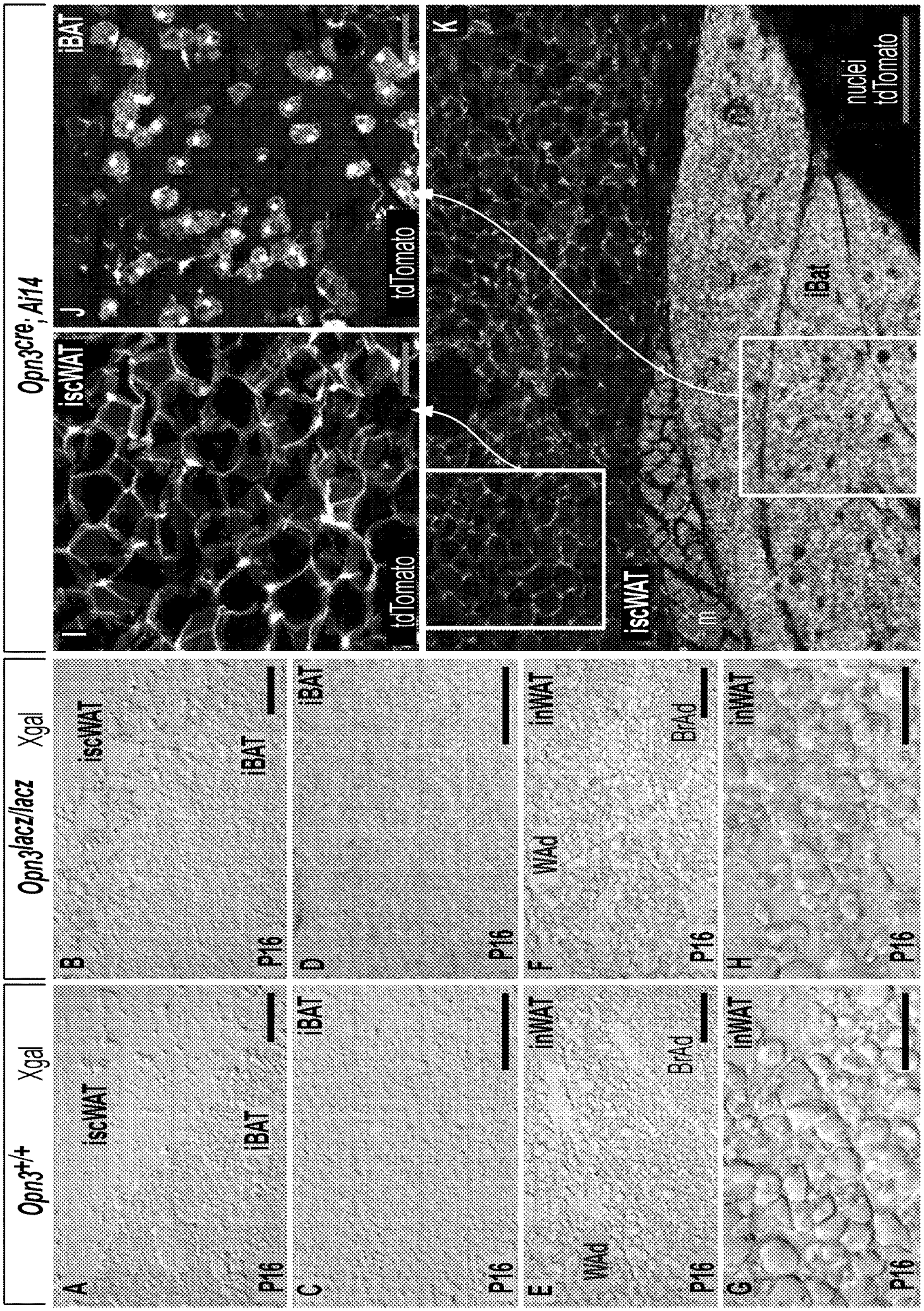
FIG. 8 illustrates, according to some embodiments, expression of OPN3 in iAT and inWAT.

No reliable antibodies for murine OPN3 are presently available, so expression of OPN3 was assessed by taking advantage of three alleles: $OPN3^{lacz}$, $OPN3^{cre}$ (in combination with the tdTomato reporter Ai14), and OPN3-eGFP, an expression reporter transgene based on a bacterial artificial chromosome (GENSAT 030727-UCD). The interscapular adipose tissue (iAT) depot comprises interscapular subcutaneous white adipose tissue (iscWAT) and interscapular brown adipose tissue (iBAT). X-gal labeling of control cryosections from postnatal day (P) 16 iAT showed no background labeling in wild-type mice (FIG. 8A) but intense labeling in the $OPN3^{lacz/lacz}$ iscWAT (FIG. 8B). Labeled adipocytes were not detected in control iBAT (FIG. 8C). In iBAT from $OPN3^{lacz/lacz}$ X-gal-labeled cells were not readily apparent, but at higher magnification and bright transillumination, a subset expressing brown adipocytes was detected (FIG. 8D).

Neonatal inguinal white adipose tissue (inWAT) has a high content of brite adipocytes (FIGS. 8E and 8F, BrAd). In control P16 inWAT, neither the large unilocular white adipocytes nor the smaller brite adipocytes were X-gal labeled (FIGS. 8E and 8G). By contrast, the large, unilocular white adipocytes from $OPN3^{lacz/lacz}$ mice were X-gal positive (FIGS. 8F and 8H). When $OPN3^{cre}$ allele was used to convert the tdTomato reporter Ai14 (FIGS. 8I-8K), cryosections showed that almost all adipocytes within iscWAT were positive (FIGS. 81 and 8K). In iBAT, a subset of brown adipocytes was positive (FIGS. 8J and 8K). The OPN3-eGFP reporter confirmed expression of OPN3 in most white and brown adipocytes. Finally, Genotype-Tissue Expression (GTEx; accession phs000424.v7.p2, accessed on Feb. 21, 2018) data report low to moderate expression of OPN3 in human subcutaneous and omental adipose tissue (2.9 and 3.1 tags/million, respectively). These data indicate that both mouse and human adipose tissues express OPN3 and raise the possibility of direct light responsiveness.

Photon Flux within iscWAT and iBAT is Sufficient for Opsin Activation

Figure 9A:
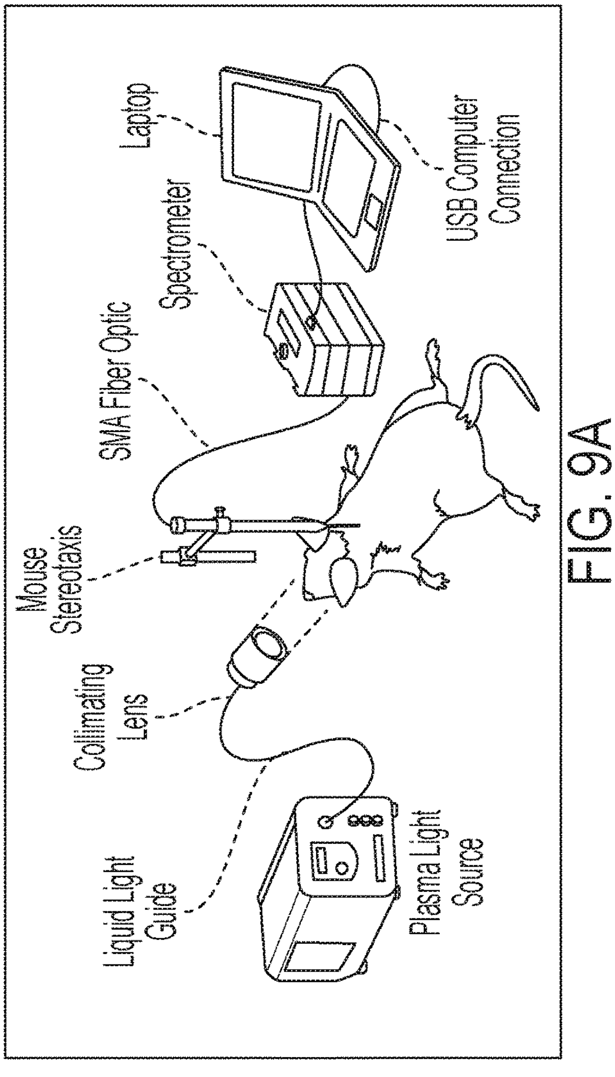
FIG. 9 illustrates, according to some embodiments, measurement of photon flux within iBAT and iscWAT.
Figure 9B:
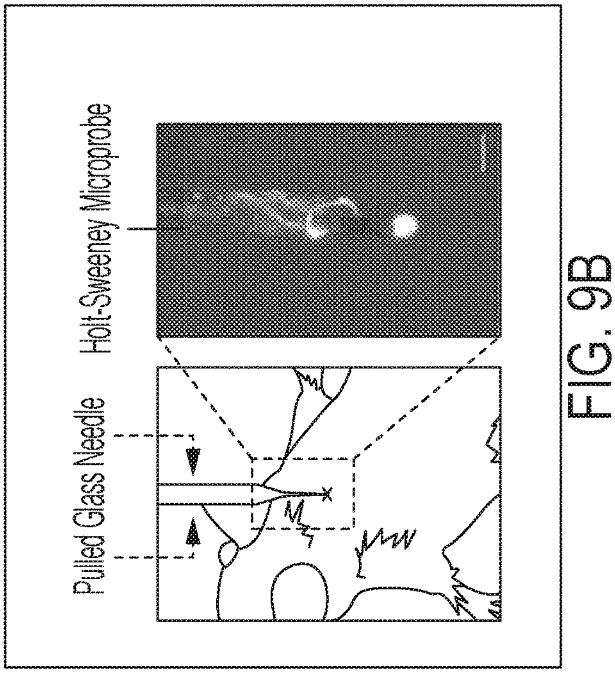
Figure 9C:
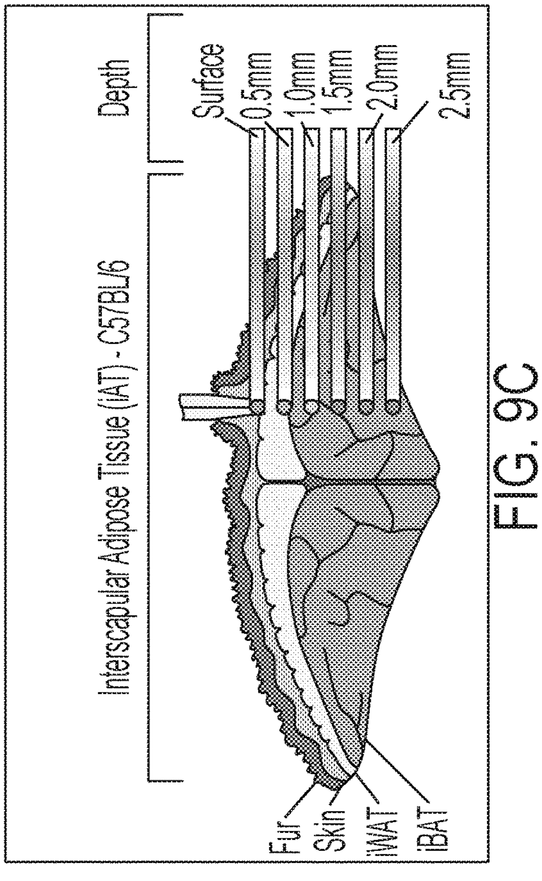
Figure 9D:
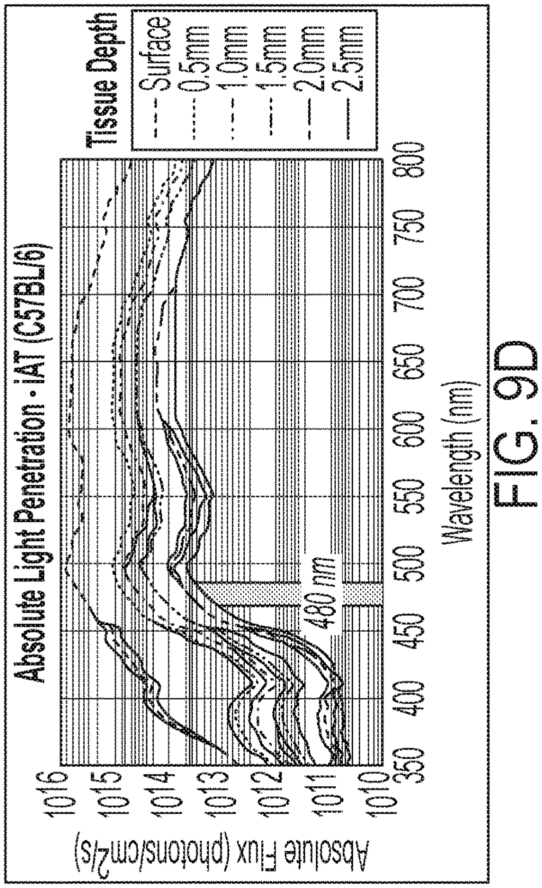

To measure photon flux within the iAT of a pigmented mouse (FIG. 9A), the Holt-Sweeney microprobe (HSM) (FIG. 9B) was fabricated from a light-shielded optic fiber and attached a transparent spherical collecting tip, permitting omnidirectional measurements of scalar irradiance under constant angular sensitivity. The microprobe is mounted within a pulled Pasteur pipette and lowered into the iAT with a stereotaxic frame. Photon flux measurements across the 350-800 nm spectral range were taken every 0.5 mm up to a 2.5 mm total depth (FIG. 9C). At the $\lambda_{max}$ of 480 nm for OPN3 (FIG. 9D), the measured photon flux was $5\times10^{14}$ photons $cm^{-2}s^{-1}$ at 0.5 mm (deepest point within iscWAT) (FIG. 9C) and $2\times10^{13}$ photons $cm^{-2}s^{-1}$ at 2.5 mm (deepest point within iBAT) (FIG. 9C). Surface illumination was controlled to 1% of clear sky sunlight intensity (direct sunlight intensity was measured to be $2\times10^{17}$ photons $cm^{-2}s^{-1}$). Total light attenuation ranged from less than one log quanta at 0.5 mm to just over two log quanta at 2.5 mm. Extrapolating for full sunlight, iscWAT photon flux would be approximately $5\times10^{16}$ photons $cm^{-2}s^{-1}$. Signaling thresholds for atypical opsins are as low as $10^{10}$ photons $cm^{-2}s^{-1}$ (Wong, 2012). Thus, these data indicate that iscWAT and iBAT photon flux is sufficient for opsin stimulation.

Transcriptome Analysis Suggests that OPN3 Regulates Metabolism

To address OPN3 function, a microarray-based transcriptome analysis was performed on P16 control and OPN3 germline null mice. iAT and inWAT were harvested alongside liver (low-expression control). Using the AltAnalyze suite, Z score significant clustering of differentially regulated transcripts (red, upregulated; blue, downregulated) was identified into select WikiPathway models, with a more detailed schematic included. As expected, the OPN3 transcript showed the highest negative fold change in OPN3 null iAT (3.0-fold down, $p=1.5\times10^{-4}$) and inWAT (5.6-fold down, $p=7.6\times10^{-3}$) but was not significantly changed in liver. Overall, transcriptome analysis indicated that OPN3 activity was required for normal regulation of metabolism, as evidenced by deregulation of the adipocyte extracellular matrix, lipid, glucose, and energy generation pathways.

The following are shown in FIG. 8, e.g., expression of OPN3 in iAT and inWAT:

(A-D) X-gal-labeled wild-type (A and C) and $OPN3^{lacz/lacz}$ (B and D) cryosections of iAT, including iscWAT (A and B) and iBAT (C and D) at P16. (E-H) X-gal-labeled wild-type (E and G) and $OPN3^{lacz/lacz}$ (F and H) cryosections of inWAT, including white adipocytes (WAd) and brite adipocytes (BrAd).

(G and H) Higher magnification of inWAT in wild-type (G) and $OPN3^{lacz/lacz}$ (H) cryosections.

(I-K) Detection of tdTomato (red, grayscale) in $OPN3^{cre}$; Ai14 mice for iAT showing positive cells in iscWAT (I, enlarged region in K) and iBAT (J, enlarged region in K). iscWAT and iBAT are separated by a leaflet of muscle (m). Labeling of nuclei with Hoechst 33258 is presented in green.

Scale bars: (A, B, E, F, and K) 100 μm and (C, D, and G-J) 50 μm.

Figure 10A:
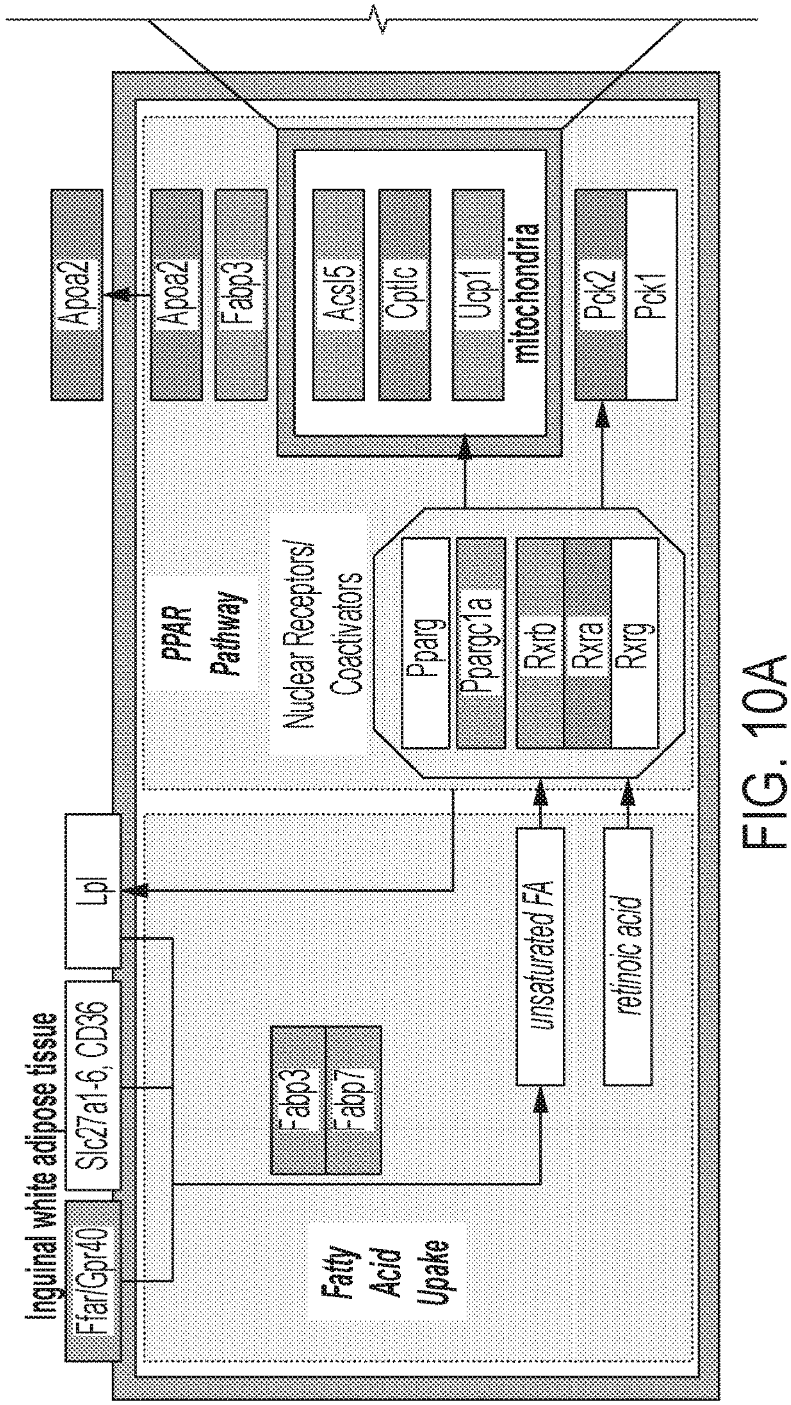
FIG. 10 illustrates, according to some embodiments, OPN3 null and minus blue reared mouse inwat phenotype.

In inWAT, OPN3-dependent, differentially regulated transcripts cluster within the peroxisome proliferator-activated receptor (PPAR) pathway and the mitochondrial electron transport chain (ETC) (FIG. 10A). The PPAR pathway regulates adipocyte size, as well as lipid metabolism and energy generation. This pathway regulates energy generation in part because multiple components of the lipolysis pathway, including HSL (hormone-sensitive lipase), ATGL (adipose triglyceride lipase), and perilipin (PLIN), directly or indirectly depend on the transcriptional co-activator PGC1a for their expression. Furthermore, UCP1 is downregulated, presumably as a response to deregulation of its transcription factors PGC1a and RXRa/b. Notably, the transcript for lipoprotein lipase (Lpl), an enzyme with a role in extracellular lipolysis is deregulated in the liver of OPN3 null mice. Finally, inWAT from OPN3 null mice showed a striking cluster of 17 downregulated ETC transcripts (FIG. 10A). Combined, these data suggest deregulated energy metabolism in OPN3 null mice.

Figure 10B:
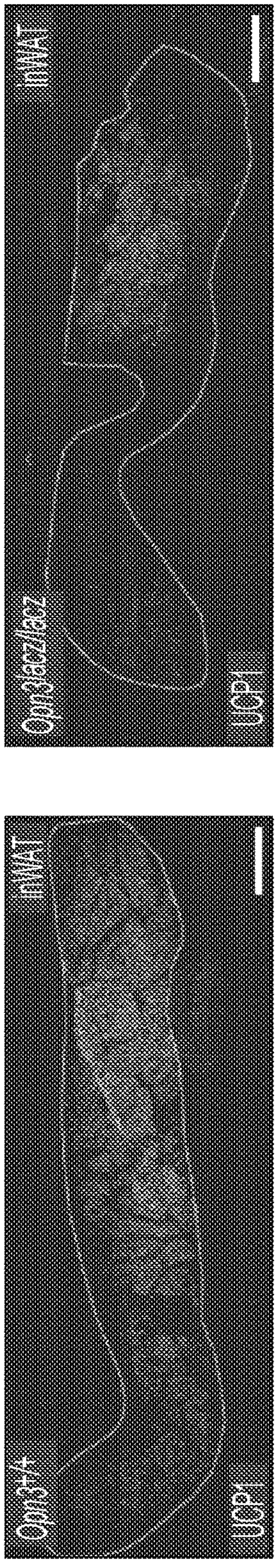
Figure 10C:
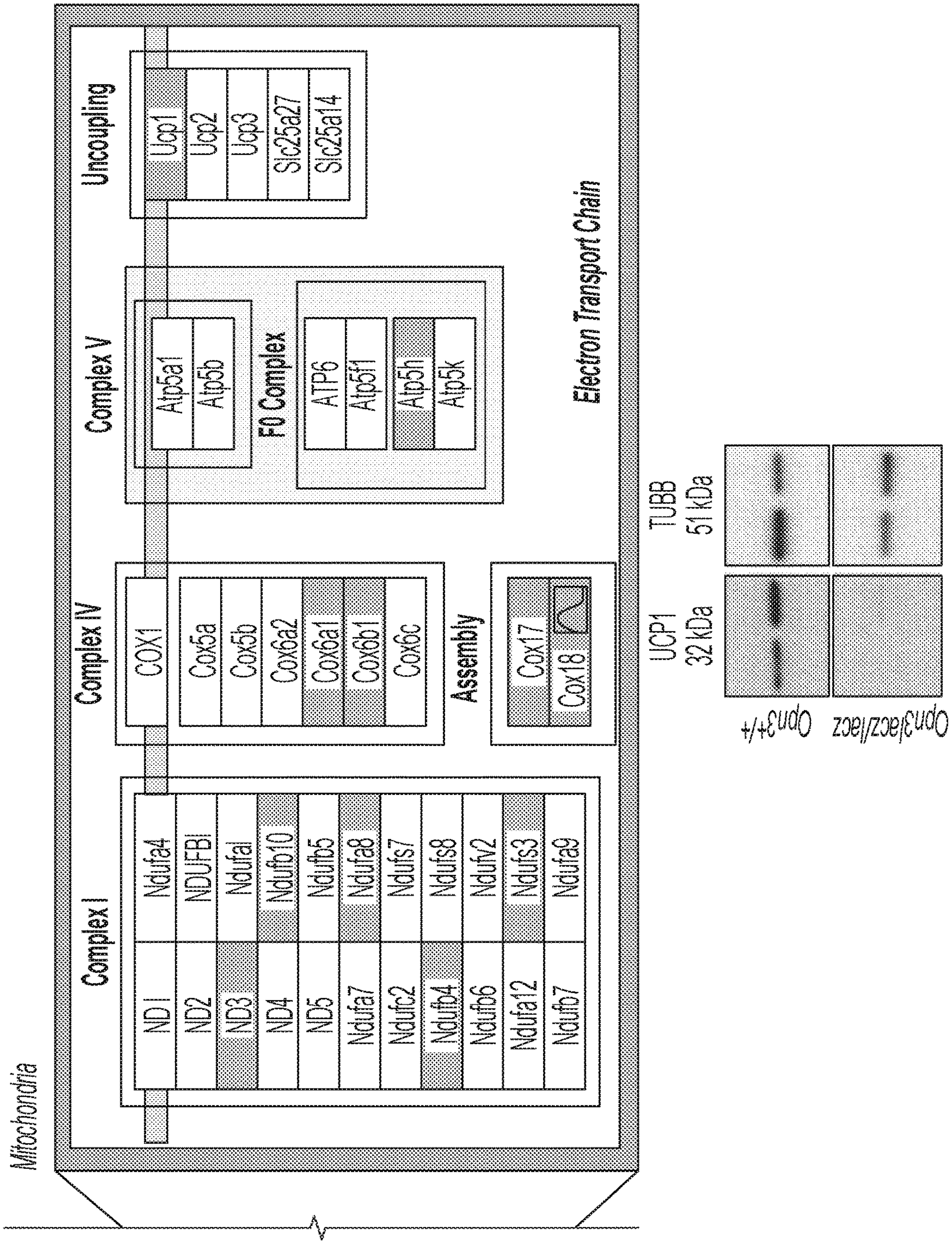
Figure 10D:
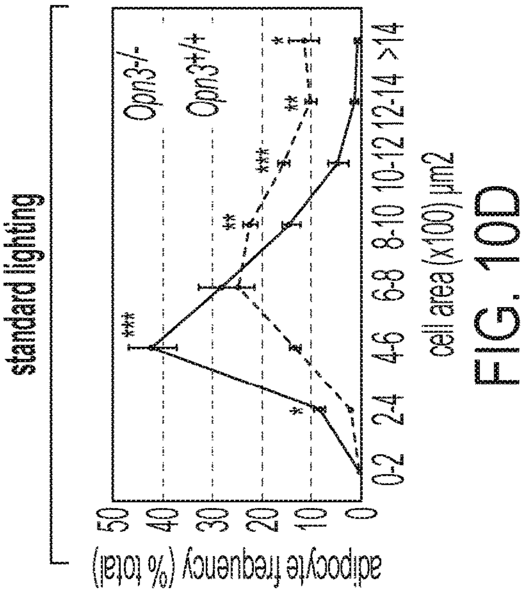
Figure 10E:
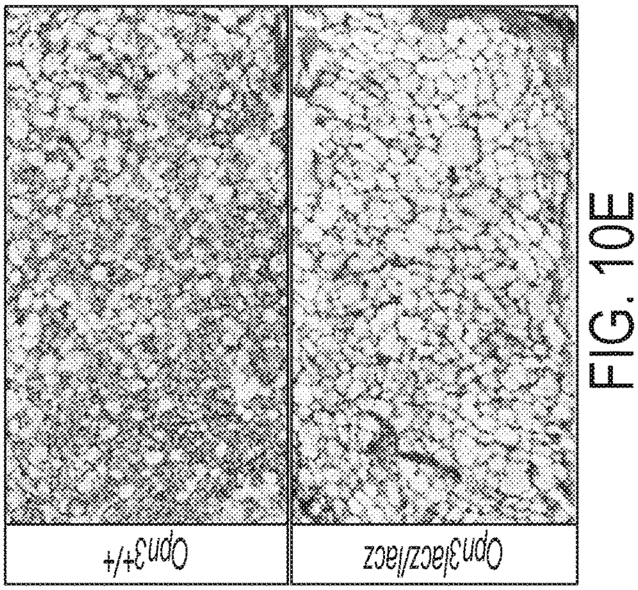

Detection of UCP1 in inWAT either by immunofluorescence (FIG. 10B) or by immunoblot (FIG. 10C) confirmed the comparatively low levels in OPN3 null mice. inWAT cell-size assessment showed that OPN3 null mice had, on average, larger adipocytes (FIG. 10D). Hematoxylin inWAT staining also show lower proportions of the smaller brite adipocytes (FIG. 10E), consistent with adipocyte size assessment.

Figure 10F:
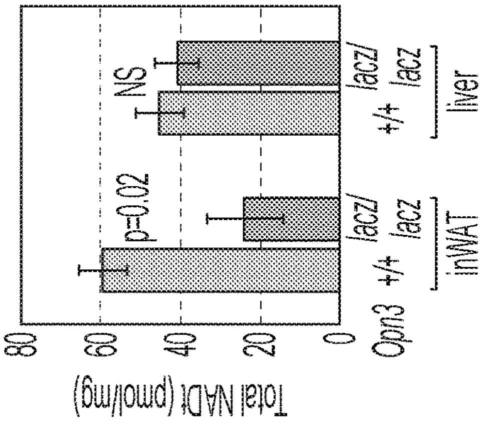
Figure 10G:
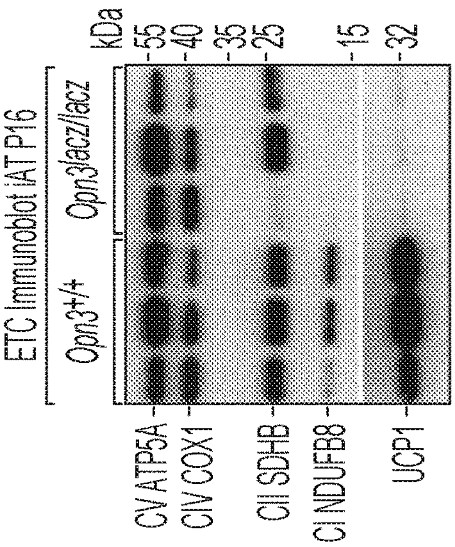
Figure 10H:
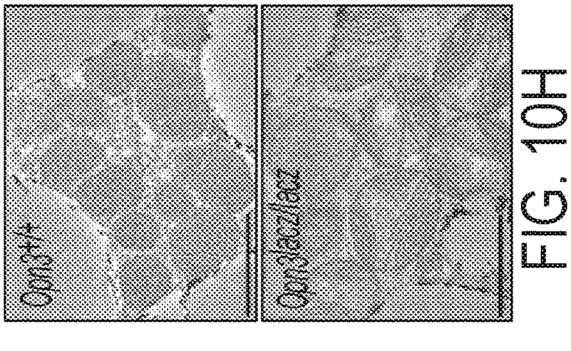

Total NAD content was then measured in OPN3 null mice to assess mitochondrial function. Quantification showed no change in liver NAD in OPN3 null mice but a reduction in inWAT (FIG. 10F), consistent with reduced mitochondrial content. Though transcriptome analysis for OPN3 null iBAT did not cluster the ETC, we were prompted by the effects of OPN3 deficiency on inWAT to assess mitochondrial status in iBAT. Immunoblotting for the ETC components ATP5A (Complex V), COX1 (Complex IV), SDHB (Complex II), NDUFB8 (Complex I), and UCP1 revealed some variability in the presence of SDHB in OPN3 null mice but a consistently low level of both NDUFB8 and UCP1 (FIG. 10G). Correspondingly, iBAT transmission electron microscopy (TEM) at P28 shows disorganized organellar cristae (FIG. 10H), similar to that of Ucp1 null mice, implying in part, OPN3-dependent changes in mitochondrial maintenance and/or organization.

The following are shown in FIG. 9, e.g., Measurement of Photon Flux within iBAT and iscWAT:

(A) Schematic describing set up for measuring intra-tissue photon flux. Collimated photons from a plasma source are directed toward an anesthetized mouse, into which the fiber probe is guided via a stereotaxic frame. Spectra are measured by an OceanOptics spectrometer.

(B) Holt-Sweeney microprobe (scale bar: 100 μm) is an optic fiber with a transparent spherical tip that accepts photons over approximately 4c steradians.

(C) Measurement depths along iAT.

Figure 10I:
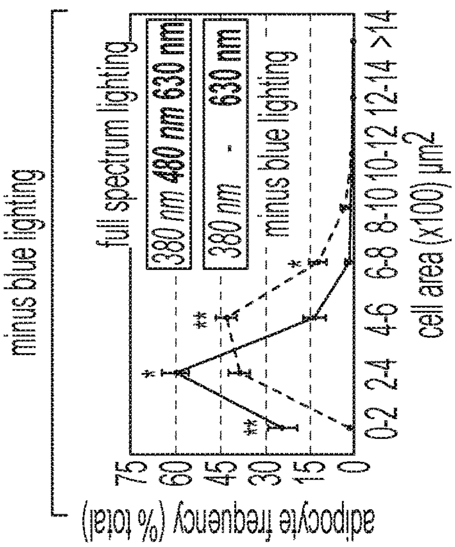
Figure 10J:
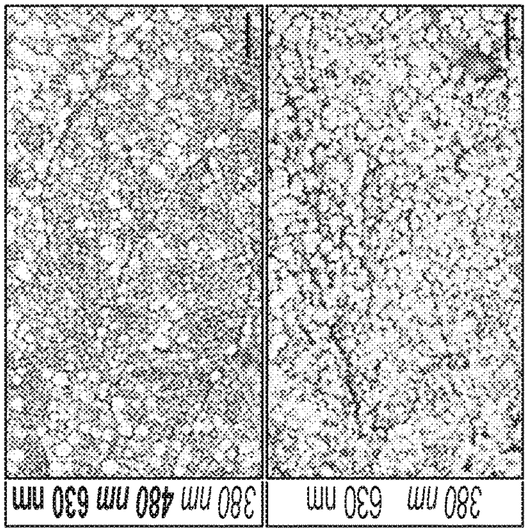
Figure 10K:
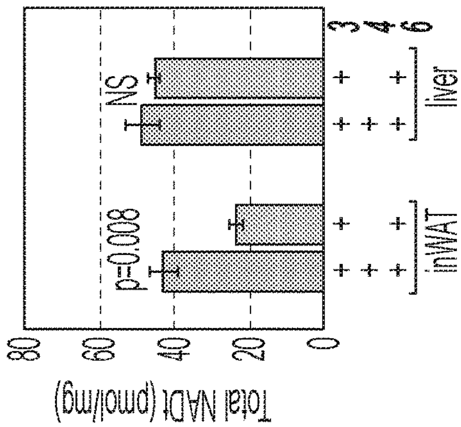
Figure 10L:
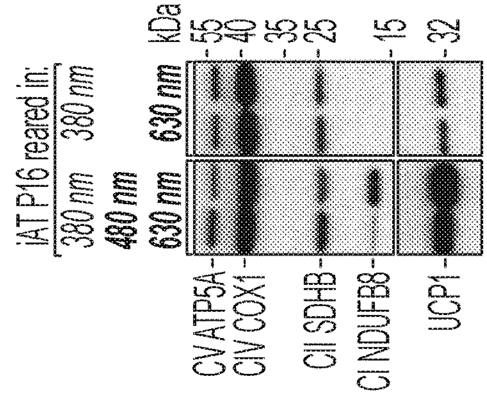

(D) Absolute photon flux within interscapular adipose color coded for depth. The uppermost blue trace is surface flux and, at the $\lambda_{max}$ for OPN3, is about $2\times10^{15}$ photons $cm^{-2}s^{-1}$. At the maximum 2.5 mm depth (brown trace), the flux at the OPN3 $\lambda_{max}$ is approximately $1\times10^{13}$ photons $cm^{-2}s^{-1}$. Each trace is averaged data from n 3 mice. Color shading is ±SEM To assess OPN3 function as a photoreceptive opsin, C57BL/6J mice were raised in "minus blue" lighting conditions from embryonic day (E) 16.5 (see STAR Methods) and compared with mice raised under full spectrum conditions. Subtracting 480 nm wavelengths reduces total photon flux, but because opsins are sensitive to specific wavelengths, this lighting paradigm ensures that any non-blue opsin receives unchanged stimulation. Minus blue lighting resulted in inWAT with quantifiably larger adipocytes (FIG. 10I), lower brite adipocyte content (FIG. 10J), and lower total NAD (FIG. 10K). Furthermore, minus blue iBAT showed lower levels of NDUFB8 and UCP1 (FIG. 10L). When compared with OPN3 null mice, the minus blue phenotype is milder. This might be explained by residual activation of OPN3 resulting from low-efficiency absorption of violet and red photons. Altogether, these data support the hypothesis that OPN3 functions as a light sensor that regulates adipose tissue development.

Adaptive Thermogenesis in Mice Is Promoted by Blue Light in an OPN3-Dependent Manner In mice, body temperature is partly maintained by heat that is generated by skeletal muscle shivering or within BAT via NST pathways that employ UCP1, creatine metabolism, and calcium cycling. The energy for thermogenesis is provided partly by the oxidative metabolism of FFAs that are stored in adipocytes. The process of lipolysis liberating FFAs is thus crucial for normal NST. Furthermore, it has been shown that lipolysis in white adipocytes is directly required to fuel NST. According to some embodiments, several features of OPN3 null and minus blue mice suggested defects with NST.

The following are shown in FIG. 10, e.g., OPN3 Null and Minus Blue Reared Mouse inWAT Phenotype:

(A) Schematic of clustered OPN3-dependent transcript changes in PPAR (WP2316), lipid uptake, and mitochondrial ETC (WP295) pathways (red, upregulated; blue, downregulated).

(B) UCPJ (green) labeling of inWAT in control and $OPN3^{lacz/lacz}$ animals at P16.

(C) Immunoblot detecting UCP1 and β-tubulin (TUBB) in P16 inWAT from $OPN3^{+/+}$ and $OPN3^{lacz/lacz}$ mice.

(D-L) Adipocyte size distribution (D and I) in inWAT comparing control and $OPN3^{lacz/lacz}$(D) and full spectrum versus minus blue raised (I) mice at P16. Data are presented as mean±SEM, n=3 for each genotype. Direct comparisons between genotypes at each interval were performed with Student's t test, *p<0.05, p<0.01, *p<0.001.

(E and J) Hematoxylin staining of histological sections of P16 inWAT from $OPN3^{+/+}$ $OPN3^{lacz/lacz}$ (E) and full spectrum (380, 480, and 630 nm) reared versus minus blue (380 and 630 nm) reared (J) mice. (F and K) Total NAD levels in inWAT and liver for P16 $OPN3^{+/+}$ and $OPN3^{lacz/lacz}$ mice (F, n=4) or for mice reared either in full spectrum or minus blue lighting (K, n=3). p values calculated using Student's t test.

(G and L) Immunoblots detecting multiple components of the ETC (ATP5A, COX1, SDHB, NDUFB8, and UCP1) in P16 iAT for $OPN3^{+/+}$, $OPN3^{lacz/lacz}$ and minus blue reared mice.

(H) TEM showing abnormal mitochondrial morphology in the OPN3 null iBAT at P28. Scale bars: (B) 500 μm, (E and J) 100 μm, and (H) 2 μm. The following are shown in FIG. 11, e.g., OPN3 Is Required for Light-Dependent Enhancement of the Thermogenesis Response:

CBT assessments over a time course after a 4° C. cold exposure for P21-P24 (neonatal) or adult mice of the indicated genotypes. Lighting conditions during cold exposure are indicated by the colored lines above the chart's horizontal axis.

(A) CBTs during cold exposure in $OPN3^{lacz/lacz}$ and control $OPN3^{+/+}$ in full spectrum (380+480+630 nm) lighting.

(B) CBTs during cold exposure in $OPN3^{\Delta Ex2/\Delta Ex2}$ and control $OPN3^{+/+}$ C57BL/6J background mice in full spectrum lighting.

(C) CBTs during cold exposure for C57BL/6J mice raised either in full spectrum (gray trace) or in minus blue (380+630 nm, blue trace) lighting.

(D) CBTs during cold exposure in the same cohorts of mice shown in (A) except in minus blue lighting.

(E) As in (D) except for adult mice (2 months).

(F) CBTs during cold exposure in $OPN3^{lacz/lacz}$ and control $OPN3^{+/+}$ in full spectrum (380+480+630 nm) lighting for 180 min and minus blue (480 nm withdrawn) lighting for a further 120 min.

Data are presented as mean±SEMI.

Figure 11A:
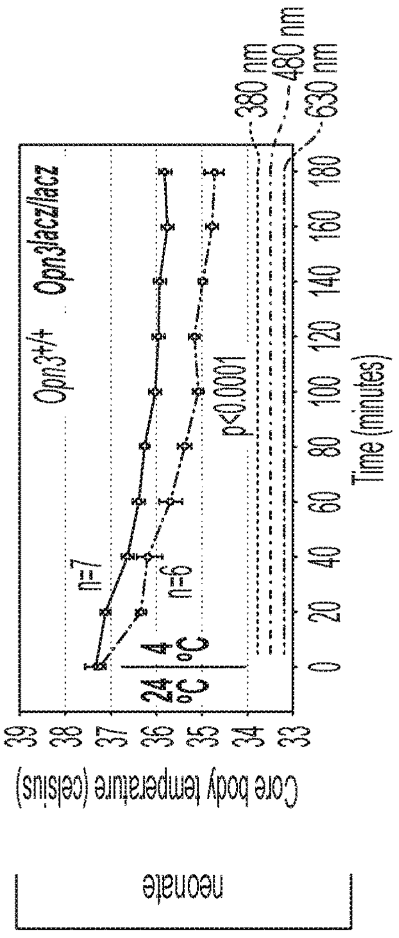
FIG. 11 illustrates, according to some embodiments, OPN3 is required for light-dependent enhancement of the thermogenesis response.
Figure 11B:
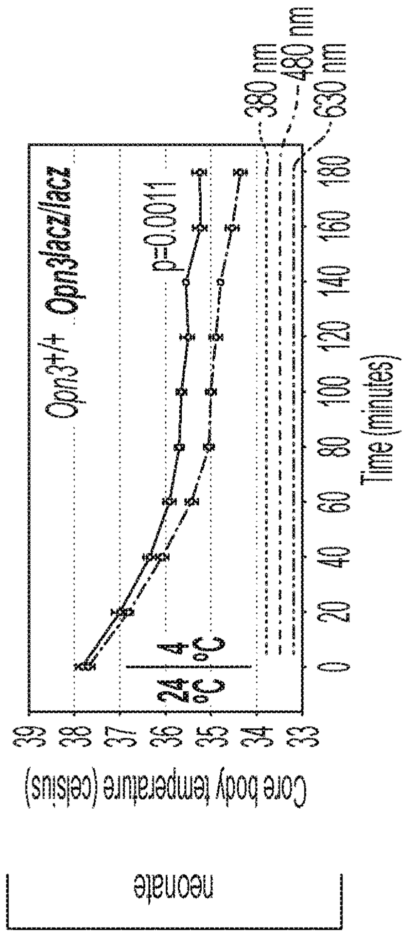
Figure 11C:
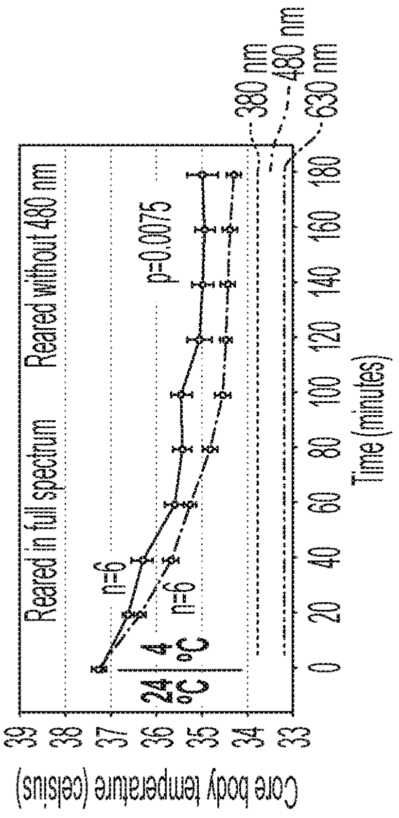
Figure 11D:
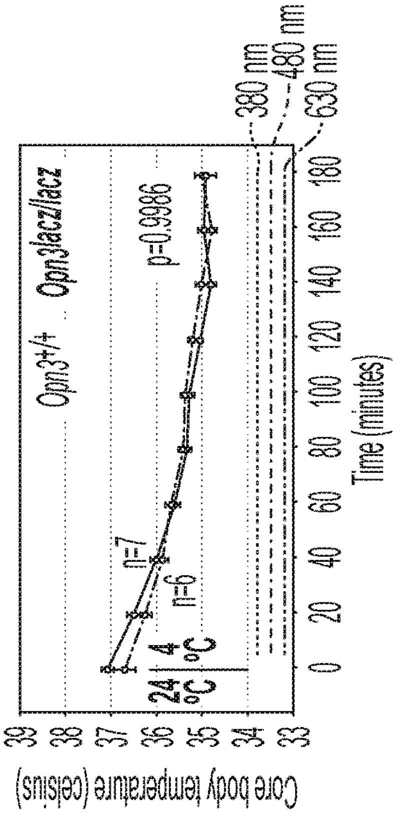

According to some embodiments, when $OPN3^{+/+}$ and $OPN3^{lacz/lacz}$ neonatal mice were exposed to 4° C. over the course of 3 h under full spectrum lighting, core body temperatures (CBTs) of OPN3 null mice were lower than those of wild-type mice (FIG. 11A). To account for possible thermogenic influences caused by the mixed genetic background of $OPN3^{lacz/lacz}$ mice, a new OPN3 loss-of-function allele was generated on a pure C57BL/6J background by CRISPR ($OPN3^{\Delta Ex2}$) and the analysis was repeated. $OPN3^{\Delta Ex2/\Delta Ex2}$ mice also show lower defended CBTs (FIG. 11B), confirming the reduction in NST to be OPN3 dependent. According to some embodiments, the assertion that OPN3 functions as a light sensor by assessing NST in minus blue mice could be tested again. After 3 h of cold exposure, minus blue mice similarly showed lower defended CBTs than mice reared under full spectrum lighting (FIG. 1C). These data show that the absence of 480 nm light that normally stimulates OPN3 during development mimics genetic loss of function.

At the same time, it was possible that OPN3 could mediate acute light responses. According to some embodiments, this was tested by cold exposing the same cohort of OPN3 wild-type and null mice (FIG. 11A) under minus blue lighting. Interestingly, the CBTs of control and OPN3 null mice were statistically indistinguishable (FIG. TTD). This suggests that blue light can, via OPN3, acutely promote adaptive NST and that the activity of OPN3 is necessary for this effect.

Figure 11F:
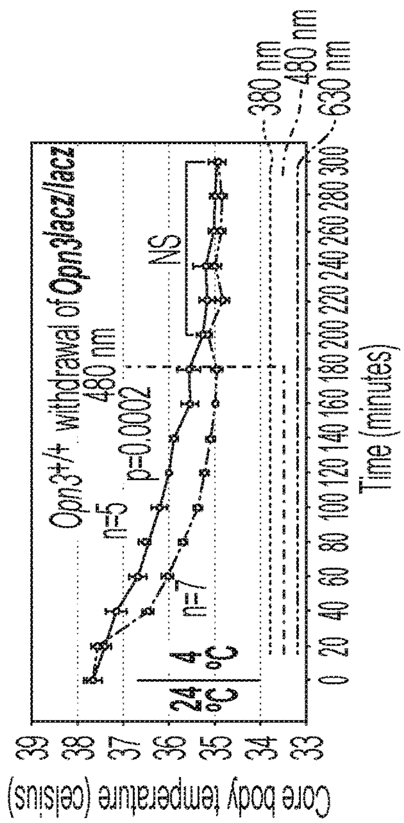
Figure 11E:
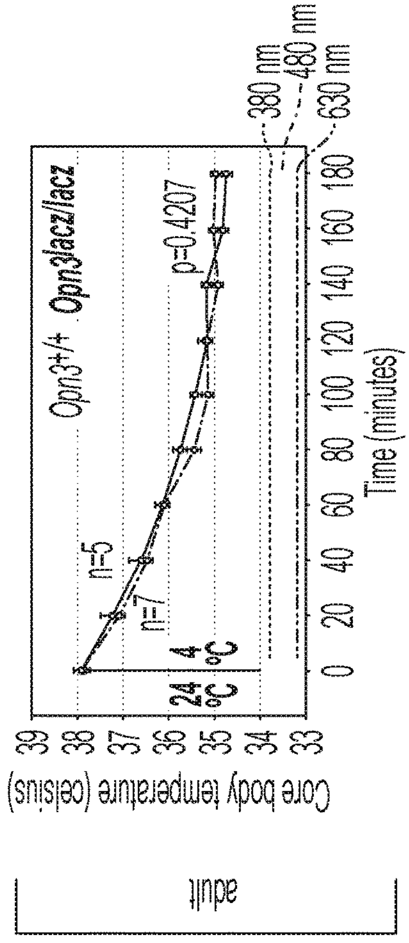

Neonatal mice have a beige adipocyte content that is higher than it is in adult mice, and this may reflect special NST requirements given their low mass-to-surface area ratio. Thus, it was also sought to establish whether adult mice showed a blue-light-promoted, OPN3-dependent NST response. For the analysis, two types of experiments were performed. In the first, CBTs were assessed in cohorts of adult control and OPN3 null mice in the minus blue condition and showed that they were indistinguishable (FIG. 11E). Then, with the same cohorts of mice, the assessment was repeated in full spectrum lighting and showed that over 3 h of cold exposure, wild-type mice CBTs were higher than those of OPN3 null mice (FIG. 11F, to minute 180). This shows that as in neonatal mice, adult NST is promoted by light and by OPN3 activity. At minute 180, the 480 nm light was turned off and a decrease was observed in CBTs of wild-type mice to become indistinguishable from that of OPN3 null mice. This provides further evidence that blue light can acutely regulate adaptive thermogenesis in an OPN3-dependent manner and that this can occur in both neonatal and adult mice.

White Adipocyte OPN3 is Required for a Normal Thermogenesis Response

Figure 12A:
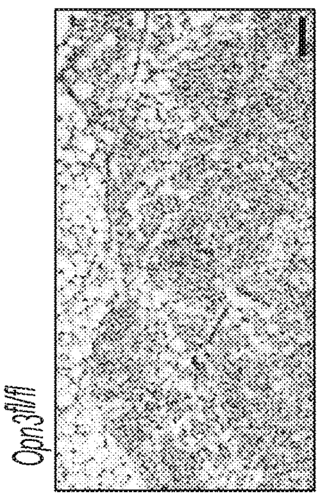
FIG. 12 illustrates, according to some embodiments, white adipocyte OPN3 is required for a normal thermogenesis response.
Figure 12B:
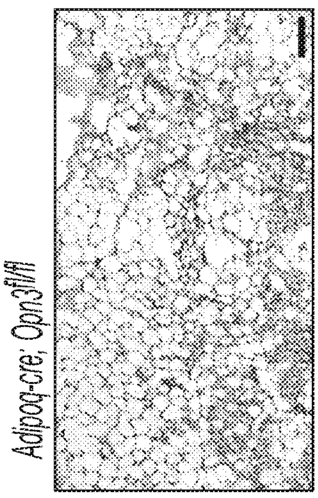
Figure 12C:
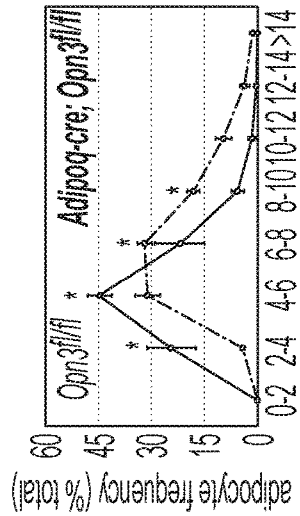

To determine whether aspects of the germline null phenotype could be attributed to adipocyte OPN3, we conditionally deleted OPN3 with pan-adipocyte Adipoq-cre. The inWAT of neonatal Adipoq-cre; OPN3/fl mice shows low beige content (FIGS. 12A and 12B) and larger adipocyte size distribution (FIG. 12C) similar to $OPN3^{lacz/lacz}$ and minus blue mice. This is consistent with the hypothesis that OPN3 functions as a light sensor within adipocytes to regulate adipose tissue development.

Figure 12D:
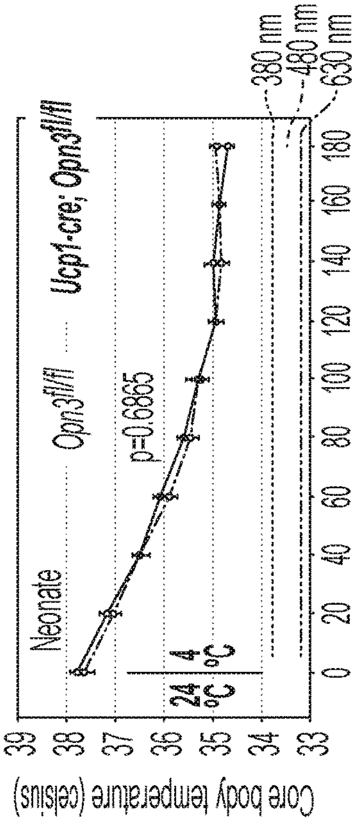
Figure 12E:
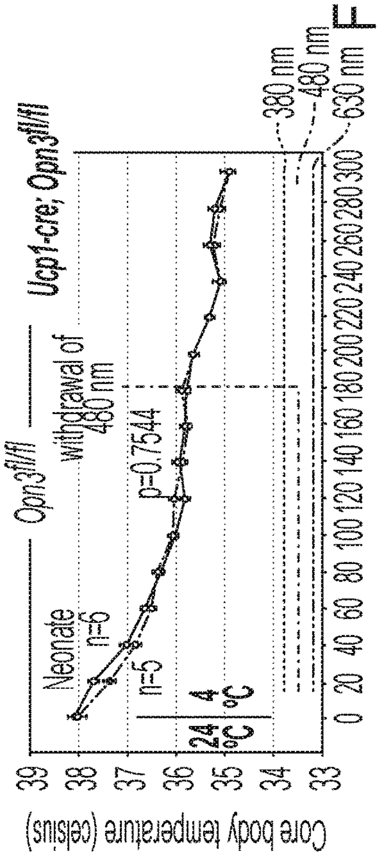

Because both brown and white adipocytes express OPN3, it was possible that the reduced NST in OPN3 null mice could be explained by either BAT or WAT defects (or both). Thus, CBTs were measured in cohorts of neonatal mice in which OPN3 was conditionally deleted either from only brown adipocytes with Ucp1-cre or from all adipocytes with Adipoq-cre. Efficient cre-mediated deletion of the floxed region of OPN3 in both Ucp1-cre; $OPN3^{fl/fl}$ and Adipoq-cre; $OPN3^{fl/fl}$ mice were first confirmed by PCR. Cold-exposed Ucp1-cre; $OPN3^{fl/fl}$ mice had CBTs indistinguishable from those of control $OPN3^{fl/fl}$ mice in any lighting condition (FIGS. 12D and 12E). This indicated that brown adipocyte OPN3 was not required for normal NST.

Figure 12F:
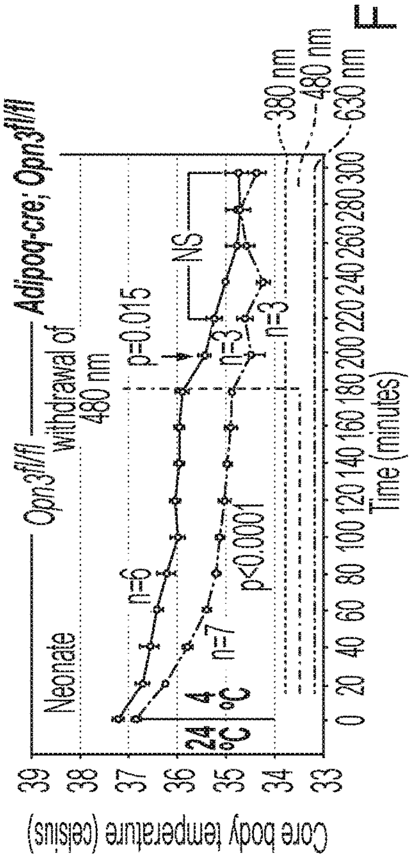
Figure 12G:
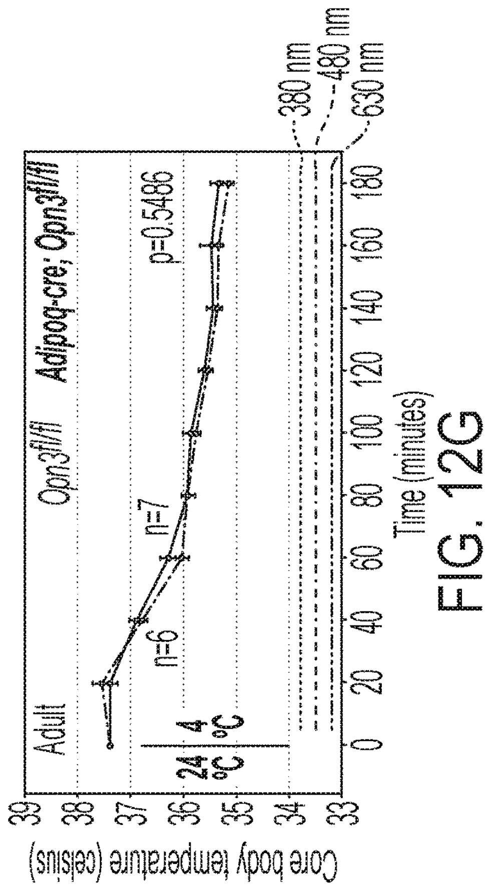
Figure 12H:
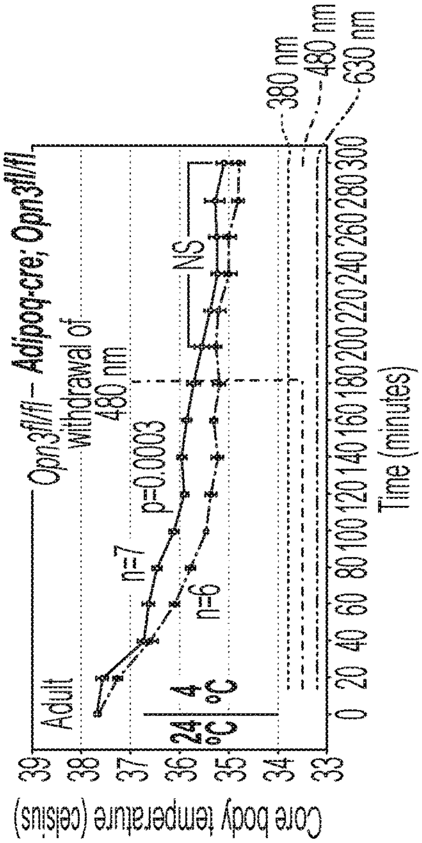
Figure 12I:
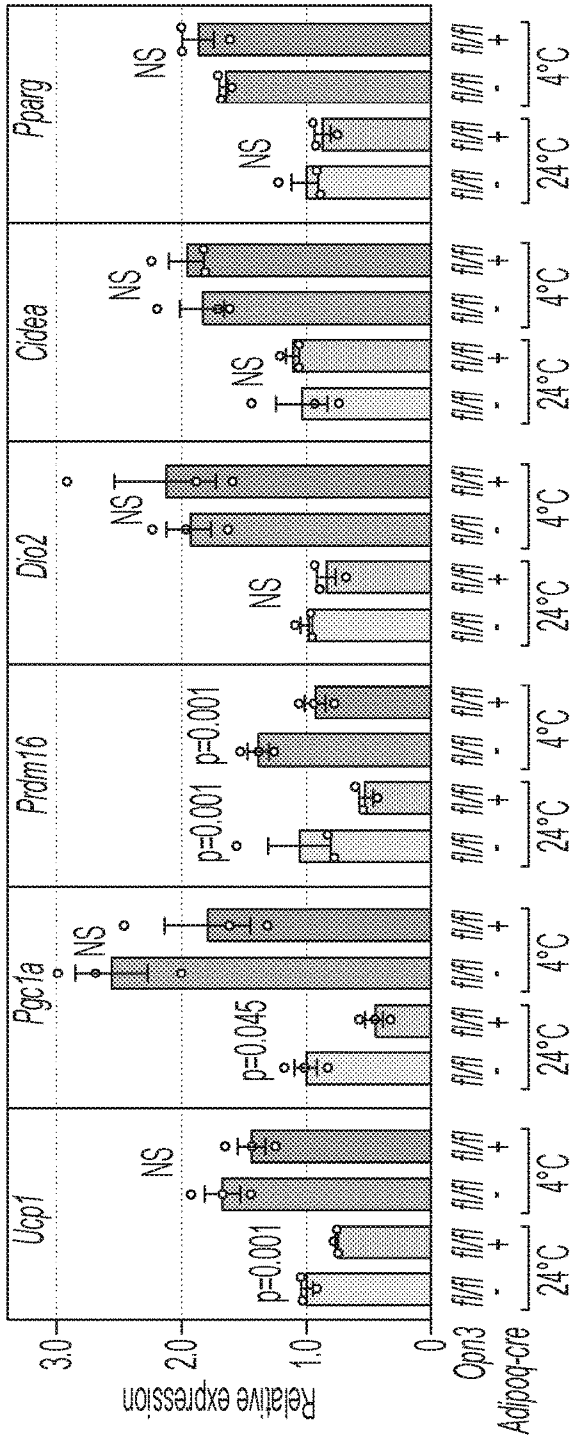

By contrast, neonatal Adipoq-cre; $OPN3^{fl/fl}$ mice in full spectrum lighting showed a more limited ability than $OPN3^{fl/fl}$ control mice to defend their body temperature (FIG. 12F). When 480 nm light was withdrawn at minute 180, CBTs of $OPN3^{fl/fl}$ mice rapidly dropped to the level of the conditional null (FIG. 12F). Repetition of cold exposure experiments in adult $OPN3^{fl/fl}$ and Adipoq-cre; $OPN3^{fl/fl}$ null mice showed a similar thermogenesis deficit (FIGS. 12G and 12H) in which the absence of blue light, either throughout the cold exposure (FIG. 12G) or acutely at minute 180 (FIG. 12H), could mimic the conditional loss of adipocyte OPN3. The absence of an NST deficit in Rx-cre; $OPN3^{fl/fl}$ mice, in which OPN3 is conditionally deleted from retinal neurons, confirms that retinal OPN3 is not necessary for this pathway. Furthermore, unchanged tail temperature measured via infrared thermography in Adipoq-cre; $OPN3^{fl/fl}$ mice indicates that the observed CBT differences are unlikely to be a consequence of cutaneous vasodilation and conductive heat loss. Finally, qPCR assessment of a set of thermogenesis pathway transcripts (Ucp1, Pgc1a, Prdm16, Dio2, Cidea, and Pparg) in iAT showed, consistent with transcriptome analysis and the NST deficit, that loss of adipocyte OPN3 resulted in diminished expression of Ucp1, Pgc1a, and Prdm16 (FIG. 12I). Combined, these data suggest that OPN3 expression in white adipocytes, but not in retina or BAT, is required for the light-dependent component of the thermogenesis response.

Loss of OPN3 Results in Decreased Energy Expenditure

Figures 13A, 13B:
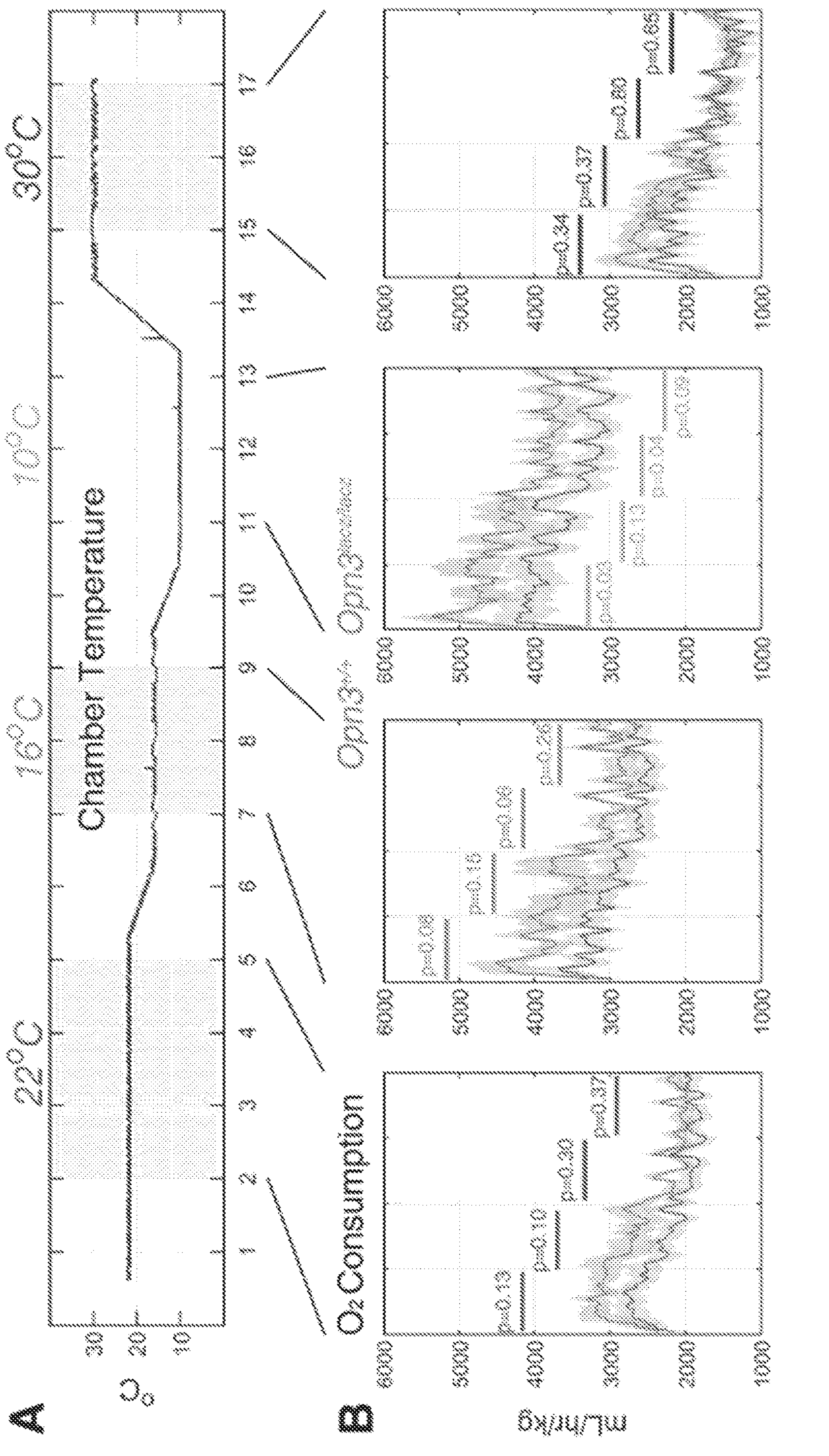
FIG. 13 illustrates, according to some embodiments, Loss of OPN3 alters energy metabolism.
Figures 13C, 13D:
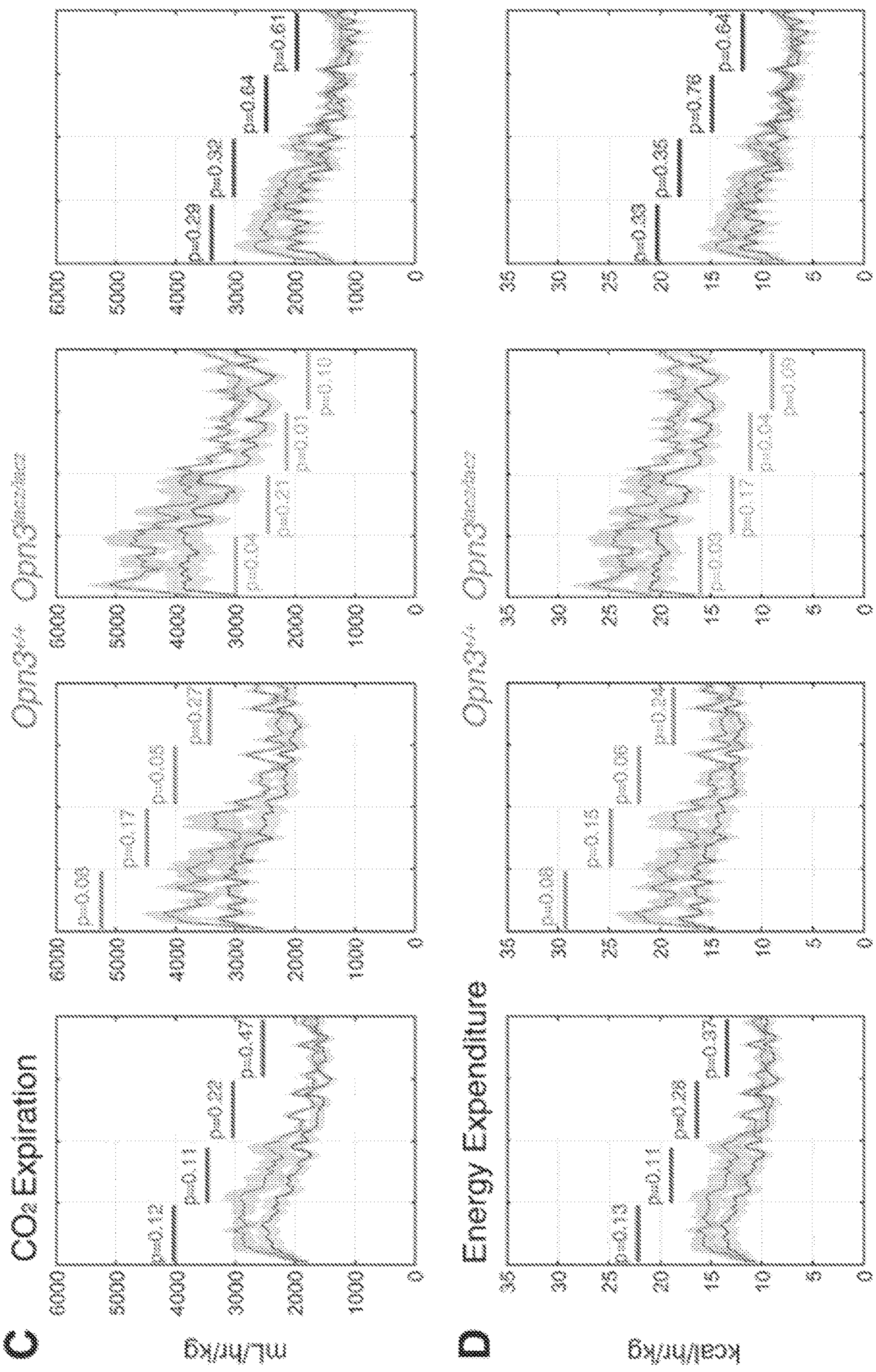
Figures 13E, 13F:
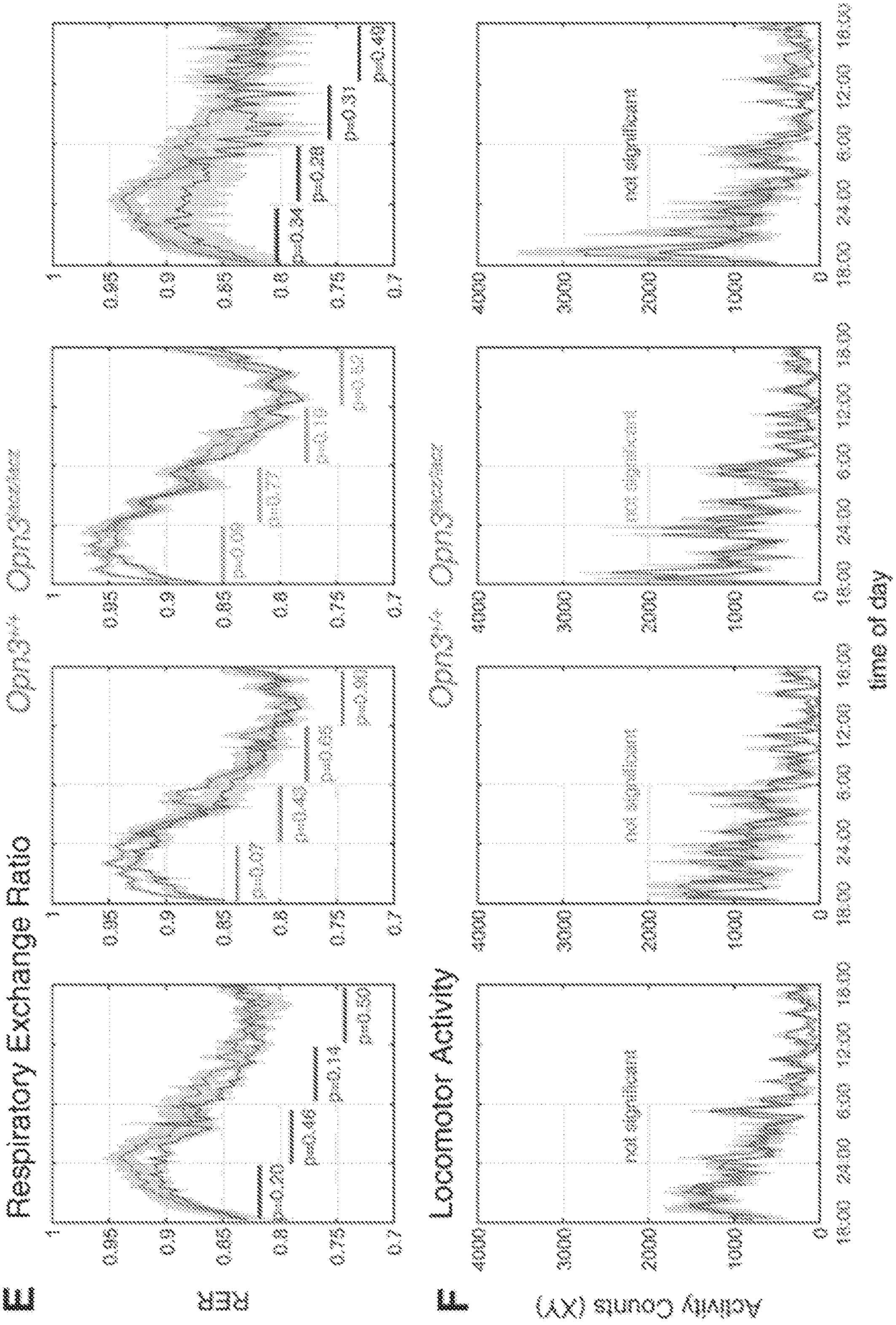

To determine how OPN3 contributes to longitudinal energy balance and homeostasis, indirect calorimetry was performed in 4-month-old $OPN3^{+/+}$ (n=5) and $OPN3^{lacz/lacz}$ (n=10) male mice. Animals were acclimated and individually housed in metabolic chambers (TSE Systems, PhenoMaster Cages), to assess energy expenditure at 22° C., 16° C., 10° C., and 30° C. (FIG. 13A). On average, $OPN3^{lacz/lacz}$ mice showed lower oxygen consumption (FIG. 13B) and carbon dioxide expiration (FIG. 13C) than controls, with the differences becoming significant at the lowest ambient temperatures (p=0.03 and p=0.04 for 02, separate repeated-measures ANOVA conducted across a 5-h period during lights off and lights on, respectively). These differences disappeared once the ambient temperature was restored to thermoneutrality (30° C.), suggesting that these differences represent adaptive, not pathological, responses. Correspondingly, $OPN3^{lacz/lacz}$ animals show lower energy expenditure (FIG. 13D), with significant differences at 10° C. Unnormalized energy expenditure data also argue for differences in energy expenditure between $OPN3^{+/+}$ and $OPN3^{lacz/lacz}$ mice that are exacerbated by decreasing ambient temperature.

The following are shown in FIG. 12, e.g., White Adipocyte OPN3 Is Required for a Normal Thermogenesis Response (A and B) Hematoxylin staining of $OPN3^{fl/fl}$ (A) and Adipoq-cre; $OPN3^{fl/fl}$ (B) inWAT at P16.

(C) Adipocyte size assessment in $OPN3^{fl/fl}$ and Adipoq-cre; $OPN3_{fl/fl}$ inWAT at P16. *=p<0.05 by Student's t test.

(D-H) CBT assessments over a time course after a 4° C. cold exposure for adult mice of the indicated genotypes. Lighting conditions during cold exposure are indicated by the colored lines above the chart's horizontal axis.

(D and E) CBTs of $OPN3^{fl/fl}$ and Ucp1-cre; $OPN3^{fl/fl}$ mice (D) under minus blue conditions and (E) in full spectrum lighting for 180 min and then for a further 120 min in minus blue.

(F) As in (E) except for cohorts of neonatal Adipoq-cre; $OPN3^{fl/fl}$ and control $OPN3^{fl/fl}$ mice.

(G) As in (D) except for cohorts of adult Adipoq-cre; $OPN3^{fl/fl}$ and control $OPN3^{fl/fl}$ mice.

(H) As in (F) except for adult mice.

(I) Relative expression of transcripts for the thermogenesis pathway genes Ucp1, Pgc1a, Prdm16, Dio2, Cidea, and Pparg in iBAT from mice of the indicated genotypes. iBAT was harvested from control mice in ambient temperature (24° C.) and those exposed to 4° C. for 3 h.

Data are presented as mean±SEM Scale bars: 100 μm.

The following are shown in FIG. 13, e.g., Loss of OPN3 Alters Energy Metabolism:

(A) Schematic detailing the ambient temperature throughout the experiment and the durations of measurement intervals.

(B-D) $VO_2$ (B), $VCO_2$ (C), and energy expenditure (EE, D) measurements by indirect calorimetry (TSE Systems, PhenoMaster Cages) were obtained for 22° C., 16° C., 10° C., and 30° C. from $OPN3^{+/+}$ (gray trace, n=5) and $OPN3^{acz/lacz}$ (blue trace, n=10) animals. Each graph shows a 24-h period of averaged data±SEM for the corresponding ambient temperature. The lighting conditions were maintained at a standard 12L:12D cycle, depicted as lights off 6 PM-6 AM (gray shaded region) followed by lights on 6 AM-6 PM (yellow shaded region).

(E) Respiratory exchange ratio (RER) was calculated by the ratio $VCO_2/VO_2$.

(F) Spontaneous locomotor activity (XY) was measured by infrared beam breaks.

(G and H) 24-h average food (G) and water consumption (H) were measured by differential weight-based sensors and plotted per ambient temperature.

(I) Postmortem fat depot masses in iAT, inWAT, and pgWAT. All statistics performed on the data in (B)-(F) are repeated-measures ANOVA across 5-h time intervals: 7 PM-12 AM, 12 AM-5 AM, 7 AM-12 PM, and 12 PM-5 PM Statistics performed on the data in (G)-(I) are 2-way ANOVAs with p values reported from Holm-Šiddk corrected multiple comparisons.

The respiratory exchange ratio (RER) was estimated by calculating the ratio of $VCO_2/VO_2$ and was not significantly changed between $OPN3^{+/+}$ and $OPN3^{lacz/lacz}$ animals throughout the experiment. This suggests the absence of substrate utilization preference and reflects the overall decreased metabolic demand caused by the loss of OPN3. This is supported by the lack of locomotor activity differences between $OPN3^{+/+}$ and $OPN3^{lacz/lacz}$ animals (FIG.

Figures 13G, 13H, 13I:
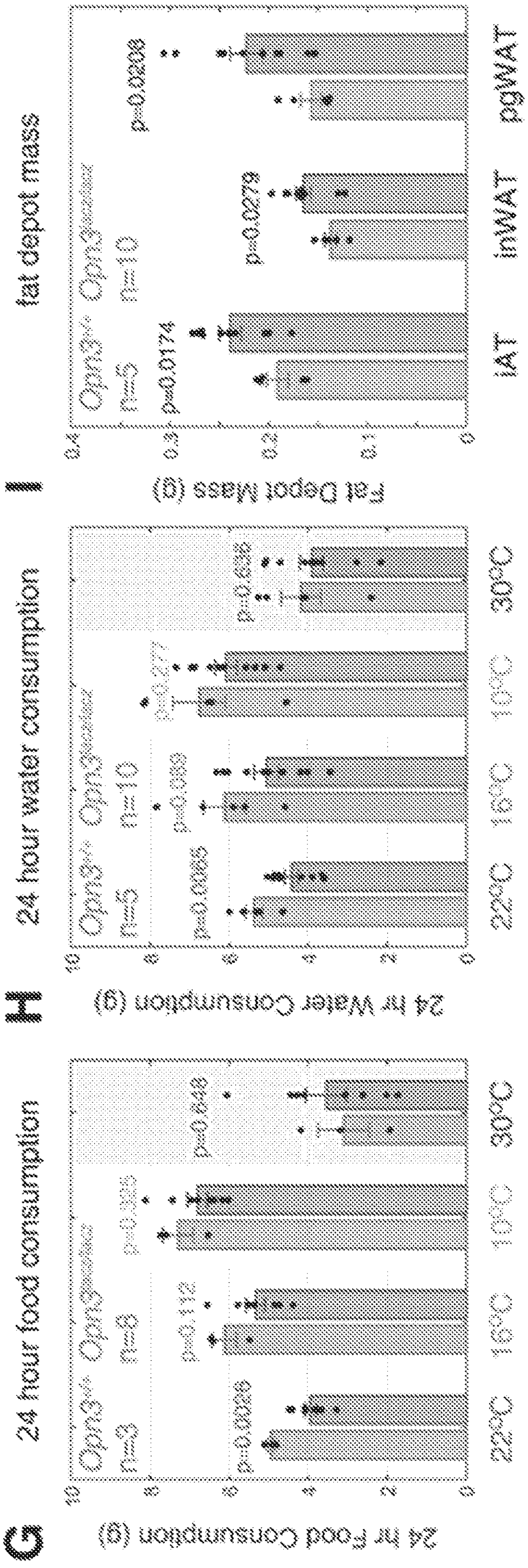

13F), which decouples the observed changes in energy expenditure from gross activity levels. In addition, locomotor activity data strongly suggest the absence of change in circadian phasing between $OPN3^{+/+}$ and $OPN3^{lacz/lacz}$ animals, implying that loss of OPN3 does not result in an altered activity cycle. Finally, $OPN3^{lacz/lacz}$ animals consumed less food (FIG. 13G) and water (FIG. 13H) compared with controls, consistent with their lower energy expenditure. Postmortem fat depot masses were higher in the $OPN3^{lacz/lacz}$ animals, perhaps suggesting diminished fat mobilization (FIG. 13I). Altogether, these data argue for the importance of OPN3 for adaptive thermogenesis, with direct consequences for whole-organism energy storage and utilization.

White Adipocyte OPN3 is Required for Normal Lipolysis During Cold Exposure

According to some embodiments, the long-standing belief that BAT lipolysis is essential for NST was challenged, e.g., analyses showing that inhibiting lipolysis in BAT does not compromise defended CBTs as long as WAT or cardiac muscle lipolysis is intact. Because this distinction mimicked the CBT differences between the Ucp1-cre; $OPN3^{fl/fl}$ and Adipoq-cre; $OPN3^{fl/fl}$ mice, it was asked whether OPN3 in white adipocytes was necessary to provide thermogenic fuel during cold exposure. This was addressed with two complementary approaches: First, an in vivo fasting experiment aimed at augmenting the use of fat reserves via lipolysis during cold exposure was performed.

Figure 14A:
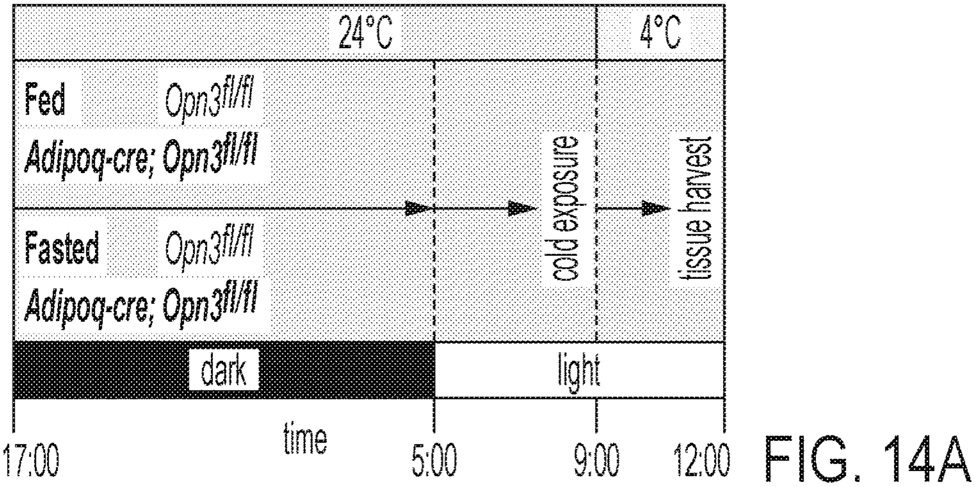
FIG. 14 illustrates, according to some embodiments, OPN3-dependent fat mass utilization in vivo and light- and OPN3-dependent lipolysis activation in vivo and in vitro.
Figure 14B:
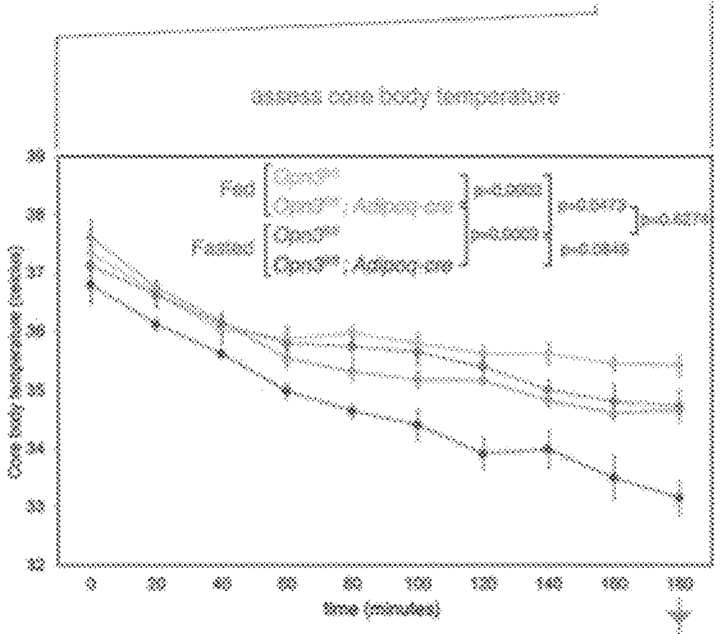
Figure 14C:
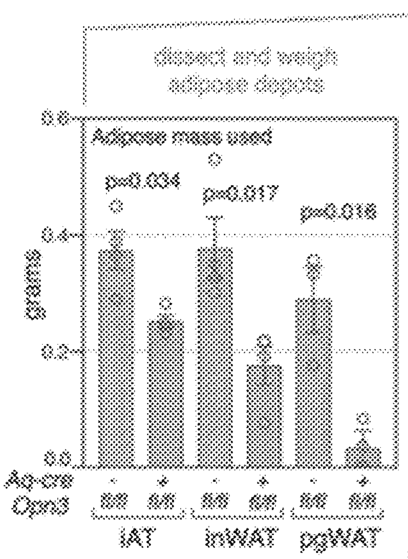

In this analysis, cohorts of control ($OPN3^{fl/fl}$) and experimental (Adipoq-cre; $OPN3^{fl/fl}$) mice were either fed ad libitum or fasted overnight and then exposed to 4° C. for 3 h (FIG. 14A). At the termination of the experiment, fat depots were dissected and weighed. After subtracting fat mass differences between fed and fasted animals, we found that Adipoq-cre; $OPN3^{+/+}$ animals mobilized significantly less fat mass than controls (380 versus 230 mg iAT, 380 versus 180 mg inWAT, and 300 versus 33 mg perigonadal white adipose tissue [pgWAT]) (FIG. 14C). This was consistent with the hypothesis that adipocyte OPN3 is required for a normal utilization of fat mass. Fat mass changes under conditions of fed versus fasting state have been documented previously and illustrate the need for lipolysis under conditions of nutritional deprivation.

Figure 14D:
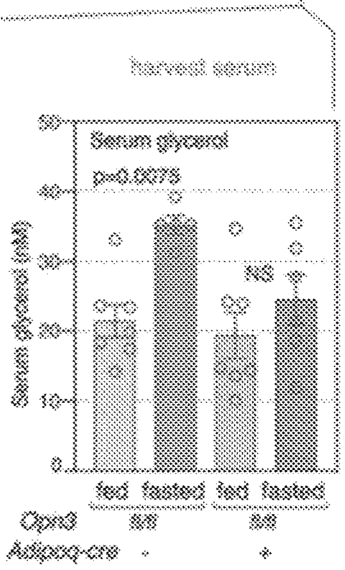
Figure 14E:
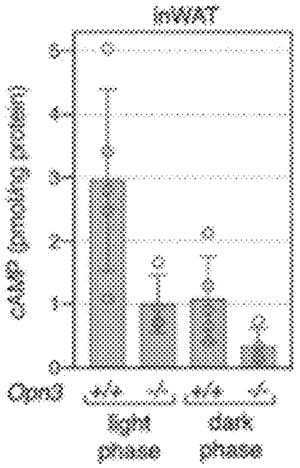

Lipolysis is initiated by 0-adrenergic receptor activation of Gαs and adenyl cyclase. This elevates cyclic AMP (cAMP) and engages targets of protein kinase A (PKA), including HSL, PLIN, and cAMP response element-binding protein (CREB), liberating glycerol and FFAs from stored triglycerides. Fasted mice showed significantly elevated serum glycerol compared with fed mice, but this difference was diminished in Adipoq-cre; $OPN3^{fl/fl}$ mice compared with controls (FIG. 14D). Assessment of cAMP from inWAT lysates revealed that control mice show significantly elevated cAMP compared with Adipoq-cre; $OPN3^{fl/fl}$ mice during the light phase of a 12:12 h light-dark (12L:12D) cycle (FIG. 14E). However, this difference was abolished during the dark phase. Thus, both measurements of serum glycerol and cAMP in inWAT support the hypothesis that OPN3 is required for a light-dependent regulation of the lipolysis response.

Figure 14F:
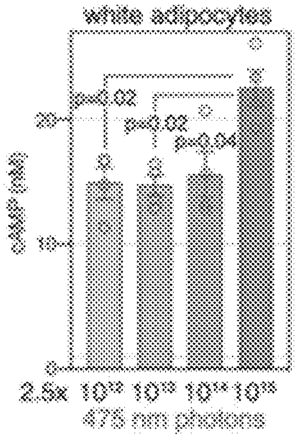
Figure 14G:
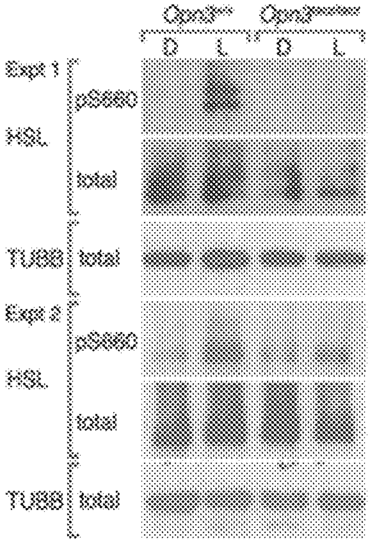
Figure 14H:
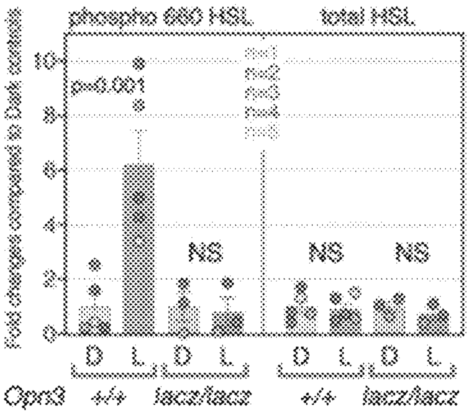
Figure 14I:
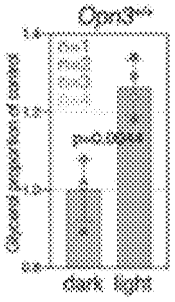
Figure 14J:
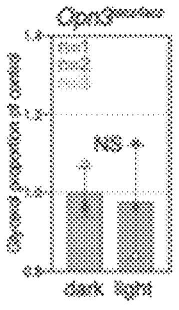

In a second approach, it was asked whether adipocytes could respond to light in isolation. Therefore, adipocytes were differentiated from the stromal vascular fraction (SVF) of inWAT from $OPN3^{+/+}$ and $OPN3^{lacz/lacz}$ mice. cAMP measurements from these white adipocytes follow a dose-dependent response to photon flux (FIG. 14F). Cultured adipocytes of both genotypes were then exposed to 480 nm light and compared levels of phosphorylated PKA substrates to unexposed cultures. Consistently elevated phosphorylated HSL (phospho-HSL) in light-stimulated $OPN3^{+/+}$ adipocytes compared with dark ones were observed (FIG. 14G). However, this light-dependent elevation was absent from $OPN3^{lacz/lacz}$ adipocytes. Quantification of this response shows significantly higher light-induced phospho-HSL in $OPN3^{+/+}$, but not $OPN3^{lacz/lacz}$ cultured adipocytes (FIG. 14H). Light-induced OPN3-dependent changes in other PKA targets were also observed. Free glycerol in culture media from differentiated white adipocytes were also measured and a significant elevation of free glycerol in blue-light-stimulated control adipocytes was found (FIG. 14I), but not OPN3 null adipocytes (FIG. 14J). These data argue for direct light responsiveness in isolated adipocytes that requires OPN3.

According to some embodiments, it has been suggested that OPN4 can mediate light responses in cultured primary adipocytes. The possibility of OPN3-OPN4 interaction in light-mediated adipocyte function was therefore explored. Assessment of OPN4 expression in iscWAT and iBAT from $OPN4^{cre}$; Z/EG mice revealed no lineage marking in adipocytes, despite a robust signal in the retina. To address a potential role for OPN4 in NST, CBTs were measured in cold-exposed cohorts of OPN4 wild-type and null mice, but no significant differences were found.

Finally, differentiated adipocytes from $OPN4^{+/+}$ and OPN4 null inWAT were stimulated with blue light and a robust induction of phospho-HSL was shown in both. These data were inconsistent with an in vivo role for adipocyte OPN4 in local light responses. The involvement of Rhodopsin (Opsin 2 [OPN2]), the photopigment-mediating vision under dim light, was also tested in defending CBTs on cold exposure. A mouse with a P23H mutation in the OPN2 gene that produces a nonfunctional Rhodopsin protein was used. Assessment of defended CBTs during cold exposure revealed no significant differences. These data argue against a nonvisual function of OPN2 in NST.

The following are shown in FIG. 14, e.g., OPN3-Dependent Fat Mass Utilization In Vivo and Light- and OPN3-Dependent Lipolysis Activation In Vivo and In Vitro:

(A) Schematic describing the timeline of a fasting-cold exposure experiment.

(B) CBT offed and fasted $OPN3^{fl/fl}$ and Adipoq-cre; $OPN3^{fl/fl}$ mice during 180 min of cold exposure.

(C) Fat mass used by $OPN3^{fl/fl}$ and Adipoq-cre; OPN3, fed and fasted, cold-exposed mice.

(D) Serum glycerol levels from the same fed and fasted $OPN3^{fl/fl}$ and Adipoq-cre; $OPN3^{+/+}$ mice as in (C) after the 180 min of cold exposure.

(E) Chart showing that $OPN3^{+/+}$ mice have elevated cAMP levels in lysates of inWAT during the light phase versus the dark phase, while the cAMP levels in the inWAT of $OPN3^{lacz/lacz}$ mice are similar in both phases, comparable to levels observed in the $OPN3^{+/+}$ dark phase and significantly lower than those seen in the $OPN3^{+/+}$ light phase.

(F) Cultured in vitro differentiated adipocytes show 475 nm light-dependent, dose-response elevation of cAMP.

(G) Two examples of immunoblots showing light-dependent and OPN3-dependent induction of phospho-660-HSL in cultured in vitro differentiated adipocytes. Each set of immunoblots (experiment 1 and experiment 2) was performed using white adipocytes isolated from separate mice.

(H) Quantification of phospho-HSL induction in wild-type control (OPN3$^{+/+}$, n=5 mice) and OPN3 loss-of-function (OPN3$^{lacz,lacz}$, n=3 mice) white adipocytes.

(I and J) Quantification of glycerol released from in vitro differentiated OPN3$^{+/+}$ (I) and OPN3$^{C}$Z acz (J) cells in response to 2 h of blue light stimulation compared with darkness.

Discussion

According to some embodiments, an assessment of OPN3 (encephalopsin) function is presented in the mouse, in which adipocytes use OPN3-dependent light sensing to regulate metabolic physiology. Extraocular photoreception is exhibited in many species, including vertebrates such as fish and birds. To date, however, there are only a few examples of extraocular light reception in mammals. Non-canonical opsins may function within adipocytes and within the skin and may mediate a vasorelaxation response and induce autophagy in human colon cancer cells. According to some embodiments, adipocyte OPN3 may have an important role in regulating lipid homeostasis.

OPN3 Activity Mediates a Light-Dependent Pathway that Regulates Energy Metabolism OPN3 has all the crucial molecular characteristics of the opsin family of light-responsive G protein-coupled receptors. Thus, one hypothesis to explain the OPN3 phenotype places OPN3 as the candidate detector for decoding light information to regulate energy homeostasis. This hypothesis was tested by raising C57BL/6J mice in minus blue conditions that exclude 480 nm wavelengths known to stimulate OPN3 homologs in other vertebrates. Remarkably, minus blue mice show the same abnormal WAT histology and low NAD, reduced iAT ETC complexes, low UCP1, and NST deficits characteristic of OPN3 null mice. This outcome is consistent with the existence of an OPN3-dependent, light-decoding metabolic regulation pathway. According to some embodiments, it suggests that OPN3 functions during development to establish the histological and functional characteristics of metabolic tissues.

A characteristic of non-canonical opsins is that they can mediate acute responses to light. OPN4 mediates the pupillary light reflex and light-aversive behavior in neonatal mice. According to some embodiments, OPN3 could mediate light responses over a similar timescale by demonstrating light- and OPN3-dependent changes in CBTs during cold exposure. When blue light was withdrawn, wild-type mice rapidly reduced their CBTs to abnormally low OPN3 null levels. According to some embodiments, CBTs of OPN3 null and wild-type mice were indistinguishable in minus blue conditions, indicating that OPN3 activity is necessary for the acute enhancement of body temperature by blue light. However, because minus blue reared animals also show deficits in NST, even under blue light stimulation (FIG. 11*c*), OPN3 likely possesses additional developmental roles that are not addressed in the current study.

Acute light stimulation enhances body temperature in humans, and this response is mediated by 460 nm light, but not 550 nm light. Though OPN4 has been implicated due to known circadian regulation of CBTs, the current analysis suggests the alternative hypothesis that OPN3-dependent light responses are central to this physiology. According to some embodiments, acute light exposure may cause elevated temperature preference, suggesting that this configuration of light information decoding is deeply conserved. Humans differ from mice in that we are a diurnal species, and the metabolic interaction between OPN3 and human circadian clock remains an open question. Even so, it is very likely that the activity of OPN3 in the light-dependent regulation of metabolic pathways and body temperature will be tightly integrated with OPN4-dependent circadian and ocular photic input pathways that also regulate this physiology.

White Adipocytes are a Site of OPN3 Metabolic Activity

Many cell types express OPN3, and this raises the possibility that extraocular light reception in mammals is commonplace. According to some embodiments, white adipocytes are a crucial site of OPN3 function for NST. Moreover, there are likely to be additional adipocyte-independent activities of OPN3 (e.g., brown adipocyte OPN3 activity from involvement in NST).

Prompted partly by transcriptome analysis, according to some embodiments, lipolysis is shown in cultured white adipocytes is enhanced by blue light in an OPN3-dependent manner. As illustrated by the lower-than-normal body temperature that results when lipid mobilization enzymes are compromised, lipolysis is an essential component of a normal thermogenesis response in mice. Blue-light-stimulated white adipocytes show elevated cAMP and, importantly, dramatic elevation of phospho-HSL, the rate-limiting enzyme in the lipolysis pathway, a response lost in OPN3 null adipocytes. Because lipolysis is an essential response for normal body temperature maintenance and the resulting FFAs are required for the activation of UCP1, according to some embodiments, a mechanistic explanation for the OPN3-dependent deficit in NST is provided. According to some embodiments, the reduced ability of Adipoq-cre; OPN3$^{fl/fl}$ mice to use fat mass in response to fasting and cold exposure is consistent with a role for OPN3 in enhancing lipolysis in vivo. Moreover, elucidating the specific OPN3-dependent signaling mechanisms in adipose tissue may enable a better understanding of the direct link between blue-light-sensing OPN3 and lipolytic enzymes.

According to some embodiments, OPN3 mediates light-dependent regulation of cellular physiology in mice and diverse human cell types. Accordingly, key evidence is provided that OPN3 can regulate physiology at the organismal level, at least in the mouse. Both the primary amino acid sequence and the expression pattern of OPN3 are highly conserved. If the light-OPN3 adipocyte pathway exists in humans, there are potentially broad implications for human health. Our modern lifestyle subjects us to unnatural lighting spectra, exposure to light at night, shift work, and jet lag, all of which result in metabolic disruption. Based on the current findings, it is possible that insufficient stimulation of the light-OPN3 adipocyte pathway is part of an explanation for the prevalence of metabolic deregulation in industrialized nations where unnatural lighting has become the norm.

KEY RESOURCES TABLE

| REAGENT or RESOURCE | SOURCE | IDENTIFIER |
|---|---|---|
| Antibodies | | |
| Rabbit polyclonal anti-UCP1 | Abeam | ab10983; RRID: AB_2241462 |
| Chicken polyclonal anti-GFP | Abeam | ab13970; RRID: AB_330798 |

KEY RESOURCES TABLE-continued

| | | |
|---|---|---|
| Rabbit polyclonal anti-TUBB3 | BioLegend | 802001; RRID: AB_2564645 |
| Rabbit polyclonal anti-Recoverin | Millipore Sigma | AB5585; RRID: AB_2253622 |
| Phalloidin (Alexa Fluor 594) | Thermo Fisher Scientific | A12381; RRID: AB_2315633 |
| Mouse monoclonal anti-Rhodopsin | Abeam | ab3267; RRID: AB_303655 |
| Isolectin IB4 (Alexa Fluor 488) | Thermo Fisher Scientific | I21411; RRID: AB_2314662 |
| Anti-Phospho-PKA (pThr197) | Cell Signaling Technology | 5661S; RRID: AB_10707163 |
| Anti-PKA C-a | Cell Signaling Technology | 5842S; RRID: AB_10706172 |
| Anti-Phospho-PKA Substrate (RRxpS/T) | Cell Signaling Technology | 9624S; RRID: AB_331817 |
| Anti-Phospho-HSL (pSer660) | Cell Signaling Technology | 4126S; RRID: AB_490997 |
| Anti-HSL | Cell Signaling Technology | 18381T; RRID: AB_2798800 |
| Anti-Phospho-PLIN1 (pSer522) | Vala Sciences | 4856 |
| Anti-Phospho-CREB (pSer133) | Cell Signaling Technology | 9198S; RRID: AB_2561044 |
| Anti-phospho-ERK (p44/42) | Cell Signaling Technology | 9102S; RRID: AB_330744 |
| **Chemicals, Peptides, and Recombinant Proteins** | | |
| DMEM High Glucose | Thermo Fisher Scientific | 11965-092 |
| Insulin | Millipore Sigma | I2643 |
| Rosiglitazone | Millipore Sigma | R2408 |
| Dexamethasone | Millipore Sigma | D1756 |
| IBMX | Millipore Sigma | I5879 |
| 9-cis-Retinal | Millipore Sigma | R5754 |
| **Critical Commercial Assays** | | |
| cAMP Assay Kit (Competitive ELISA, Fluorometric) | Abeam | ab138880 |
| OxPhos Rodent WB Antibody Cocktail | Thermo Fisher Scientific | 45-8099; RRID: AB_2533835 |
| Free Glycerol Reagent | Millipore Sigma | F6428 |
| GeneJET RNA Purification Kit | Thermo Fisher Scientific | K0732 |
| Verso cDNA Synthesis Kit | Thermo Fisher Scientific | AB1453 |
| NAD/NADH Assay Kit (Colorimetric) | Abeam | ab65348 |
| **Deposited Data** | | |
| Gene Expression Dataset | GEO NCBI | GEO: GSE140757 |
| **Experimental Models: Organisms/Strains** | | |
| Mouse: Adipoq-cre: B6.FVB-$Tg^{(Adipoq-cre)1Evdr}$/J | The Jackson Laboratory | 010803; RRID: IMSR_JAX: 010803 |
| Mouse: Ucp1-cre: B6.FVB-$Tg^{(Ucp1-cre)1Evdr}$/J | The Jackson Laboratory | 024670; RRID: IMSR_JAX: 024670 |
| Mouse: Ai14: B6; 129S6-Gt(ROSA)$26Sor^{tm14(CAG-tdTomato)Hze}$/J | The Jackson Laboratory | 007908; RRID: IMSR_JAX: 007908 |
| Mouse: OPN2: B6.129S6(Cg)-$^{Rhotm1.1Kpal}$/J | The Jackson Laboratory | 017628; RRID: IMSR_JAX: 017628 |
| Mouse: C57BL/6J | The Jackson Laboratory | 000664; RRID: IMSR_JAX: 000664 |
| Mouse: Rx-cre: B6.Cg-Tg($^{Rax-cre)1Zkoz/Ph}$/J | Klimova et al., 2013 | N/A |
| Mouse: $OPN3^{lacZ/lacZ}$ | This paper | N/A |
| Mouse: $OPN^{fl/fl}$ | This paper | N/A |
| Mouse: $OPN3^{\Delta Ex2/DEx2}$ | This paper | N/A |

KEY RESOURCES TABLE-continued

| | | |
|---|---|---|
| Mouse: OPN3$^{cre}$ | This paper | N/A |
| Mouse: OPN3-eGFP: B6-Tg($^{OPN3-EGFPJY3Gsat/Mmucd}$)/J | GENSAT | 030727-UCD; RRID: MMRRC_030727-UCD |
| **REAGENT or RESOURCE** | **SOURCE** | **IDENTIFIER** |
| Mouse: OPN4: OPN4$^{tm1skay}$ | KOMP Repository | MGI: 2449695 |
| Mouse: OPN3: OPN3$^{tm2a/(UCOMM)Wtsi}$ | EuMMCR Repository | MGI: 4434308 |
| Mouse: OPN4$^{cre}$; Z/EG | Ecker et al., 2010 | N/A |
| Oligonucleotides | | |
| Dio2 F: CAGTGTGGTGCACGTCTCCAATC | This Paper | N/A |
| Dio2 R: TGAACCAAAGTTGACCACCAG | This Paper | N/A |
| Prdm16B: CAGCACGGTGAAGCCATTC | This Paper | N/A |
| Prdm16R GCGTGCATCCGCTTGTG | This Paper | N/A |
| Pgc1α F: CCCTGCCATTGTTAAGACC | This Paper | N/A |
| Pgc1α R: TGCTGCTGTTCCTGTTTTC | This Paper | N/A |
| Cidea F: TGCTCTTCTGTATCGCCCAGT | This Paper | N/A |
| Cidea R: GCCGTGTTAAGGAATCTGCTG | This Paper | N/A |
| Ucp1 F: ACTGCCACACCTCCAGTCATT | This Paper | N/A |
| Ucp1 R: CTTTGCCTCACTCAGGATTGG | This Paper | N/A |
| Pparγ F: GTGCCAGTTTCGATCCGTAGA | This Paper | N/A |
| Pparγ R: GGCCAGCATCGTGTAGATGA | This Paper | N/A |
| Hprt1 F: TCAGTCAACGGGGGACATAAA | This Paper | N/A |
| Hprt1 R: GGGGCTGTACTGCTTAACCAG | This Paper | N/A |
| TbpF: GAAGCTGCGGTACAATTCCAG | This Paper | N/A |
| TbpR: CCCCTTGTACCCTTCACCAAT | This Paper | N/A |
| Software and Algorithms | | |
| GraphPad Prism 8.2.1 | GraphPad | GraphPad.com |
| MATLAB 2018a | Mathworks | Mathworks.com |
| ImageJ/Fiji 2.0.0 | ImageJ | ImageJ.nih.gov |
| AltAnalyze | Salomonis, 2012 | AltAnalyze.org |
| FLIR Tools Version 2.1 | FLIR | Flir.com |
| | Other | |
| Infrared Thermal Camera | FLIR | T530 |
| Rectal Thermometer Probe | Physitemp | RET-3 |
| TSE PhenoMaster | TSE Systems Inc. | N/A |
| JAZ Spectrometer | Ocean Optics | JAZ |

Experimental Model and Subject Details

All experiments were approved by Cincinnati Children's Hospital Medical Center, The University of Michigan Ann Arbor, and The University of Washington Institutional Animal Care and Use Committees and were in accordance with the National Institute of Health guidelines. Ages of mice used in this study include P16 (immunohistochemical analyses and microarray), P21-P24 (neonatal cold exposure), P28 (transmission electron microscopy), 2 months (adult cold exposure), and 3-4 months (fiber radiometry and indirect calorimetry). Male and female mice were used for all studies unless otherwise stated.

Mice

Animals were housed in a pathogen-free vivarium in accordance with institutional policies. Genetically modified mice used in this study were: B6; FVB-Tg(Adipoq-cre)1Evdr/J (Eguchi et al., 2011)(Jax stock #010803), Ai14 (Madisen et al., 2010)(Jax stock #007914), OPN4 (Panda et al., 2003), and Tg(OPN3-EGFP)JY3Gsat (MMRRC stock number 030727-UCD). The Ucp1cre mouse line used in the thermoregulation assay studies was obtained from Jackson Laboratories: B6.FVB-Tg(Ucp1-cre)1Evdr/J (Jax stock #024670). The OPN4cre; Z/EG mouse line was generously donated by Kwoon Y. Wong from the University of Michigan Ann Arbor. OPN3tm2a(EUCOMM)Wtsi mice were generated from C57BL/6N ES cells obtained from EUCOMM (ES clone ID: EPD0197_3_E01). The ES cells harbor a genetic modification wherein the lacz-Neomycin cassette is flanked by FRT sites and a loxp site separates lacz from the neomycin coding region. Loxp sites also flank exon 2 of OPN3 allowing multiple mouse lines that can serve as reporter nulls, conditional floxed and null mice. The OPN3Lacz reporter null line was created by crossing OPN3tm2a(EUCOMM)Wtsi mice to FVB/N-Tg(EIIa-cre)C5379Lmgd/J mice (Lakso et al., 1996)(Jax stock #003314). OPN3fl/lf line was created by crossing the OPN3tm2a(EUCOMM)Wtsi mice to 129S4/SvJaeSor-Gt(ROSA)26Sortm1(FLP1)Dym/J (Jax stock #003946) to remove the lacZ cassette. This means that OPN3lacz mice are of mixed C57Bl6/6N, FVB/N background and that Adipoq-cre; OPN3fl mice are of mixed C57Bl6/6N, 129S4/Sv, B6; FVB background. Littermate control animals were used for all experiments with the exception of C57BL/6J mice reared under different lighting conditions.

The OPN3cre was generated in-house using CRISPR-Cas9 technology. Four gRNAs that target exon 2 of OPN3 were selected to knock in the Cre cassette. Plasmids containing the gRNA sequence were transfected into MK4 cells (an in-house mouse cell line representing induced metanephric mesenchyme undergoing epithelial conversion). The editing efficiency of gRNA was determined by T7E1 assay of PCR products of the target region amplified from genomic DNA of transfected MK4 cells. The sequence of the gRNA that was subsequently used for the transfection is TACCGTGGACTGGAGATCCA (SEQ ID NO: 17). Sanger sequencing was performed to validate the knock-in sequence of founder mice.

The OPN3ΔEx2 allele was generated in-house using CRISPR-Cas9 technology as above. Four gRNAs that target exon 2 of OPN3 were selected. The sequences of the gRNAs are: for the 50 end: TAGCAACGAATGCAAAGGTA GGG (SEQ ID NO: 18) and ATCCACATGTTCTGCC CAGGAGG (SEQ ID NO: 19). For the 30 end: GCGCTATGTTGGTAAGGTGT GGG (SEQ ID NO: 20) and TGTGGTTTTAATCAGCACAGGGG (SEQ ID NO: 21). Out of the 6 pups derived from one injection, the founder animal had a 2203 bp deletion that was also confirmed by Sanger sequencing. The proximal breakpoint of this deletion is intron 1 (bp 175,667,424) to intron 2 (bp175,665,054) thus deleting the entirety of exon 2.

Mice were placed on normal chow diet (NCD: 29% Protein, 13% Fat and 58% Carbohydrate kcal; LAB Diet #5010) ad libitum with free access to water.

Genotyping

Primer sequences and pairs for genotyping each of the alleles in this study are listed in the table below:

| Allele | Primers | Pairs | bp |
|---|---|---|---|
| OPN3 | F1: ACCCAGGCTTCTTTTGGTCT | F1R1-Wild-type | 1191 |
| | R1: AGAGTCGTTGGCATCCTTGG | F1R1-OPN3$^{fl}$ | 1231 |
| | F2: ACTATCCCGACCGCCTTACT | F1R2-OPN3$^{fl}$ | 1610 |
| | R2: GAACTGATGGCGAGCTCAGA | F1R2-OPN3$^{cko}$ | 640 |
| | | F2R2-OPN3$^{lacz}$ | 701 |
| OPN3$^{cre}$ | F1: TGCTGGCCTATGAACGTTATATCC | F1R1-Wild-type | 401 |
| | R1: TCAGTTCTGGGTGACTAACTGATC | F1R2-OPN3$^{cre}$ | 390 |
| | R2: CACTCGTTGCATCGACCGGTAATGC | | |
| Adipoq$^{cre}$ | F: GCATTACCGGTCGATGCAACGAGTGATGAG | FR - cre | 450 |
| Ucp1$^{cre}$ | R: GAGTGAACGAACCTGGTCGAAATCAGTGCG | | |
| Rx$^{cre}$ | | | |
| OPN3$^{\Delta Ex2}$ | F1: CTCAGAACCCACAAAGTGCTGG | F1R1-Wild-type | 307 |
| | R1: GTGGACTGCAATGTCCCATCTATC | F1R2-OPN3$^{\Delta Ex2}$ | 191 |
| | R2: GTGGGCATCATAGCCCATTGCTAC | | |
| OPN4 | F1: AGGAGTGTATAGAGCCGGAAGTCTG | F1R1 - Wild-type | 520 |
| | R1: CCAGTCCAGAAGCCTAGGGCATGCC | F2R2-OPN4$^{-}$ | 380 |
| | F2: TGCTCCTGCCGAGTATCCATCATGGC | | |
| | R2: CGCCAAGCTCTTCATATCACGGGTAG | | |
| OPN4$^{cre}$ | F1: AGGCTGGATGGATGAGAGC | F1R1-Wild-type | 187 |
| | R1: GTTGTGAAGCTGGGATCCTG | F2R2-cre | 184 |
| | F2: CGACCAGGTTCGTTCACTCA | | |
| | R2: CAGCGTTTTCGTTCTGCCAA | | |
| Z/EG | F: CCCCTGCTGTCCATTCCTTA | FR-Z/EG | 224 |
| | R: TGACCATGATTACGCAAGC | | |

OPN3 Mouse Lines

All OPN3 mouse lines used in this study, along with the scientific rationale, are detailed in the table below:

| Allele | Mouse Lines | Rationale & Data |
|---|---|---|
| OPN3$^{IKMC}$ | | Parent allele used to derive other modular alleles. |
| OPN3$^{lacZ}$ | OPN3$^{lacZ/lacZ}$ | Reporter null allele. Key data presented for this mouse line includes FIGS. 1, 3, 4, 6, and 7, where we show adipocyte expression, adipocyte morphometric differences, NAD, ETC, body temperature, gene expression differences, and adipocyte specific light responses. |
| OPN3$^{fl}$ | Adipoq$^{cre}$; OPN3$^{fl/fl}$ | Conditional deletion of OPN3 from adipocytes. Key data for this mouse line are presented in FIGS. 5 and 7 where we directly measure markers of lipolysis that are OPN3- and light-dependent. This allele is crucial because it permits us to focus on analyses that explore adipocyte-specific OPN3 functions. |
| | Ucpl$^{cre}$; OPN3$^{fl/fl}$ | Conditional deletion of OPN3 from brown adipocytes. Key data for this mouse line are presented in FIG. 5E showing no difference between OPN3$^{fl/fl}$ and Ucpl$^{cre}$; OPN3$^{fl/fl}$ adult mice in defended body temperature following cold exposure. |
| | Rx$^{cre}$; OPN3$^{fl/fl}$ | Conditional deletion of OPN3 from retinal progenitors. |
| OPN3$^{cre}$ | OPN3$^{cre}$; Ai14 | In house developed and validated constitutive Cre driver line used in combination with Ai14 (Jax #007908) to characterize OPN3 expression in iscWAT and iBAT via the fluorescent tdTomato reporter. Key data presented for this line are in FIGS. 1I-1K. |
| OPN3$^{\Delta Ex2}$ | OPN3$^{\Delta Ex2/\Delta Ex2}$ | In house generated CRISPR-Cas9 mediated 2203 bp deletion of exon 2 of the OPN3 locus. Key data presented for this mouse line is in FIG. 4B, showing persistence of defended core body temperature differences between controls and OPN3 loss-of-function animals on a congenic C57BL/6J background. |

Method Details

Lighting Conditions

Animals were housed in standard fluorescent lighting (photon flux 1.62×1015 photons/cm2/sec) on a 12L:12D cycle except where noted. For full spectrum lighting, LEDs were used to yield a comparable total photon flux of 1.68×1015 photons/cm2/sec. Spectral and photon flux information for LED lighting: near violet (λ max=380 nm, 4.23×1014 photons/cm2/sec in the 370-400 nm range), blue (λ max=480 nm, 5.36×1014 photons/cm2/sec in the 430-530 nm range), and red (λ max=630 nm, 6.72×1014 photons/cm2/sec in the 590-660 nm range). Photon fluxes were measured at approximately 24" from source and through an empty standard mouse cage. For wavelength restricted experiments, C57BL/6J animals were housed in a 12L:12D cycle starting late gestation (embryonic day E16) either in full spectrum (380 nm+480 nm+630 nm LEDs) or in "minus blue" (380 nm+630 nm LEDs) lighting.

Intra-Adipose Tissue Radiometry

Fabrication of the Holt-Sweeney microprobe (HSM) is described as follows (Holt et al., 2014). The termination of one end of a 100 mm silica core fiber optic patch cable (Ocean Optics, Dunedin, Fla., USA) was removed. The fiber's furcation tubing and jacketing was stripped, and the fiber's polyimide buffer was removed 5 cm from the fiber's end using a butane torch. A 10 g weight was attached to the end of the fiber and then pulled upon heating with the butane torch, narrowing the diameter. The narrowed region of the fiber was then cut using carborundum paper, to yield a flat fiber end with a diameter of 30-50 μm. The sides of the narrowed fiber were painted with a film opaquing pen to prevent stray light from entering, while leaving a small transparent opening at the fiber tip. For structural support, this bare, tapered fiber was then secured in the tip of a pulled glass Pasteur pipette using a drop of cyanoacrylate glue, leaving only 6-9 mm of bare optical fiber protruding. A small light-scattering ball was added to the end of the tapered optical fiber for spectral scalar irradiance measurements. To do this, titanium dioxide was thoroughly mixed with a high-viscosity UV-curable resin, DELO-PHOTOBOND, GB368 (DELO Industrie Klebstoffe, Windach, Germany). The tip of a pulled fiber was quickly inserted and removed from a droplet of the resin and titanium dioxide mixture, resulting in a sphere with a diameter of approximately twice that of the tapered fiber. As all measurements from a given probe were normalized to the signal from the same probe in a gelatin blank, small variations in the probe diameter have no effect on our results. The sphere was cured for 12 h using a Thorlabs fiber coupled LED light source (M375F2, Thorlabs Inc, Newton, N.J., USA).

For intra-tissue radiometric measurements in mice, 4 month-old adult animals were anesthetized under ventilated isoflurane and placed in a mouse stereotaxic frame (Stoelting Co, Wood Dale, Ill., USA). The hair overlying the intrascapular region was shaved and a small 10 mm rostro-caudal incision was made through the dorsal skin to expose the underlying tissue. A 21-gauge needle attached to the stereotaxic frame was first lowered through the intrascapular region to produce a pilot hole through the adipose tissue. Following, the Holt-Sweeney microprobe was affixed to the stereotaxic frame and lowered through the pilot hole. After the probe is in position, the dorsal skin was repositioned to cover as much of the incision site as possible without obstructing the probe's descent. For broadband light illumination, a Thorlabs plasma light source (HPLS345, Thorlabs Inc, Newton, N.J., USA) was positioned above and in front of the mouse stereotaxic frame. The light was delivered to the animal via a 5 mm liquid light guide connected to a 2 in. collimating lens secured in a vice. The distance from the collimating lens to the animal was approximately 2 ft.

Scalar irradiance measurements as a function of wavelength were obtained at the surface of the adipose tissue and at probe depth increments of 0.5 mm up to 2.5 mm. Spectral irradiance data were collected using an Ocean Optics 200-850 nm spectrometer (JAZ series, Ocean Optics, Dunedin, Fla., USA).

Immunohistochemistry and Tissue Processing

Animals were anesthetized under isoflurane and sacrificed by cervical dislocation. Adipose tissue depots (interscapular adipose tissue complex and inguinal WAT) from P16 male mice were harvested and fixed in ice cold 10% zinc formalin for 1 hour at 4° C. After washing in PBS, adipose tissue samples were prepared for cryosectioning as described previously. Gelatinembedded tissues were sectioned at 16 μm in a cryostat and labeled with primary antibodies as previously described. Chicken antibodies to GFP (ab13970, 1 in 500), and rabbit antibodies to UCP1 (ab10983, 1 in 500), were purchased from Abcam. Alexa 488 conjugated isolectin (1 in 300) and Alexa 594 conjugated F-actin were purchased from Thermo Fisher Scientific. Alexa 488 conjugated secondary antibodies (1 in 300) were purchased from Jackson ImmunoResearch.

X-Gal Staining

For X-Gal labeling, tissue samples were fixed in X-Gal fixative (1% formaldehyde, 0.2% glutaraldehyde, 2 mM MgCl2, 5 mM EGTA, and 0.01% Nonidet P-40) for two hours at room temperature. Tissues were cryosectioned as described above and then labeled with X-Gal. The reaction was monitored closely and stopped when background started to appear in control (wild-type) tissues. Following two washes in PBS, cryosections were imaged using a bright field microscope.

Hematoxylin Labeling and Cell-Size Quantification

Gelatin-embedded frozen sections of inguinal WAT (as described above) were stained with hematoxylin and imaged under brightfield. Samples were imaged with a rhodamine filter to assess adipocyte size distribution. Using the free hand selection tool on ImageJ, adipocytes were outlined and the area measured in μm2. Cell size distribution was determined by quantifying 60 cells from at least 10 regions, for a total of approximately 600 cells per animal. Cell areas were binned into 200 μm2 intervals and the frequency of total cells (%) charted for each interval.

Pre-Adipocyte Differentiation and Light Induction

IngWAT dissociation and extraction of stromal vascular fraction was performed as described before (Liu et al., 2017). Briefly, the inguinal fat pads were collected in PBS and digested in 1.5 mg/ml Collagenase A in PBS with 4% BSA and penicillin/streptomycin at 37° C., with intermittent agitation over 40 minutes. The stromal vascular fraction was extracted by passing the enzymatically dispersed cells through a 100 μm cell strainer and cultured in basal media (DMEM containing 10% fetal bovine serum and penicillin/streptomycin). For differentiation, the stromal vascular cells were plated on day 1 such that the cells reached confluency on day 3. On day 4, the basal media was replaced with induction media containing Insulin (100 nM), Rosiglitazone (1 μM), IBMX (0.5 mM) and Dexamethasone (2 μg/ml) in basal media. Thereafter, the differentiating cells were maintained in basal media containing insulin (100 nM) until the day of experimentation.

Light inductions to assay lipolysis responses were typically done on day 13-day 15 of differentiation. For this, cultures were moved to a dark, 37° C. incubator, protected from light, overnight. The next day, the cultures were serum-starved, under dim red light, where the complete basal medium was washed out using serum-free medium (at least three washes) and the cells were left in serum-free media for 3 hours, before light inductions. For light inductions, half the OPN3+/+ and OPN3Lacz/Lacz cultures were left in the dark incubator, while the rest were moved to an adjacent incubator that housed a light set-up to deliver 5×1014 photons/cm2/sec of 480 nm wavelength. The culture conditions in the two incubators were comparable except for the lighting. Prior to stimulation, any movement between incubators was accomplished with care and within a matter of seconds so as to avoid any potential temperature shock. Wild-type controls were always processed alongside OPN3 null samples. Light inductions were carried out for 30 minutes, after which the cells were washed in PBS and snap frozen by immersing the culture plates in liquid nitrogen and frozen at −80° C. until lysate preparations for western blotting.

For the light-induced cyclic AMP response, in vitro differentiated OPN3+/+ and OPN3Lacz/Lacz adipocytes were used between days 7 and 10 of differentiation. The cells were incubated with 9-cis-Retinal (5 mM) the day before the assay and one hour before the light induction, the cells were incubated in fresh DMEM without phenol red. The light pulses (465 nm) were delivered for 30 minutes with varying intensities as indicated in the results. The cells were then harvested to quantify cAMP levels by direct immunoassay (fluorometric kit by Abcam, ab138880) as per manufacturer's instructions. For ex vivo cAMP quantification from harvested tissue, dissected inguinal white adipose tissue samples were homogenized by a pellet pestle in ice cold lysis buffer. Briefly, all samples and standards (50 μl each) were tested in duplicates, to which 25 mL of 1×HRP-cAMP was added. The plates were incubated at room temperature for 2 hours and after the washing steps, 100 μL of AbRed indicator was added. The plates were incubated for 1 hour and the fluorescence was measured at Ex/Em=540/590 nm using a Biotek Synergy4 microplate reader.

Western Blotting

Western blots were performed using standard protocols. Adipose tissue lysates were made in NP40 lysis buffer: 150 mM NaCl, 1% NP40, 50 mM Tris 8.0 with phosphatase inhibitors. Lysates were prepared by sonication and the lysates were separated from overlaying fat layer by three rounds of centrifugation. After BCA method of protein quantification, lysates were boiled in Laemmli sample buffer (4% SDS, 20% glycerol, 10% 2-mercaptoethanol, 0.004% bromophenol blue and 0.125 M Tris HCl, pH 6.8). Blots were incubated with OxPhos antibodies (Thermofisher 45-8099 1:1000) and UCP-1 (Abcam ab10983). HRP-conjugated secondary antibodies were used at 1:5000 dilution and detected by enhanced chemiluminescence (ThermoFisher Scientific).

Glycerol Assay

Glycerol assays were performed using free glycerol detection reagent (Sigma, F6428) as per manufacturer's instructions. For serum glycerol, terminal blood collections were performed using cardiac puncture method and sera were frozen immediately at −80° C. until use. For glycerol detection, 1:20 ratio of sera to free glycerol reagent was used to perform the assay.

For in vitro differentiated adipocytes, wild-type and OPN3 null cells were dark adapted overnight on Day 13 or Day 14 of differentiation and serum starved for at least 3 hours on the day of the experiment. All cells were given fresh serum-free media before stimulating one set of wild-type and OPN3 null cells with blue light, while another set of cells were left in the dark incubator. Culture media was collected at the end of 2 hours of incubation in blue light or darkness and frozen on dry ice immediately for storage at −80C until use. For the glycerol assay, a 1:10 ratio of culture media to free glycerol reagent was used to determine the amount of glycerol released during the 2 hours of darkness or blue light stimulation.

Microarray Analysis

Interscapular adipose tissue complex and inguinal white adipose tissue from P16 mice were harvested at one hour after lights on (ZT1) and snap frozen on dry ice. Tissue pieces were homogenized in TRIzol (TriReagent Invitrogen) using RNase-free Zirconium oxide beads (2.0 mm) in a TissueLyser II (QIAGEN). Phase separation was achieved using chloroform and RNA in the aqueous phase was precipitated using ethanol. RNA was purified by column method using GeneJET RNA purification kit (ThermoFisher Scientific #K0732) and eluted into RNase-free water. RNA quality was assessed using the Agilent 2100 Bioanalyzer and an RNA-integrity number cut-off of 7 was applied for selecting samples for microarray assay. RNA from biological triplicates were submitted for microarray assay (ClariomD, Affymetrix) to the Technology Center for Genomics and Bioinformatics, University of California, Los Angeles.

Data analysis including normalization, gene expression changes and gene-enrichment analysis was performed using AltAnalyze, developed by Nathan Salomonis at Cincinnati Children's Hospital Medical Center. AltAnalyze uses the robust multi-array average method of normalization. Briefly, the raw intensity values are background corrected, log 2 transformed and then quantile normalized. Next, a linear model is fit to the normalized data to obtain an expression measure for each probe set on each array. Gene expression changes greater than 1.1 fold were calculated using unpaired t test, where a p value <0.05 was used as a cut-off.

Quantitative RT-PCR

Intrascapular adipose depots were harvested immediately following cold challenge assays. Snap frozen tissue was homogenized and processed for RNA as described above. RNA was treated with RNase-free DNase I (ThermoFisher Scientific #EN0521) and cDNA was synthesized using a Verso cDNA synthesis kit (ThermoFisher Scientific AB1453/B). Quantitative RT-PCR was performed with Radiant SYBR Green Lo-ROX qPCR mix (Alkali Scientific Inc.) in a ThermoFisher QuantStudio 6 Flex Real-Time PCR system. Primer information for quantitative PCR is included in the Table. Relative expression was calculated by the ΔΔCT method using Tbp (TATA binding protein) as the normalizing gene. Statistical significance was calculated by an unpaired t test, using a p value cutoff of <0.05.

The primers used for the corresponding target gene are as follows:

| Target | Forward primer | Reverse primer |
|---|---|---|
| Dio2 | CAGTGTGGTGCACGTCTCCAA TC | TGAACCAAAGTTGACCACC AG |
| Prdm16 | CAGCACGGTGAAGCCATTC | GCGTGCATCCGCTTGTG |
| Pgc1a | CCCTGCCATTGTTAAGACC | TGCTGCTGTTCCTGTTTTC |
| Cidea | TGCTCTTCTGTATCGCCCAGT | GCCGTGTTAAGGAATCTGCT G |
| Ucp-1 | ACTGCCACACCTCCAGTCATT | CTTTGCCTCACTCAGGATTG G |
| Pparg | GTGCCAGTTTCGATCCGTAGA | GGCCAGCATCGTGTAGATG A |

-continued

| Target | Forward primer | Reverse primer |
|---|---|---|
| Hprt1 | TCAGTCAACGGGGGACATAA A | GGGGCTGTACTGCTTAACC AG |
| Tbp | GAAGCTGCGGTACAATTCCAG | CCCCTTGTACCCTTCACCAA T |

Transmission Electron Microscopy

Freshly dissected adipose tissues from P28 male mice were collected and 1 mm samples from approximately similar areas were fixed in 2% glutaraldehyde, 1% paraformaldehyde in PBS for 1 hour at room temperature before processing and sectioning for transmission electron microscopy as described before.

NAD/NADH Quantification

NAD levels were measured using NAD/NADH assay kit from Abcam (ab65348). Briefly, tissues samples (inguinal adipose tissue and liver) from P16 mouse pups were snap frozen in liquid nitrogen, homogenized in NADH/NAD extraction buffer and filtered through a 10 kD spin column (ab93349) to remove enzymes. Assay procedure was followed per kit instructions and levels of NADH and NAD+ were determined normalized to tissue weight.

Thermoregulation Assay

Core body temperature assessment upon acute cold exposure was performed on control and experimental male and female mice with the OPN3 reporter null (OPN3+/+ and OPN3lacz/lacz), with the exon 2 deletion on the C57BL/6J background (OPN3ΔEx2), with panadipocyte conditional deletion of OPN3 (OPN3fl/fl and Adipoq-cre; OPN3fl/fl), with brown adipocyte conditional deletion of OPN3 (OPN3fl/fl and Ucp1cre; OPN3fl/fl), with retinal conditional deletion of OPN3 (OPN3fl/fl and Rx-cre; OPN3fl/fl), and control and OPN4 null mice. In addition, C57BL/6J mice reared under wavelength restriction (with or without blue, as described previously) were subject to this assay. Littermates were separated from their home cage and individually housed in a home-built lighting chamber situated in an electronically monitored 4° C. cold room for 3 or 5 hours depending on the assay. While the mouse was conscious, body temperature was measured rectally with a RET-3 Microprobe Thermometer (Kent Scientific) every 20 minutes for the duration of the assay. Food and water were available ad libitum for all mice except when Adipoq-cre; OPN3fl/fl mice were fasted overnight, where food withdrawal was maintained during the cold assay. The thermo probe operator was blinded to mouse genotype and prior temperature measurements throughout the study. At the end of the cold exposure, mice were euthanized and relevant tissues were collected. The 3-hour cold exposure assays subjected mice to either a red (630 nm) and violet (380 nm) LED illumination combination (RV), or a red (630 nm), blue (480 nm) and violet (380 nm) LED combination (RBV). For the 5-hour cold exposure assays, the entirety of the 3-hour assay was extended by 2 hours following withdrawal of the 480 nm wavelength LED illumination. Two different ages of animals, postnatal day 21 (P21) and 2 month-old adults, were selected for these cold exposure assays. The order of cage placement was randomized at this time, such that the thermo probe operator remained blinded. For all cold exposure assays involving fed or overnight fasted Adipoqcre; OPN3fl/fl animals, intrascapular (iAT), inguinal (inWAT), and perigonadal (pgWAT) adipose tissues were harvested. Following animal euthanasia, the fat pads were manually dissected, and their weight recorded. For fat depots with left and right pads, both were harvested and weighed, and the average recorded per animal.

Indirect Calorimetry and Energy Expenditure 12-16-week-old OPN3+/+ and OPN3lacz/lacz male mice were acclimated in metabolic chambers (PhenoMaster®, TSE Systems GmbH, Germany) for 3 days before the start of the study. Mice were continuously recorded for a total of 17 days with the following measurements taken every 15 minutes: gas exchange (O2 and CO2), food intake, water intake, and spontaneous locomotor activity (in the XY plane). Ambient temperature was adjusted via climate-controlled chambers that housed the metabolic chambers. VO2, VCO2, and energy expenditure (EE) were calculated according to the manufacturer's guidelines (PhenoMaster® Software, TSE Systems GmbH, Germany), with EE estimated via the abbreviated Weir formula. The respiratory exchange ratio (RER) was calculated by the ratio VCO2/VO2. Where appropriate, values were normalized by body weight (mL/hr/kg for VO2 and VCO2, and kcal/hr/kg for EE). Food and water intake were measured by top-fixed load cell sensors, from which food and water containers were suspended into the sealed cage environment. For food consumption, mice demonstrating excessive food grinding behavior were excluded from statistical analyses. After 9 days of continuous recording, cages were replaced with fresh ones and sealed, and gas exchange re-equilibration completed all within 2 hours.

Tail Infrared Thermography (FLIR)

Adult OPN3fl/fl and Adipoq-cre; OPN3fl/fl animals were placed in a tubular mouse restraint (Kent Scientific, Torrington, Conn.). These restraints permitted respiration via a slotted nose cone but immobilized the animal while exposing the tail through a rear port. IR thermographic images were taken with a FLIR T530 infrared camera (FLIR® Systems, Wilsonville, Oreg.). Tail temperatures were quantified by describing a pixel-averaged circular region of interest of consistent size and rostrocaudal distance from the base of the tail.

Quantification and Statistical Analysis

Statistical analyses were performed using GraphPad Prism version 4.00 (GraphPad Software), Microsoft Excel and MATLAB 2018a (FIG. 6). Two-tailed distribution, two-sample unequal variance t-test was used to determine the statistical significance between two independent groups. Time series datasets between two groups (FIGS. 4, 5, and 6) were analyzed via one-way repeated-measures ANOVA. Datasets involving two or more factors (FIGS. 6G-6I) were analyzed by 2-way ANOVAs with Holm-Šdák corrected multiple comparisons.

Data and Code Availability

Whole-genome expression profiles are available at accession number GEO: GSE140757.

Neuropsin (OPN5) Mediates Local Light-Dependent Induction of Circadian Clock Genes and Circadian Photoentrainment in Exposed Murine Skin Highlights. According to some embodiments, OPN5 may be expressed in murine melanocytes in outer ear and vibrissal pad skin.

According to some embodiments, OPN5 may be necessary for ex vivo photoentrainment of circadian clocks in murine skin According to some embodiments, OPN5 may be necessary for normal light-mediated expression of clock genes in vivo According to some embodiments, dermal circadian clocks in blind mice may photoentrain in vivo In Brief. The main circadian clock within the mammalian brain is thought to dictate the phase of peripheral clocks. According to some embodiments, it is demonstrated that circadian clocks within exposed regions of a mouse's skin can respond directly to environmental light cues.

Summary

Nearly all mammalian tissues have functional, autonomous circadian clocks, which free-run with non-24 h periods and must be synchronized (entrained) to the 24 h day. This entrainment mechanism is thought to be hierarchical, with photic input to the retina entraining the master circadian clock in the suprachiasmatic nuclei (SCN) and the SCN in turn synchronizing peripheral tissues via endocrine mechanisms. Here, the function of a population of melanocyte precursor cells in hair and vibrissal follicles that express the photopigment neuropsin (OPN5) was assessed. Organotypic cultures of murine outer ear and vibrissal skin entrain to a light-dark cycle ex vivo, requiring cis-retinal chromophore and OPN5 gene function. Short-wavelength light strongly phase shifts skin circadian rhythms ex vivo via an OPN5-dependent mechanism. In vivo, the normal amplitude of Period mRNA expression in outer ear skin is dependent on both the light-dark cycle and OPN5 function. In $OPN4^{-/-}$; $Pde6b^{rd1/rd1}$ mice that cannot behaviorally entrain to light-dark cycles, the phase of skin-clock gene expression remains synchronized to the light-dark cycle, even as other peripheral clocks remain phase-locked to the free-running behavioral rhythm. Taken together, these results demonstrate the presence of a direct photic circadian entrainment pathway and direct light-response elements for clock genes in murine skin, similar to pathways previously described for invertebrates and certain non-mammalian vertebrates.

Introduction

Peripheral tissues of mammals can maintain circadian rhythms of gene expression for months when cultured in vitro, but synchronization of these peripheral clocks to each other and to the 24 h light-dark (LD) cycle in vivo is thought to be mediated through signals emanating from the SCN. An alternate mechanism, whereby the light cycle directly entrains peripheral oscillators through local photopigments, is utilized by invertebrates such as *Drosophila* and non-mammalian vertebrates such as zebrafish. To date, however, direct light entrainment of non-ocular tissues in mammals has not been demonstrated.

Expression of opsin family members in skin has been reported in several organisms including mammals. The functions of these opsins are still being determined and may be diverse. Light exposure causes chromatophore expansion in *Xenopus* dermal melanocytes, and this is mediated by melanopsin (OPN4). Similarly, opsin-mediated photoreception is thought to cause chromatophore expansion in octopus skin. Short-wavelength light has been shown to induce a local, delayed electrical response from the skin of the outer ear in mammals, although the photoreceptor responsible for this effect is unknown.

Neuropsin (OPN5) is an opsin family member known to function as a photopigment responsive to wavelengths in the near UV (λ max=380 nm). OPN5 is expressed in paraventricular organ neurons in birds, where it is suggested to mediate photoreception relating to seasonality. In mammals, OPN5 is required for photoentrainment of the local circadian oscillator in the murine retina and cornea. OPN5 expression has been found in the outer ear skin of mice, but its function in this tissue is unknown. According to some embodiments, short-wavelength light can directly photoentrain circadian rhythms in murine skin and can induce clock gene expression both in vitro and in vivo through an OPN5-dependent mechanism, suggesting that mammals may utilize local photic cues in peripheral tissue for circadian entrainment.

Results

Localization of OPN5-Expressing Cells in Dermal Melanocytes

Figure 15A:
FIG. 15 illustrates, according to some embodiments, OPN5 is expressed in lef1 positive hair follicle stem cells.
Figure 15B:
Figure 15C:
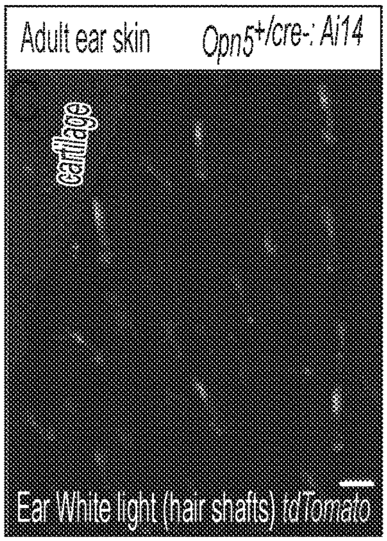
Figure 15D:
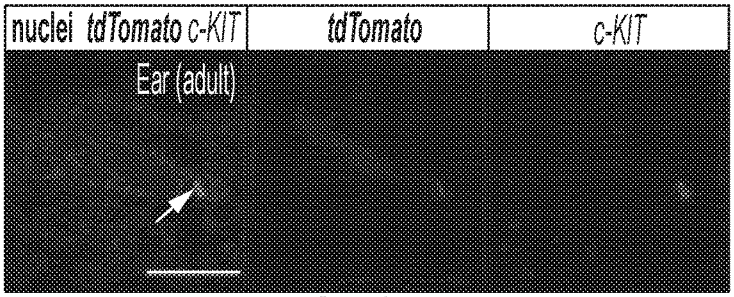
Figure 15E:
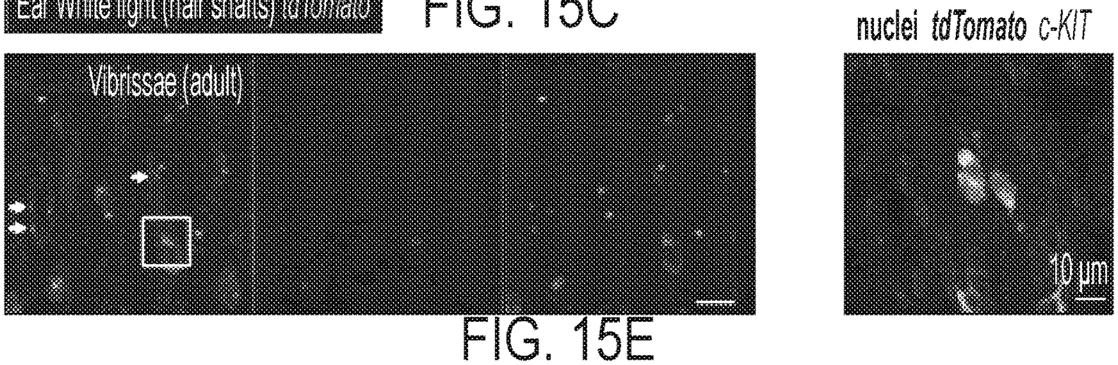
Figure 15F:
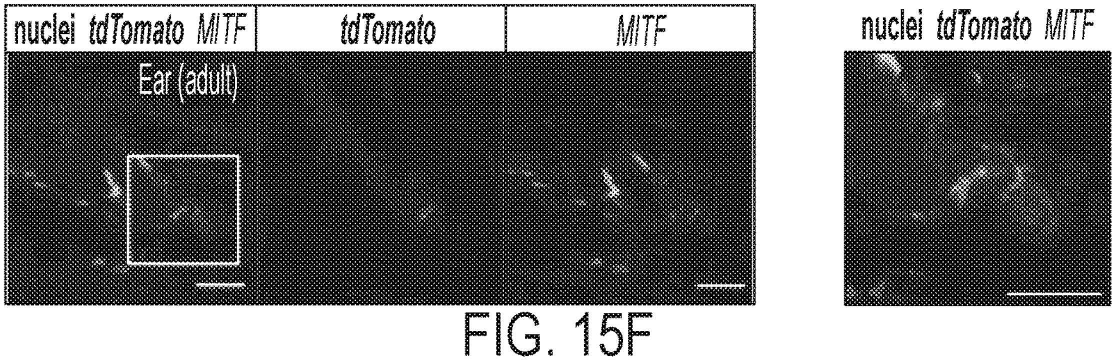
Figure 15G:
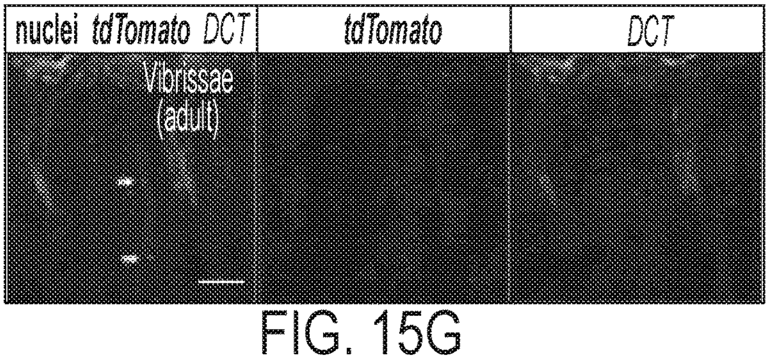
Figure 15H:
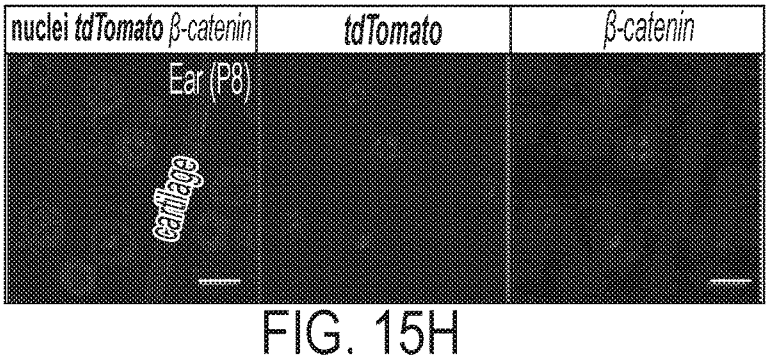
Figure 15I:
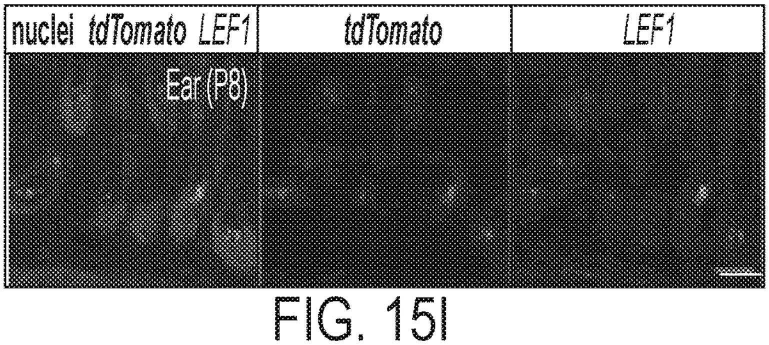
Figure 15J:
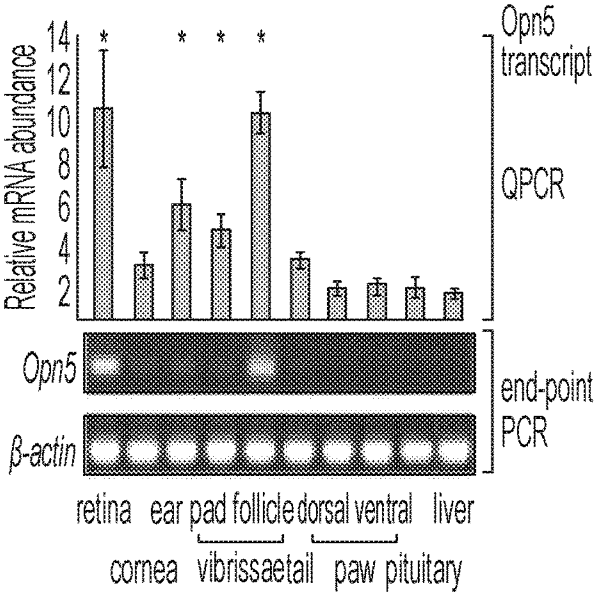
Figure 15K:
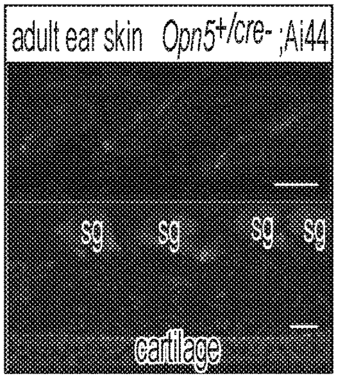

To analyze the expression of OPN5 in skin, a Cre-recombinase knock-in allele of OPN5 was utilized, crossed to the tdTomato-expressing Ai14 reporter (as no validated anti-OPN5 antibody has been reported to date, and published antibodies show non-specific staining in knockout strains). According to some embodiments, histologic analysis of ear (pinna) and vibrissal pad skin from P8 mice revealed reporter expression in two populations of cells: a diffusely distributed, minor population under the epidermis (FIG. 15B, dashed line) and a more-numerous population in the base of hair follicles (FIGS. 15A-15C). These clusters of OPN5-expressing cells co-labeled for c-KIT, MITF, DCT (TRP-2), β-catenin, and LEF1 (FIGS. 15D-15I). These represent markers for melanocyte progenitor cells within the hair bulb. However, it should be noted that $OPN5^{-/-}$ mice do not exhibit overt hyperpigmentation or albinism. In adult mice, a PCR-based survey confirmed OPN5 expression in retina, ear pinna, and nose skin vibrissae (FIG. 15J). OPN5 transcript was observed neither in the ventral or dorsal skin of the forepaw nor in pituitary or liver. Assessment of skin from adult ear pinnae from $OPN5^{cre}$; Ai14 mice showed an expression pattern like that observed in P8 mice with positive cells within the hair follicle base (FIG. 15K). These data indicate that the predominant population of OPN5-expressing cells in pinna and vibrissal pad resides within the hair and vibrissal follicles.

The level of transcription of other opsins was also analyzed in various regions of adult mouse skin. OPN5 expression was observed in skin of the dorsal back and tail in addition to the ear pinnae and vibrissae. OPN2 (rhodopsin) was also detected in the vibrissal pad and dorsal skin. OPN4, OPN3, and OPN1sw were not detected at levels above baseline (liver) in any skin area. OPN3 was qualitatively observed in in most tissues as assayed by presence of correct amplicon size using gel electrophoresis.

Ex Vivo Photoentrainment of Skin Circadian Clocks

Figures 16A, 16B, 16C, 16D, 16E, 16F, 16G, 16H, 16I, 16J:
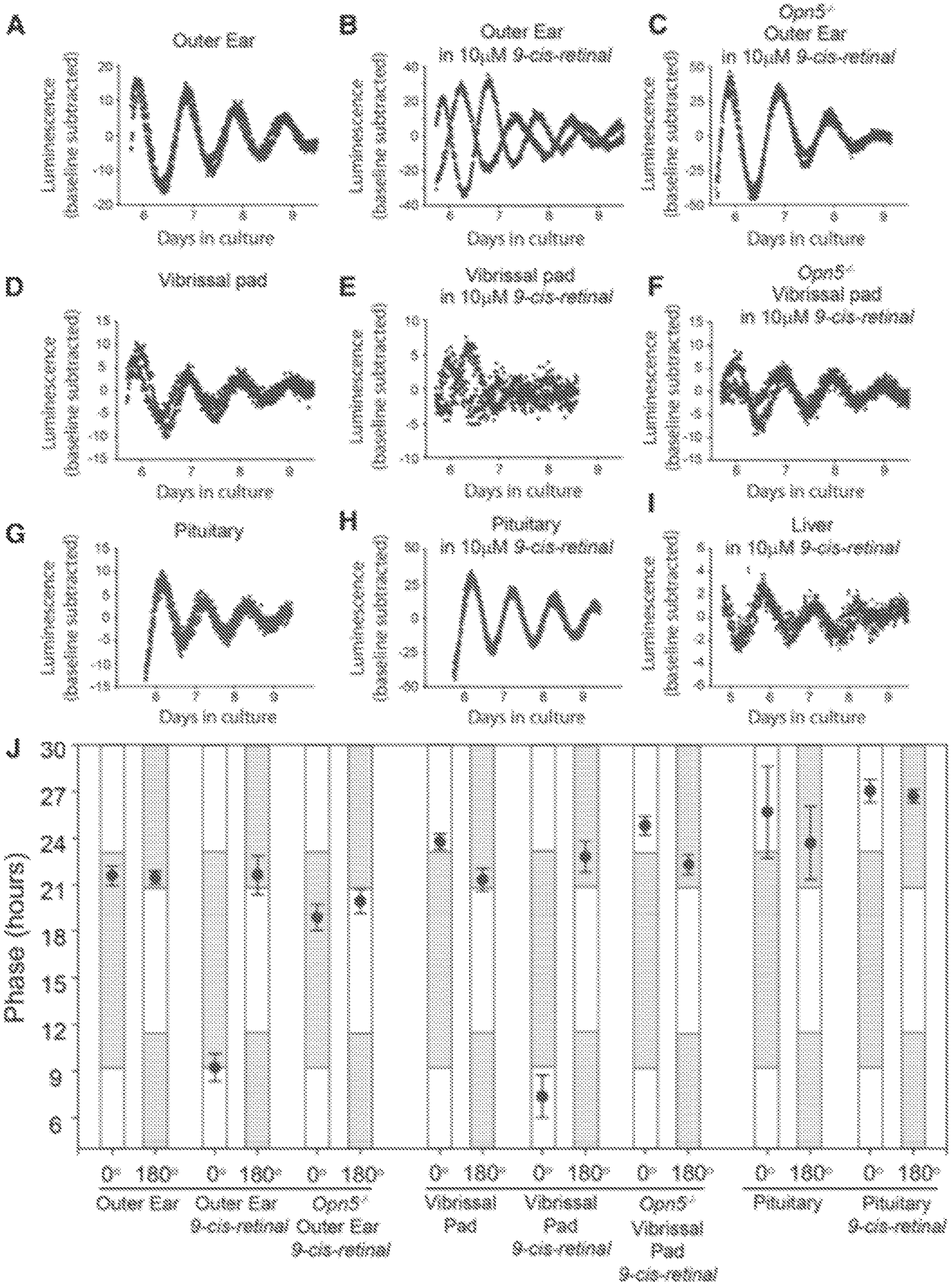
FIG. 16 illustrates, according to some embodiments, cultures of outer ear and vibrissal pad exhibit OPN5-mediated photoentrainment.

The absence of photoentrainment has been previously reported in cultured pinna tissue from $Per2^{Luc}$ mice. This could indicate a lack of sufficiency for OPN5 in photoentrainment of ear skin. However, previous studies were performed in the absence of exogenous chromophore, which may be required for production of functional photopigment. Exogenous retinaldehyde is necessary to elicit light responses in tissue culture experiments using *Xenopus* melanocytes as well as mammalian cells transfected with human OPN5 or OPN4. Thus, ex vivo photoentrainment of outer ear cultures supplemented with exogenous 9-cis-retinaldehyde or all-trans-retinaldehyde was attempted. Dissected outer ears (pinnae) of $Per2^{Luc}$ mice were bisected along the cartilage and each pinna half was cultured separately. The two cultures were then exposed to oppositely phased (referred to as 0° and 180°) 10 h light: 14 h dark cycles for 5 full cycles with or without 10 μM 9-cis-retinal. The tissues were then maintained in constant darkness to determine the circadian phase of the $Per2^{Luc}$ reporter. Without exogenous retinaldehyde, pinna cultures failed to photoentrain (FIG. 16A). However, in the presence of 9-cis-retinal, pinna cultures adopted antiphase $Per2^{Luc}$ luminescence rhythms (FIGS. 16B and 16J). An assessment of photoentrainment in the vibrissal pad (3 vibrissal follicles including surrounding fat, dermis, and epidermis) similarly showed the 0° and 180° cultures adopting antiphase $Per2^{Luc}$ rhythms but only in the presence of 9-cis-retinal (FIG. 16D, E, J). When incubated in the presence of all-trans-retinal, ear pinna cultures did not exhibit photoentrainment. This is perhaps due to an inability of mammalian OPN5 to bind to retinaldehyde in its all-trans state. These data indicate that skin of the pinna and vibrissal pad photoentrain their circadian clocks ex vivo.

To determine whether OPN5 was required for ex vivo photoentrainment in pinnae and vibrissae, tissues from $OPN5^{-/-}$ mice were tested under identical conditions to the wild-type experiments. Neither cultures of pinnae nor vibrissal pads of $OPN5^{-/-}$ mice displayed photoentrainment ex vivo, even in the presence of 9-cis-retinal (FIG. 16C, F, J). Wild-type tissues in which OPN5 was undetectable by RT-PCR, including the pituitary and liver, were not photoentrainable ex vivo either with or without 9-cis-retinal (FIG. 16G, H, I, J). Thus, the dermal tissues of the outer ear and macrovibrissal pad contain photoentrainable circadian clocks that require OPN5 and retinaldehyde chromophore, suggesting that this opsin is functioning as a photopigment in these tissues.

Figures 17A, 17B, 17C, 17D, 17E, 17F, 17G, 17H, 17I, 17J:
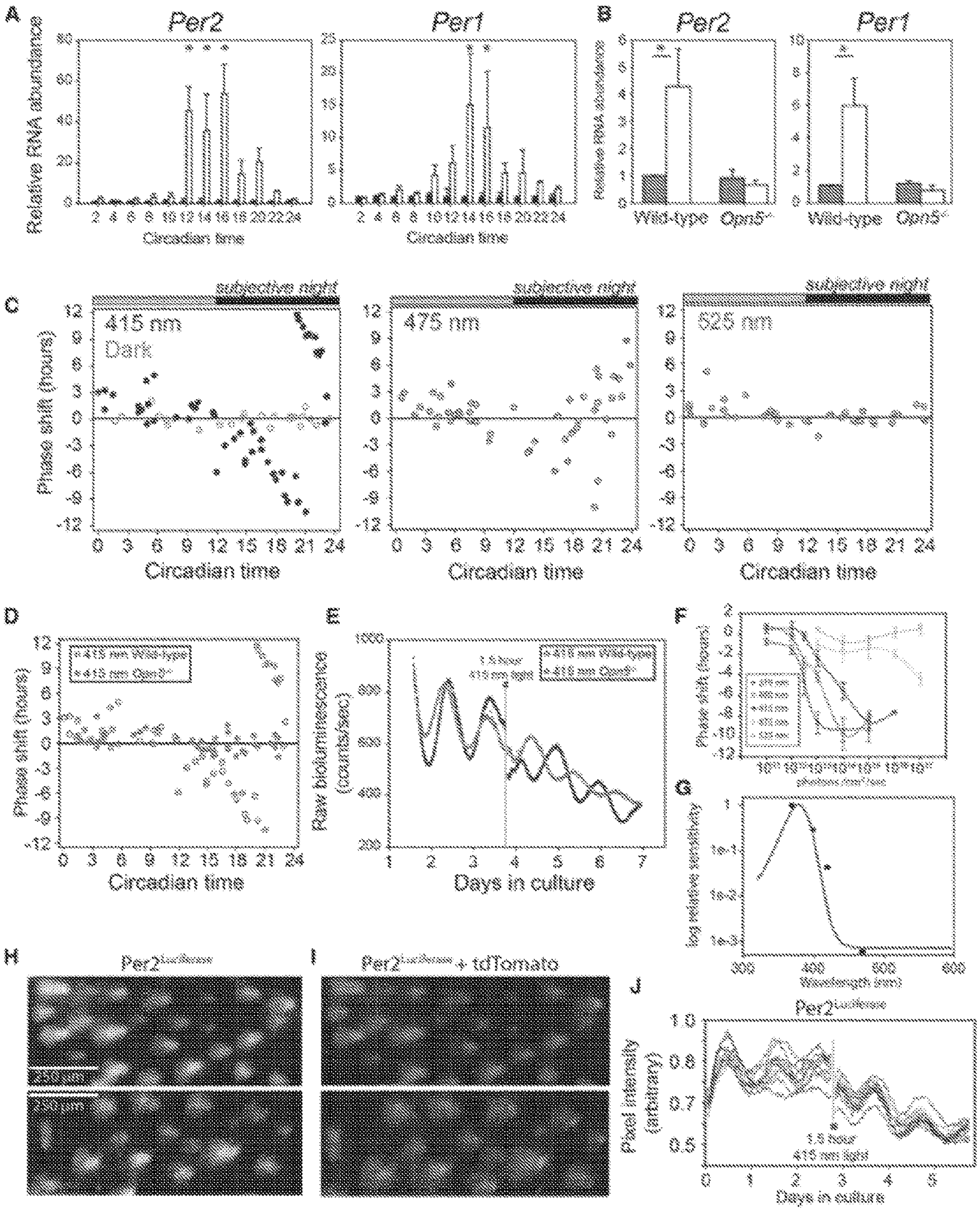
FIG. 17 illustrates, according to some embodiments, induction of per genes and phase shifts from acute light exposure.

When vertebrate circadian systems undergo a phase shift, a common feature is the photic induction of genes of the Per family. In mammals, acute light causes a phase-dependent induction of Per1 and Per2 in the SCN. To further evaluate the direct effect of light on the circadian clock in mouse skin, light induction of Per genes in pinnae ex vivo was measured. Tissues from $Per2^{Luc}$ mice were held in darkness for at least 36 h before exposure to a 90 min light pulse from a violet light-emitting diode (peak λ=415 nm, $2\times10^{14}$ photons $cm^{-2}$ $s^{-1}$) at times across a circadian cycle based on the phase of $Per2^{Luc}$ luminescence. Both Per2 and Per1 mRNA were strongly induced by the violet light, and the response was gated by the phase of the circadian clock (FIG. 17A). Similar to SCN clock phase-dependent behavioral responses to light, we observed a "dead zone" during the times of day when the tissue would have been in the light phase of an LD cycle (subjective day), during which the bright violet light elicited no response of the Per genes. However, at times nearing the light-to-dark transition (dusk) and into the subjective night, both Per genes responded robustly to light (FIG. 17A). In vivo, violet light administered to mice at circadian time (CT) 13 elicited strong induction of Per1 and Per2 transcripts, which was abrogated in $OPN5^{-/-}$ mice (FIG. 17B). These results suggest photic induction of Per1 and Per2 in skin is gated by the circadian clock and that OPN5 is serving as photoreceptor for this induction.

Light-induced phase shifts of $Per2^{Luc}$ luminescence rhythms in cultured pinnae displayed a similar pattern of sensitivity during the subjective night, with a 'Type 0' strong resetting waveform (FIG. 17C). To ascertain the spectral sensitivity of the phase shifting effect we used light pulses of equal photon flux ($2\times10^{14}$ photons $cm^{-2}$ $s^{-1}$) of 475-nm (blue) and 525-nm (green) light. A similar phase-dependent response, but of reduced magnitude was observed for 475-nm light, while there was no observable photic response during the subjective night to 525-nm light (FIG. 17C). Violet light pulses (415 nm) as given in FIG. 17C were not sufficient to elicit phase shifts from cultured pinnae from $OPN5^{-/-}$ mice at any phase of the circadian cycle (FIGS. 17D and 17E). According to some embodiments, OPN5 is required for chromophore-dependent photoentrainment of ear skin ex vivo, and for circadian-gated light induction of Per mRNA. While the spectral sensitivity peak of mammalian OPN5 in in the UVA range, we used 415-nm light in the majority of these ex vivo experiments to avoid long term exposure of cell culture media and cultured to UV light. To better test the spectral tuning of the photic phase-shifting response, phase delaying light pulses (CT 17-19) were administered using 5 wavelengths from 370 nm to 525 nm over a 10,000-fold intensity range for each wavelength (FIG. 17F). According to some embodiments, the strongest phase setting effects were observed with 370 nm near-UV with a monotonic decrease in efficacy with increasing wavelength. Analysis of the relative potency of light of different wavelengths results in an action spectrum for circadian phase shifting that is coincident with the reported absorption spectrum for OPN5 (FIG. 17G), these data strongly suggest that OPN5 is acting as the primary photoreceptor for circadian entrainment in skin. Importantly, significant phase shifting activity was not seen with light of 475 nm or 525 nm, a wavelength range encompassing maximally sensitivity for melanopsin (OPN4) and rhodopsin (OPN2).

When luminescence from $Per2^{Luc}$ ear cultures was imaged using a cooled charged-coupled device (CCID) camera, areas of strong luminescence appeared around the areas of hair follicles (FIG. 17H). The bioluminescence from hair follicles was spatially associated with groups of Ai14-expressing cells in $OPN5^{cre}$; Ai14 tissue (FIG. 17I). When imaged continuously for days, the follicles showed robust circadian oscillations, confirming previous reports of strong circadian activity within hair follicles. When measured as independent regions of interest from time-lapse images of a cultured ear, the luminescence rhythms of individual hair follicles within a single tissue drift in phase over days in culture but are returned to a common phase by a 90 min, 415-nm light pulse (FIG. 17J). According to some embodiments, this suggests that local entrainment of the circadian clock through OPN5 mediates coordination of circadian phase via daily resetting.

In Vivo Effects of OPN5 Loss on Skin Circadian Clocks

Figures 18A, 18N:
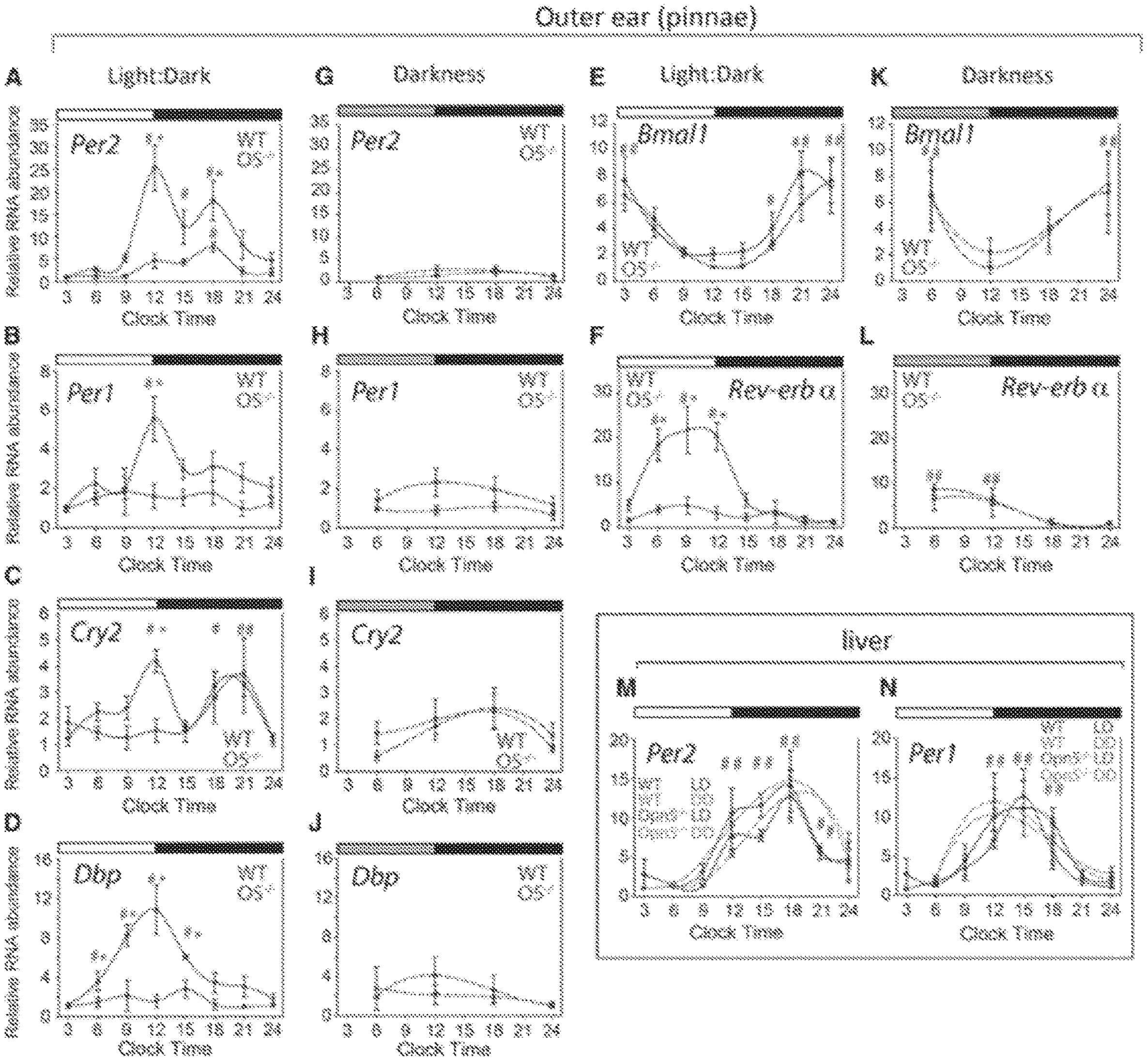
FIG. 18 illustrates, according to some embodiments, expression of clock genes in wild-type and OPN5–/– outer ear.

To determine the extent to which this photoreceptive system functions in vivo, clock gene expression was assessed by qPCR in pinnae over a 24 h time-course of a 12:12 LD cycle or after 36 h of constant darkness (DD). In wild-type pinnae in LD, Per1 and Per2 showed robust mRNA expression amplitude (FIGS. 18A and 18B, blue lines). By contrast, $OPN5^{-/-}$ animals in the same LD cycles did not show the same amplitude of clock gene expression. In particular, a large induction of transcript was observed at around clock time 12 in wild-type mice (or dusk) for Per2, Per1, Cry2, and Dbp, but this induction was absent in $OPN5^{-/-}$ ear skin (FIGS. 18A-18D). A similar pattern was observed for Rev-erba but with a prolonged high-amplitude expression through the light phase (FIGS. 18F and 18L). In constant darkness (DD), the skin of wild-type animals showed reduced amplitudes of the same genes that showed the strong amplitude of expression in LD and were not statistically different from $OPN5^{-/-}$ tissue (FIGS. 18G-18J and 18L). Interestingly, the expression of the core clock gene Bmal1 was unchanged by lighting conditions or genotype (FIGS. 18E and 18K). This suggests that the light-induced amplitude enhancement is acting over an already active circadian clock and is not necessary for the function of the core clock itself. Additionally, a noticeable "hump" of expression occurs in Per2 and Cry2 in mid to late night in $OPN5^{-/-}$ skin, indicating the presence of systemic light cues, in addition to the OPN5-driven light sensitivity in the early night (FIGS. 18A and 18C). An examination of the expression of Per1 and Per2 in the liver (FIGS. 18M and 18N) shows that the anticipated expression is unchanged in OPN5 null mice in both LD and DD conditions. According to some embodiments, this suggests that the action of OPN5 in regulating the amplitude of clock gene expression in ear skin is local to the skin and is not a result of decreased central entrainment. According to some embodiments, photic modulation of Per gene expression is suggested as a fundamental mechanism for photic entrainment of the SCN clock by the retina. These results reveal a similar strong diurnal induction of clock-related genes in areas of exposed skin.

Photic Entrainment of Skin Clocks In Vivo

The currently accepted model for peripheral circadian oscillator entrainment in mammals posits that entrainment cues for peripheral tissues emanate from the photoentrained SCN. According to some embodiments, the behavior of some peripheral circadian clocks may not be consistent with this model, as they are able to synchronize in the absence of a functional SCN. This leaves open the possibility that peripheral opsin expression could substitute for the SCN in providing photoentrainment cues in vivo. To assess the relative contributions of central (SCN dependent) and local phase control of the skin circadian clock, mice lacking photic input to the SCN but with intact OPN5 function in skin were utilized. Mice that are null for melanopsin ($OPN4^{-/-}$) and have rod and cone degeneration ($Pde6b^{rd1/rd1}$) do not deliver photic entrainment signals to the SCN and "free run" their locomotor activity cycle through light-dark cycles. Thus, there will be days during which the activity phase of $OPN4^{-/-}$; $Pde6b^{rd1/rd1}$ mice has advanced to become exactly opposite of the LD cycle phase. According to some embodiments, this provides an opportunity to determine whether the ear skin clock is entrained independently by the light-dark cycle or oscillates in phase with the SCN.

Figures 19A, 19B, 19C, 19D, 19E:
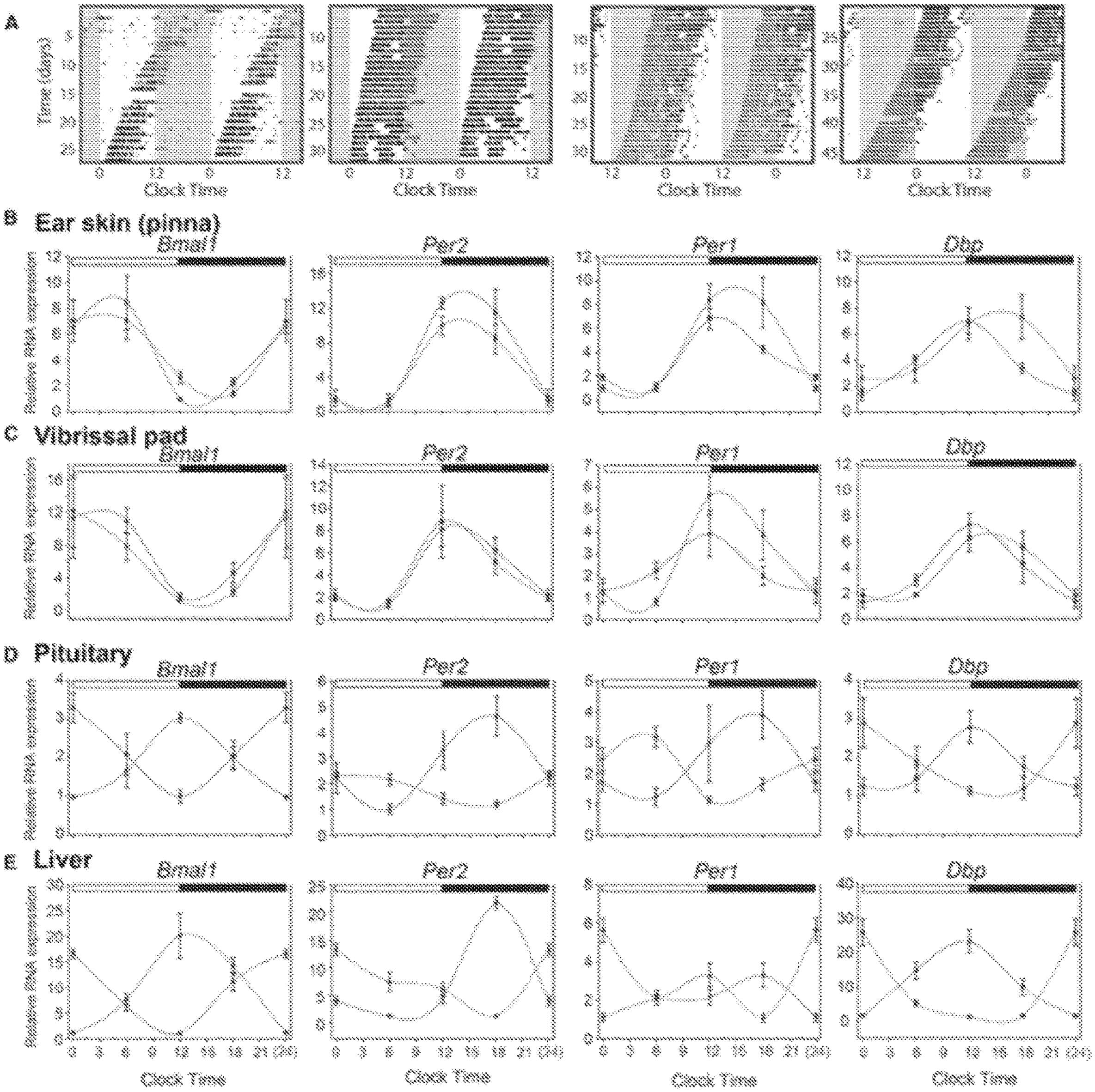
FIG. 19 illustrates, according to some embodiments, circadian transcripts in the skin are entrained to LD cycles in vivo.

After a minimum of 3 weeks' exposure to the 12 h light:12 h dark cycle, wheel running behavior of $OPN4^{-/-}$; $Pde6b^{rd1/rd1}$ mice was recorded and used as an indication of clock phase for the SCN (FIG. 19*a*). Clock gene expression rhythmicity was analyzed in two cohorts of mice. In one cohort, activity onset was coincident with lights on (diurnal-like) (FIG. 19A, red boxes), and in the other cohort, activity onset was coincident with lights off (nocturnal-like) (blue boxes). RT-PCR analysis showed that in both pinna and vibrissal pad, the phases of Bmal1, Per2, Per1, and Dbp expression were the same in both cohorts (FIGS. 19B and 19C, red and blue traces), indicating synchronization with the LD cycle. In contrast, clock gene expression in the liver and pituitary remained synchronized with behavior and SCN phase (FIGS. 19D and 19E). This strongly suggests that (1) the photoreceptors present in the skin are capable of photoentraining the local circadian clock in vivo and (2) these signals are capable of overriding signals from the central circadian pacemaker controlling behavior in the presence of an LD cycle.

The following are shown in FIG. 15, e.g., OPN5 Is Expressed in LEF1 Positive Hair Follicle Stem Cells:

(A and B) Overview images from labeled cryosections from P8 $OPN5^{+/cre}$; Ai14 mice for dorsal ear skin (A) and P8 vibrissal pad skin (B). For these and all figure panels, blue shows nuclear labeling with Hoechst 33258 and red indicates expression of the Ai14 tdTomato cre activity reporter. Clusters of tdTomato positive cells are observed in hair follicles (A and B) and in vibrissal follicle (VF) (B). A sparsely distributed population of tdTomato positive cells is observed outside the follicles and closer to the skin surface (B, dashed white line).

(C) td Tomato cell clusters (red) around bases of hair follicles in whole-mount adult ear images with white light to visualize hair shafts.

(D-I) In $OPN5^{+/cre}$; Ai14 dorsal ear skin (D, F, and H-I) and vibrissal pad skin (E and G). tdTomato positive cells are also viewed with antibodies to c-KIT (D and E), MITF (F), DCT (G), β-Catenin (H, transverse), and LEF1 (I). White arrows indicate strongly double-labeled cells or cell clusters.

(J) OPN5 transcript was detected in adult tissues using quantitative or end-point RT-PCR as labeled indicating active transcription of OPN5 at this stage of development. All transcript levels as measured by standard curve qPCR are shown relative to expression in the liver. Retina, n=5; cornea, n=5; ear, n=5; vibrissal pad, n=5; vibrissal follicles, n=4; tail, n=4; paw, n=4; pituitary, n=5; liver, n=5. Bars represent means±SEM *p<0.05, one-way ANOVA, Tukey's post hoc.

(K) Images from Hoechst 33258-labeled cryosections from adult OPN5$^{+/cre}$; Ai14 mice for dorsal ear skin. sg, sebaceous glands. Scale bars represent 50 μm unless otherwise noted.

The following are shown in FIG. 16, e.g., Cultures of Outer Ear and Vibrissal Pad Exhibit OPN5-Mediated Photoentrainment:

(A-C) Luminescence traces of cultured outer ear (pinna) from Per2$^{Luc}$ mice after 5 days of an LD cycle ex vivo from wild-type mice without (A) or with (B) 10 mM9-cis-retinaldehyde or from OPN5$^{-/-}$ mice with 10 μM 9-cis-retinaldehyde (C). Blue and red traces represent two pieces of tissue from the same animal in independent culture dishes exposed to oppositely phased light-dark cycles.

(D-F) The same as (A-C), but vibrissal pad tissue.

(G-I) Luminescence traces of pituitary (G and H) or liver (I) cultures after 5 days of an LD cycle ex vivo.

(J) Phase of the peak of Per2$^{Luc}$ luminescence on the day after 5 days of LD in either the 0° or 180° position of a photoentrainment apparatus. Points show mean±SEM White and gray bars represent times at which the tissues experienced light or dark in the previous LD cycle. n=5 pairs of cultures for each group.

The following are shown in FIG. 17, e.g., Induction of Per Genes and Phase Shifts from Acute Light Exposure:

(A) Relative RNA transcript from outer ear as measured by qPCR from wild-type organotypic tissue cultures. Tissues were cultured for 2 days and then given a 90 min 5 W/m$^2$ violet light pulse beginning at the phase shown (white bars) or left in darkness (dark bars). All transcripts are shown relative to β-actin and relative to their own dark control (dark bars) using ΔΔCt RT-PCR. All tissues were incubated in 10 UM 9-cis retinaldehyde.

(B) Per2 and Per1 induction in pinna skin of wild-type or OPN5$^{-/-}$ mice receiving a light pulse in vivo. Mice were entrained to an LD cycle and then placed in constant darkness for 2 days before receiving a 60 min violet light pulse of 2 W/m$^2$ beginning at circadian time 13.

(A and B) Two-way ANOVA p<0.05. *=p<0.05 in Tukey post hoc analysis. CT2 n=3, CT4 n=3, CT6 n=5, CT8 n=5, CT10 n=4, CT12 n=4, CT14 n=15, CT16 n 4, CT18 n=3, CT20 n=3, CT22 n=3, CT24 n=3. In vivo, n=5 for dark groups, n=7 for light groups.

(C) Phase response curves of cultured Per2$^{L}$uc mouse pinnae receiving 90 min, 2×10$^{14}$ photons cm$^{-2}$ s$^{-1}$, light pulses of 415 nm, 475 nm, or 525 nm. Handling controls performed in darkness are shown as gray circles. Pulse times are shown as the beginning of the pulse in which circadian time 12 corresponds to the peak of Per2$^{L}$uc luminescence.

(D) Phase response curve comparing wild-type (violet, same data as C, left) and OPN5$^{-/-}$ (gray) cultured pinnae.

(E) Raw Per2$^{luc}$ luminescence traces of wild-type (violet) or OPN5$^{-/-}$ (gray) pinnae receiving a 90 min 415-nm light pulse on the third day where indicated.

(F) Phase delays elicited by a 90 min light pulse of the indicated photic flux and wavelength. Points and error bars represent mean±SEM.

(G) Action spectrum of relative sensitivity of half maximum of data from (F) (black points) compared to mouse OPN5 absorbance spectrum (violet line) adapted from [16].

(H) Per2$^{Luc}$ bioluminescence from a cultured mouse pinna as viewed from the base of hair follicles.

(I) tdTomato expression (red) from OPN5$^{cre/+}$; Ai14 ear tissue overlaid with bioluminescence of Per2$^{Luc}$ ear (white from H).

(J) Quantification of individual bioluminescent hair follicles as in (H) imaged over 6 days. A 415 nm, 2×10$^{14}$ photons cm$^{-2}$ s$^{-1}$ light pulse was given for 90 min on day 2.7 where noted.

Discussion

According to some embodiments, OPN5 may be shown to be expressed in retinal neurons and to function in the eye to mediate local photoentrainment of the retina's intrinsic circadian clock. Moreover, according to some embodiments, it is shown that OPN5 is expressed extraocularly in vibrissal and ear pinna skin, and it functions locally in a photoreceptive mechanism to entrain the circadian rhythms of these tissues directly to the external light-dark cycle. Isolated skin is able to synchronize its circadian oscillations to the light-dark cycle ex vivo, likely through OPN5-dependent induction of Per gene expression. In vivo, this local mechanism allows skin rhythms to maintain synchrony with the light-dark cycle even under conditions in which the central oscillator (as represented by locomotor activity) is free running. OPN5 expression is also necessary for the full amplitude of diurnal rhythmic Per gene expression in LD cycles in vivo.

The requirement in cultured skin for exogenous cis-retinaldehyde to demonstrate photosensitivity and the coincidence of action spectrum and reported absorption spectrum for OPN5 strongly suggest that the skin photoreceptive mechanism utilizes OPN5 as a photopigment. Circadian clocks within mammalian skin control the response to UV light, as well as cell cycle progression in hair follicles and keratinocytes, and response to physical injury. According to some embodiments, it is suggested that light modulation of these clocks through OPN5 function may significantly influence these physiologies. Further, these results suggest that mammals, like fish, amphibians, and birds, utilize extraocular opsin photopigments for direct, light-dependent regulation of circadian clock function in some peripheral tissues. According to some embodiments, this challenges the widely held dogma that peripheral circadian rhythms within mammals are synchronized exclusively by the master SCN circadian pacemaker via ocular photoreception and suggests that mammals also use local light sensing in peripheral tissues for this purpose.

The expression of opsins in extra-retinal sites opens important questions about their physiology. In the retina, 11-cis-retinaldehyde is produced by the retinal pigment epithelium (RPE). However, in frog skin, bird hypothalamus, mammalian smooth muscle, and mammalian skin, opsins must receive the retinaldehyde from an alternate source. In culture systems, exogenous retinaldehyde is often required. It will be of interest to determine the source and processing machinery for the proper chromophore function in these extraocular sites. According to some embodiments, it has been demonstrated that the exposure of skin to short-wavelength light produces diverse systemic effects such as (3-endorphin and urocanic acid production. The photoreceptors for these important effects have not been identified. According to some embodiments, it is suggested that OPN5 could be a candidate photopigment in skin for mediating diverse light-dependent physiologies.

The following are shown in FIG. 18, e.g., Expression of Clock Genes in Wild-Type and OPN5$^{-/-}$ Outer Ear:

Pinnae were harvested from mice that were housed in either a 12 h:12 h LD cycle (A-F) or in constant darkness for at least 36 h (G-L). Transcript levels were determined using ΔΔCt RT-PCR. White and black boxes above charts indicate times of light or darkness in an LD cycle or the subjective LD cycle for groups in DD. Wild-type data are shown using blue symbols and data from OPN5$^{-/-}$ using red symbols. Charts (M and N) show data for liver from wild-type and OPN5$^{-/-}$, LD and DD as labeled. Each chartpoint indicates mean±SE for n=4 in each group. To assess significant differences across a time-course, we used the ANOVA with Tukey's post hoc statistical test: p<0.05 is indicated by the hash symbol (#). The same statistical test was used to assess difference between time-courses: p<0.05 between groups is indicated by an asterisk (*). n=4 mice for each point.

The following are shown in FIG. 19, e.g., Circadian Transcripts in the Skin Are Entrained to LD Cycles In Vivo:

(A) Representative actograms of wheel-running behavior in OPN4$^{-/-}$; Pde6b$^{rd1/rd1}$ mice in a 12 h light:12 h dark cycle. Actograms outlined in red show animals for which their behavioral onset coincides with lights on the last day shown. Actograms outlined in blue show mice in the opposite behavioral phase on the last day shown.

(B-E) Transcript abundance from pinnae ear skin (B), vibrissal pad (C), pituitary (D), or liver (E) collected at clock times indicated based on the LD cycle. Traces in red indicate animals collected on the day when behavioral coincided with light onset. Traces in blue were collected from animals when their behavioral onset coincided with dark onset. n=4 mice for each point. Two-way ANOVA results for (B) non-significant p=0.43-0.91; (C) non-significant p=0.16-0.70; (D) p=0.001-0.009, except Dbp p=0.16; and (E) p=0.001-0.043.

Star Methods

KEY RESOURCES TABLE

| REAGENT or RESOURCE | SOURCE | IDENTIFIER |
|---|---|---|
| | Antibodies | |
| c-KIT | Cell Signaling | CatmAb #3074; RRID:AB_1147633 |
| MITF | Abcam | Cat#ab12039; RRID:AB_298801 |
| DCT | Proteintech | Cat#13095-1-ap; RRID:AB_2090576 |
| LEF1 | Cell Signaling | Cat#2230S; RRID:AB_823558 |
| β-catenin | Santa Cruz | Cat#sc7199; RRID:AB_634603 |
| | Chemicals, Peptides, and Recombinant Proteins | |
| OCT | TissueTek | Cat#4583 |
| Donkey serum | Jackson Immuno | Cat# 017-000121 |
| Alexa Fluor 647 donkey anti mouse | Jackson Immuno | Cat#715-605-151 |
| Alexa Fluor 647 goat anti-rabbit | Jackson Immuno | Cat#111-605-003 |
| DMEM | GIBCO | Cat#90-013-PB |
| B27 Supplement | Thermo Fisher | Cat#0080085SA |
| D-Luciferin potassium salt | Biosynth | Cat#L-8220 |
| Hanks Balanced Salt Solution | Thermo Fisher | Cat#14025076 |
| 9-cis-retinaldehyde | Simga | Cat#R5754 |
| all-trans-retinaldehyde | Sigma | Cat#R2500 |
| RNAlater | QIAGEN | Cat#76104 |
| Tri reagent | Thermo Fisher | Cat#AM9738 |
| | Critical Commercial Assays | |
| High Capacity RNA to cDNA kit | Applied Biosystems | Cat#4387406 |
| Absolute Blue QPCR mix | Thermo Fisher | Cat#AB4163A |
| | Experimental Models: Organisms/Strains | |
| Period2: Luciferase, B6.129S6-Per2$^{tm1Jt}$/J | Jackson Laboratories | Stock# 006852 |
| OPN5$^{-/-}$ | [19] | N/A |
| OPN5$^{Cre}$; Ai14 | [57] | N/A |

-continued

| KEY RESOURCES TABLE | | |
|---|---|---|
| REAGENT or RESOURCE | SOURCE | IDENTIFIER |
| B6;129S6-Gt(ROSA)26Sortm14(CAG-tdTomato) | Jackson Laboratories | Stock#007908 |
| OPN4$^{-/-}$; Pde6b$^{rd1/rd1}$ | [27] | N/A |
| Oligonucleotides | | |
| | This paper | N/A |
| | This paper | N/A |
| Software and Algorithms | | |
| ClockLab | Actimetrics | https://www.actimetrics.com/products/clocklab/ |
| Lumicycle Analysis | Actimetrics | https://www.actimetrics.com/products/lumicycle/lumicycle-32/ |
| ImageJ | NIH | https://imagej.nih.gov/ij/ |
| Sigma Plot 11.0 | Systat | systatsoftware.com |
| Other | | |
| Zeiss LSM 700 confocal microscope | Zeiss | LSM 700 |
| Abi7500 Fast Real-time PCR machine | Abi | 7500 Fast |
| Quantum radiometer | Macam | Q203 |
| Lumicycle luminometer | Actimetrics | Lumicycle 32 |
| Retiga Lumo CCD camera | Q-imaging | Retiga Lumo |
| Microscope stage incubator | Bioscience tools | Cat#TC-MWPHB |
| Millicell cell culture inserts | Millipore | Cat#PICMORG50 |

Materials Availability

This study did not generate new unique reagents.

Experimental Model and Subject Details

Mice

All animal experiments were carried out according to protocols approved by the Institutional Animal Care and Use Committee at the University of Washington and Cincinnati Children's Hospital Medical Center. OPN5--mice were generated as described in [19]. OPN5Cre mice were generated in-house at CCHMC transgenic core using CRISPR-Cas9 targeting. See allele design for details. Four guide RNAs that target exon 1 of OPN5 were selected to knock in the Cre cassette. Plasmids containing the gRNA sequence were transfected into MK4 cells (an in-house mouse cell line representing induced metanephric mesenchyme undergoing epithelial conversion). The editing efficiency of gRNA was determined by T7E1 assay using PCR product-transfected MK 4 cells. The sequence of the gRNA that was subsequently used for the transfection is TGGAGTCC-TACTCGCGGACG (SEQ ID NO: 44). Sanger sequencing was performed to validate the knock-in sequence of founder mice. Primer sequences for genotyping the OPN5cre allele are: OPN5cre-inF1: TGGAAAGAGATGCATTTGTGAG (SEQ ID NO: 45), OPN5cre-inR1: ACAGCCTATGAAT-TCTCTCAATGC (SEQ ID NO: 46) and OPN5cre-inF2: CACTGCATTCTAGTTGTGGTTTGTCC (SEQ ID NO: 47). Primer pair OPN5cre-inF1/OPN5cre-inR1 detects wild type allele (300 bp) and OPN5cre-inF2/OPN5cre-inR1 detects cre allele (209 bp). Founder OPN5Cre mice were bred to B6; 129S6-Gt (ROSA) 26Sortm 14 (CAG-tdTomato) Hze/J mice (JAX stock number 007908) to generate OPN5Cre; Ai14 tdTomato animals.

For immunohistochemistry, mice at postnatal day 8 were used as neonatal mice, and mice older than 6 weeks but younger than 1 year were used as adults.

For behavioral studies, in vivo studies of gene expression, and ex vivo tissue culture, mice older than 6 weeks but younger than one year were used.

For behavioral free-running of OPN4$^{-/-}$; Pde6b$^{rd1/rd1}$ mice, mice were between 4 to 6 months old at the start of each experiment.

In all experiments care was taken to use both male and female mice. Mice were allowed access to food and water ad libitum, and were maintained in standard humidity with room temperature between 20° C. and 25° C. Mice were randomly assigned to experimental groups based on their genotypes.

Method Details

Immunohistochemistry

Animals were euthanized, and skin harvested at the indicated age. Tissues were fixed in 4% PFA at room temperature for two h followed by two 15-min washes in 1×PBS. Skin was cryoprotected in 30% sucrose solution in PBS, embedded in OCT (TissueTek) and sectioned at 16 μm. Slides were subjected to antigen retrieval in ice cold 10 mM sodium citrate with 0.05% Tween-20 for 10 min. Subsequently, sections were blocked in 10% donkey serum with 0.5% Triton in 1×PBS and stained with antibodies to c-KIT (1:250, CellSignaling #mAb3074), MITF (1:250, Abcam #ab12039), DCT (1:250, Proteintech #13095-1-ap), LEF1 (1:500, Cell Signaling #2230S), and β-catenin (1:500, Santa Cruz Biotechnology #sc-7199) overnight at 4° C. Following three 15-min washes in 1×PBS, secondary antibody (1:1000 Alexa 488 donkey anti-rabbit, 1:1000 Alexa 647 donkey anti-mouse, or 1:1000 Alexa 647 goat anti-rabbit) and Hoechst 33342 labeling was performed at room temperature for one h. Imaging was done on a Zeiss LSM 700 confocal microscope.

Ex Vivo Photoentrainment and Light-Induced Gene Expression

Animals were euthanized by C02 asphyxiation, and the skin was harvested and sterilized on the epidermal side with 70% isopropyl alcohol swabs before being placed into cold Hank's Balanced Salt Solution (HBSS, Thermo Fisher). Outer ears (pinna) were dissected along the cartilage layer by pulling apart the dermal layers on either side of the cartilage layer. Myostacial vibrissae pads were collected and 3 adjacent macrovibrissae were dissected including surrounding fat and muscle down to the base of the follicles. All skin explants were placed epidermal-side-up on cell-culture inserts (PICMORG50, Millipore). Pituitary and liver samples were placed immediately onto cell culture inserts. Cell culture media consisted of Dulbecco's Modified Eagle Medium (DMEM) supplemented with B-27 supplement (Thermo Fisher), 352.5 μg/mL $NaHCO_3$, 10 mM HEPES (Thermo Fisher), 25 units/mL penicillin; 25 μg/mL streptomycin (Thermo Fisher), 0.1 mM luciferin potassium salt (Biosynth) and 10 μM 9-cis retinaldehyde (Sigma) or 10 μM all-trans retinaldehyde (Sigma) where noted. Organotypic cultures were sealed with vacuum grease and maintained in 36° C. incubators without $CO_2$.

Light-dark cycles were administered to cultured tissue using a device which allows tissues at diametrically-opposed positions (designated 0° and 180°) to experience oppositely phased light-dark cycles as has been described previously [27]. Briefly, a motor drove a solid black disk with a pie-shaped transparent window at 24 h revolution such that each of the paired tissues was illuminated for 9 h in every 24-h cycle. Light came from LEDs with peak wavelengths at 415 nm, 475 nm, and 530 nm. A Macam Q203 quantum radiometer was used for radiometric light measurements.

After 5 days of light-dark cycles, the cultured tissues were placed in constant darkness in a Lumicycle luminometer (Actimetrics), in which bioluminescence was measured continuously. Bioluminescence data were de-trended by using a polynomial fit with an order of 1 to remove the steady decline of background bioluminescence. To measure the period of oscillations, a best-fit sine-wave was fit to the detrended data (Lumicycle Analysis). Phases were determined using at least three days of oscillations.

For acute light-induction and phase shift experiments, the phase of a cultured tissue was measured using the second peak of luminescence compared to non-light treated control tissue as a guide within the Lumicycle machine. Tissue was then transferred in a light-proof, insulated chamber (to maintain constant culture temperature) to an incubator with 415 nm light at 5 W/$m^2$ for 90 min. Tissues were then placed in ice cold RNAlater (QIAGEN) for later RNA extraction or monitored for luciferase expression rhythms. Phase delays are measured as expected minus observed $Per2^{Luciferase}$ rhythms after the light pulse, based on the phase and period of the rhythm before the light pulse. For the action spectrum, irradiance response curves for individual wavelengths were fit using a 4 parameter sigmoid curve with a Hill slope. Half-maximum values of these curves were then normalized to 1 for comparison with published absorption spectra.

For in vivo light-induction experiments, mice were entrained to a 12 h light: 12 h dark cycles for at least 3 weeks and then lights were turned off for 2 days of constant darkness. At the time corresponding to one h past the onset of darkness (CT13) of the previous light-dark cycle, mice were exposed to 415 nm light at 2 W/$m^2$ for 60 min before being euthanized by cervical dislocation and ears were dissected into cold RNAlater.

Imaging of Bioluminescence Ex Vivo

A custom darkbox was created to allow a Retiga Lumo CCD camera (Q-imaging) to image cultured tissue from beneath. Tissue was maintained at 36° C. using a microscope stage incubator (Bioscience Tools). Luminescence was collected at 30 min intervals to generate one image for a total of 48 images/day.

Analysis of In Vivo Clock Gene Transcription $OPN4^{-/-}$; $Pde6b^{rd1/rd1}$ mice were housed in cages equipped with running wheels. Wheel-running behavior was monitored continuously and recorded using ClockLab software (Actimetrics). Lights used included LEDs with peak spectral output at 415 nm ($4.2\times10^{14}$ photons $cm^{-2}s^{-1}$) and 475 nm ($7.2\times10^{14}$ photons $cm^{-2}s^{-1}$). After at least 3 weeks of exposure to the LD cycle, when behavioral onset of activity coincided with either lights-on or lights-off mice were euthanized using cervical dislocation and tissues were dissected under dim red light and stored in cold RNAlater. Animals were between 3 and 12 months of age and included both male and female mice. For analysis of clock gene expression in wild-type and $OPN5^{-/-}$ mice (FIG. 17), mice were housed in cages as described above for a least 3 weeks before either being euthanized using cervical dislocation at specific clock times or placed in constant darkness for at least 36 h before tissue collection.

RNA Extraction and RT-PCR

Total RNA was extracted from tissues using TRI-reagent (Thermo fisher) according to manufacturer's instructions, and cDNA was generated using High Capacity RNA to cDNA kit (Applied Biosystems). QPCR was performed using Absolute Blue QPCR mix (Thermo Fisher) on an Applied Biosystems 7500fast Real Time PCR machine. Relative quantities of transcripts were quantified using the 2^-ΔΔCt method comparing the transcript of interest to β actin and comparing light treated groups to the dark control tissue from the same animal.

For comparison of transcripts among tissue types in FIG. 15, standard curve RT-PCR was used to avoid complications of differential expression of endogenous control genes between tissues. An amplicon for OPN5 transcript was generated from cDNA from mouse retina and was cloned into a pCR 2.1 TOPO cloning vector (Life Technologies). Standard curves were generated using the OPN5-pCR 2.1 TOPO plasmid from $10^9$ to $10^2$ copies in a 1:100 dilution series.

Quantification and Statistical Analysis

For quantification of opsin transcript abundance in FIG. 15J, ANOVA was performed on the total dataset and a Tukey post hoc was run using Sigma Plot 11.0 software. N are reported in the figure legends. For ex vivo light induction of FIG. 17A, transcript abundance was compared to the abundance of dark samples collected from the same cohort of animals. For in vivo separate animals were used for light and dark experiments. ANOVA was performed on the total dataset and a Tukey post hoc was run using Sigma Plot 11.0 software. N are reported in the figure legend. For the action spectrum of FIG. 17F, the N are as follows: 370 nm light $10^{11}$ n=5, $10^{12}$ n=6, $3\times10^{12}$ n=5, $10^{13}$ n=5, $10^{14}$ n=7, $10^{15}$ n=5; 400 nm light $10^{11}$ n=4, $10^{12}$ n=6, $3\times10^{12}$ n=4, $10^{13}$ n=5, $10^{14}$ n=4, $10^{15}$ n=4; 415 nm light $10^{11}$ n=4, $10^{12}$ n=5, $3\times10^{12}$ n=6, $10^{13}$ n=7, $10^{14}$ n=8, $10^{15}$ n=7, $10^{16}$ n=4; 475 nm light $10^{13}$ n=4, $10^{14}$n=7, $10^{15}$n=4, $10^{16}$n=7, $10^{17}$ n=7; 525 nm light $10^{13}$ n=5, $10^{14}$n=7, $10^{15}$ n=5, $10^{16}$ n=6, $10^{17}$ n=6. Sigmoid Hill curves with 4 parameters were fit to data from individual wavelengths using Sigma Plot 11.0. For FIG. 18, ANOVA were run comparing both light conditions and genotype comparisons between WT and $OPN5^{-/-}$, and Tukey post hoc tests were used. For FIG. 19, ANOVA were run on data between groups for individual tissues and Tukey post hoc tests were performed. N for FIGS. 18 and 19 are listed in the figure legends. For all quantified data mean±SEM are shown. n represents individual animals for in vivo experiments and individual organotypic tissue cultures for ex vivo experiments.

Data and Code Availability

This paper did not generate any datasets or new code.

An Opsin 5-Dopamine Pathway Mediates Light-Dependent Vascular Development in the Eye During mouse postnatal eye development, the embryonic hyaloid vascular network regresses from the vitreous as an adaption for high-acuity vision. This process occurs with precisely controlled timing. According to some embodiments, it is shown that opsin 5 (OPN5; also known as neuropsin)-dependent retinal light responses regulate vascular development in the postnatal eye. In OPN5-null mice, hyaloid vessels regress precociously. According to some embodiments, it is demonstrated that 380-nm light stimulation via OPN5 and VGAT (the vesicular GABA/glycine transporter) in retinal ganglion cells enhances the activity of inner retinal DAT (also known as SLC6A3; a dopamine reuptake transporter) and thus suppresses vitreal dopamine. In turn, dopamine acts directly on hyaloid vascular endothelial cells to suppress the activity of vascular endothelial growth factor receptor 2 (VEGFR2) and promote hyaloid vessel regression. With OPN5 loss of function, the vitreous dopamine level is elevated and results in premature hyaloid regression. Accordingly, these investigations identify violet light as a developmental timing cue that, via an OPN5-dopamine pathway, regulates optic axis clearance in preparation for visual function.

Summary

Photons from the sun reach our planet at high flux. In response, organisms have evolved detection systems that decode light information for adaptive advantage. Examples from mammals include the visual system, where photons bouncing off an object are detected to decode object identity, and the circadian system, where the 24-h light cycle entrains time-of-day-dependent physiology. Most light detectors in metazoans are opsins, a class of G protein-coupled receptors that convert the energy of a photon into a cellular signaling response. Rhodopsin, the opsin of mammalian rod photoreceptors, is a well-characterized example of a visual opsin, whereas melanopsin (also known as opsin 4 (OPN4)) has a central role in circadian clock photoentrainment. Neuropsin (also known as OPN5) is another opsin family member. Relatively little is known about OPN5 except that it responds to violet-light wavelengths ($\lambda_{max}$ of 380 nm), regulates seasonal breeding behavior in birds and the activity cycle in mice, but also mediates photoentrainment of the retinal circadian clock. Here, OPN5 function is investigated in the development of the mouse eye and shown, according to some embodiments, that it is required for normal biological timing. In this case, OPN5 is required for a light response that regulates vascular regression timing.

Results

Figure 20A:
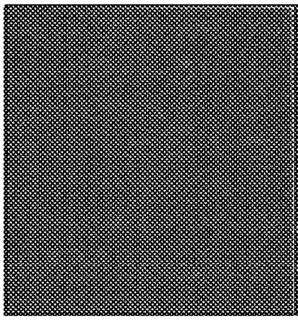
FIG. 20 illustrates, according to some embodiments, OPN5 is expressed in a distinct subset of RGCs.
Figure 20B:
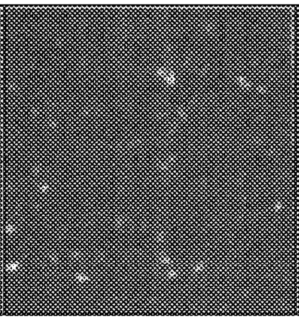
Figure 20C:
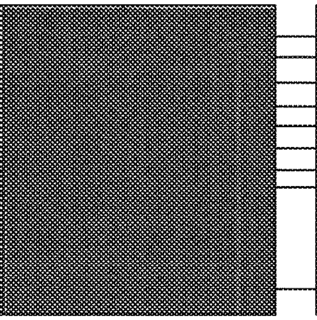
Figure 20D:
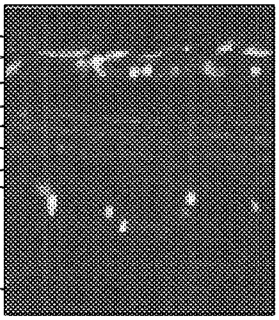

According to some embodiments, OPN5 is expressed in a retinal ganglion cell subset. OPN5 is expressed in retinal ganglion cells (RGCs) in adult mice. To further assess the features of OPN5-expressing cells, an $OPN5^{cre}$ allele was combined with Ai14, a tdTomato-expressing cre reporter. According to labelling with multiple markers, the overall architecture of the OPN5-null retina is unchanged. In P5 (5 d postnatal) retinal flat mounts, $OPN5^{cre}$; Ai14 cells were at relatively low density throughout the inner retina (FIG. 20A). In P12 calretinin-labelled cryosections, OPN5-expressing cell bodies were in the ganglion cell layer (FIG. 20C,D). At P5, Ai14-expressing processes were immature (FIG. 20A), but at P12, the processes were prominent and observed as bundles within the nerve fibre layer (NFL) and within several laminations of the inner plexiform layer (IPL; S1-S5 (the sublaminae of the IPL); FIG. 20C,D). These morphological features are consistent with the characteristics of RGCs.

Figure 20E:
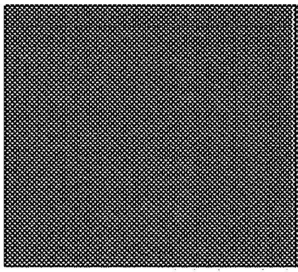
Figure 20F:
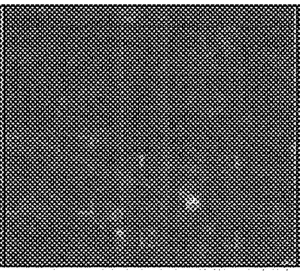
Figure 20G:
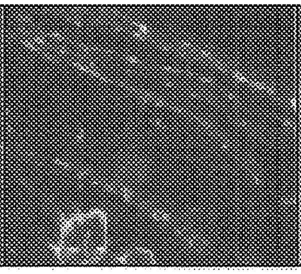
Figure 20H:
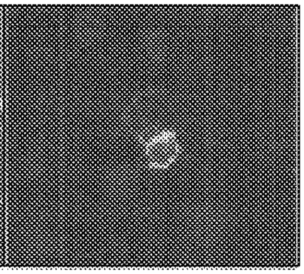
Figure 20I:
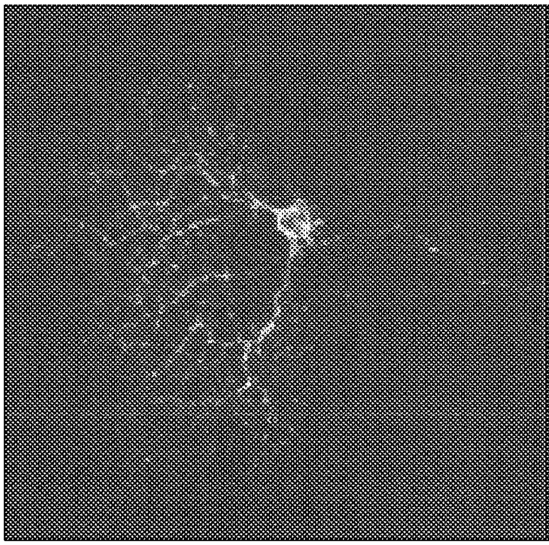
Figure 20J:
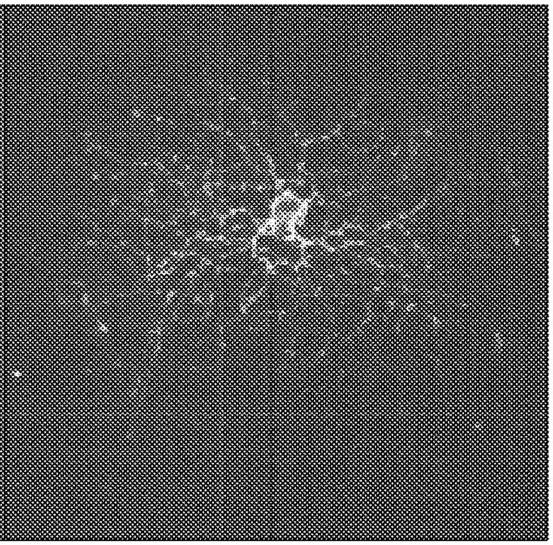

OPN4 antibody labelling in $OPN5^{cre}$; Ai14 retinae indicated that OPN4 and OPN5 are expressed in distinct RGC subsets. At P5, the density of $OPN5^{cre}$; Ai14 and OPN4-labelled cells was similar (FIG. 20B). At P12 (FIG. 20E-H), co-labelling again showed that largely, OPN4 and $OPN5^{cre}$; Ai14 cells were two distinct subsets. Prominent bundles of axons from OPN5 and OPN4 RGCs are cofasciculated (FIG. 20E-G). Rare co-labelled cells were identified (FIG. 20F,H about 50 cells per retina), but could result from cre lineage marking oversampling. At P24, $OPN5^{cre}$; $Brainbow^{20}$-labelled retinal cells (FIG. 20I,J) have the appearance of mature RGCs with extensive dendritic arbours and axons. Brain cryosections from $OPN5^{cre}$; Ai14 mice showed axons in the optic tracts, lateral geniculate nucleus and superior colliculus as might be expected for RGCs. Labelling of $OPN5^{cre}$; Ai6 retinae at P8 with the RGC marker RBPMS (RNA-binding protein with multiple splicing) and the RGC/amacrine cell marker calretinin provided evidence that OPN5 is expressed exclusively in RGCs.

The following are shown in FIG. 20, e.g., OPN5 is expressed in a distinct subset of RGCs:

Flat mount retina from P5, $OPN5^{Cre}$; Ai14 mice showing the tdTomato cre reporter (a,b), nuclear labelling with Hoechst 33258 (b), and counter labelling for OPN4 (b). c,d, Retinal cryosections from P12, $OPN5^{Cre}$; Ai14 mice showing the tdTomato cre reporter (c,d), nuclei with Hoechst 33258 (c,d) and labelling for calretinin (d). Retinal laminae are indicated by the abbreviation between the panels: GCL, ganglion cell layer; S5-S1, sublaminae of the inner plexiform layer; INL, inner nuclear layer; OPL, outer plexiform layer. e-h, As in a and b, except at P12. Magnified regions off as indicated by the white corner marks are shown (g,h). i,j, Flat mount retinae showing labelling of cell bodies (asterisks), dendritic fields and axons (arrows) for RGCs labelled by the Brainbow3.2 reporter in P24 $OPN5^{cre}$ mice. Scale bars, 20 μm. Panels a-j are representative of at least three separate experiments. Additional examples of these images are available on Figshare (https://figshare.com/articles/NCB_Additional_Images_pptx/7450961).

Figure 21A:
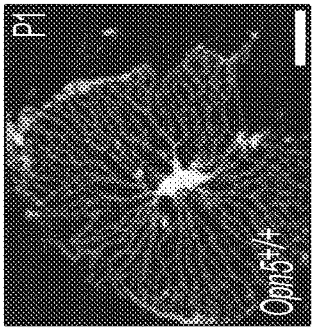
FIG. 21 illustrates, according to some embodiments, precocious hyaloid vessel regression in the OPN5-null mice and absence of 380-nm photons.
Figure 21B:
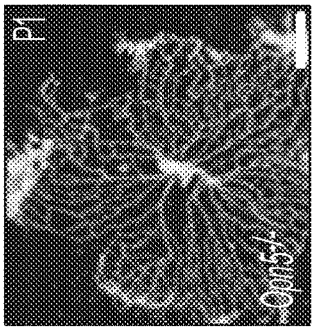
Figure 21C:
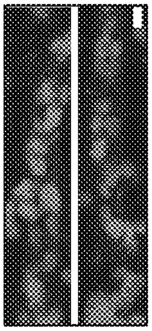
Figure 21D:
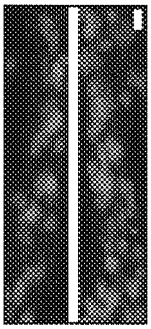
Figure 21E:
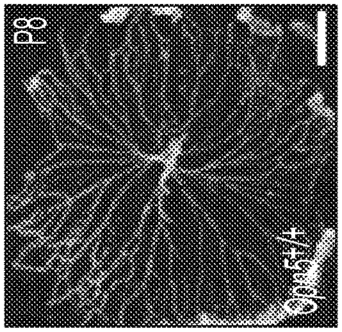
Figure 21F:
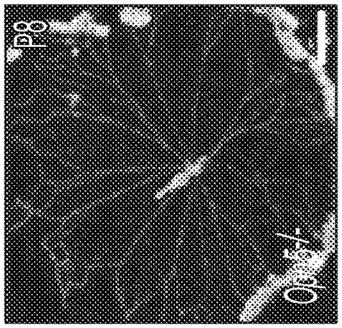
Figure 21G:
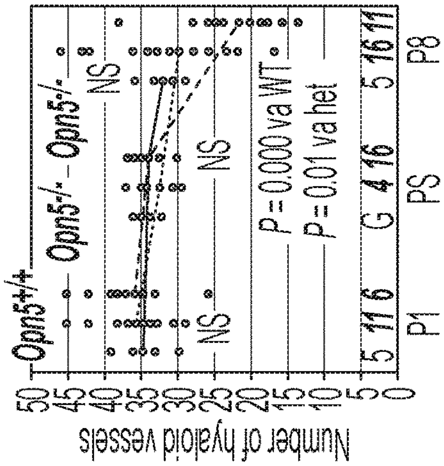
Figure 21H:
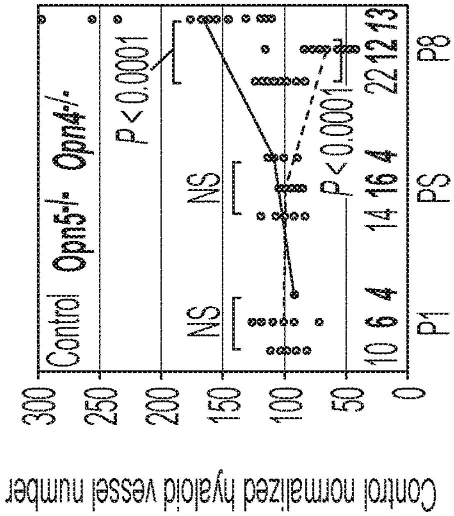
Figure 21I:
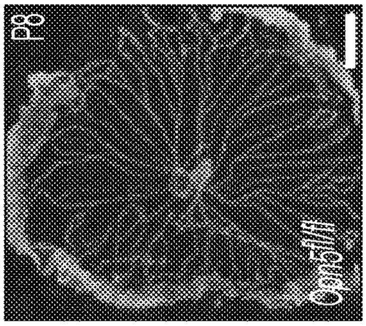
Figure 21J:
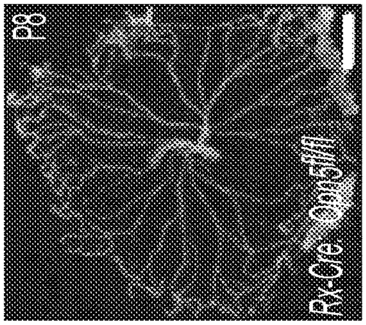
Figure 21K:
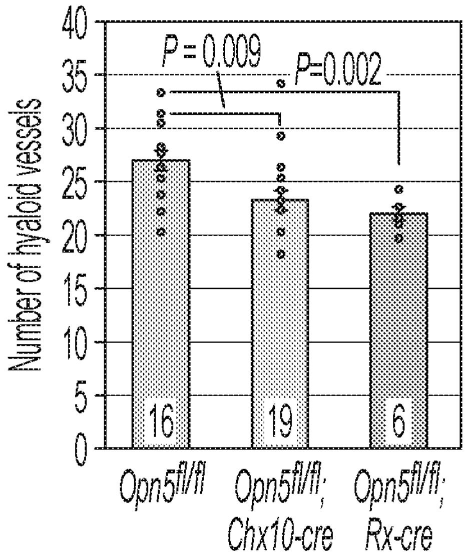

According to some embodiments, normal hyaloid vessel regression timing requires OPN5 and violet light. According to some embodiments, light stimulation of OPN4 regulates hyaloid vessel regression and retinal angiogenesis. Prompted by this, hyaloid regression was assessed in the OPN5-null mouse. At P1, OPN5-null mice showed normal hyaloid vessel numbers (FIG. 21*a,b,g,h*) and normal vessel cellularity (FIG. 21*c,d*, control: 13.3±1.2, OPN5 null: 13.2±1.6 nuclei per 100-μm length, P=0.92). At P8, OPN5-null mice had fewer hyaloid vessels (FIG. 21*e-h*), indicating precocious regression. This phenotype is unique as all hyaloid phenotypes described so far, including that of the OPN4-null mouse, show hyaloid persistence. Precocious hyaloid regression in the OPN5-null mouse is best illustrated when vessel numbers are quantified over a P1-P8 time course (FIG. 21*g,h*, blue line) and compared with the control (FIG. 21*g,h*, grey line) and the OPN4-null mouse (FIG. 21*h*, green line). When $OPN5^{fl}$ is conditionally deleted in the retina using Chx10-cre or Rx-cre, precocious hyaloid regression is observed (FIG. 21*i-k*). Thus, according to some embodiments, OPN5 is required locally within retinal neurons to regulate hyaloid regression.

Figure 21L:
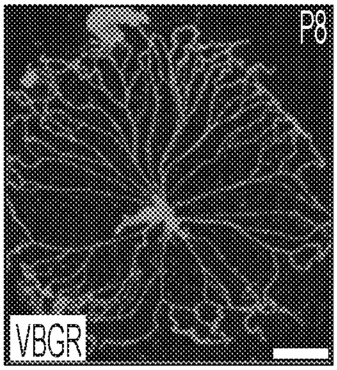
Figure 21M:
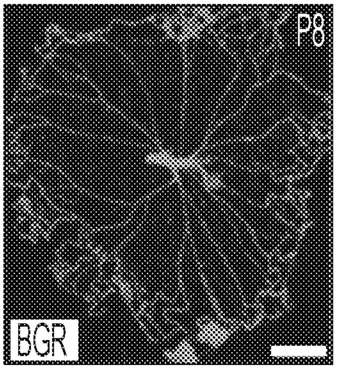
Figure 21N:
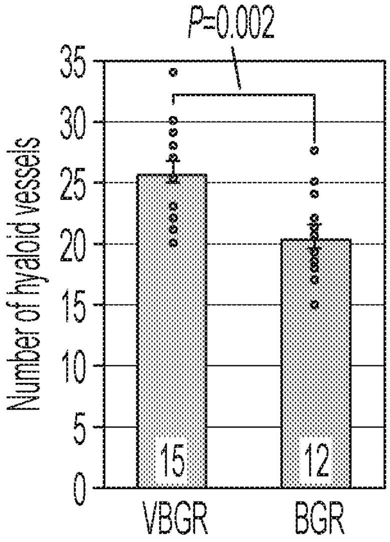

To mimic OPN5 loss of function using lighting conditions, mice were raised from birth in the absence of the 380-nm wavelengths that maximally stimulate OPN5. Control mice were raised in a light-dark cycle of 'VBGR' (violet (380 nm), blue (480 nm), green (520 nm) and red (630 nm)) lighting and showed a typical hyaloid vessel number at P8 (FIG. 21*l,n*, grey bar). By contrast, mice raised in 'BGR lighting that omitted violet light showed precocious hyaloid regression (FIG. 21*m,n*, blue bar). This phenocopies the OPN5-null mice and is consistent with a model in which 380-nm photons stimulate OPN5 to suppress hyaloid vessel regression.

The following are shown in FIG. 21, e.g., Precocious hyaloid vessel regression in the OPN5-null mice and absence of 380-nm photons:

Hoechst 33258 (blue)-labelled hyaloid vessel preparations from P1 $OPN5^{+/+}$ (a) and $OPN5^{-/-}$ (b) mice. c,d, Higher-magnification images of two examples each of P1 hyaloid vessel segments from $OPN5^{+/+}$ (c) and $OPN5^{-/-}$ (d) mice labelled with Hoechst 33258 (red) and isolectin (green). e,f Hoechst 33258-labelled hyaloid vessel preparations from P8 $OPN5^{+/+}$ (e) and $OPN5^{-/-}$ (f) mice. g, Quantification of hyaloid vessel number in $OPN5^{+/+}$ (WT), $OPN5^{+/-}$ (het) and $OPN5^{-/-}$ mice over a P1-P8 time course. h, As in e, but relative hyaloid vessel numbers for control, $OPN5^{-/-}$ and $OPN4^{-/-}$ mice. i,j, Hoechst 33258-labelled hyaloid vessel preparations from P8 $OPN5^{fl/fl}$ control (i) and $OPN5^{fl/fl}$; Rx-cre (j) mice. k, Quantification of P8 hyaloid vessel number in $OPN5^{fl/fl}$ control, $OPN5^{fl/fl}$; Chx10-cre and $OPN5^{fl/fl}$; Rx-cre mice. l,m, Hoechst 33258-labelled hyaloid vessel preparations from P8 mice raised from birth in full spectrum (VBGR) (l) or 'minus violet' (BGR) (m) lighting. n, Quantification of P8 hyaloid vessel number from P8 mice raised from birth in full spectrum (VBGR) or 'minus violet' (BGR) lighting. All P values were determined by Student's t-test; NS, not significant. The number at the base of each chart is n and represents the number of animals assessed. Error bars are s.e.m. Scale bars, 400 µm (a,b,e,f,i,j,l,m) and 20 µm (c,d).

The following are shown in FIG. 22, e.g., OPN5-dependent and light-dependent pathways regulate dopamine levels in the neonatal mouse eye:

Immunofluorescence labelling for TH (greyscale) in flat mount retinae from control $OPN5^{+/+}$ (a,b,e) and $OPN5^{-/-}$ (c,d,f mice at P8 (a-d) and P15 (e,f). Scale bars, 100 µm (a-d) and 20 µm (e,f). g-k, Charts showing ELISA quantification of dopamine in retinal lysates (g,j) and vitreous fluid (h,i,k). Dopamine levels in each tissue over a P2-P8 developmental time course are shown (g,h). Dopamine levels in retinal lysate (j) and vitreous fluid (k) from P6 $OPN5^{+/+}$ control (j,k), $OPN5^{+/-}$ heterozygote (j,k) and $OPN5^{-/-}$ homozygote (j,k) are also shown. Dopamine levels over a P2-P6 developmental time course comparing normal lighting (LD) with the consequences of dark rearing (DD) are also indicated (i). P values were determined by two-way ANOVA (g,h), Student's t-test (i) and one-way ANOVA (j, k). Error bars are s.e.m. The number at the base of each chart is n and represents the number of animals assessed. Panels a-f are representative of at least three separate experiments. Additional examples of a-d are available on Figshare (https://doi.org/10.6084/m9.figshare.7450961).

Figures 22A, 22B, 22C, 22D, 22E, 22F:
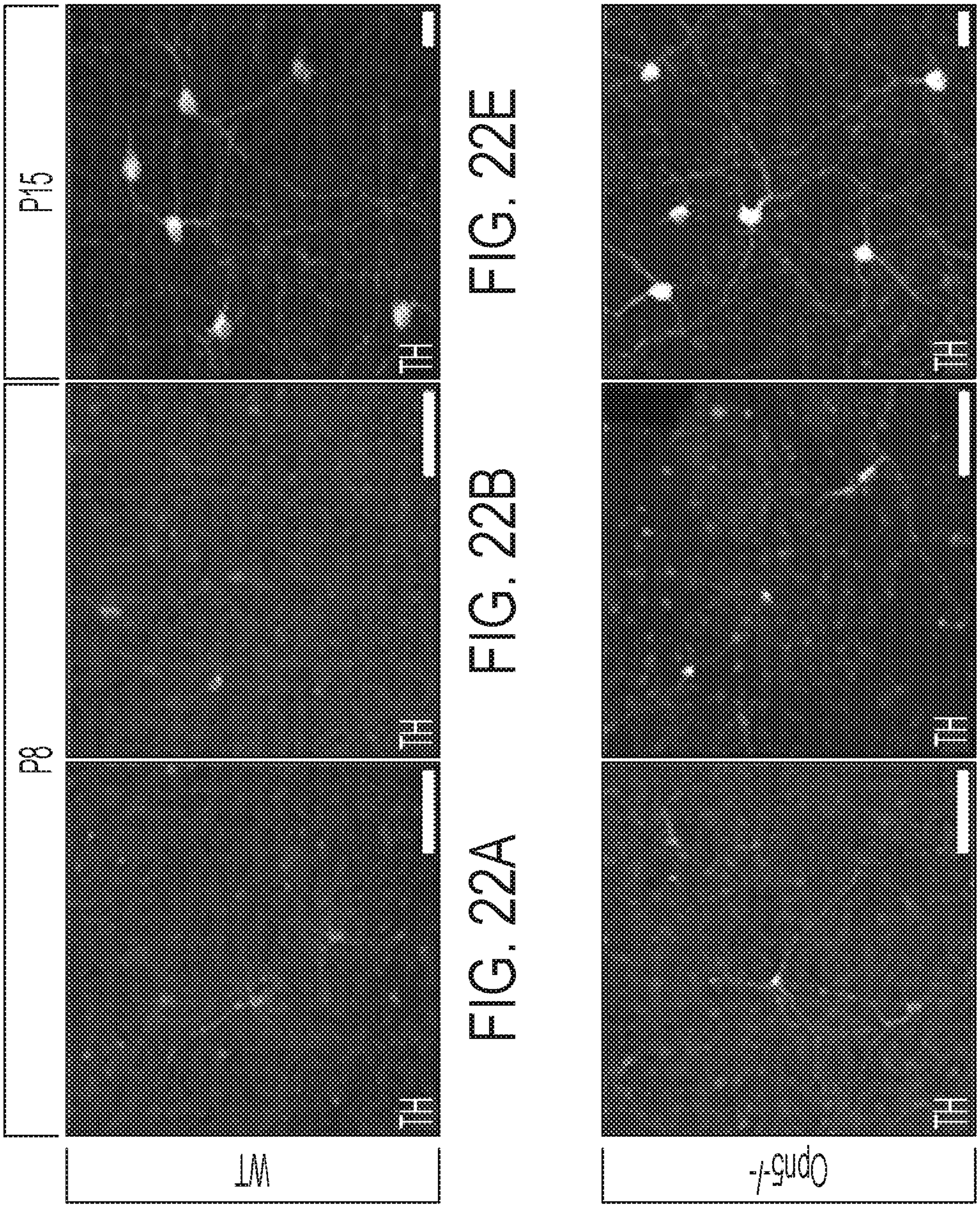
FIG. 22 illustrates, according to some embodiments, OPN5-dependent and light-dependent pathways regulate dopamine levels in the neonatal mouse eye.

According to some embodiments, a light-OPN5 pathway regulates dopamine levels in the eye. In OPN4-null mice, elevated levels of vascular endothelial growth factor A (VEGFA) explain hyaloid vessel persistence. Assessment of the levels of VEGFA and its inhibitor FLT1 in the vitreous of OPN5-null mice indicated no change. According to some embodiments, this suggested that the OPN5-light response pathway regulated hyaloid regression by a distinct mechanism. In the OPN5-null retina, an unusual labelling pattern was noted for tyrosine hydroxylase (TH). In wild-type (WT) retina at P8, TH immunoreactivity was faint and largely restricted to the perinuclear region of a subset of amacrine cells (FIG. 22*a,b*). In OPN5-null mice, TH labelling was stronger and prominent in cell processes (FIG. 22*c,d*). Elevated intensity of TH labelling in the OPN5-null retina was also evident at P15 when dopaminergic amacrine cells are more fully developed (FIG. 22*e,f*). TH is the rate-limiting enzyme that mediates the first step in the biosynthesis of dopamine. As TH levels are under feedback regulation, these data indicated that dopamine levels might be modulated in the OPN5-null eye. Interestingly, dopamine is known to have in vitro anti-vascular activity via suppression of VEGF receptor 2 (VEGFR2) signaling. This meant that OPN5-dependent regulation of dopamine could be an explanation for OPN5-dependent regulation of hyaloid regression. Thus, according to some embodiments, it was hypothesized that OPN5-dependent release of dopamine from the retina promoted hyaloid vessel regression by direct signaling.

Figure 22G:
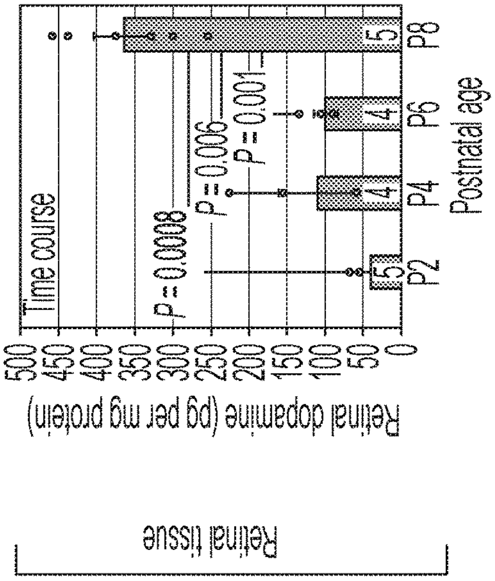
Figure 22J:
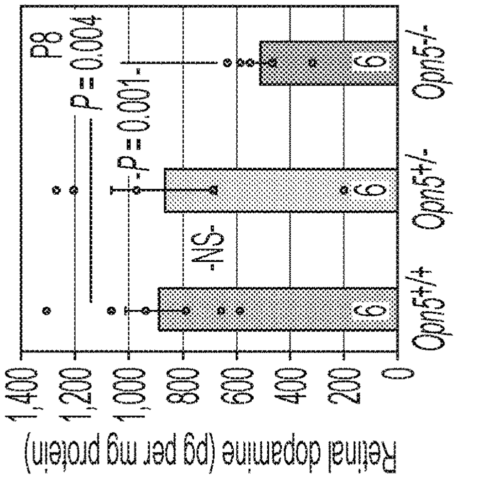
Figure 22H:
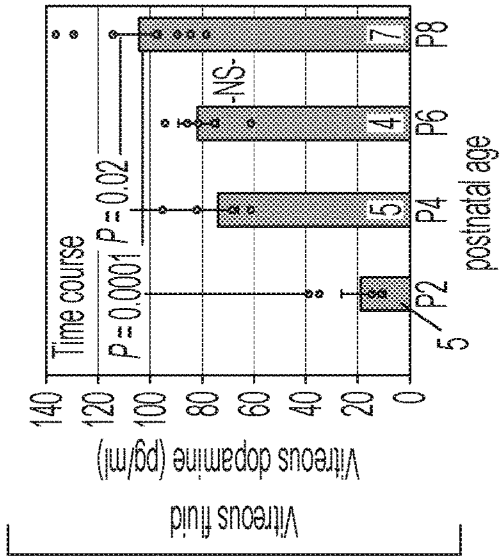
Figure 22I:
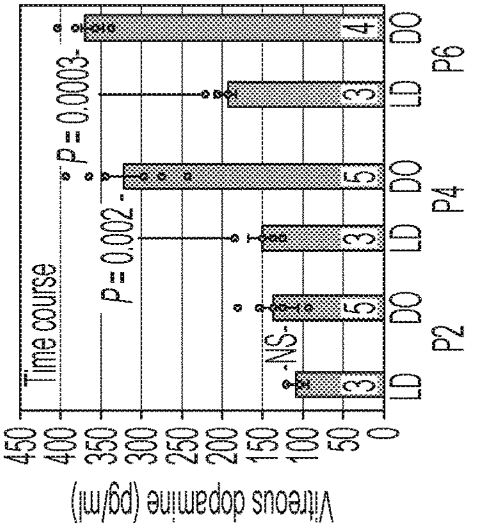
Figure 22K:
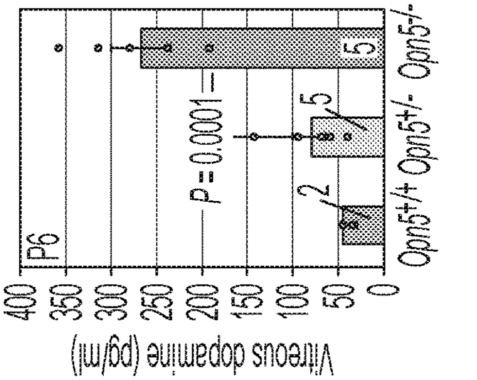

Dopaminergic amacrine cells that express TH develop in the first few days after birth in the mouse. This also means that, normally, dopamine levels in the retina climb rapidly after birth. Using enzyme-linked immunosorbent assay (ELISA) quantification, we confirmed that retinal dopamine levels rise over a P2-P8 time course (FIG. 22*g*). Dopamine in solubilized retinal tissue is primarily from intracellular stores. ELISA quantification showed that dopamine levels in the vitreous, where the hyaloid vessels reside, also rise over the postnatal period (FIG. 22*h*). In adult mice, dopamine levels in the eye are light regulated. To evaluate this possibility for neonatal mice, vitreous dopamine was quantified over a postnatal time course of normal lighting and constant darkness. At P4 and P6, vitreal dopamine levels were significantly elevated in constant darkness (FIG. 22*i*), indicating that, postnatally, light stimulation normally suppresses vitreal dopamine. To determine whether light-regulated dopamine might be a consequence of OPN5 activity, retina and vitreous was harvested from an OPN5 allelic series at P6 and quantified dopamine levels (FIG. 22*j,k*). This showed that OPN5 homo-zygote null mice had lower levels of intracellular dopamine in the retina (FIG. 22*j*), but elevated levels in the vitreous (FIG. 22*k*). According to some embodiments, these data indicate that dopamine in both compartments is regulated by OPN5.

The following are shown in FIG. 23, e.g., Light-dependent activation of phospho-T53-DAT in the IPL requires OPN5:

Labelling of P8 $OPN5^{+/+}$ retina for nuclei and phospho-T53-DAT for dark-adapted mice (a), half of which were exposed to 30 min of 380-nm light (b). NBL, neuroblastic layer. Scale bars, 50 µm. The indicated areas of each panel are exported to the chart in panel e. e, Chart showing averaged (n 3) quantification profiles for phospho-T53-DAT in retinal cryosections (a,b). The grey shading emphasizes the elevated signal of the light-induced sample. c,d, As in a and b, respectively, but for $OPN5^{-/-}$ retina. f. Chart as in e, except for $OPN5^{-/-}$ mice. Traces from the chart in panel e are reproduced on the chart in for comparison. g,h, Charts showing area-under-the-peak quantification (n 3) of phospho-T53-DAT labelling in the IPL (g) and the NFL (h) for P8 mice of the labelled genotype and light exposure. The vertical dashed lines in e and f indicate the areas that were quantified i, Immunoblot detecting DAT, phospho-T53-DAT (pDAT) and β-tubulin (TUBB) in retinae harvested from $OPN5^{+/+}$ and $OPN5^{-/-}$ mice during the light phase. Phospho-T53-DAT expression is lower than normal in the OPN5-null mice. Quantification of P8 hyaloid vessels in WT mice injected with vehicle (veh) or with the DAT inhibitor (DATi) raised from E17 either in normal lighting or in constant darkness. k, Quantification of P8 hyaloid vessels in $OPN5^{+/+}$, $OPN5^{+/+}$ and $OPN5^{-/-}$ mice injected from P1-P8 with the DAT inhibitor. P values were determined by two-way ANOVA. Error bars are s.e.m. The number at the base of each chart is n and represents the number of animals assessed. Panels a-d are representative of three separate experiments.

According to some embodiments, a light-OPN5 pathway suppresses dopamine release to the vitreous by enhancing DAT activity. The biological effects of dopamine are regulated by its release, signaling and reuptake. A key regulator of uptake, and thus a good candidate for an OPN5-dependent activity, is the dopamine transporter DAT (also known as SLC6A3). Threonine 53 of DAT is phosphorylated and enhances the rate of dopamine uptake by DAT. This activation marker can be detected with a phospho-specific antibody. Basal phosphorylation stoichiometry of T53-DAT is typically 50% but is increased by stimuli that elevate dopamine uptake. To determine whether phos-pho-T53-DAT levels were regulated by light and were OPN5 dependent, retinal cryosections from cohorts of P8 littermate $OPN5^{+/+}$ and $OPN5^{-/-}$ mice were labelled after they were dark adapted followed by ±30 min of 380-nm light at $1\times10^{12}$ photons $cm^{-2}$ $s^{-1}$. Labelling for phospho-T53-DAT was found throughout the IPL and NFL of all samples (FIG. 23*a-d*). The phospho-T53-DAT signal was quantified by averaging pixel intensity across horizontal pixel rows of images aligned like those shown (FIG. 23*a-d*), generating intensity profiles (FIG. 23*e*, grey and blue profiles) and calculating the area under the peaks (indicated by the grey vertical dashed lines in FIG. 23*e,f*). This revealed that, for the IPL (FIG. 23*g*, grey and blue bars), but not for the NFL (FIG. 23*h*, grey and blue bars), the phospho-T53-DAT signal was significantly increased in response to the 380-nm light.

Figures 23E, 23F, 23G, 23H, 23I, 23J, 23K:
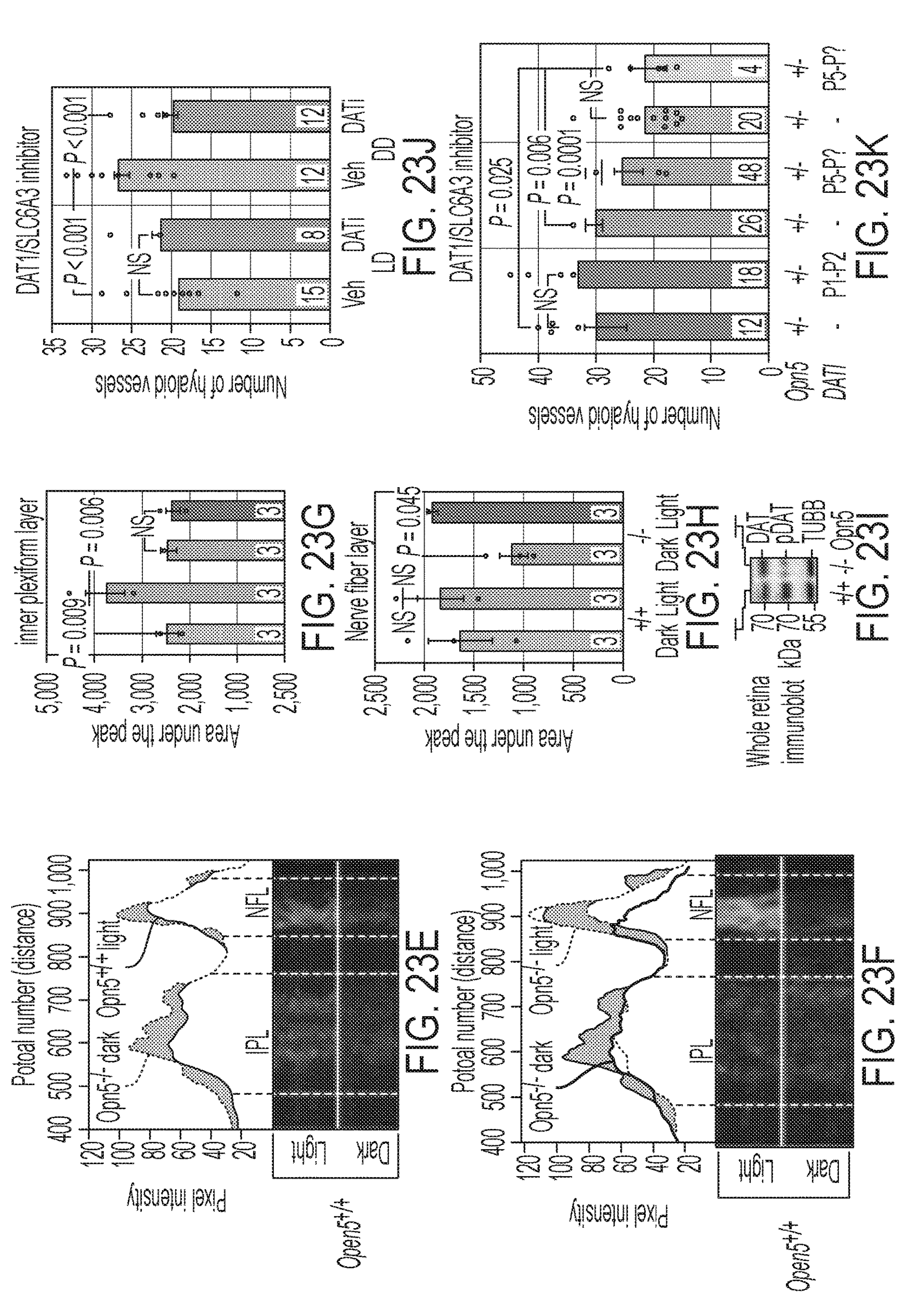
FIG. 23 illustrates, according to some embodiments, light-dependent activation of phospho-T53-DAT in the IPL requires OPN5.

To determine whether light induction of the phospho-T53-DAT signal was OPN5 dependent, the same analysis was performed in OPN5-null mice (FIG. 23*c,d,f-h*). This revealed that, in the OPN5-null retina, the phospho-T53-DAT signal for the IPL did not elevate in response to light exposure (FIG. 23*g*, orange and red bars), indicating OPN5 dependence. Interestingly, in the NFL, OPN5-null mice have a lower level of phospho-T53-DAT independent of light exposure (FIG. 23*h*, compare grey bar and orange bar). However, this low level of phospho-T53-DAT can be rescued by light exposure (FIG. 23*h*, compare orange and red bars). This indicates that NFL phospho-T53-DAT levels are regulated both by OPN5 (negatively, light independent) and by a distinct light response pathway (positively). Although the pathway for the positive regulation of phospho-T53-DAT in the NFL (other opsins are obvious candidates) may not be fully understood, it serves as a useful internal control to show that the OPN5-null retina can be light responsive. An immunoblot detecting phospho-T53-DAT in total solubilized retina from the light phase (FIG. 23*i*) revealed that, overall, the level is lower in the OPN5-null mice, suggesting that NFL phospho-T53-DAT is the smaller proportion of the total. Collectively, according to some embodiments, analysis of T53-DAT indicates that OPN5 is required for a light-dependent upregulation within the IPL. As T53-phosphorylated DAT sequesters dopamine with higher efficiency, this finding is consistent with a model in which loss of OPN5 function results in diminished dopamine uptake by DAT, and thus elevated levels of vitreal dopamine.

Inhibition of DAT promotes hyaloid regression in an OPN5-dependent manner. To determine whether DAT had a functional role in the regulation of hyaloid regression in vivo, advantage was taken of the DAT inhibitor GBR12909. Based on data showing that dopamine signaling can suppress VEGFR2 activation via the phosphatase SHP2, according to some embodiments, it was predicted that suppressing DAT activity would elevate dopamine levels in the eye and thus should counter the consequences of dark rearing because the latter elevates levels of VEGFA. To test this, the effects of P1-P8 GBR12909 injection on hyaloid vessel regression were compared in C57BL/6J mice raised either in normal lighting or in constant darkness. This showed that GBR12909 had no significant effect on mice raised in normal lighting (FIG. 23*j*, normal lighting), but could reverse the hyaloid vessel persistence resulting from dark rearing (FIG. 23*j*, constant darkness). According to some embodiments, this shows that DAT activity is an important light-dependent regulator of hyaloid vessel regression.

The following are shown in FIG. 24, e.g., OPN5 RGCs use Vgat in a hyaloid regression pathway: a model for OPN4-VEGFA and OPN5-dopamine pathway integration:

a, Quantification of hyaloid vessels in P8 $OPN5^{+/+}$; $Vglut2^{+/+}$, $OPN5^{+/cre}$; $Vglut2^{+/+}$, $OPN5^{+/cre}$; $Vglut2^{fl/fl}$ and $OPN5^{+/cre}$; $Vglut2^{fl/fl}$ mice. b-e, Hyaloids from P8 $OPN5^{+/+}$; $Vgat^{+/+}$ (b), $OPN5{+}1^{cre}$; $Vgat^{+/+}$ (c), $OPN5^{+/cre}$; $Vgat^{fl/+}$ (d) and $OPN5^{+/cre}$; $Vgat^{fl/fl}$ (e) mice. f Quantification of hyaloid vessels in P8 mice with genotypes listed in b-e. g-j, Retinal cryosections imaged for phospho-T53-DAT and Ai6-cre from P8 $OPN5^{Cre}$, Ai6; $Vgat^{+/+}$ (g,h) or $OPN5^{cre}$; Ai6; $Vgat^{fl/fl}$ (i,j) mice. Additional examples of g-j are available on Figshare (https://doi.org/10.6084/m9.figshare.7450961). The sample sizes (n) for a and f are shown at the base of each bar and represent the number of mice. P values were determined by one-way ANOVA. Error bars are s.e.m. Images in b-e represent at least six, and in g-j at least three, separate experiments. Scale bars, 200 μm (b-e) and 20 μm (g-j). k, Schematic describing the integration of the OPN4-VEGFA and OPN5-dopamine hyaloid regression pathways. The schematic identifies two phases of development, E16-E18 (k) and P3-P8 (1), when OPN4 and OPN5 are each required. In late gestation, blue-light stimulation of OPN4 RGCs suppresses retinal cellularity. In dark-reared or in OPN4-null mice, elevated cellularity increases oxygen demand ([02]) and, via the hypoxia response pathway, increases VEGFA expression in amacrine cells and RGCs. Elevated levels of VEGFA cause promiscuous retinal angiogenesis and suppresses hyaloid vessel regression.

According to the present analysis, violet-light stimulation of OPN5 RGCs postnatally suppresses dopamine in the vitreous by upregulating T53 phosphorylation of the dopamine transporter in neurons in the IPL. Normally, OPN5-dependent phosphorylation of DAT results in elevated dopamine uptake and a reduced flux of dopamine from dopaminergic amacrine cells to the vitreous. In the absence of OPN5, or the violet light that stimulates OPN5, the vitreous dopamine level is precociously elevated. This results in premature activation of the dopamine receptor DRD2 in hyaloid VECs, suppression of VEGFR2 survival signaling and precocious regression. These data indicate that both 480-nm blue light via OPN4 and 380-nm violet light via OPN5 function as developmental timing cues.

To assess DAT activity in OPN5-dependent regulation of hyaloid regression, GBR12909 was injected daily from P1-P8 into $OPN5^{+/+}$, $OPN5^{+/-}$ and $OPN5^{-/-}$ mouse pups. Quantification of hyaloid vessels at P8 showed that WT mice did not respond significantly (FIG. 23*k*), but that in heterozygote mice, GBR12909 produced a precocious hyaloid regression equivalent to the OPN5 homozygote phenotype (FIG. 23*k*). GBR12909 produced no change in homozygote mice (FIG. 23*k*). Inhibitor activity may be buffered by the intact feedback regulation of the WT mouse. However, in OPN5 heterozygote mice, in which dopamine levels are elevated (FIG. 22*k*) and feedback regulation may be compromised, the DAT inhibitor was able to convert the hyaloid phenotype from normal to precocious regression. It is likely that the inhibitor produces no effect in the OPN5 homozygote because the endogenous vitreal dopamine level is already high (FIG. 22*k*) and signaling activity may be close to maximal. These data indicate a finely balanced interaction between OPN5 and DAT that is consistent with OPN5-dependent regulation of DAT activity via phosphorylation.

Figure 24A:
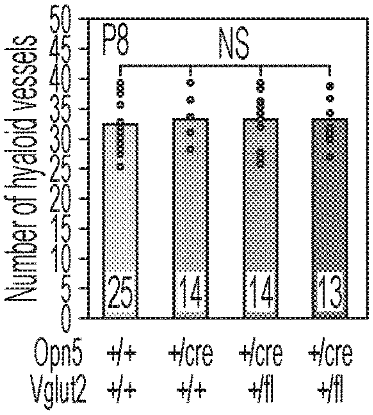
FIG. 24 illustrates, according to some embodiments, OPN5 RGCs use VGAT in a hyaloid regression pathway: a model for OPN4-VEGFA and OPN5-dopamine pathway integration.
Figure 24B:
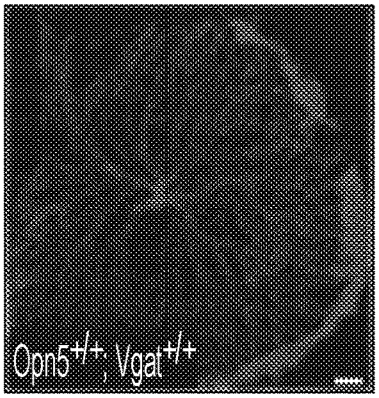
Figure 24C:
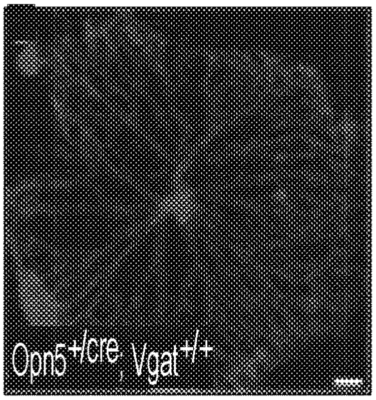
Figure 24F:
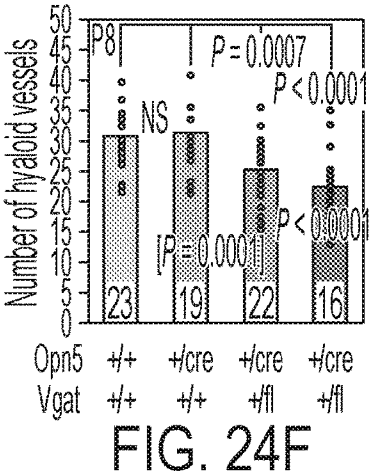
Figure 24D:
Figure 24E:
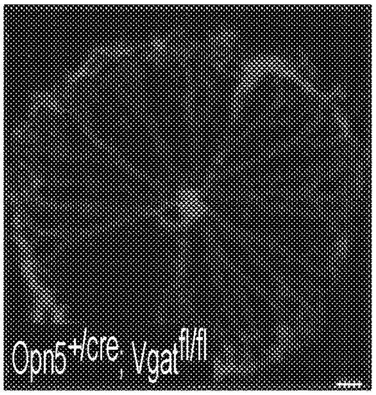
Figures 24G, 24H, 24I, 24J:
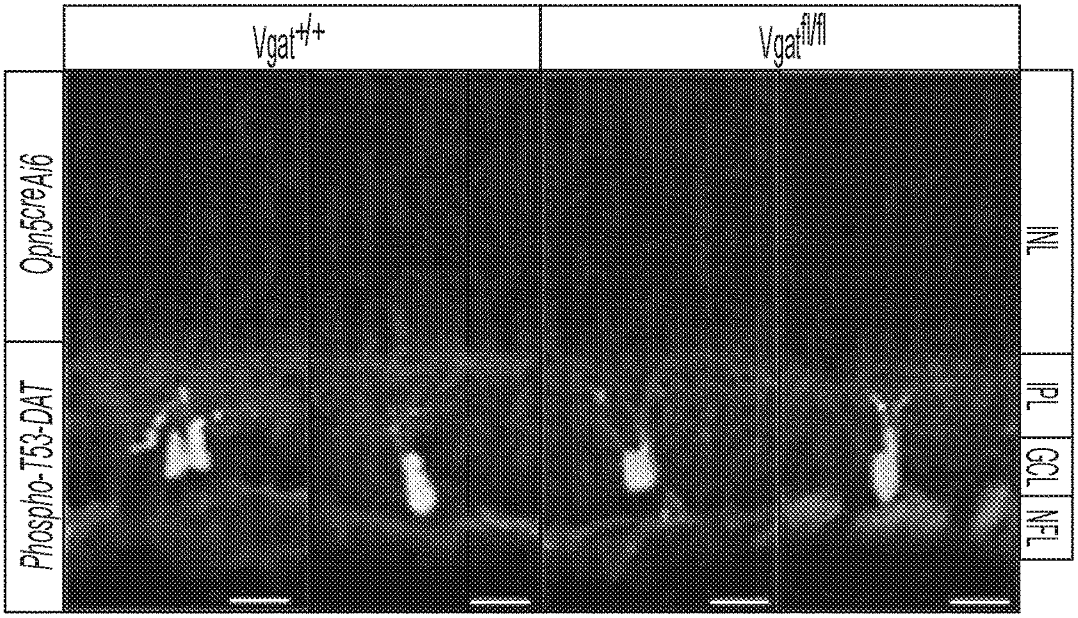
Figure 24K:
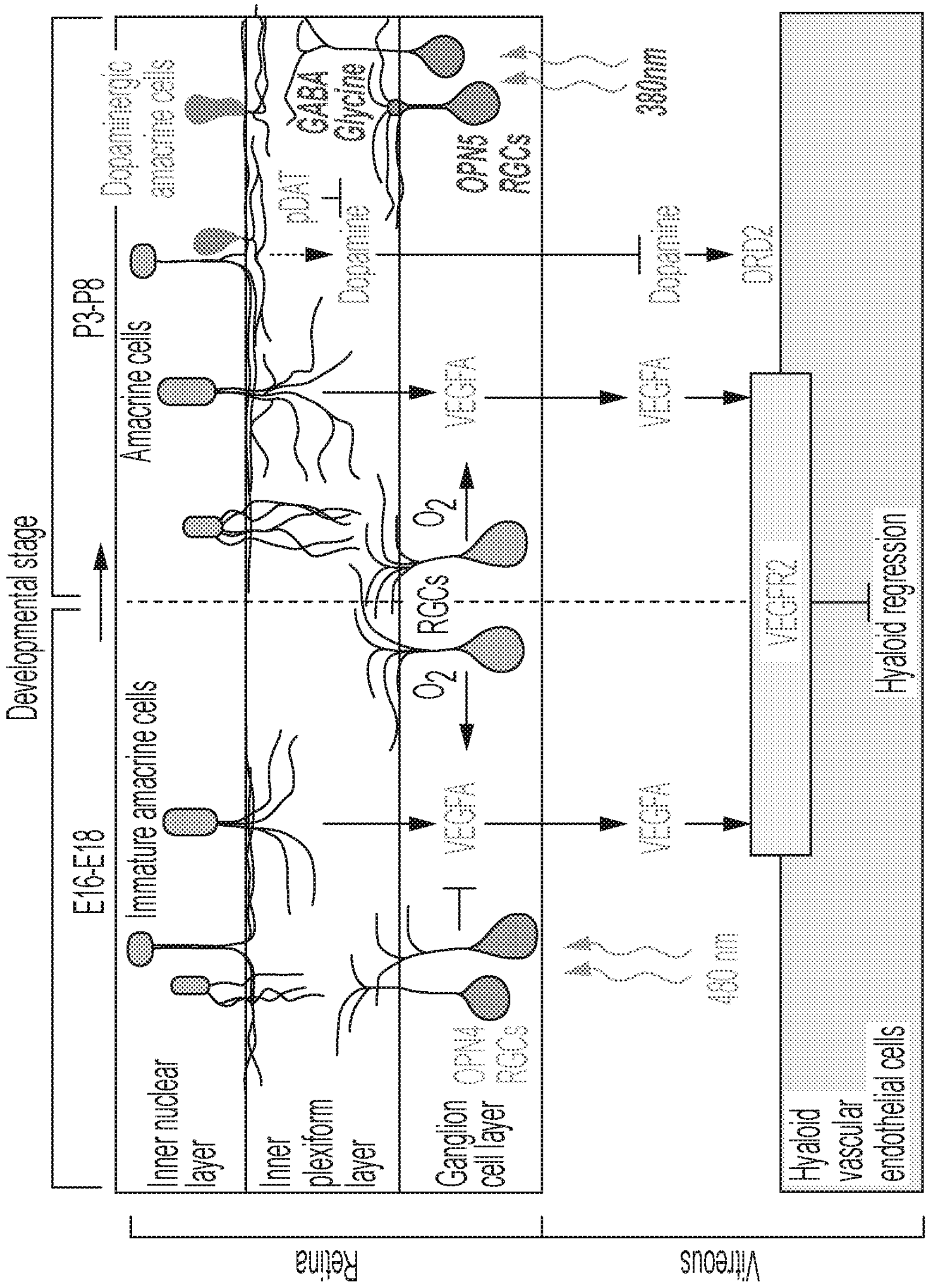

According to some embodiments, VGAT in OPN5 RGCs is required for regulation of phospho-T53-DAT and hyaloid regression. Glutamate, γ-aminobutyric acid (GABA) and glycine are neurotransmitters important for visual function. In the adult mouse, glutamate is used as an excitatory neurotransmitter by canonical photoreceptors and OPN4 RGCs. GABA and glycine are inhibitory neurotransmitters and their receptors are detected in various retinal neurons, including amacrine cells and RGCs. Glutamate and GABA/glycine are loaded into presynaptic vesicles by the VGLUT (vesicular glutamate transporter) and VGAT (vesicular GABA transporter) family of transporters, respectively. During mouse retinal development, VGAT is expressed soon after birth and precedes the expression of VGLUT2. Loss of function of these transporters eliminates neurotransmitter activity. To determine whether OPN5 RGCs might use one of these neurotransmitters for the vascular response pathway, hyaloid vessels were quantified in $OPN5^{cre}$ conditional deletion mutants of Vglut2 and Vgat. Although deletion of Vglut2fl had no consequence (FIG. 24*a*), homozygous deletion of $Vgatf^{f}$ phenocopied the OPN5 germline null precocious hyaloid regression (FIG. 24*b-f*). Furthermore, the $OPN5^{cre/+}$ heterozygote showed no hyaloid phenotype, but $OPN5^{+/cre}$; $Vgat^{fl/+}$ mice showed a significant precocious regression (FIG. 24*d,f*). This transheterozygote phenotype is genetic evidence that OPN5 and Vgat function in the same pathway and in the same cell type. If this is true, then we would predict that the Vgat conditional deletion would, like OPN5 loss of function, result in diminished levels of phospho-T53-DAT under lighted conditions. This was confirmed using immunofluorescence labelling of the retina from $OPN5^{+/cre}$; $Vgat^{fl/+}$ (FIG. 24*g,h*) and $OPN5^{+/cre}$; Vgatfl/fl mice (FIG. 24*i,j*). These data indicate that OPN5 RGCs use VGAT to signal within the vascular regression pathway.

Figure 25A:
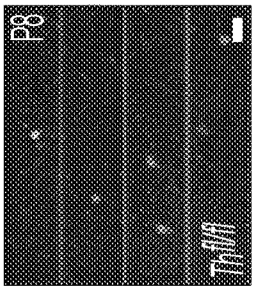
FIG. 25 illustrates, according to some embodiments, retinal dopamine promotes hyaloid vessel regression via DRD2-dependent suppression of VEGFR2 activity.
Figure 25B:
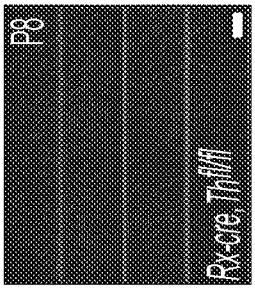
Figure 25C:
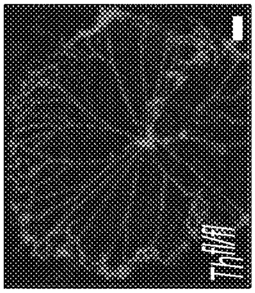
Figure 25D:
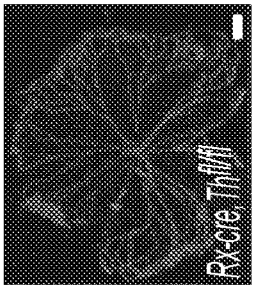
Figure 25E:
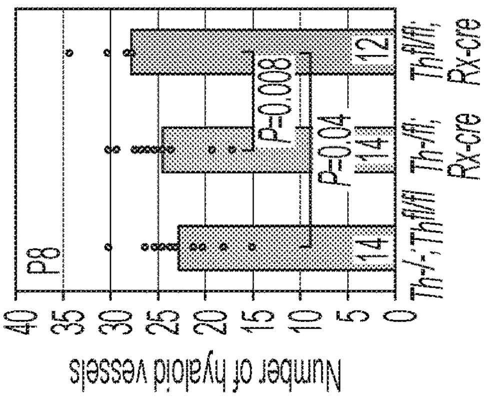

According to some embodiments, dopamine has a direct action on hyaloid vascular endothelial cells to promote hyaloid regression. According to some embodiments, it has been hypothesized that dopamine release from the neonatal retina is light and OPN5 dependent and that dopamine then signals directly to hyaloid vascular endothelial cells (VECs) to promote regression. To assess whether a retinal source of dopamine regulated hyaloid regression, a $Th^{fl}$ allele was conditionally deleted. Chx10-cre, although effective for studies of TH function in adult mice, did not delete $Th^{fl}$ efficiently during the postnatal period. However, Rx-cre was effective (FIG. 25*a,b*) and resulted in a hyaloid vessel persistence (FIG. 25*c-e*), indicating that the active dopamine is produced locally in the retina.

To assess the involvement of dopamine receptors in hyaloid regression, advantage was first taken of SK38393, a receptor agonist. SK38393 was injected daily into $OPN5^{+/+}$, $OPN5^{+/-}$ and $OPN5^{-/-}$ mouse pups from P1-P8. Although SK38393 had no significant effect on WT mice, it produced precocious hyaloid regression in heterozygous mice. SK38393 did not produce a significant reduction in hyaloid vessel numbers in OPN5-null mice. This pattern of response is very similar to that observed with the DAT inhibitor (FIG. 23*k*). Again, this pattern of modulation is probably explained by the resilience of an intact dopamine feedback pathway in WT animals, the sensitized background of the heterozygote and the already saturated level of dopamine signaling in the homozygote. Injection of two different dopamine receptor antagonists from P1-P8 in WT mice produced elevated numbers of hyaloid vessels. Thus, according to some embodiments, pharmacological manipulations indicate that hyaloid vessel regression can be regulated both positively and negatively by dopamine receptor modulators.

Figure 25F:
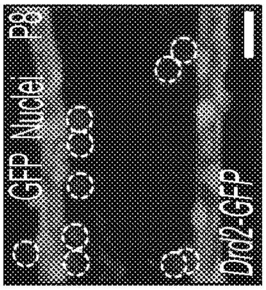
Figure 25G:
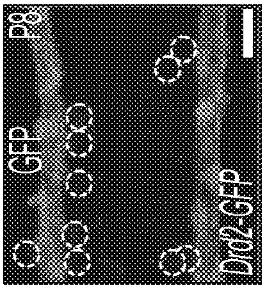
Figure 25H:
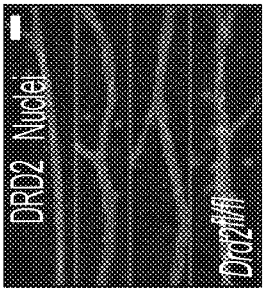
Figure 25I:
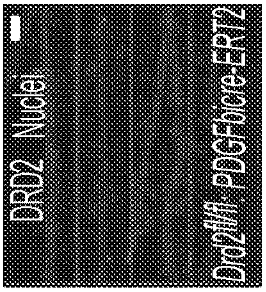

According to some embodiments, one prediction of the hypothesis that retinal dopamine regulates hyaloid regression was that dopamine receptors would be expressed within the hyaloid vessels. As dopamine receptor D2 (DRD2) was implicated in the suppression of VEGFR2 signaling, this member of the family was focused on. Vascular cells, but not hyaloid-associated myeloid cells, showed Drd2-GFP reporter expression (FIG. 25*f,g*). Furthermore, labelling with an anti-DRD2 antibody detected cells within the hyaloid vessels (FIG. 25*h*) and this was eliminated in the $Drd2^{fl/fl}$; Pdgfb-icreERT2 conditional deletion that targets VECs (FIG. 25*i*). According to some embodiments, these data show that DRD2 is expressed in hyaloid VECs.

Figure 25J:
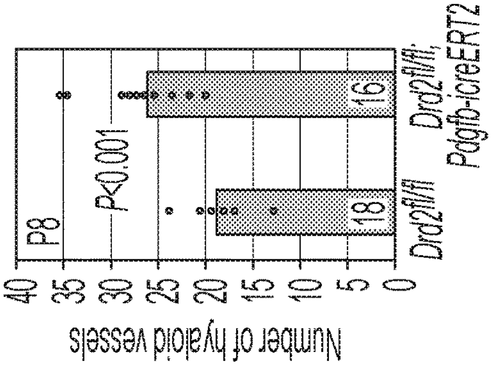
Figure 25K:
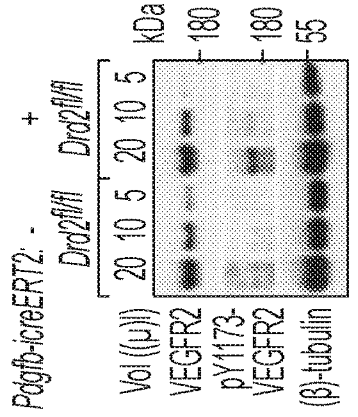

In $Drd2^{fl/fl}$; Pdgfb-icreERT2 mice, the hyaloid vessels are persistent (FIG. 25*j*), but there are no quantifiable consequences for the development of the superficial retinal vasculature. According to some embodiments, this identifies hyaloid VECs as a dopamine-responsive cell and indicates that dopamine signaling promotes hyaloid regression. A further prediction of the hypothesis is that, in hyaloid VECs, dopamine signaling would suppress the activation of VEGFR2. To test this, immunoblotting was performed for VEGFR2 and the activated, phosphotyrosine-1173 form of VEGFR2 (pY1173-VEGFR2), from both $Drd2^{fl/fl}$ control and $Drd2^{fl/fl}$; Pdgfb-icreERT2 hyaloid vessels at P5. Pooling dissected hyaloids from six animals of each genotype allowed threshold detection of the pY1173-VEGFR2 in the control (FIG. 25*k*, left lane). To assess the reliability of comparative immunoblotting, a three step, twofold loading dilution was performed and immunoblot band intensities were quantified. Presented graphically, band intensities for VEGFR2, pY1173-VEGFR2 and 0-tubulin showed high Pearson coefficients, indicating a linear relationship between lysate quantity and band intensity. When pY1173-VEGFR2 values were normalized to VEGFR2 (FIG. 6*l*), $Drd2^{fl/fl}$; Pdgfb-icreERT2 genotype values were much higher (FIG.

Figure 25L:
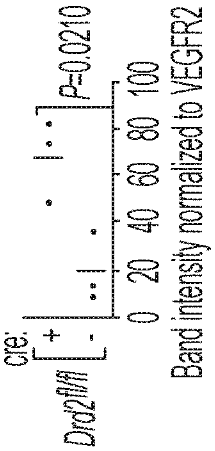
Figure 25M:
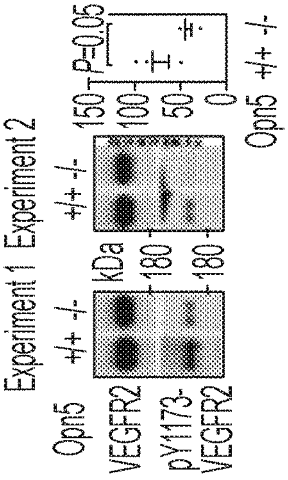
Figure 25N:
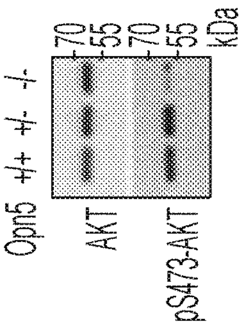

25*l*), consistent with the observed band intensities on the immunoblot (FIG. 25*k*). According to some embodiments, these data show that deletion of Drd2 in hyaloid VECs permits elevated activation of VEGFR2 and indicates that, normally, dopamine signaling suppresses VEGFR2 activity. In an additional test of this model, pY1173-VEGFR2 was assessed and pS473-AKT levels in the OPN5-null mice. pY1173-VEGFR2 levels were lower in the hyaloid vessels of the OPN5-null mice (FIG. 25*m*). In addition, across an allelic series, pS473-AKT levels were lower only in the OPN5 homozygote, consistent with precocious hyaloid regression only in this genotype (FIG. 25*n*). As dopamine levels are high in the OPN5-null mice, these data are consistent with a model in which dopamine promotes hyaloid vessel regression by suppressing VEGFR2 activity and the downstream survival signaling mediated by AKT.

Figure 25O:
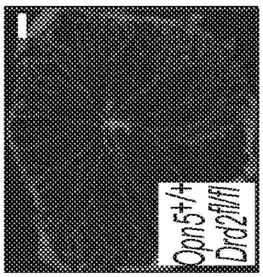
Figure 25P:
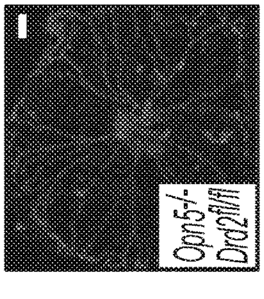
Figure 25Q:
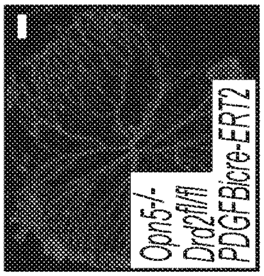
Figure 25R:
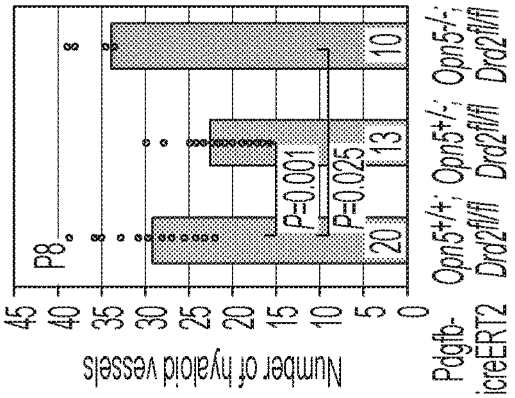

As a genetic test of the relationship between OPN5 and vascular signaling, it was determined whether deletion of Drd2 in VECs would reverse precocious hyaloid regression in the OPN5-null mice. P8 hyaloid vessel numbers were compared in mice of genotype $OPN5^{-/-}$, with $OPN5^{+/+}$; Pdgfb-icreERT2; $Drd2^{fl/fl}$ and with $OPN5^{-/-}$; Pdgfb-icreERT2; $Drd2^{fl/fl}$. According to some embodiments, this experiment confirmed the precocious regression of hyaloid vessels due to OPN5 loss of function (FIG. 25*o,p,r*, light blue bar), but showed that deletion of Drd2 in VECs could switch the hyaloid phenotype to persistence (FIG. 25*q,p*, dark blue bar). This outcome establishes that OPN5 and Drd2 function in the same developmental pathway and have opposing influences on hyaloid regression.

The following are shown in FIG. 25, e.g., Retinal dopamine promotes hyaloid vessel regression via DRD2-dependent suppression of VEGFR2 activity:

TH labelling (green) in four regions of P8 flat mount retinae from $Th^{fl/fl}$ (a) and Rx-cre; $Th^{fl/fl}$ (b) mice. c,d, Hyaloids from P8 control $Th^{fl/fl}$ (c) and Rx-cre; $Th^{fl/fl}$ (d) mice. e, P8 hyaloid vessel numbers in control ($Th^{+/+}$ or $Th^{+/fl}$), Rx-cre; $Th^{+/fl}$ and Rx-cre; $Th^{fl/fl}$ mice. f,g, Hyaloid vessels from Drd2-GFP mice showing reporter expression (green) in vessels but not macrophages (circles). GFP, green fluorescent protein. h,i, Immunolabelling for DRD2 in P8 hyaloids from tamoxifen-treated $Drd2^{fl/fl}$ (h) and $Drd2^{fl/fl}$; Pdgfb-icreERT2 (i) mice. j, P8 hyaloid vessel numbers in $Drd2^{fl/fl}$ and $Drd2^{fl/fl}$; Pdgfb-icreERT2 mice. k, Immunoblots for VEGFR2, pY1173-VEGFR2 and β-tubulin in P6 hyaloid vessel lysates from $Drd2^{fl/fl}$ and $Drd2^{fl/fl}$; Pdgfb-icreERT2 mice. Hyaloid lysate is loaded in successively halved volumes to ensure linear range detection. 1, Band intensity of n=3 mice, pY1173-VEGFR2, normalized to total VEGFR2 from k confirms that, in the Drd2 mutant, active VEGFR2 expression is higher. m,n, Immunoblots for VEGFR2 and pY1173-VEGFR2 (m), and AKT and pS473-AKT (n) from P6 hyaloids of the indicated genotypes. In the graph in m, quantification of pY1173-VEGFR2 relative to VEGFR2 in $OPN5^{+/+}$ and $OPN5^{-/-}$ hyaloid vessels is shown. pY1173-VEGFR2 and pS473-AKT levels are lower in $OPN5^{-/-}$. n=3 mice. o-q, P8 hyaloids from tamoxifen-treated $OPN5^{+/+}$; $Drd2^{fl/fl}$ (o), $OPN5^{-/-}$; $Drd2^{fl/fl}$ (p) and $OPN5^{-/-}$; $Drd2^{fl/fl}$; Pdgfb-icreERT2 (q) mice. r, P8 hyaloid vessel numbers in $OPN5^{+/+}$; $Drd2^{fl/fl}$, $OPN5^{-/-}$; $Drd2^{fl/fl}$ and $OPN5^{-/-}$; $Drd2^{fl/fl}$; Pdgfb-icreERT2 mice. s-u, P8 hyaloid preparations from $Flt1^{fl/fl}$ (s), Rx-cre; $Flt1^{fl/fl}$ (t) and SKF38393-injected Rx-cre; $Flt1^{fl/fl}$ (u) mice. v, P8 hyaloid vessel numbers in control $Flt1^{fl/fl}$, Rx-cre; $Flt1^{fl/fl}$ and SKF38393-injected Rx-cre; $Flt1^{fl/fl}$ mice. Scale bars, 20 μm (a,b,f-i) and 200 μm (c,d,o-q, s-u). The number at the base of each chart bar is n and represents the number of mice (e,j,r,v). P values were determined by one-way ANOVA (e,r,v) and Student's t-test (j,l,m). Error bars are s.e.m. Images are representative of at least three separate experiments.

Figure 25S:
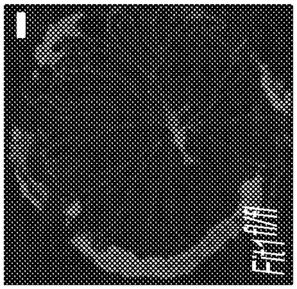
Figure 25T:
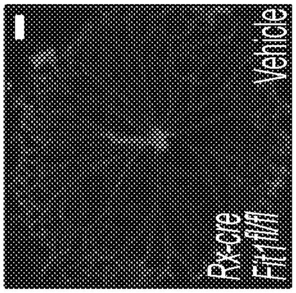
Figure 25U:
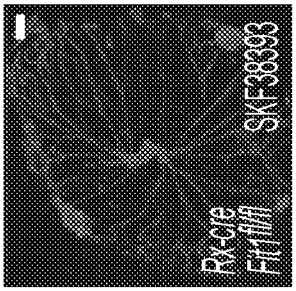
Figure 25V:
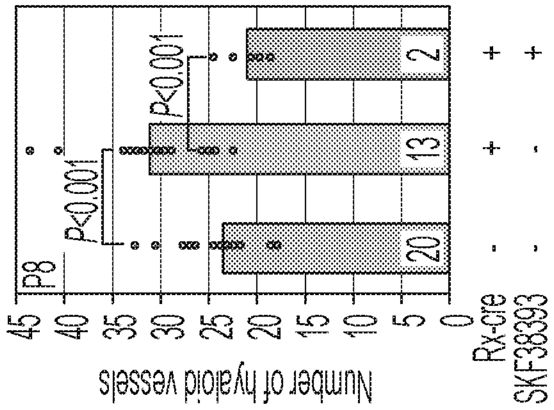

One implication of immunoblotting data for pY1173-VEGFR2 (FIG. 25*k*) and the genetic analysis (FIG. 25*o-r*) is that a balance of VEGFA and dopamine signaling determines the fate of the hyaloid vessels. To determine whether this balance could be demonstrated at the level of receptor ligands, a rescue experiment was designed. An elevated level of VEGFA activity was generated, and thus hyaloid vessel persistence, by conditionally deleting the gene encoding the naturally occurring VEGFA inhibitor FLT1 in the retina. Chx10-cre deletion of $Flt1^{fl/fl}$ produces hyaloid persistence, but in this case, Rx-cre was used (FIG. 25*s,t,v*, light blue bar). To determine whether dopamine receptor signaling could reverse the hyaloid persistence, a littermate cohort of Rx-cre; $Flt1^{fl/fl}$ mice was injected (each day, from P1 to P8) with the dopamine receptor agonist SKF38393. This resulted in a reversal of the hyaloid persistence (FIG. 6*s-v*), an outcome that illustrates, according to some embodiments, the balance of VEGFA and dopamine signaling that regulates hyaloid regression.

Discussion

According to some embodiments, an unanticipated vascular development pathway in the eye has been identified. OPN5, an atypical opsin known to respond to near-UV photons, initiates the pathway response and functions postnatally (FIG. 25*l*). Dopamine, a broadly functional neurotransmitter and neuromodulator, is a signaling intermediate that is regulated by OPN5 and elicits a direct response in hyaloid VECs to limit VEGFR2 signaling via DRD2 (FIG. 25*l*). Based on OPN5-dependent and light-dependent phosphorylation at T53, and its pharmacological inhibition, according to some embodiments, the dopamine transporter DAT is a key component of this pathway that normally suppresses the levels of dopamine in the vitreous (FIG. 25*l*). In addition, the GABA transporter VGAT is implicated in OPN5 RGC signaling as its conditional deletion in OPN5 RGCs phenocopies the OPN5-null precocious hyaloid regression and low phospho-T53-DAT level. Thus, the light-OPN5-VGAT-dopamine-DRD2-VEGFR2-hyaloid pathway is characterized by two suppressive steps: light-OPN5 suppresses the levels of dopamine in the vitreous, whereas dopamine suppresses VEGFR2 signaling in the hyaloid vessels (FIG. 25*l*).

Light-dependent regulation of vitreal dopamine occurs against a backdrop of generally rising levels of dopamine in the postnatal eye. This means that, whereas the function of dopamine is to promote hyaloid vessel regression, the effect of 380-nm photons and OPN5 is to suppress regression of the hyaloid vessels. It is likely that this has evolved as a mechanism to optimize the timing of hyaloid vessel regression and ensure that they remain functional postnatally until the superficial retinal vascular plexus is complete. According to some embodiments, OPN4 also mediates light-dependent vascular development in the eye and suppresses VEGFA levels because it keeps retinal cellularity in check, and thus limits the oxygen demand that can elevate levels of VEGFA (FIG. 25*l*). The crucial window for activation of the OPN4 response is in late gestation and requires a direct light stimulation of the mouse fetus. Thus, the OPN4 and OPN5 response pathways use distinct mediators to regulate vascular development and, as they function at different stages of development, can be thought of as developmental timing cues (FIG. **25*l***). Notably, the spontaneous waves of neuronal activity that arise in the neonatal mouse retina are partly dependent on OPN4 modulation of gap junctions that are, in turn, regulated by dopamine. According to some embodiments, the relationship of retinal wave activity to vascular development may be assessed.

OPN5 is highly conserved and it may bet anticipated that the described pathway (FIG. **25*l*) will be relevant to human biology. According to some embodiments, the latter steps in the pathway involving DRD2-dependent suppression of VEGFR2 activity may be an explanation for the observation that premature infants treated with dopamine (for hypotension) have a higher risk of retinopathy of prematurity, a vascular overgrowth disease. According to some embodiments, therapeutic dopamine promotes regression of the hyaloid vessels and thus exacerbates the hypoxia that leads to rebound vascular overgrowth. Furthermore, the risk of retinopathy of prematurity in premature infants is partly dependent on their season of gestation, with short days and lower light exposure associated with higher risk. It is possible that the OPN5-dopamine pathway is a component of this risk equation because insufficient light would be expected to result in elevated levels of vitreal dopamine, precocious hyaloid regression and thus a more profound hypoxia in the premature eye. An understanding of the relationship between OPN4-dependent and OPN5-dependent regulation of vascular development in the eye (FIG. 25*l***) raises the interesting possibility that, according to some embodiments, premature infants at risk for retinopathy of prematurity might be treated with a light therapy that differentially targets each pathway response. Moreover, according to some embodiments, both violet light in the 360-400-nm range and dopamine are key regulators of refractive development and that each can suppress progression to myopia. The current observations suggest that the OPN5-dopamine pathway is likely to be involved.

Methods

Mice. Animals were housed in a pathogen-free vivarium and all pharmacological treatments were in accordance with protocols approved by the Institutional Animal Care and Use Committee at Cincinnati Children's Hospital Medical Center. This study is compliant with all relevant ethical regulations regarding animal research. Day of birth is defined as P1. Genetically modified mice used in this study were: Chx10-cre (Tg(Chx10-eGFP/cre-ALPP)2Clc/J) (Jax source 005105), Pdgfb-icreER(T2)[60], Rx-cre[49], Ai14 (Jax stock 007914), Brainbow (Jax stock 021227; Brainbow 3.2), $Drd2^{eGFP}$ (Tg(Drd2-eGFP)S118Gsat)[61], $Drd2^{loxp}$ (Jax stock 020631), $Flt1^{flox}$ (Jax stock 02809 Vegfr-1flox), $TH^{flox}$ (ref[48]), $Vglut2^{fl}$ (Jax stock 012898), $Vgat^{fl}$ (Jax stock 012897), OPN4 (ref.[62]) and $OPN5^{tm1a(KOMP)Wtsi}$, that were generated from C57BL/6N embryonic stem cells obtained from KOMP (embryonic stem clone ID: KOMP-(HTGRS6008_A_B12-OPN5-ampicillin). The embryonic stem cells harbour a genetic modification in which a Lacz-Neomycin cassette is flanked by FRT sites, between exon 3 and exon 4, and a loxp site separates Lacz from the neomycin coding region. Loxp sites also flank exon 4 of OPN5, allowing multiple mouse lines that can serve as reporter nulls, conditional floxed and null mice. The OPN5fl allele was created by crossing the $OPN5^{tm1a(KOMP)Wtsi}$ mice to FLPeR (Jax stock 003946) to remove the LacZ cassette. The $OPN5^{-/-}$ line was created by crossing the $OPN5^{fl}$ mice to E2a-cre (Jax stock 003724). Littermate control animals were used for all experiments with the exception of C57BL/6J mice, which were reared under different lighting conditions.

The genotyping primers and protocol for alleles except OPN5 are described in the cited publication or on the Jackson Labs website. Primer sequences for genotyping the OPN5−/− or OPN50/f alleles are: F1: CACAGTATGTGTGACAACCT (SEQ ID NO: 48); R1: GTGGACAGATTAACTGAAGC (SEQ ID NO: 49); R2: GAACTGATGGCGAGCTCAGA (SEQ ID NO: 25). F1-R1 gives a 626-bp WT band and also gives a 700-bp band from the $OPN50^{fl}$ allele. F1-R2 gives a 376-bp band for $OPN5^{null}$ and a 1,617-bp band from the $OPN5^{fl}$ allele. Primer sequences for genotyping the OPN5cre allele are: OPN5creF1: TGGAAAGAGATGCATTTGTGAG (SEQ ID NO: 45); OPN5creF2: CACTGCATTCTAGTTGTGGTTTGTCC (SEQ ID NO: 47); OPN5creR1: ACAGCCTATGAATTCTCTCAATGC (SEQ ID NO: 46). F1-R1 gives a 300-bp band for WT allele and F2-R1 gives a 209-bp band for the cre allele.

The OPN5cre mice were generated in-house using CRISPR (clustered regularly interspaced short palindromic repeats)-Cas9 (CRISPR-associated protein 9) technology. Four guide RNAs that target exon 1 of OPN5 were selected to knock in the Cre cassette. Plasmids containing the guide RNA sequence were transfected into MK4 cells (an in-house mouse cell line representing induced metanephric mesenchyme undergoing epithelial conversion). The editing efficiency of guide RNA was determined by the T7E1 assay of PCR products of the target region amplified from genomic DNA of transfected MK4 cells. The sequence of the guide RNA that was subsequently used for the transfection is TGGAGTCCTACTCGCGGACG (SEQ ID NO: 44). Sanger sequencing was performed to validate the knock-in sequence of founder mice.

Mice were placed on a normal chow diet (29% protein, 13% fat and 58% carbohydrate kcal; LAB Diet 5010) ad libitum with free access to water. Littermate controls were used for genetic crosses and both male and female pups were included in the study.

Lighting conditions. Animals were housed in standard fluorescent lighting (photon flux: $1.62\times10^{15}$ photons $cm^{-2}s^{-1}$) in a 12 light/12 dark cycle except where noted. For full-spectrum lighting (VBGR), LEDs were used to yield a comparable total photon flux of $1.68\times10^{15}$ photons $cm^{-2}s^{-1}$. Spectral and photon flux information for LED lighting: violet ($\lambda_{max}$=380 nm, $4.23\times10^{14}$ photons $cm^{-2}s^{-1}$ in 370-400-nm range), blue ($\lambda_{max}$=480 nm, $5.36\times10^{15}$ photons $cm^{-2}s^{-1}$ in 430 530-nm range), green ($\lambda_{max}$=530 nm, $5.82\times10^{15}$ photons $cm^{-2}s^{-1}$ in 480-600-nm range) and red ($\lambda_{max}$=630 nm, $1.93\times10^{15}$ photons $cm^{-2}s^{-1}$ in 590-660-nm range). For wavelength-restricted hyaloid assessment, C57BL/6J animals were housed in a 12 light/12 dark cycle starting at late gestation (embryonic day 18 (E18)) either in full spectrum (VBGR) or without violet (BGR) lighting. For dark-reared experiments, pregnant dams were moved to the dark at gestation age E16. For light induction experiments, on P7 at lights off, nursing females and pups were moved to the dark for 24-h dark adaptation. $OPN5^{+/+}$ and $OPN5^{-/-}$ pups were subjected to ±30 min of 380-nm light at $1\times10^{12}$ photons $cm^{-2}s^{-1}$ (approximately 1% of clear sky summer day sunlight at this wavelength) at 2 h after subjective lights off.

Immunohistochemistry and imaging. Animals were anaesthetized under isoflurane and killed by cervical dislocation or decapitation for early post-natal pups. Preparation and immunofluorescence staining of retinae and hyaloid vessels were as described previously[39]. For phospho-T53-DAT quantification, the retinae of each genotype and light condition were collected in dim red light (dark adapted) or normal light from at least three different induction experiments and mounted in the same OCT (optimal cutting temperature) blocks. Retinal sections were processed, stained and imaged together to compensate for batch differences. Alexa-conjugated secondary antibodies were purchased from Jackson ImmunoResearch. Images were captured using Zeiss ApoTome AX10 or Zeiss LSM700 confocal microscopes and processed by ImageJ (NIH) and Adobe Photoshop (Adobe Systems).

ELISA. Vitreous and retinae from pups were collected and rapidly frozen on dry ice. To detect dopamine levels, vitreal samples were pooled from three to six pups depending on age and six retinae for each n. Dopamine extraction and ELISA were performed according to the manufacturer's protocol using BA E-5300 (Rocky Mountain Diagnostics). For dark-adapted experiments, the vitreous and retinae were collected under dim red light. To detect VEGFA and FLT1 levels, samples from P5 pups were pooled from six eyes for each n. The mouse VEGFA kit Quantikine (MMV00) and the mouse VEGFR1 (FLT1) kit Quantikine (MVR100) from R&D systems were used. ELISA was read by using the EnVision Multimode Plate Reader (Perkin Elmer).

Pharmacological reagents and treatments. All dopamine pharmacological modulators, except for the antagonist 2-CMDO (2-chloro-11-(4-methylpiperazino) dibenz(Z)[b,f] oxepin maleate), were injected at 1 mg per kg body weight intraperitoneally into nursing dams on the day of birth and at P2, then directly into pups until P8. 2-CMDO was injected into pups at P5-P8 at 2 mg per kg body weight. Injection was done in dim red light 1 h before the lights were turned on. Dopamine agonist SKF38393 hydrobromide, the high-affinity D2 antagonist L-741626, the dopamine transporter 1 inhibitor GBR12909 dihydrochloride and 2-CMDO were all purchased from Tocris Biosciences. For experiments with Pdgfb-icreERT2 mouse lines, 2 mg tamoxifen was injected into nursing dams on the day of birth and on P2 to activate tamoxifen-dependent cre.

Western blotting. Western blots were performed using standard protocols. Immediately after dissection, 12 hyaloid vascular tissues or retinae of P6 (6 pups) were pooled in 100 μl of 1× Laemmli sample buffer and sonicated. After centrifugation, 20 μl supernatant was loaded on 4-20% gradient protein gel (Thermo Fisher Scientific). Separated protein bands were transferred to a PVDF (polyvinylidene difluoride) membrane, and bands were visualized by chemiluminescence (Thermo Fisher Scientific). Band intensity was measured by ImageJ (NIH). The following antibodies were used for western blotting: VEGFR2 (9698, Cell Signaling Technology), phospho-VEGFR2 (2478, Cell Signaling Technology), 0-tubulin (ab6046, Abcam), DAT (NB300-254, Novus), phospho-DAT (PA5-35414, Thermo Fisher Scientific), AKT (4691, Cell Signaling Technology) and phospho-AKT S473 (4060, Cell Signaling Technology). All antibodies were used at 1:1,000 dilution.

Statistics and reproducibility. Samples for immunoblots were pooled from multiple animals (six pups for hyaloid vasculature and six retinae) and each experiment was repeated at least twice with independent samples. ELISA assessment was performed at least twice with independent biological samples. Each n in this analysis is a separate animal with the exception of immunoblots and ELISA, for which pooled samples from animals of the same genotype represent one n. Retinal images with immunofluorescence labelling represent n=3 independent biological samples from separate litters. Data gathered for hyaloid vessel quantification represent samples from multiple litters to reach n indicated on charts for each genotype and condition. Data are presented as mean±s.e.m. (standard error of the mean) in aligned dot plots overlaid with a bar or line graph. Statistical analyses were performed using GraphPad Prism version 4.00 (GraphPad Software) and Microsoft Excel for two-tailed Student's t-test, one-way or two-way analysis of variance (ANOVA) as indicated. Two-tailed distribution, two-sample unequal variance t-test was used to determine the statistical significance between two independent groups except for FIG. 25*m*, which is one-tailed. Sidak's or Tukey's multiple comparison test were performed post-hoc when significance differences were found in ANOVA.

Reporting Summary

Statistics

Data collection: Perkin Elmer Envision Plate Reader: Wallac Envision Manager version 1.12. Zeiss Zen Software for image acquisition Data analysis: Fiji by ImageJ (NIH) Photoshop CS3 (Adobe) Excel 2016 (Microsoft) GraphPad Prism v4.00 (GraphPad Software, Inc.)

Data

Data exclusions: No data was excluded

Replication: For all genetic models and pharmacological treatments, multiple litter cohorts were measured to eliminate the effect of litter and demonstrate reproducibility. For all immunohistochemistry, tissues from multiple animals (n>=3) across different litters were collected and analyzed. Drd2-eGF hyaloid images were from 2 Drd2-eGFP+ eyes (A generous gift from Dr. D. Copenhagen). For Western blot experiments, hyaloids were pooled from different litters (n=8 eyes) for each genotype and experiments were repeated three times. For VEGFA and FLT1 ELISA, vitreal for each genotype was pooled from 6 individual eyes for each n, n=3. For Dopamine extraction and ELISA, vitreal fluid for each genotype was pooled from >=6 eyes for each n, n=3 except for OPN5+/+ (n=2). Retinal tissue from six individual eyes were pooled for each n of dopamine extraction and ELISA. 2-3 independent ELISA were performed, depending the genotype and tissues. For pDAT quantification, retinae of each genotype and light condition were collected from at least 3 different induction experiments and mounted in the same OCT blocks. Retinal sections were processed, stained, and imaged together to compensate for batch differences. For C57BL/6J LD and DD dopamine time course, pups from each litter were split randomly to different time points.

Randomization: The studies conducted in this manuscript compared wildtype (control) and mutant (experimental) animals, which were allocated into groups based on genotype. There was randomization while assigning litters from genetic models to different experiments. Pups from C57BL/6J litters were randomly selected and designated for pharmacological or vehicle treatment. Animals were randomized into different experiments from a cohort of litters, where one control and experimental animal from each litter was designated for a particular experiment while the littermates were assigned to another purpose. For light induction experiments, pups of different genotype were randomly assigned to dark-adapted only or dark-adapted plus light-induced from different litters to achieve enough sample size.

Blinding: For all pharmacological treatments, the investigators were blinded to the genotype during the course of treatment except for C57BL/6J. For Western blot and ELISA investigators were not blinded to the genotypes of the animals since samples were pooled. Investigators were not blinded for experiments with differential lighting conditions (hyaloid vessel and retinal labelling). Investigators were blinded to the genotype for other hyaloid vessel and retinal vessel quantification, and genotype was assigned to data at the end point.

Antibodies

Antibodies used: Primary antibody for IF Source Calretinin (1:100) MAB1568 (Millipore) Drd2 (1:200) ADR-002 (Alomone) ChAT (1:200) AB144 (Millipore) DAT/SLC6A3 (1:200) MAB369 (Millipore) RBPMS (1:200) AB194213 (Abcam) Melanopsin (1:1000) AB-N38 (Advance Targeting Systems) pDAT (1:500) PA5-35414 (Thermo Fisher Scientific) Tyrosine Hydroxylase (1:1000) AB1542 (Millipore) Primary antibody for Western Source AKT (1:1000) #4691 (Cell Signaling Technology) pAKT-Ser473 (1:1000) #4060 (Cell Signaling Technology) DAT (1:1000) NB300-254 (Novus) pDAT (1:1000) PA5-35414 (Thermo Fisher Scientific) VEGFR2 (1:1000) #9698 (Cell Signaling Technology) pVEGFR2 (1:1000) #2478 (Cell Signaling Technology)-Tubulin (1:1000) ab6046 (Abcam)

Validation: All antibodies were validated by both the manufacturer and using negative controls in this study Eukaryotic Cell Lines Cell line source(s): MK4 cells were used within the CCHMC Gene Targeting Core Facility to test the efficacy of guide RNAs for CRISPR Authentication: MK4 cells were generated at CCHMC (from mouse metanephric mesenchyme) and so are the original source material Mycoplasma contamination: We do not have information on whether this cell line was tested for mycoplasma contamination.

Commonly misidentified lines (See ICLAC register): MK4 are an original, in house isolate Animals and Other Organisms Laboratory animals: Animals were housed in a pathogen-free vivarium and all pharmacological treatments were in accordance with CCHMC institutional policies. Afternoon on day when pups were seen in the morning is defined as P1. Genetically modified mice used in this study were: Chx10crel (Jax stock #00515), PdgfbicreER (T2) 2, Rxcre3, Ai144 (Jax stock #007914), Brainbow5 (Jax stock #021227 Brainbow 3.2), Drd2EGFP (ref 6) (Tg (Drd2-EGFP) S118Gsat), Drd2loxp (Jax stock #020631), Flt1flox (ref 8) (Jax stock #02809 Vegfr-1flox), THflox (ref 9) OPN410 and OPN5tmla (KOMP) Wtsi that were generated from C57BL/6N ES cells obtained from KOMP (ES clone ID: KOMP-(HTGRS6008 A B12-OPN5-amplicillin). The ES cells harbour a genetic modification wherein a Lacz-Neomycin cassette is flanked by FRT sites, between exon 3 and exon 4 and a loxp site separates Lacz from the neomycin coding region. Loxp sites also flank exon 4 of OPN5 allowing multiple mouse lines that can serve as reporter nulls, conditional floxed and null mice. The OPN5fl allele was created by crossing the OPN5tmla (KOMP) Wtsi mice to FLPeR11 (Jax stock #003946) to remove the LacZ cassette. The OPN5−/−line was created by crossing the OPN5fl/fl mice to E2a-Cre12 Jax stock #003724). Littermate control animals were used for all experiments with the exception of C57BL/6J mice reared under different lighting conditions. The OPN5cre was generated in-house using CRISPR-Cas9 technology. Four gRNAs that target exon 1 of OPN5 were selected to knock in the Cre cassette. Plasmids containing the gRNA sequence were transfected into MK4 cells (an in-house mouse cell line representing induced metanephric mesenchyme undergoing epithelial conversion). The editing efficiency of gRNA was determined by T7E1 assay of PCR products of the target region amplified from genomic DNA of transfected MK4 cells. The sequence of the gRNA that was subsequently used for the transfection is TGGAGTCCTACTCGCGGACG (SEQ ID NO: 44). Sanger sequencing was performed to validate the knock-in sequence of founder mice. Mice were placed on normal chow diet (NCD: 29% Protein, 13% Fat and 58% Carbohydrate kcal; LAB Diet #5010) ad libitum with free access to water. With the neonatal stage for this analysis, animals were not matched for sex.

A Direct and Melanopsin-Dependent Fetal Light Response Regulates Mouse Eye Development Summary Vascular patterning is critical for organ function. In the eye, there is simultaneous regression of embryonic hyaloid vasculature (important to clear the optical path) and formation of the retinal vasculature (important for the high metabolic demands of retinal neurons). These events occur postnatally in the mouse. According to some embodiments, a light-response pathway is identified that regulates both processes. According to some embodiments, when mice are mutated in the gene (OPN4) for the atypical opsin melanopsin, or are dark-reared from late gestation, the hyaloid vessels are persistent at 8 days post-partum and the retinal vasculature overgrows. Evidence is provided that these vascular anomalies are explained by a light-response pathway that suppresses retinal neuron number, limits hypoxia and, as a consequence, holds local expression of vascular endothelial growth factor (VEGFA) in check. It is also shown that the light response for this pathway occurs in late gestation at about embryonic day 16 and requires the photopigment in the fetus and not the mother. Measurements show that visceral cavity photon flux is probably sufficient to activate melanopsin-expressing retinal ganglion cells in the mouse fetus. These data thus show, according to some embodiments, that light—the stimulus for function of the mature eye—is also critical in preparing the eye for vision by regulating retinal neuron number and initiating a series of events that ultimately pattern the ocular blood vessels.

Figures 26A, 26B, 26C:
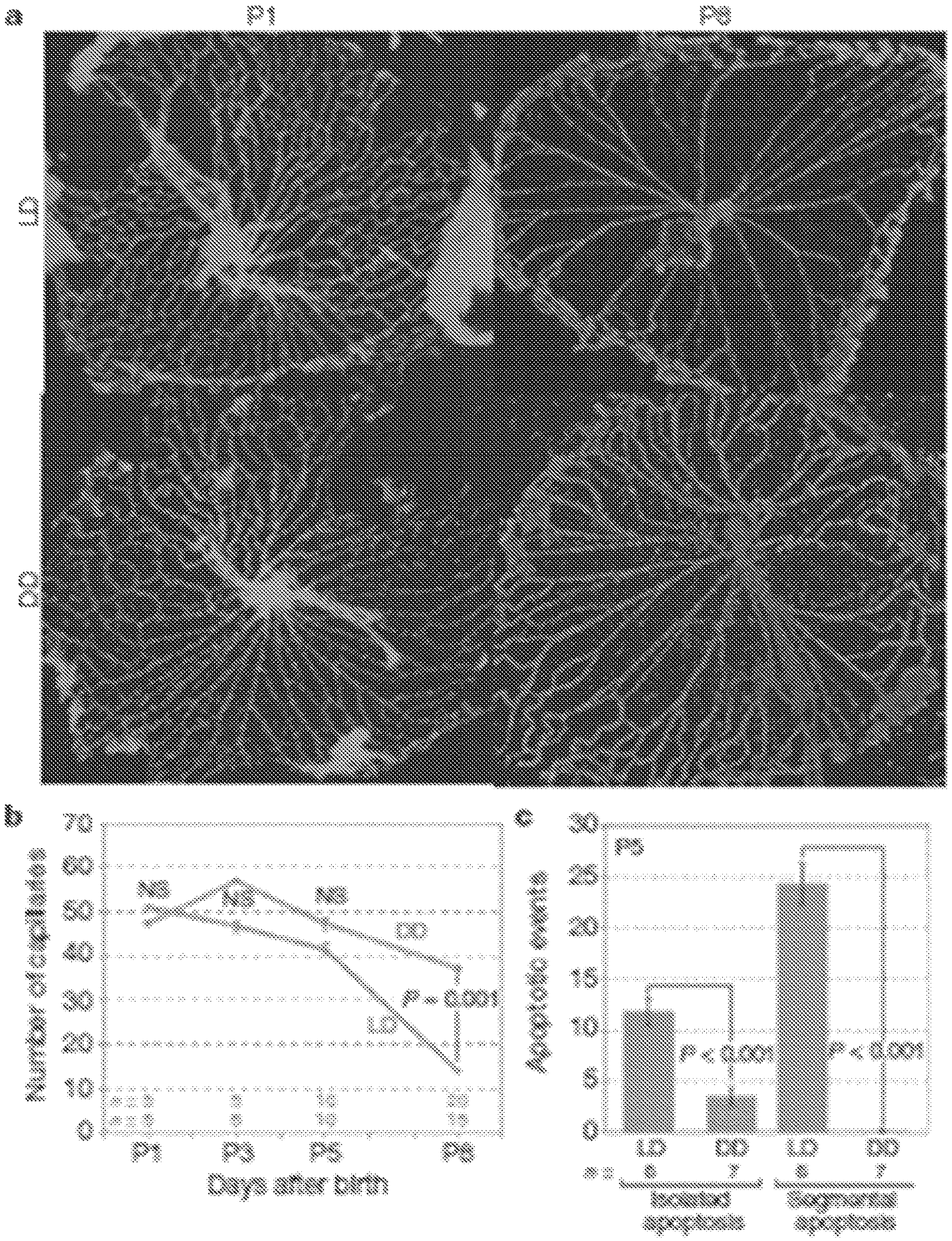
FIG. 26 illustrates, according to some embodiments, hyaloid regression is regulated by light.

Prompted by the recognition that newborn mice are light-responsive and show light-dependent neuronal connectivity changes, according to some embodiments, a pathway exists in which light responsiveness in the early retina might trigger hyaloid regression and thus clearance of the optic axis. To test this, pregnant dams were placed in the dark at late gestation (embryonic (E) day 16-17): pups raised in the dark until 8 days postpartum (P8) showed persistent hyaloid vessels (FIG. 26*a*) and this was confirmed by quantification over a P1-P8 time course (FIG. 26*b*). Assessment of hyaloid vessel numbers at P15 showed that by this stage they had regressed. This indicated that dark-rearing resulted in a regression delay. Quantification of apoptosis at P5 showed that regardless of whether we quantified the isolated events that predominate early in hyaloid regression or the segmental pattern of apoptosis that follows, there was a reduction (FIG. 26*c*) similar quantitatively to previously characterized hyaloid persistence mutants. These data suggest that a light-response pathway promotes hyaloid regression.

Hyaloid vessel regression and superficial layer retinal angiogenesis occur at the same time in the mouse, and this indicated that dark-rearing might affect both processes. Retinal angiogenesis in mice begins at the day of birth with the extension of vessel precursors from the head of the optic nerve. A superficial layer of vasculature within the retinal ganglion cell (RGC) layer extends to the retinal periphery by P7. Starting at about P8, angiogenic sprouts extend vertically downwards into the deeper layers of the retina and ultimately form the deep vasculature at the outer edge of the inner nuclear layer and the intermediate plexus within the inner plexiform layer2. In mice dark-reared from E16 to E17, the superficial vascular plexus showed an increase in density regardless of whether the region was simple plexus or at a vein. Depth-coded P8 image stacks showed that there were many more descending vessels than in the wild type and many of these were abnormally located. These changes were confirmed by quantification. Thus, the retinal vasculature is a second vascular structure in the eye where normal development is disrupted by the absence of light.

The following are shown in FIG. 26, e.g., Hyaloid regression is regulated by light:

a, Hyaloid vessel preparations at the indicated postnatal (P) days from pups reared under normal light conditions (LD) or under constant darkness (DD) from E16-17. Original magnification, 350. b, As in a but a quantification of vessel number from P1 to P8. P values obtained by analysis of variance (ANOVA). c, P5 apoptotic index in hyaloid vascular cells (isolated apoptosis) or vessels undergoing a segmental pattern of apoptosis. P values obtained by Student's t-test. Sample size (n) as labelled. NS, not significant. Error bars are s.e.m.

Figure 27A:
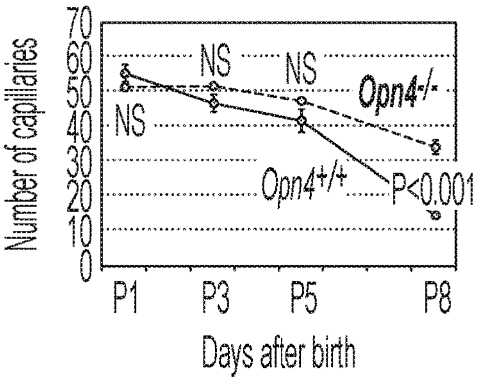
FIG. 27 illustrates, according to some embodiments, hyaloid regression and retinal angiogenesis are regulated by melanopsin.
Figure 27J:
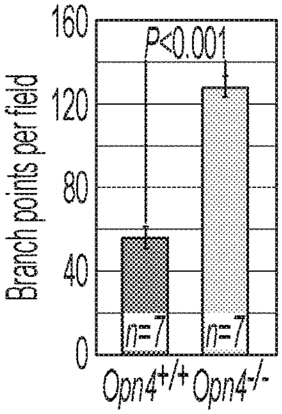
Figure 27K:
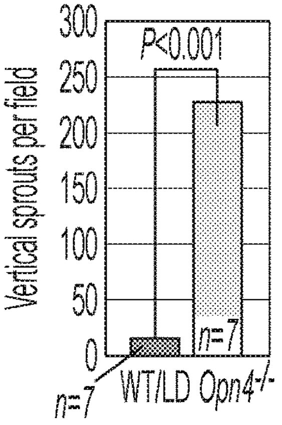
Figures 27B, 27C, 27D, 27E:
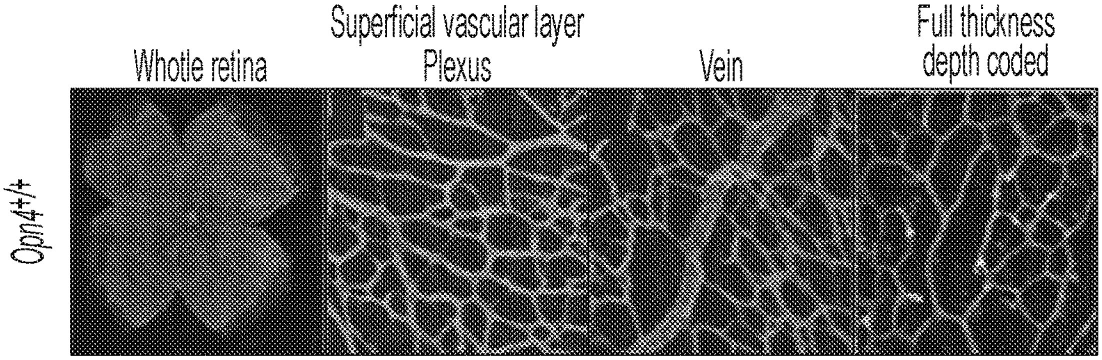
Figures 27F, 27G, 27H, 27I:
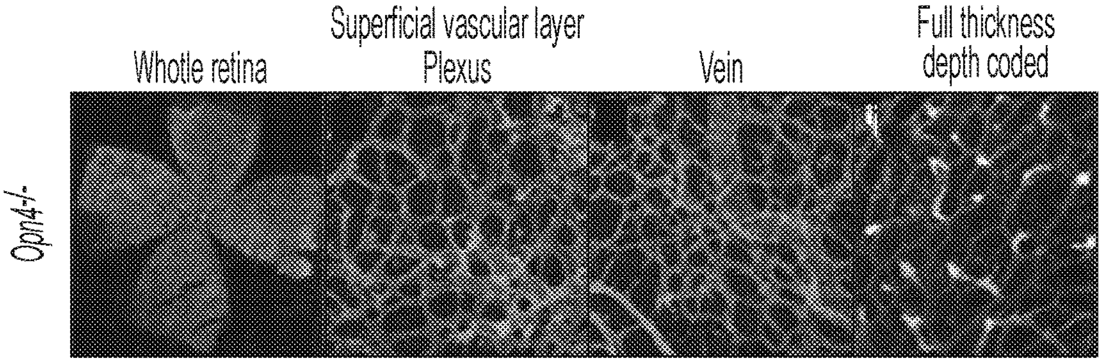

Melanopsin is expressed from an early stage of both mouse and human gestation and unlike photoreceptor opsins, is known to function in the mouse eye before P10. Melanopsin-expressing intrinsically photosensitive retinal ganglion cells (ipRGCs) are a subset of RGCs that function in circadian entrainment and the pupillary reflex. ipRGCs are located in the superficial layers of the retina adjacent to both the retinal and hyaloid vasculatures. This location, the pre-photoreceptor functions of melanopsin and the vascular anomalies present in mice that are missing RGCs, suggested, according to some embodiments, that it was a good candidate to mediate light-dependent vascular development in the eye. To test this possibility, hyaloid vessel regression and retinal vascular development were assessed in mice mutated in Opn4, the melanopsin-encoding gene. Opn4−/− mice showed normal hyaloid vessel numbers at P1 but persistence at P8 (FIG. 27*a*). Examination of P15 eyes showed that hyaloid regression was complete in the Opn4−/− mice, indicating that, as with dark-reared mice, hyaloid persistence was not long term. Opn4−/− mice also showed a retinal vascular overgrowth phenotype that qualitatively and quantitatively (FIG. 27*b-k*) mimicked the changes resulting from dark rearing. To determine whether changes in retinal vascular density endured, a quantitative assessment was performed at P15, P25 and P180 that showed that elevated vascular density was regionally sustained until at least P180. More generally, the vascular phenotype of the Opn4−/− mice phenocopies that observed in dark-reared mice. This provides an independent means of implicating a light-response pathway in vascular development of the eye and identifies melanopsin as the opsin required.

Figure 28A:
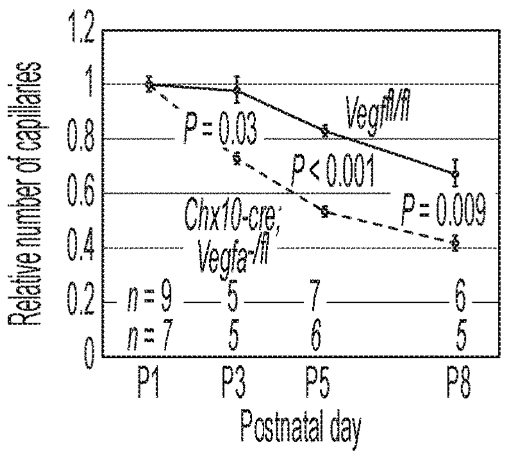
FIG. 28 illustrates, according to some embodiments, light and melanopsin-dependent regulation of VEGFA expression and hypoxia in the retina.
Figure 28B:
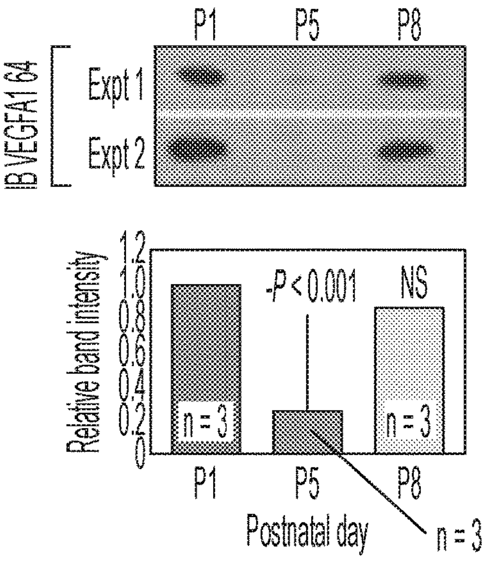

VEGFA is a potent signal for vascular endothelial cell survival that is required for retinal angiogenesis and is also present in the vitreous of the rodent and human eye where the hyaloid vessels reside. According to some embodiments, light-dependent vascular development might be explained by modulation of VEGFA. Consistent with this, homozygous and heterozygous deletion of $Vegfa^{fl}$ with the Chx10-cre retinal driver[18] gave, respectively, either a hyaloid development failure or diminished hyaloid regression (FIG. 28*a*). An immunoblot for vitreous VEGFA over the P1-P8 time course revealed that in control mice, VEGFA164 levels were reduced at P5 but rose again by P8 (FIG. 3*b*). When three different time courses of VEGFA immunoblots were quantified, the P5 VEGFA signal was about fivefold reduced compared with P1 (FIG. 28*b*). A low level of VEGFA at P5 is consistent with the idea that it is a key regulator of hyaloid regression because P5 is the time when there are peak levels of vascular endothelial cell apoptosis.

Figure 28C:
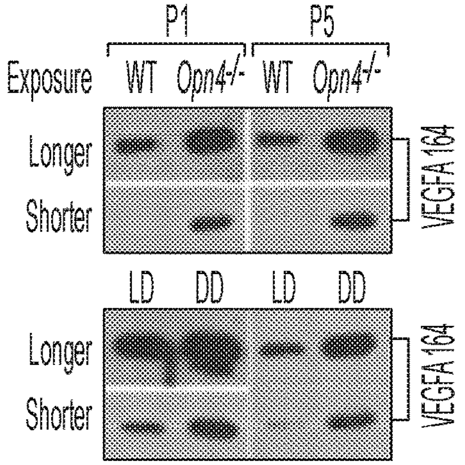
Figure 28D:
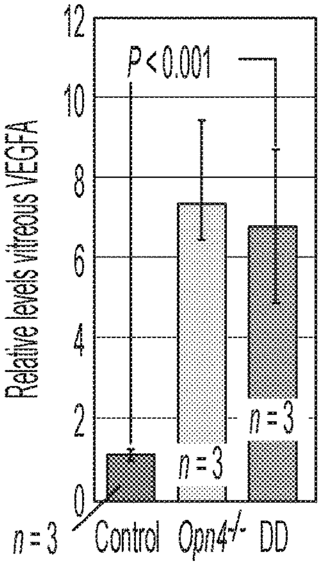
Figure 28E:
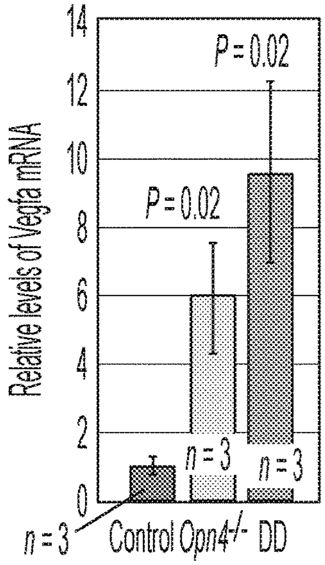

Using dark rearing and the $Opn4^{-/-}$ mice, it was determined whether actual or functional darkness resulted in a modulation of vitreous VEGFA. In four independent experiments it was consistently observed that vitreous VEGFA levels were increased regardless of how light responsiveness was compromised (FIG. 28*c*). Furthermore, an enzyme-linked immunosorbent assay (ELISA)-based assessment of VEGFA in the P5 vitreous showed that whether pups were dark-reared or mutated in Opn4, the levels of VEGFA were about sevenfold higher than in the control (FIG. 28*d*). A sevenfold increase in VEGFA in the vitreous of dark-reared and $Opn4^{-/-}$ mice was reflected in similar fold increases in the level of retinal Vegfa messenger RNA as indicated by quantitative polymerase chain reaction (qPCR) (FIG. 28*e*). Flow sorting/qPCR further showed that $Thy1.11^{+}$ RGCs and $Thy1.1^{-}Vc1.11^{+}$ amacrine/horizontal cells exhibited an increase in Vegfa mRNA, although $Thy1.1^{-}Vc.1^{-}PDGFR^{+}$ astrocytes did not. Given the VEGFA dependence of hyaloid vessels and of retinal angiogenesis, elevated retinal VEGFA expression is an explanation for the vascular anomalies observed in dark-reared and $OPN4^{+/+}$ mice.

The following are shown in FIG. 27, e.g., Hyaloid regression and retinal angiogenesis are regulated by melanopsin:

a, Quantification of hyaloid vessels in Opn4+ and $Opn4^{-/-}$ mice over a P1 to P8 time course. P values obtained by ANOVA. b-i, Low (×100; b, f) and high (λ200; c-e, g-i) magnification images of isolectin-labelled P8 retina from wild-type (b-e) and Opn4-(f-i) pups raised in normal lighting. e, i, Depth-coded z stack images for wild type (e) and Opn4 (i) indicate the appearance of vertical angiogenic sprouts. j, k, Graphs show quantification of branch points (j) and vertical sprouts (k) in animals of the indicated genotypes. WT, wild type. P values obtained by Student's t-test. Errors bars are s.e.m. Sample sizes (n) as labelled.

The following are shown in FIG. 28, e.g., Light and melanopsin-dependent regulation of VEGFA expression and hypoxia in the retina:

a, Hyaloid vessel number from P1 to P8 in mice of labelled genotypes. P values obtained by ANOVA. b, Vitreous VEGFA immunoblot (IB) for wild-type mice at P1, P5 and P8 with quantification histogram. c, Immunoblot for P1 or P5 vitreous VEGFA in wild-type and $OPN4^{-/-}$ mice or in mice reared in LD or DD light conditions as labelled. d, ELISA quantification of VEGFA levels in the P5 vitreous of control/LD mouse pups (grey bar) from $OPN4^{-/-}$ mice (pale blue bar) or those raised in constant darkness from E16-17 (DD, blue bar). e, qPCR detection of Vegfa mRNA in P5 retina from control/LD (grey bar), $OPN4^{-/-}$ mice (light blue bar) and dark-reared mice (DD, dark blue bar). P values in b, d, e were obtained by Student's t-test. Sample sizes (n) as labelled. Error bars are s.e.m. f, g, Labelling of flat-mount P5 retinas from wild-type (f) and OPN4-(g) mice for blood vessels (isolectin, green) and for hypoxia (red). Retinal myeloid cells label faintly with isolectin. Original magnification, 3100. h, i, Quantification of the relative levels of hypoxyprobe labelling in the retinas of LD and DD mice (c) and wild-type versus $OPN4^{-/-}$ (d) retinas.

Figure 28F:
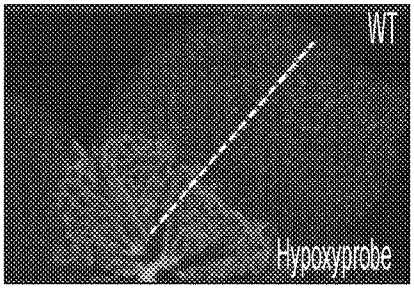
Figure 28G:
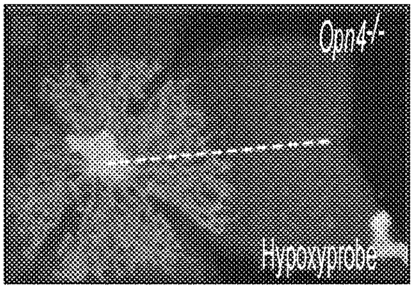
Figure 28H:
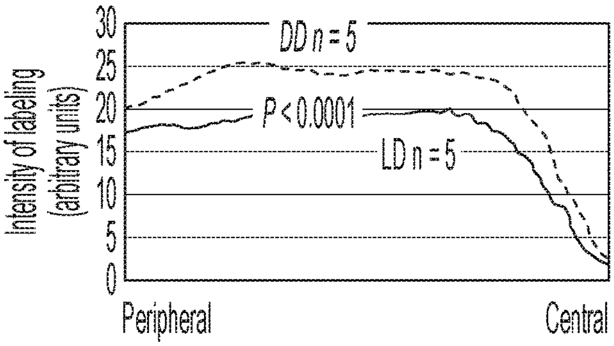
Figure 28I:
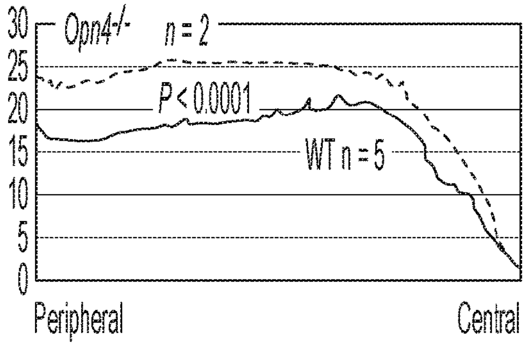

Quantification of BRN3B+ RGCs and calretinin+ amacrine cells in P5 OPN4−/− mice revealed modest increases in the numbers of both cell types. It has been shown that retinal angiogenesis in the mouse is driven by a hypoxia-response pathway that upregulates VEGFA expression. Because increased cell number can increase oxygen demand, it was tested whether the OPN4 mutation and dark rearing resulted in retinal hypoxia (FIG. 28*f, g*). Quantification of labelling with hypoxyprobe at P5 (FIG. 28*h, i*) revealed that increased signal was a consequence of both OPN4 mutation and dark rearing. This is consistent with, according to some embodiments, that elevated VEGFA expression in the retina is a consequence of increased oxygen demand due to higher numbers of retinal neurons.

The following are shown in FIG. 29, e.g., Gestational light controls vascular development in the eye:

a, Quantification of hyaloid vessels in mice raised in normal lighting (LD, grey bar) and those dark-reared from E16-17 (dark-blue bar), E17-18 (medium-blue bar), or after E18 (light-blue bar). b, c, P8 hyaloid vessel preparations from a wild-type embryo transferred into a wild-type pseudopregnant female (WT>WT) and an $OPN4^{-/-}$ embryo transferred into a wild-type pseudopregnant female ($OPN4^{-/-}$>WT). Original magnification, 350. d, Left panel: quantification of hyaloid vessels in P8 WT>WT (n 5) and $OPN4^{-/-}$>WT (n 6) pups. Right panel: quantification of hyaloid vessels in normal control pups at P8 (C; n=8) and P8 pups (n 8) born to an enucleated female (EN). Sample sizes (n) as labelled. P values in a by ANOVA; P values in d were obtained by Student's t-test. Errors bars are s.e.m.

Figure 29A:
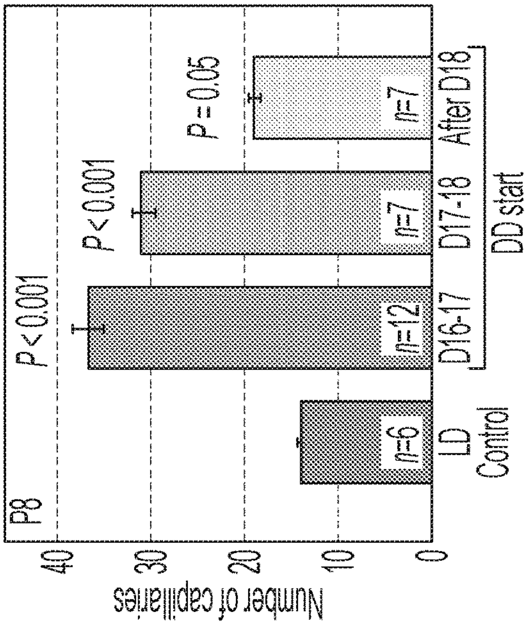
FIG. 29 illustrates, according to some embodiments, gestational light controls vascular development in the eye.
Figure 29B:
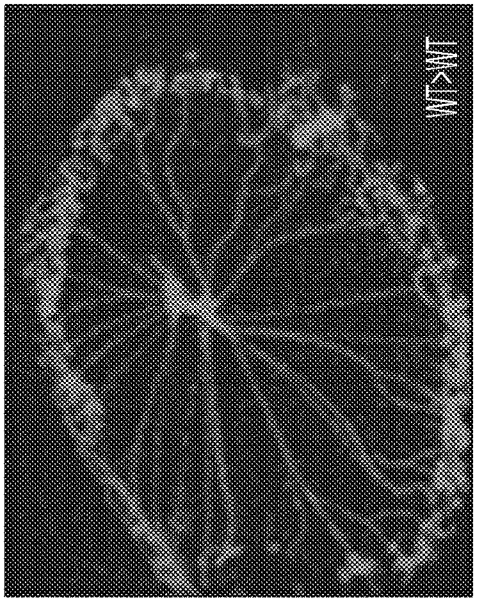
Figure 29C:
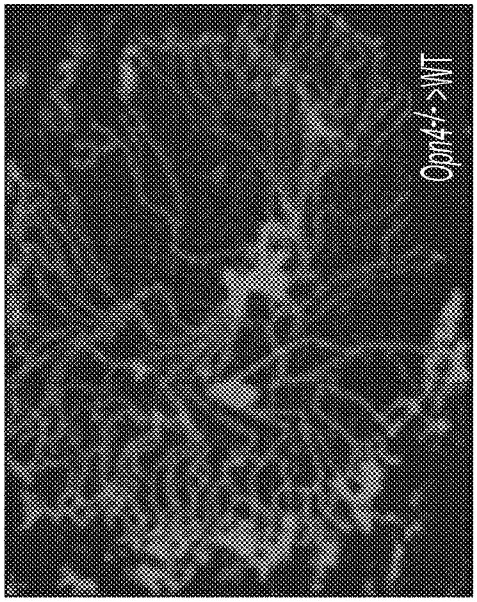
Figure 29D:
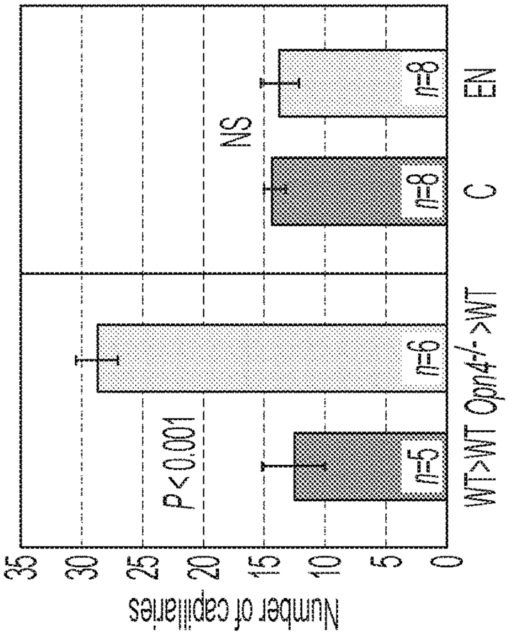

In assessing the role of light responses in vascular development of the eye, according to some embodiments, a presumption had been that birth was probably a triggering event because vascular patterning events occur after birth and because light levels to the eye of the newborn would increase. To test this, pups were dark-reared from different points of late gestation (E16-17, E17-E18 or after E18) and assessed hyaloid persistence. A dose response was observed where the hyaloid vessels were progressively more persistent with an earlier dark-rearing start (FIG. 29*a*). In particular, if dark rearing was started after E18 (the day of birth is usually E19) there was almost no effect (FIG. 29*a*, light blue bar). These data indicate the surprising outcome that, according to some embodiments, the critical light-response period stimulating hyaloid regression is gestational, at or before E16-17. This further raised the possibility that, according to some embodiments, this developmental pathway required a direct fetal light response. To test this assertion directly, embryos were transferred from an OPN4+/−×OPN4+/− cross into a pseudo pregnant wild-type female and hyaloid regression was assessed. Control, wild-type pups in the transferred litter showed normal hyaloid regression (FIG. 29*d, b*, grey bar), whereas the OPN4−/− mice showed persistence at P8 (FIG. 29*d, c*, blue bar). In addition, to test the reciprocal possibility—that the light response of the mother might influence vascular development of the fetal eye—female mice were enucleated and allowed to gestate and raise litters under normal lighting conditions. This did not produce hyaloid persistence (FIG. 29*d*). Combined, these experiments show that, according to some embodiments, melanopsin in the fetus, not the mother, is critical to regulate vascular development of the eye.

Measurements of the light level in the visceral cavity of adult mice living under mouse room fluorescent lights revealed flux densities of $1.4\times10^{13}$ (for BALB/c) and $1.1\times10^{12}$ (for C57BL/6) photons $cm^{-2}$ $s^{-1}$. Published response thresholds for rodent ipRGCs range upwards from approximately $1.2\times10^{10}$ photons $cm^{-2}$ $s^{-1}$ (refs 21-23). Furthermore, according to some embodiments, ipRGCs have the ability to respond continuously to light stimulation, via melanopsin, for up to 10 h. Although it has been suggested that, according to some embodiments, ipRGCs in newborn mouse pups are less sensitive than in adults, the reduced sensitivity is about 1.5 log quanta and so the visceral light level in a pigmented animal of $1.1\times10^{12}$ photons $cm^{-2}$ $s^{-1}$ may still be above the threshold. These data are consistent with the hypothesis that, according to some embodiments, the mouse fetus can respond directly to light via melanopsin.

These experimental studies identify, according to some embodiments, light as a trigger for hyaloid vessel regression and for suppression of promiscuous angiogenesis in the retina. The observation that dark rearing from late gestation or OPN4 mutation produces essentially identical perturbations of vascular development provides corroborating evidence for involvement of a melanopsin-dependent, light-response pathway. Moreover, the data also indicates that, according to some embodiments, the origin of the hyaloid persistence and deregulated retinal angiogenesis is increased levels of VEGFA originating in retinal neurons. These findings are surprising because, with the exception of neuronal connectivity, it has not been shown previously that light can trigger changes in developmental programs. The data indicates that, according to some embodiments, the primary light-dependent change is an increase in the number of retinal neurons and that the vascular changes occur in response to increased oxygen demand considerably later in developmental time. This pathway is an interesting example of one where events unfold slowly over the course of nearly 2 weeks. According to some embodiments, it will be interesting to determine whether this pathway influences susceptibility to retinopathy of pre-maturity, the retinal vasculopathy of pre-term infants in which promiscuous angiogenesis can cause blindness.

Methods Summary

VEGFA was detected in the vitreous of OPN4 mutant and dark-reared mice using standard immunoblotting and ELISA (R&D) techniques. Retinal neurons were identified and enumerated using standard techniques of immunofluorescence labelling. The level of retinal hypoxia in OPN4 mutant and dark-reared mice was assessed using detection of injected pimonidazole hydrochloride (Hypoxyprobe). All animal experiments were performed in accordance with IACUC-approved guidelines and regulations.

Methods

Mice. Genotyping of $Vegfa^{fl}$ (ref. 26), Chx10-cre (ref. 18), $OPN4^{cre}$ (ref. 27), Ai4 (ref. 28) and $OPN4^{-/-}$ was performed as described. All animal experimentation was carried out using protocols approved by the Institutional Animal Care and Use Committee at Cincinnati Children's Hospital Medical Center and at the University of California San Francisco.

Hyaloid and retinal labelling and quantification. Hyaloid vessels were collected and stained with Hoechst as well as for TdT-mediated dUTP nick end labelling (TUNEL) as described. Retinal flat-mounts were prepared and labelled with isolect or for melanopsin. Hyaloid vessel quantification has been described previousl[1]. Retinal vessel density was quantified by counting vessel junctions using ImageJ for many X200 microscope fields. Depth-coded three-dimensional image reconstructions were generated using a Zeiss Apotome-equipped microscope in conjunction with Axiovision software. Antibodies for labelling of retinal flat-mounts included anti-Bm3b (Abcam), anti-calretinin (Millipore) and anti-melanopsin (ATS).

Assessment of hypoxia. P5 mouse pups were injected with 60 mg $kg^{-1}$ (about 180 μg per pup) pimonidazole hydrochloride (Hypoxyprobe), and after 45 min were killed and retinas collected. The rabbit primary antibody to pimonidazole hydrochloride was then used in conjunction with an anti-rabbit Alexa594 secondary to label retinal tissue. We quantified labelling by generating intensity values along line intervals extending from the retinal centre to the periphery. Pixel intensity values from 20 to 25 line intervals per retina and 5 to 6 retinas per genotype were averaged. Significance values were calculated using the MatLab ANOVA test.

Isolation and analysis of vitreous. Vitreous was collected from dark-reared pups in a room using red illumination. Eyes from P1 and P5 pups were washed twice in sterile ice cold PBS. Excess PBS was blotted using a kimwipe, a small slit was made through the retina and vitreous collected. ELISA was performed on the vitreous using the Vegfa Quantikine kits (R&D) that include recombinant protein standards. Immunoblots were probed with a unique carboxy-terminal antibody for VEGFA from Santa Cruz. Quantification was performed using ImageJ.

Cell sorting. For flow sorting using markers for retinal neurons, retina was dissociated as described[25] except 16 mg $ml^{-1}$ of liberase CI (Roche) and 20 μg $ml^{-1}$ of DNase I (Sigma) was used. Cells were then labelled on ice for 30 min with goat PDGFR-α, washed with PBS and labelled with PerCP-conjugated anti-CD90 (clone OX-7), FITC-conjugated anti-CD57 (clone VC1.1), Alexa fluor 350 and 7-AAD. Cells were sorted with FACSAria II running DiVa software.

RNA isolation and qPCR. RNA was isolated using RNeasy (Qiagen). qPCR was performed with QuantiTect SYBR green (Qiagen) using amplification of actin for normalization. In analyzing qPCR data, the P values refer to a comparison of the ΔΔCT values. Primers were as follows: Vegfa 5'-GACAGAACAAAGCCAGA-3' (SEQ ID NO: 50), 5'-CACCGCCTTGGCTTGTCAC-3' (SEQ ID NO: 51).

Light measurements. To estimate the radiant flux density impinging a mouse housed in a cage in the UCSF animal care facilities, we determined the spectral distribution of fluorescent lights, S(λrelative), illuminating the room and the absolute power (watts $cm^{-2}$ $s^{-1}$) of these lights. Both measurements were done at floor level. S(λrelative) was measured (Photo Research, PR670 spectraradiometer) as light reflected from a spectrally flat reflective surface (Spectralon Target, Labsphere). The radiant power was measured using a calibrated radiometric detector (UDT Instruments; model S471). S(λrelative) was converted to S (λabsolute) by scaling the area under S(λrelative) to match the radiant power and then converting these values to photons $cm^{-2}$ $s^{-1}$ for each wavelength. The melanopsin spectral absorbance curve was then convolved with S(λabsolute). The area under this curve was used as a measure of the radiant flux density capable of stimulating the melanopsin pigment (λmax 5 479 nm). We calculate that the equivalent of at least $5\times10^{13}$ photons $cm^{-2}$ $s^{-1}$ was available to stimulate melanopsin. Similar measurements and calculations for sunlight (12:00, 20 Dec. 2011) revealed a radiant flux density of $2.6\times10^{16}$ photons $cm^{-2}$ $s^{-1}$.

To estimate attenuation of light that could stimulate melanopsin in mouse fetuses in utero, we directed a blue LED (Philips Lumileds Lighting Company; model: Luxeon III star, LXHL-LB3C, peak wavelength 5 470 nm) that was positioned 1 inch from the skin to a miniature silicon photodiode light detector placed inside the abdominal cavity. Light penetrated both the skin and sub-dermal muscle layer. The measurements were done on live, anaesthetized adult mice (intramuscular (IM) injections of ketamine/xylazine).

Figure 30:
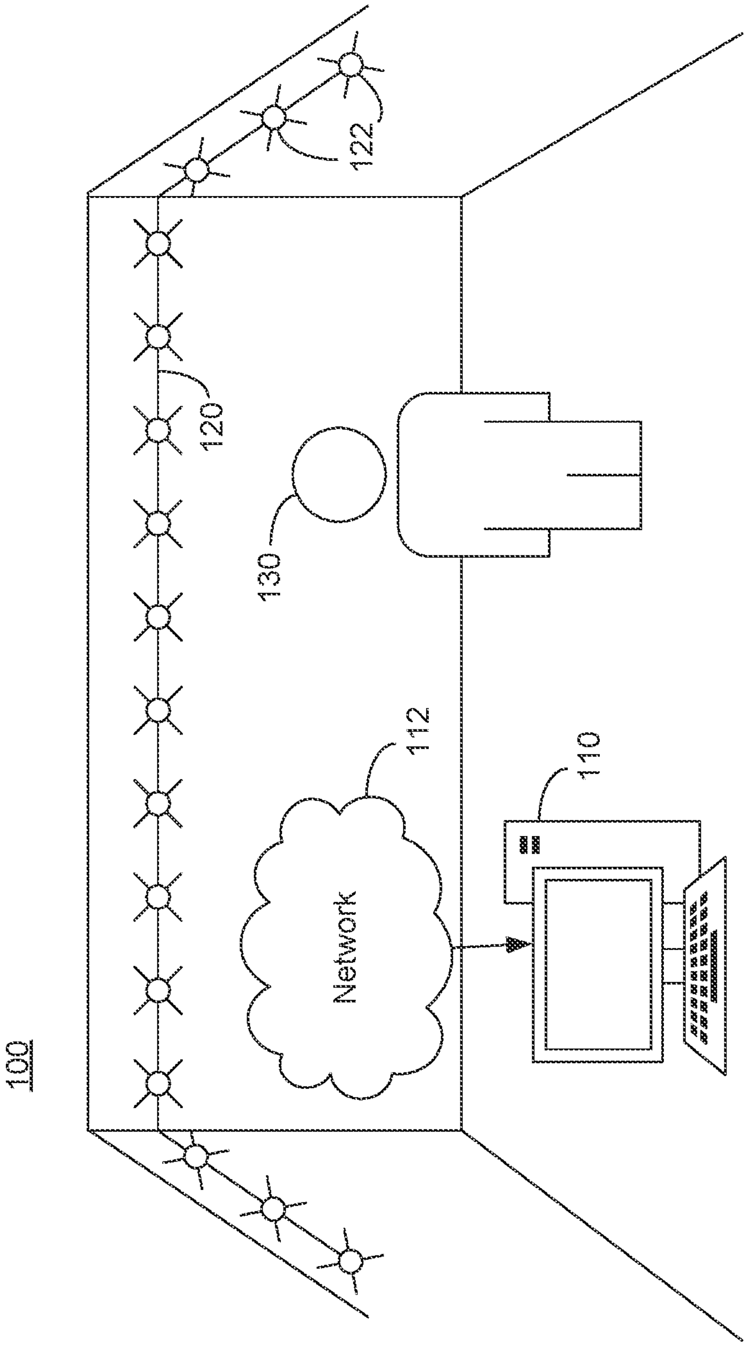
FIG. 30 illustrates an exemplary system architecture for using artificial lighting to promote circadian health of a patient, among other things.

FIG. 30 illustrates an exemplary system architecture 100 using artificial lighting to promote circadian health of a patient, among other things. System architecture 100 may include a computer 110, a network 112, a lighting device 120 (e.g., including one or more LEDs 122), and a patient 130.

In an embodiment, lighting device 120 may provide interior lighting (e.g., in a commercial health care facility). Moreover, the lighting device 120 or computer 110 may include a controller for controlling one or more of the LEDs 122. For example, the controller may control a rhythmic intensity or spectral modulation of the lighting device 122 or LEDs 122. Moreover, an emitted wavelength of the LEDs 122 may be targeted to specific human opsin absorption spectra. Specific emitted wavelengths of the LEDs 122 may include 380 nm, 430 nm, 480 nm, 530 nm, 580 nm, and 630 nm.

In some embodiments, by stimulating the opsins (e.g., OPSIN 3, 4, 5) of the patient 130, the lighting device may regulate a circadian clock of the patient 130. For example, an emitted wavelength of 480 nm may stimulate OPSIN 4 in the patient 130 or an emitted wavelength of 380 nm may stimulate OPSIN 5 in the patient 130.

Moreover, in some embodiments, the lighting device 120 may simulate normal sunlight by reproducing dawn and dusk transitions, e.g., intensity and spectrum. In some embodiments, the LEDs 122 may be distributed around an interior perimeter of a room in order to further simulate a direction of normal sunlight (e.g., rising of the sun in the east or setting of the sun in the west).

Moreover, the lighting device 120 may replicate spectral composition changes that occur in different seasons. For example, the lighting device 120 may provide a specific spectrum associated with a given season (e.g., winter, spring, summer, or fall) or a particular day or time of a calendar year (e.g., including a transitional spectrum). As another example, a period of lighting may change within a given season based on the length of day associated with the season (e.g., period of light may be shorter in the winter than in the summer).

Accordingly, the lighting device 120 may promote the health and well being of the patient 130 by regulating the circadian clock of the patient 130.

Figure 31:
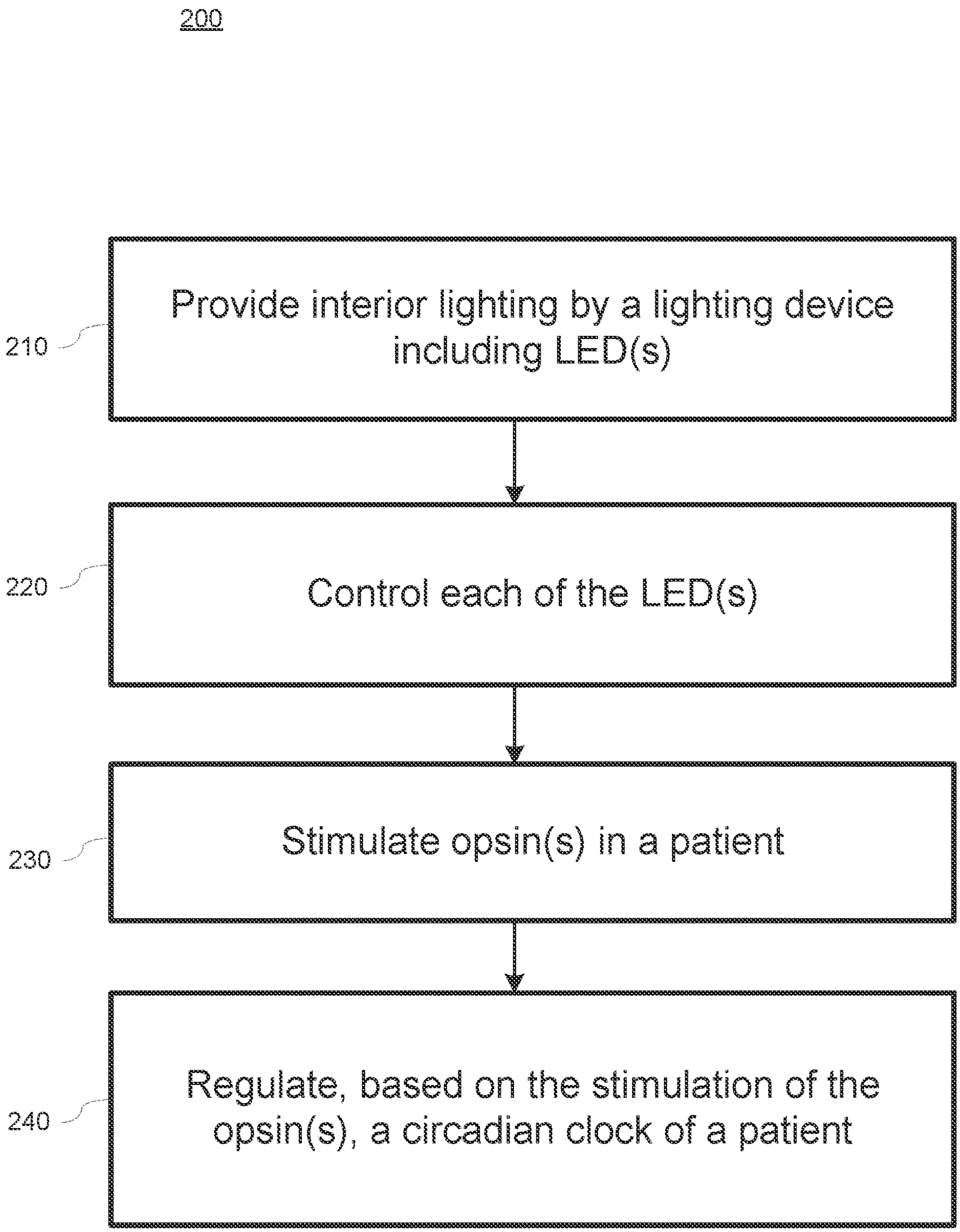
FIG. 31 illustrates an exemplary method of using artificial lighting to promote circadian health of a patient, among other things.

FIG. 31 illustrates an exemplary method 200 for using artificial lighting to promote circadian health of a patient, among other things. In some examples, the method 200 is performed by a device or machine (e.g., computer 110). Moreover, the method 200 may be performed at a network device, desktop, laptop, mobile device, server device, or by multiple devices in communication with one another. In some examples, the method 200 is performed by processing logic, including hardware, firmware, software, or a combination thereof. In some examples, the method 200 is performed by a processor executing code stored in a computer-readable medium (e.g., a memory).

At block 210, the method 200 provides interior lighting by a lighting device, where the lighting device includes one or more LEDs. For example, the LEDs of the lighting device may be located about a perimeter of the patient's room, may be located in one or more overhead lights, or may be part of a floor or desk lamp.

At block 220, the method 200 controls each of the LEDs. For example, the method 200 may control an intensity of one or more of the LEDs in order to control a rhythmic intensity, spectral modulation, spectral composition, etc.

At block 230, the method 200 stimulates one or more opsins in a patient. For example, the LEDs may target one or more human opsin absorption spectra by emitting specific wavelengths (e.g., 380 nm, 430 nm, 480 nm, 530 nm, 580 nm, or 630 nm).

At block 240, the method 200 regulates, based on the stimulation of the opsin(s), a circadian clock of the patient. For example, the method 200 may simulate normal sunlight by reproducing dawn and dusk transitions. In some embodiments, the method 200 may replication color separations typical of dawn and dusk, e.g., including a direction of specific colors based on a time of day. Moreover, the method 200 may replicate spectral composition changes that occur in different seasons (e.g., spring, summer, fall, and winter).

Examples of the methods disclosed herein may be performed in the operation of such computing devices. The order of the blocks presented in the examples herein can be varied. For example, blocks can be re-ordered, combined, or broken into sub-blocks. Certain blocks or processes can be performed in parallel.

Figure 32:
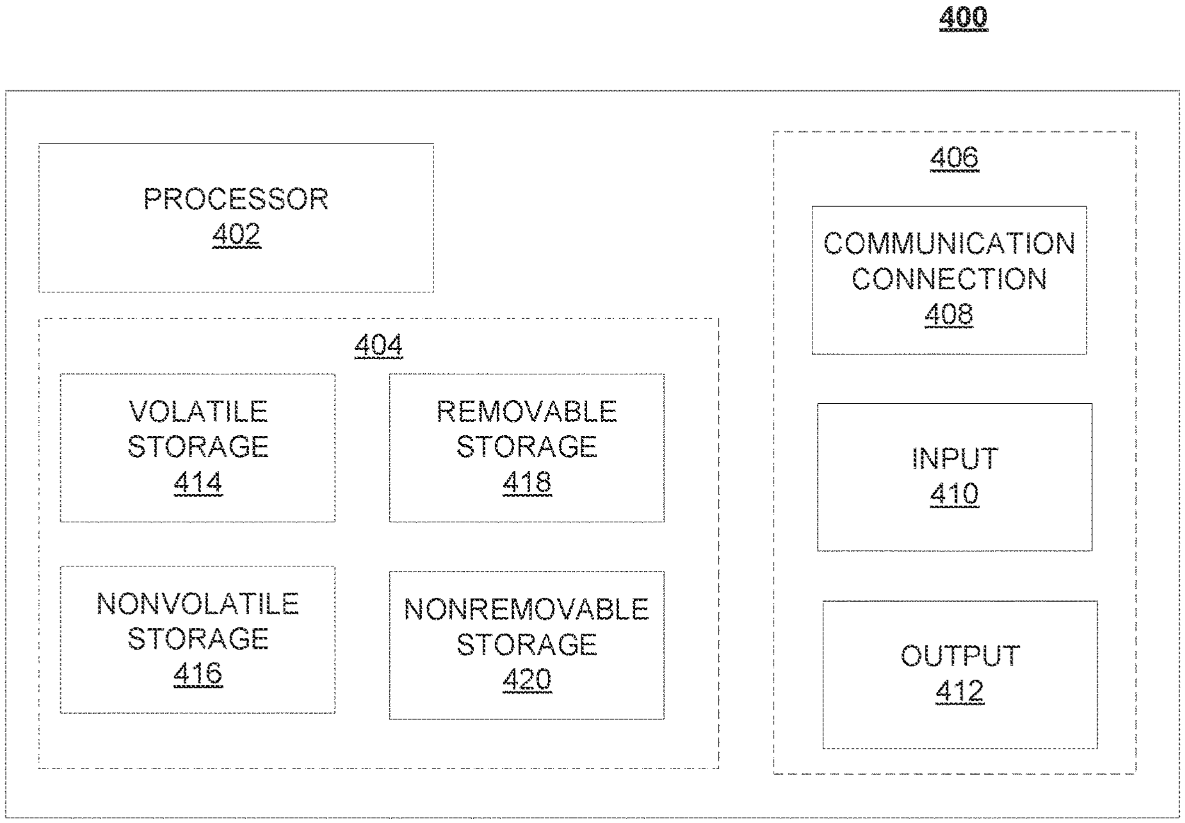
FIG. 32 illustrates a schematic of an exemplary network device.

FIG. 32 is a block diagram of network device 400 that may be connected to or comprise a component of network 112. Network device 400 may comprise hardware or a combination of hardware and software. The functionality to facilitate communications via a communications network may reside in one or a combination of network devices 400. Network device 400 depicted in FIG. 32 may represent or perform functionality of an appropriate network device 400, or a combination of network devices 400, such as, for example, a component or various components of a cellular broadcast system wireless network, a processor, a server, a gateway, an LTE or 5G anchor node or eNB, a mobile switching center (MSC), a short message service center (SMSC), an automatic location function server (ALFS), a gateway mobile location center (GMLC), a serving gateway (S-GW) 430, a packet data network (PDN) gateway, an RAN, a serving mobile location center (SMLC), or the like, or any appropriate combination thereof. It is emphasized that the block diagram depicted in FIG. 32 is exemplary and not intended to imply a limitation to a specific example or configuration. Thus, network device 400 may be implemented in a single device or multiple devices (e.g., single server or multiple servers, single gateway or multiple gateways, single controller or multiple controllers). Multiple network entities may be distributed or centrally located. Multiple network entities may communicate wirelessly, via hard wire, or any appropriate combination thereof.

Network device 400 may comprise a processor 402 and a memory 404 coupled to processor 402. Memory 404 may contain executable instructions that, when executed by processor 402, cause processor 402 to effectuate operations associated with using artificial lighting to promote circadian health of a patient. As evident from the description herein, network device 400 is not to be construed as software per se.

In addition to processor 402 and memory 404, network device 400 may include an input/output system 406. Processor 402, memory 404, and input/output system 406 may be coupled together (coupling not shown in FIG. 32) to allow communications between them. Each portion of network device 400 may comprise circuitry for performing functions associated with each respective portion. Thus, each portion may comprise hardware, or a combination of hardware and software. Accordingly, each portion of network device 400 is not to be construed as software per se. Input/output system 406 may be capable of receiving or providing information from or to a communications device or other network entities configured for telecommunications. For example, input/output system 406 may include a wireless communications (e.g., 3G/4G/5G/GPS) card. Input/output system 406 may be capable of receiving or sending video information, audio information, control information, image information, data, or any combination thereof. Input/output system 406 may be capable of transferring information with network device 400. In various configurations, input/output system 406 may receive or provide information via any appropriate means, such as, for example, optical means (e.g., infrared), electromagnetic means (e.g., RF, Wi-Fi, Bluetooth®, ZigBee®), acoustic means (e.g., speaker, microphone, ultrasonic receiver, ultrasonic transmitter), or a combination thereof. In an example configuration, input/output system 406 may comprise a Wi-Fi finder, a two-way GPS chipset or equivalent, or the like, or a combination thereof.

Input/output system 406 of network device 400 also may contain a communication connection 408 that allows network device 400 to communicate with other devices, network entities, or the like. Communication connection 408 may comprise communication media. Communication media typically embody computer-readable instructions, data structures, program modules or other data in a modulated data signal such as a carrier wave or other transport mechanism and includes any information delivery media. By way of example, and not limitation, communication media may include wired media such as a wired network or direct-wired connection, or wireless media such as acoustic, RF, infrared, or other wireless media. The term computer-readable media as used herein includes both storage media and communication media. Input/output system 406 also may include an input device 410 such as keyboard, mouse, pen, voice input device, or touch input device. Input/output system 406 may also include an output device 412, such as a display, speakers, or a printer.

Processor 402 may be capable of performing functions associated with using artificial lighting to promote circadian health of a patient, as described herein. For example, processor 402 may be capable of, in conjunction with any other portion of network device 400, determining a type of patient or targeted opsin and controlling the lighting device accordingly, as described herein.

Memory 404 of network device 400 may comprise a storage medium having a concrete, tangible, physical structure. As is known, a signal does not have a concrete, tangible, physical structure. Memory 404, as well as any computer-readable storage medium described herein, is not to be construed as a signal. Memory 404, as well as any computer-readable storage medium described herein, is not to be construed as a transient signal. Memory 404, as well as any computer-readable storage medium described herein, is not to be construed as a propagating signal. Memory 404, as well as any computer-readable storage medium described herein, is to be construed as an article of manufacture.

Memory 404 may store any information utilized in conjunction with communications. Depending upon the exact configuration or type of processor, memory 404 may include a volatile storage 414 (such as some types of RAM), a nonvolatile storage 416 (such as ROM, flash memory), or a combination thereof. Memory 404 may include additional storage (e.g., a removable storage 418 or a non-removable storage 420) including, for example, tape, flash memory, smart cards, CD-ROM, DVD, or other optical storage, magnetic cassettes, magnetic tape, magnetic disk storage or other magnetic storage devices, USB-compatible memory, or any other medium that can be used to store information and that can be accessed by network device 400. Memory

404 may comprise executable instructions that, when executed by processor 402, cause processor 402 to effectuate operations to use artificial lighting to promote circadian health of a patient.

Figure 33:
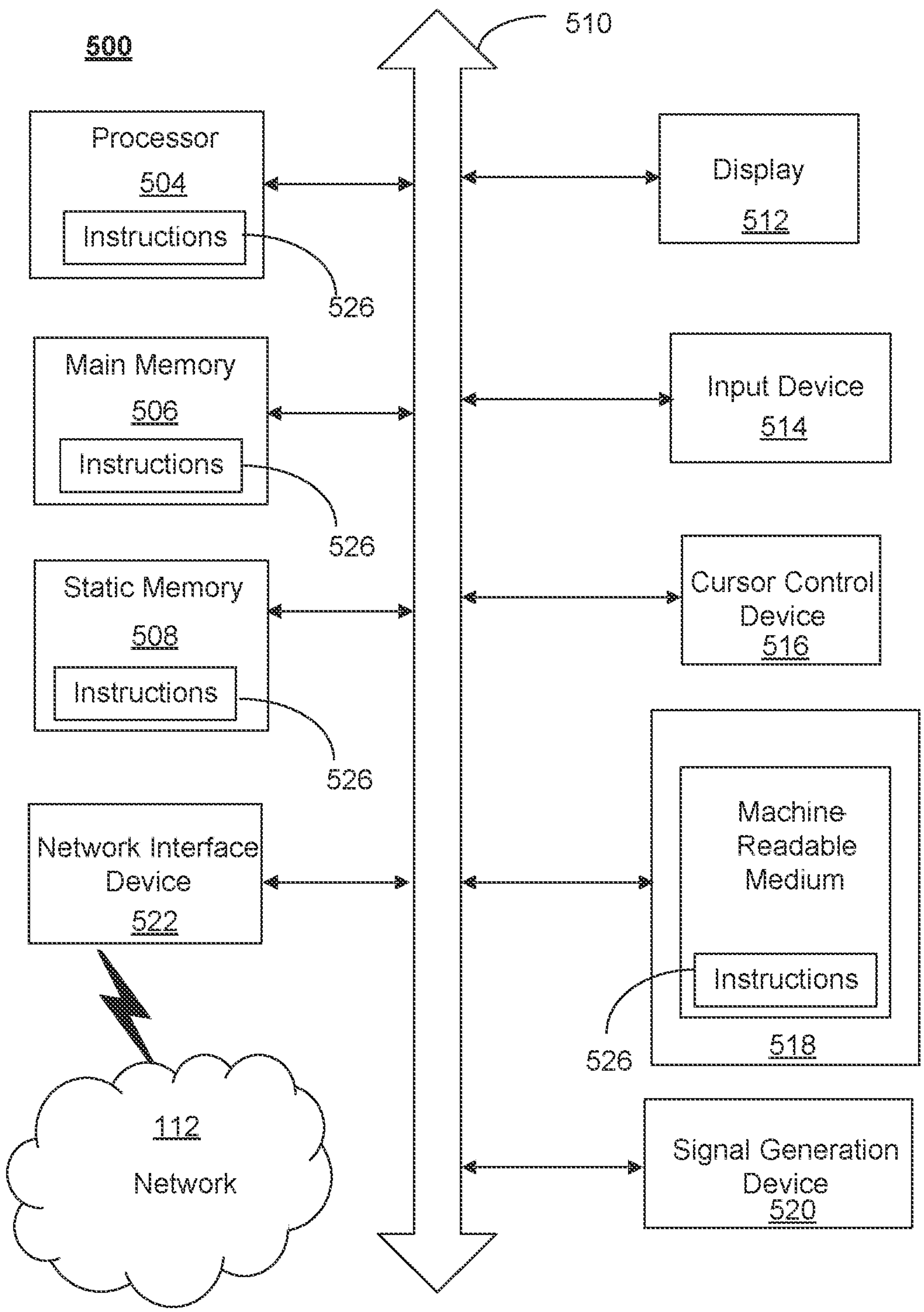
FIG. 33 illustrates an exemplary diagrammatic representation of a machine in the form of a computer system.

FIG. 33 depicts an exemplary diagrammatic representation of a machine in the form of a computer system 500 within which a set of instructions, when executed, may cause the machine to perform any one or more of the methods described above. One or more instances of the machine can operate, for example, as processor 402, computer 110, and other devices of FIGS. 1-32. In some examples, the machine may be connected (e.g., using a network 112) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

Computer system 500 may include a processor (or controller) 504 (e.g., a central processing unit (CPU)), a graphics processing unit (GPU, or both), a main memory 506 and a static memory 508, which communicate with each other via a bus 510. The computer system 500 may further include a display unit 512 (e.g., a liquid crystal display (LCD), a flat panel, or a solid-state display). Computer system 500 may include an input device 514 (e.g., a keyboard), a cursor control device 516 (e.g., a mouse), a machine readable medium 518, a signal generation device 520 (e.g., a speaker or remote control) and a network interface device 522. In distributed environments, the examples described in the subject disclosure can be adapted to utilize multiple display units 512 controlled by two or more computer systems 500. In this configuration, presentations described by the subject disclosure may in part be shown in a first of display units 512, while the remaining portion is presented in a second of display units 512.

The disk drive unit 518 may include a tangible computer-readable storage medium on which is stored one or more sets of instructions (e.g., instructions 526) embodying any one or more of the methods or functions described herein, including those methods illustrated above. Instructions 526 may also reside, completely or at least partially, within main memory 506, static memory 508, or within processor 504 during execution thereof by the computer system 500. Main memory 506 and processor 504 also may constitute tangible computer-readable storage media.

Figure 34:
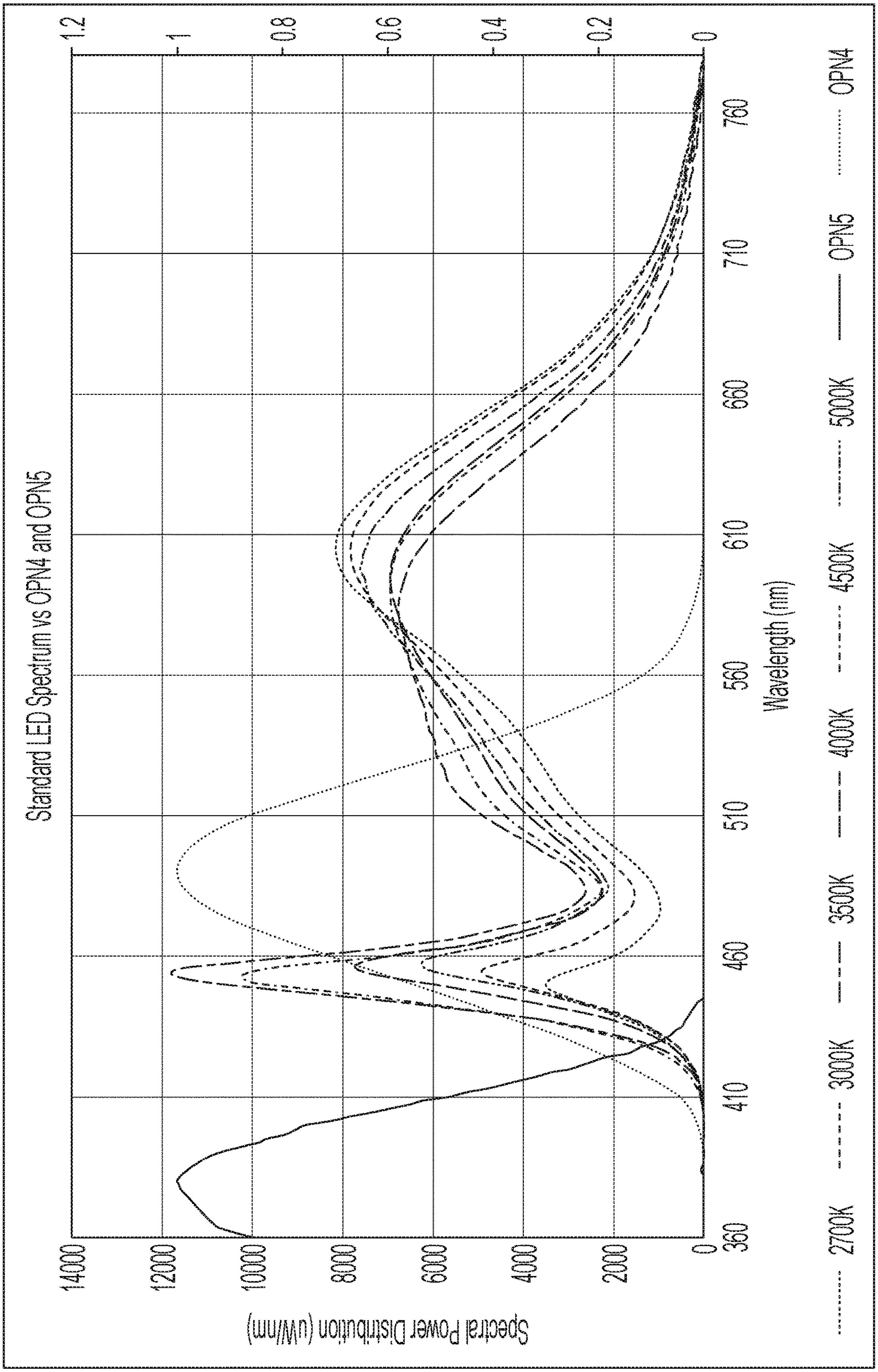
FIG. 34 illustrates, according to some embodiments, a graph of the spectral power distribution (SPD(λ)) of standard LED lights compared to melanopsin (OPN4(λ)) and neuropsin (OPN5(λ)).

FIG. 34 illustrates, according to some embodiments, a graph of the spectral power distribution (SPD(λ)) of standard LED lights compared to melanopsin (OPN4(λ)) and neuropsin (OPN5(λ)). LED lighting is growing in adoption due to its inherent benefits including long lifetime, scalable size and tremendous energy efficiency. For example, LEDs can very efficiently produce a very specific wavelength of light. Standard LEDs produce a narrow blue peak around 450 nm that partially transmit through and excite an amalgam of phosphors to generate a desired resulting spectrum. An example of this method is shown in FIG. 34, which illustrates that no matter what the resulting color of the light source, the strategy is still the same. Moreover, the energy efficiency has been engineered toward visual efficiency. However each of these LED spectra are deficient in OPN4 stimulating energy (e.g., blue light within a range of 400-525 nm). Additionally, each of these spectra from FIG. 34 are devoid in any type of energy to stimulate OPN5 (e.g., violet light within a range of 360-420 nm).

According to some aspects, OPN5 activation and OPN4 activation are relative numbers that are calculated for comparative purposes, e.g., such as comparing activation potential of different spectral power distributions and for creating a unitless OPN5/OPN4 ratio. Each of these activations are calculated by taking the dot product of the normalized sensitivity functions for each opsin type by the candidate spectral power distribution over the wavelength range 360 nm to 780 nm. Equations as follows:

$$OPN5 = \sum_{n=360}^{780} (OPN5(\lambda) * SPD(\lambda) * \delta\lambda)$$

$$OPN4 \text{ activation} = \sum_{n=360}^{780} (OPN4(\lambda) * SPD(\lambda) * \delta\lambda)$$

Where:

OPN4(λ) is a normalized spectral sensitivity function of OPN4 shown in FIG. 1

OPN5(λ) is the spectral sensitivity of OPN5 shown in FIG. 1.

SPD(λ) is the spectral power distribution of a given light source being evaluated.

OPN5/OPN4 refers to the ratio of OPN5 activation to OPN4 activation.

$$\frac{OPN5}{OPN4} = \frac{OPN5 \text{ activation}}{OPN4 \text{ activation}}$$

Figure 35:
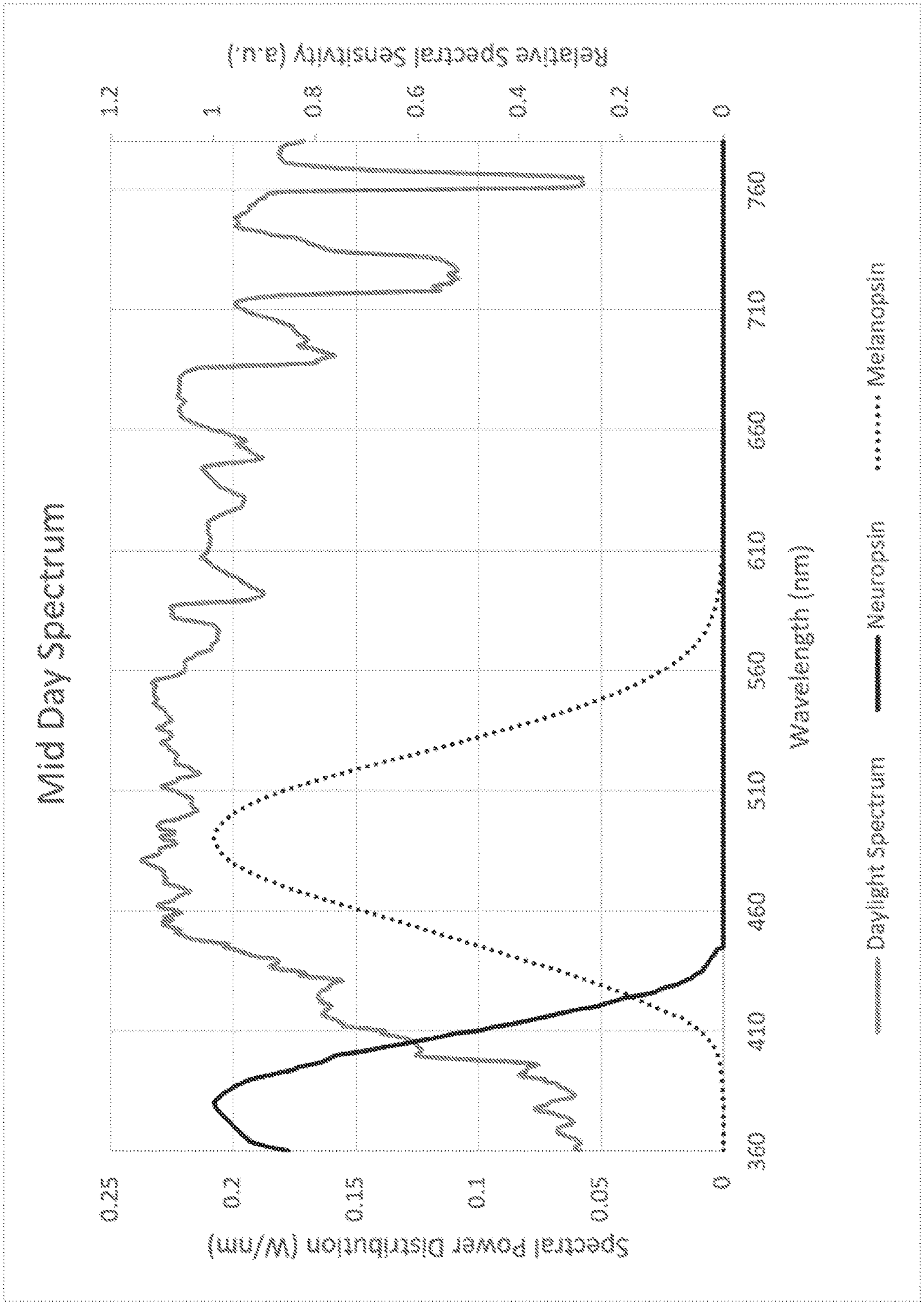
FIG. 35 illustrates, according to some embodiments, a graph of the spectral power distribution (SPD(λ)) of daylight midday compared to melanopsin (OPN4(λ)) and neuropsin (OPN5(λ)).

FIG. 35 illustrates, according to some embodiments, a graph of the spectral power distribution (SPD(λ)) of daylight midday compared to melanopsin (OPN4(λ)) and neuropsin (OPN5(λ)). Looking at the daylight spectrum from FIG. 35, there is a broad spectral power distribution which contains sufficient excitation of both OPN4 (melanopsin) and OPN5 (neuropsin).

Figure 36:
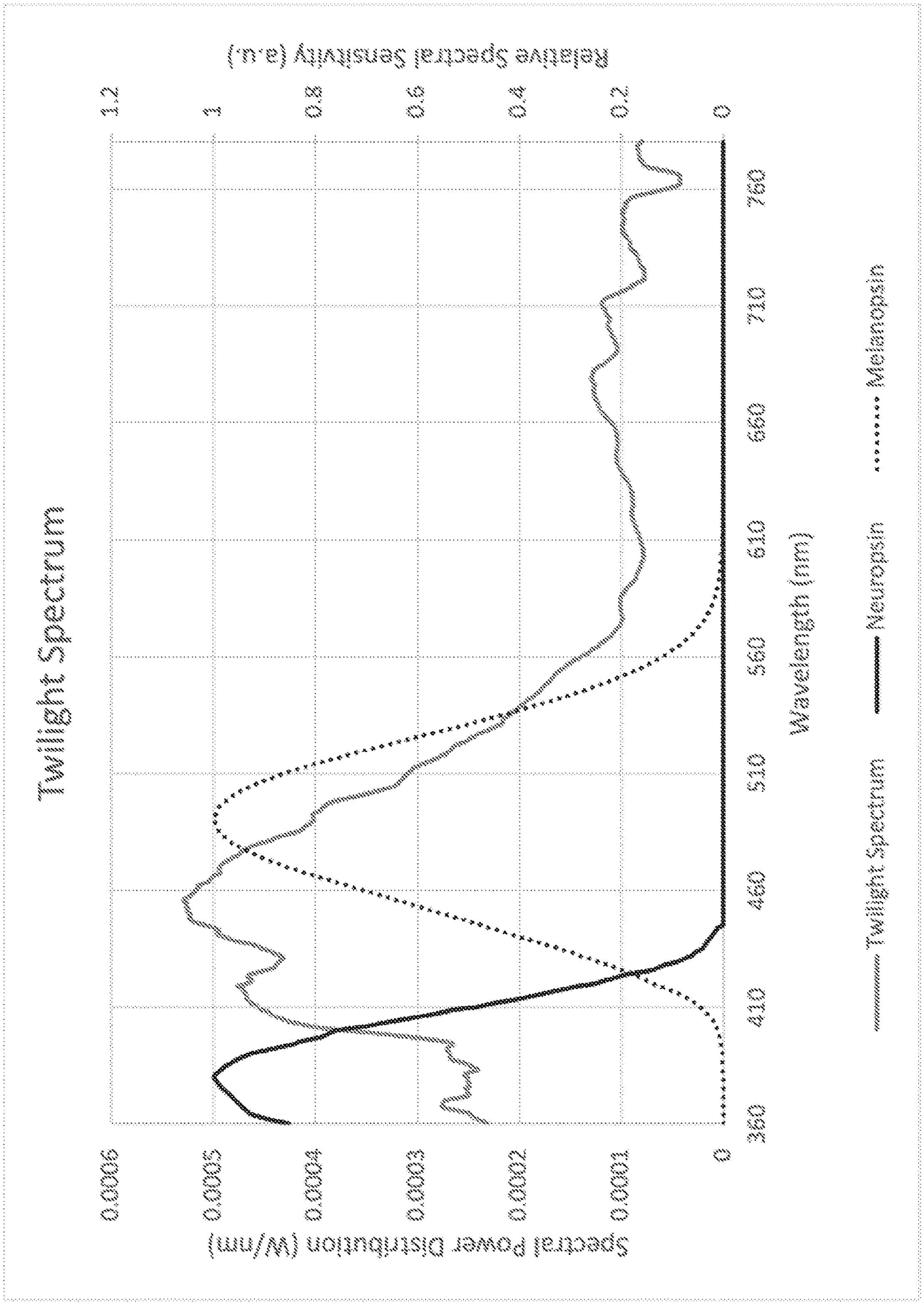
FIG. 36 illustrates, according to some embodiments, a graph of the spectral power distribution (SPD(λ)) of daylight at twilight compared to melanopsin (OPN4(λ)) and neuropsin (OPN5(λ)).

FIG. 36 illustrates, according to some embodiments, a graph of the spectral power distribution (SPD(λ)) of daylight at twilight compared to melanopsin (OPN4(λ)) and neuropsin (OPN5(λ)). As the sun goes down and the remaining skyglow of twilight remains, the spectral power distribution changes as well (e.g., FIG. 36), leaving behind a higher amount of OPN5 stimulation relative to OPN4 stimulation.

Figure 37:
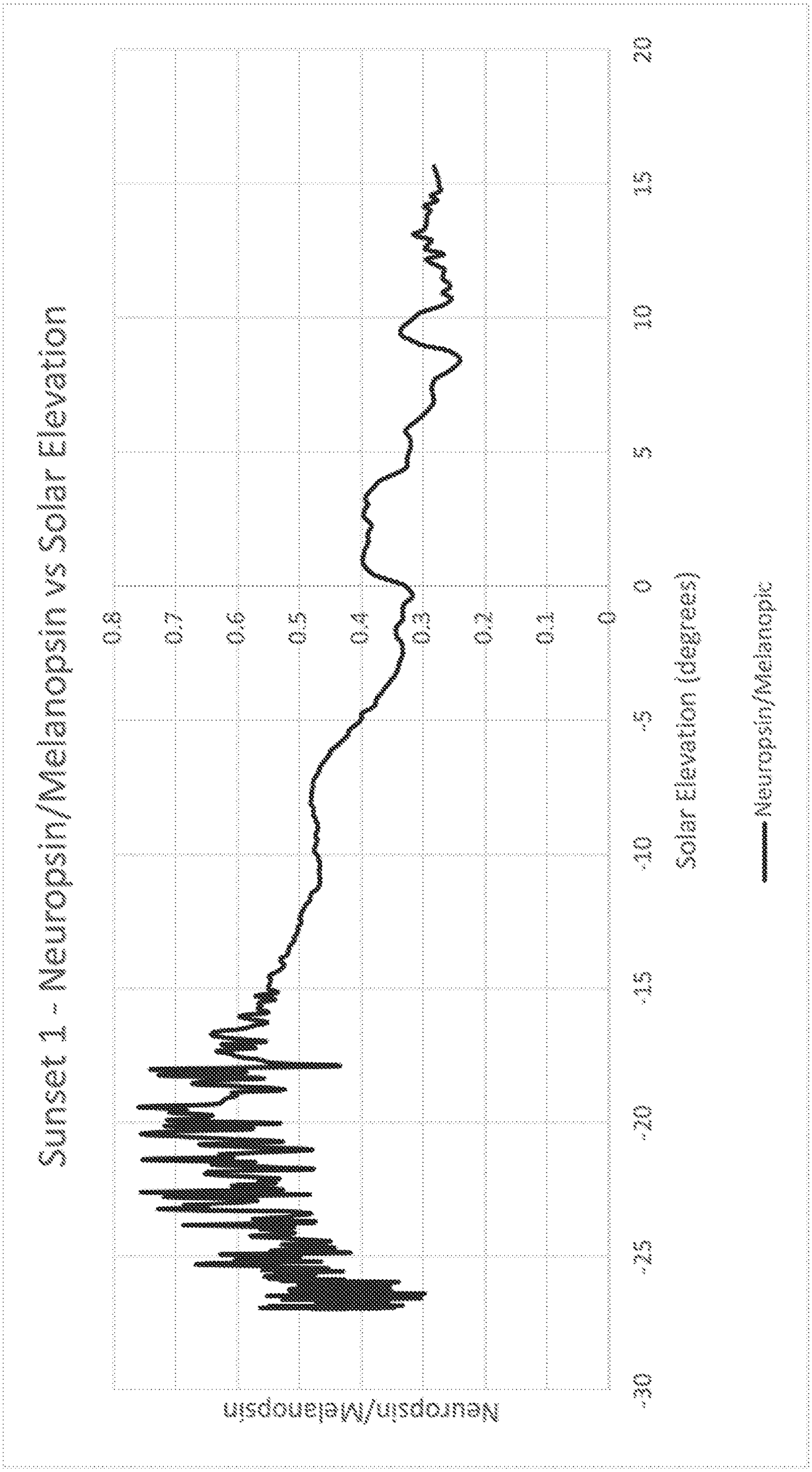
FIG. 37 illustrates, according to some embodiments, a graph of the OPN5/OPN4 ratio of a setting sun versus solar elevation, e.g., where 0 degrees represents actual sunset.
Figure 38:
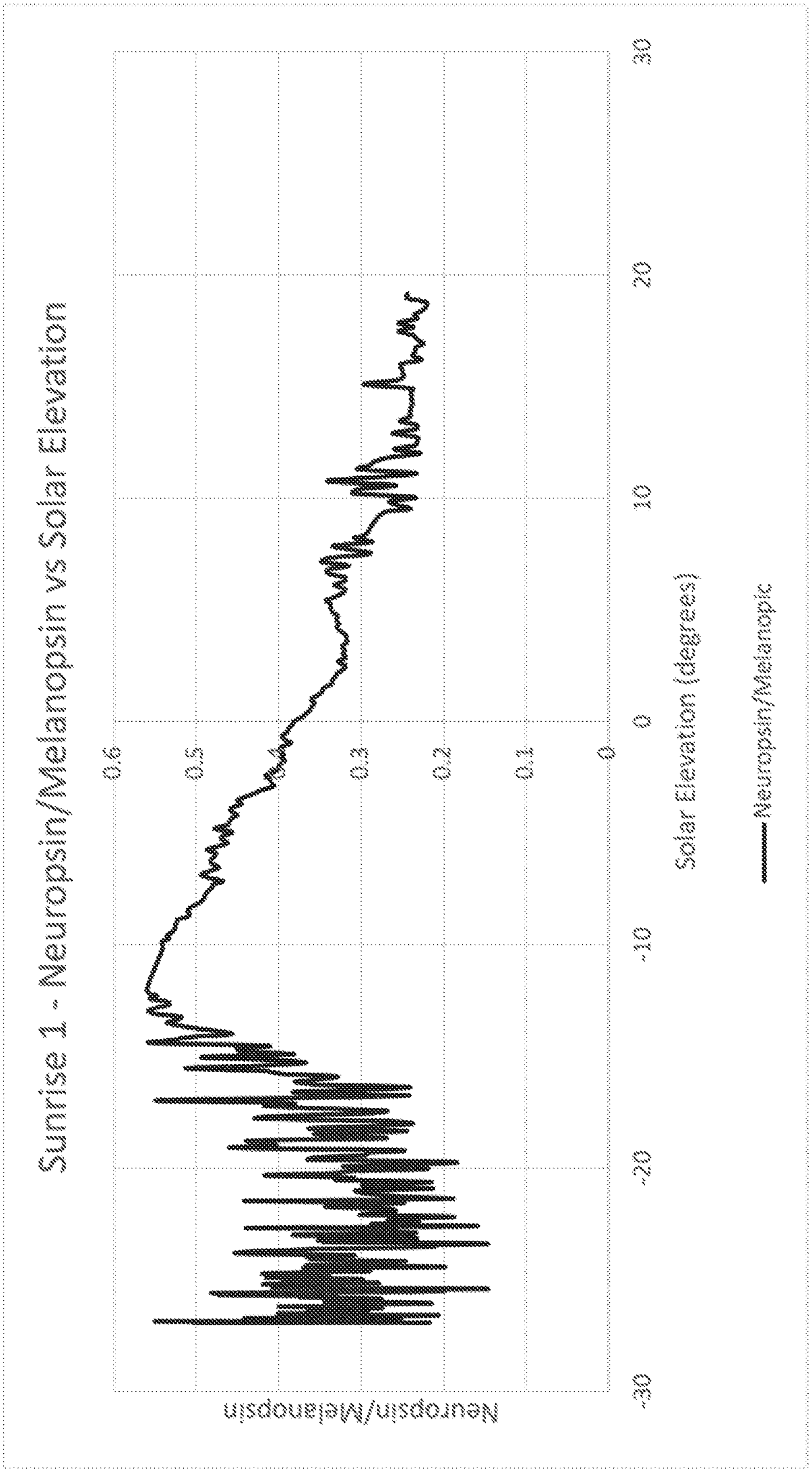
FIG. 38 illustrates, according to some embodiments, a graph of the OPN5/OPN4 ratio of a rising sun versus solar elevation, e.g., where 0 degrees represents actual sunrise.
Figure 39:
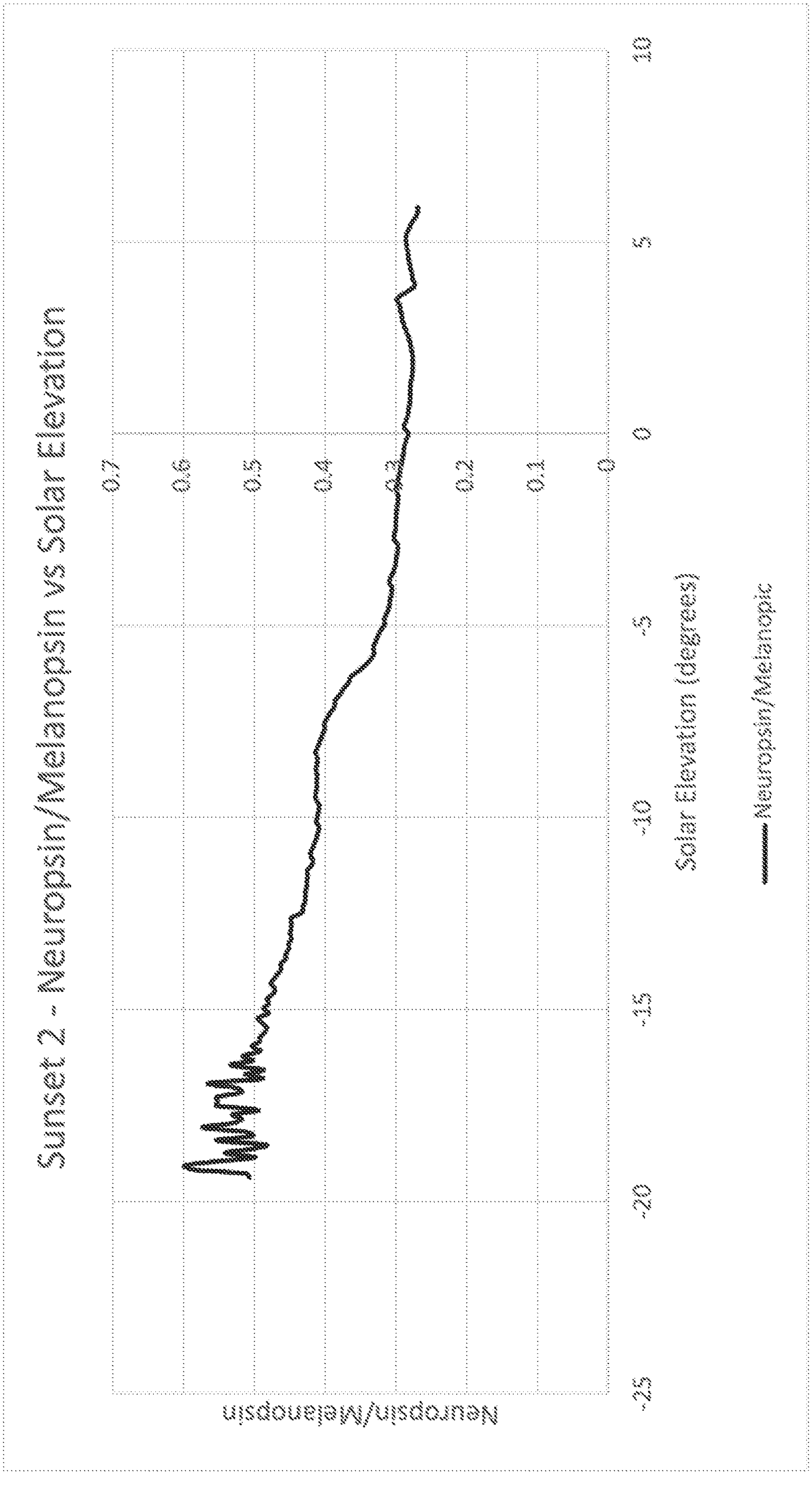
FIG. 39 illustrates, according to some embodiments, a graph of the OPN5/OPN4 ratio of a second setting sun versus solar elevation, e.g., where 0 degrees represents actual sunset.

This OPN5/OPN4 ratio is illustrated in FIGS. 37, 38, and 39. FIG. 37 illustrates, according to some embodiments, a graph of the OPN5/OPN4 ratio of a setting sun versus solar elevation, e.g., where 0 degrees represents actual sunset. FIG. 38 illustrates, according to some embodiments, a graph of the OPN5/OPN4 ratio of a rising sun versus solar elevation, e.g., where 0 degrees represents actual sunrise. FIG. 39 illustrates, according to some embodiments, a graph of the OPN5/OPN4 ratio of a second setting sun versus solar elevation, e.g., where 0 degrees represents actual sunset.

When the sun is above the horizon, the OPN5/OPN4 ratio is less than 0.4. However, when the sun drops below the horizon, the OPN5/OPN4 ratio is greater than 0.4. Evolutionarily speaking, this ratio is believed to be of particular importance as ratios of light are consistent in a variety of habitats. A similar approach has been demonstrated to be important in plants, such that phytochrome photostationary state, a ratio of far-red light to red light, is important for denoting the beginning and end of day for plants.

Figure 40:
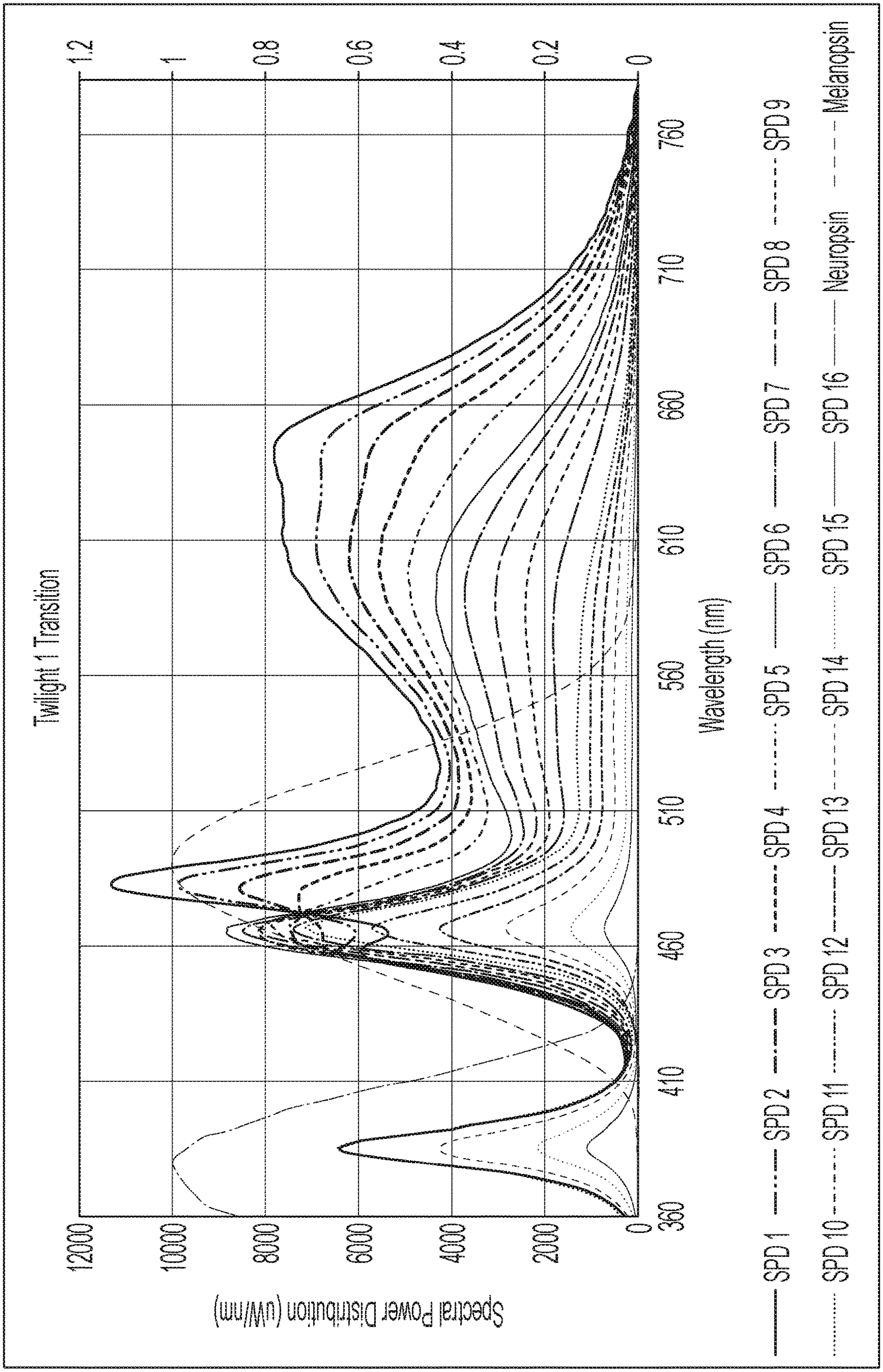
FIG. 40 illustrates, according to some embodiments, a graph of a spectral power distribution that transitions its OPN5/OPN4 ratio similarly to a rising or setting sun.
Figure 41:
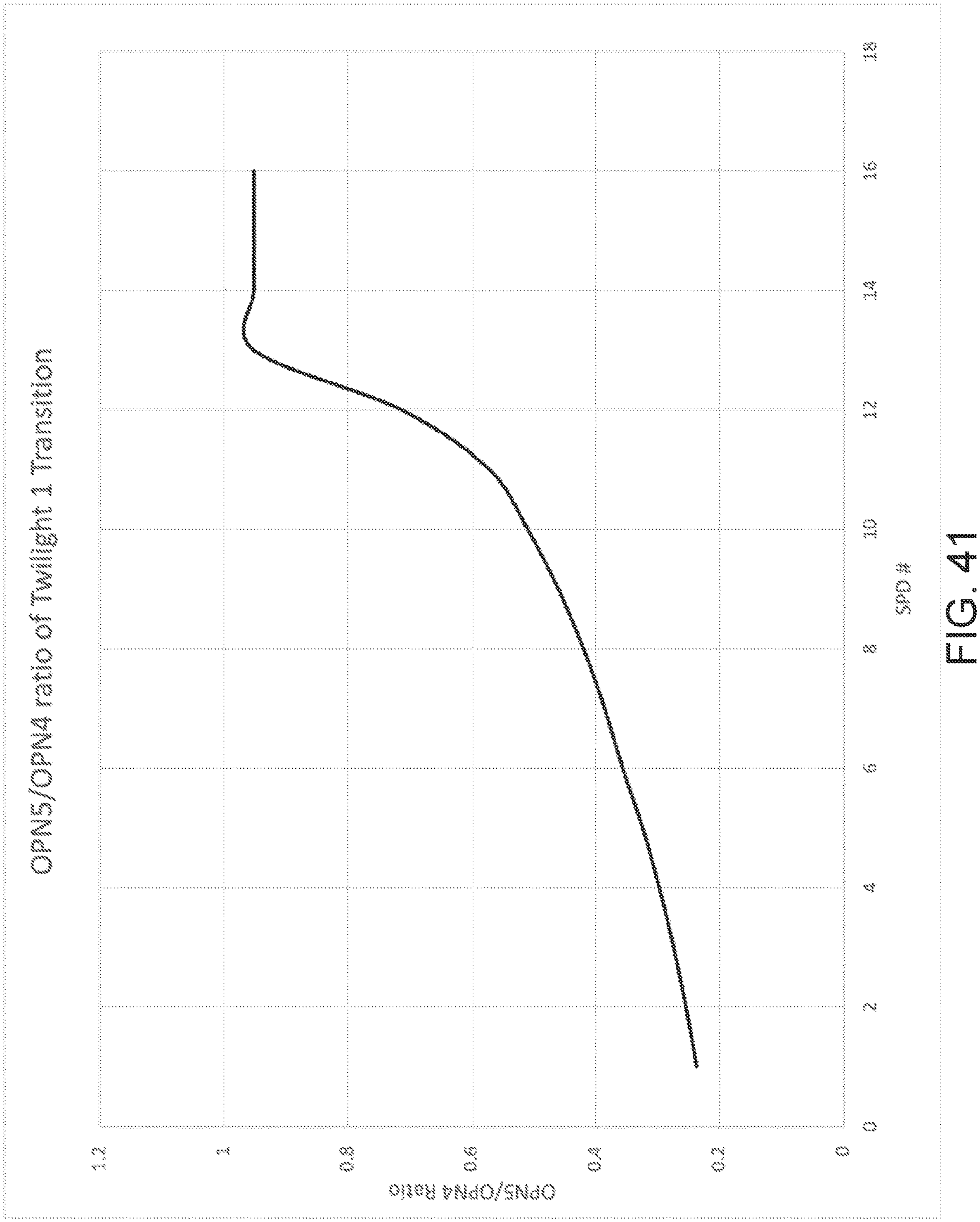
FIG. 41 illustrates, according to some embodiments, a graph of the OPN5/OPN4 ratio of the spectral transitions illustrated in FIG. 40.
Figure 42:
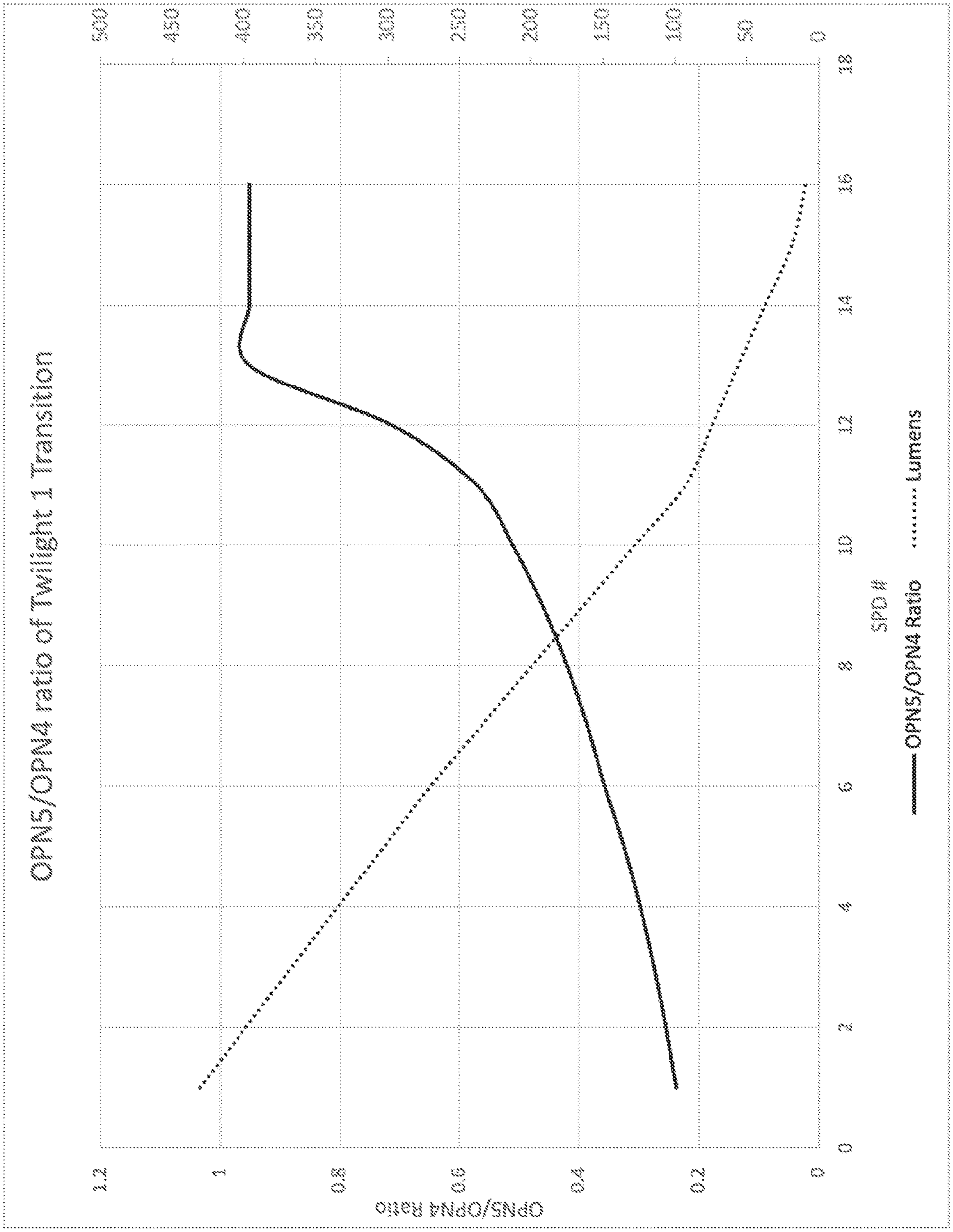
FIG. 42 illustrates, according to some embodiments, a graph of the OPN5/OPN4 ratio of the spectral transitions illustrated in FIG. 40 as well as lumens, e.g., where the OPN5/OPN4 ratio is inversely proportional to lumens.

FIG. 40 illustrates, according to some embodiments, a graph of a spectral power distribution that transitions its OPN5/OPN4 ratio similarly to a rising or setting sun. FIG. 40 represents one embodiment of spectra that represents a twilight transition that also transitions from a day with OPN5/OPN4 ratio less than 0.4 to a twilight with OPN5/OPN4 ratio greater than 0.4. This OPN5/OPN4 transition is shown in FIG. 41. Within this embodiment shown in FIG. 40, the "SPD" lines are illumination sources transmitting light in the wavelength and intensity ranges as illustrated by the graph. This particular embodiment is one that changes the resulting color to be more purple as the OPN5/OPN4 stimulation increases, similar to how the sky turns purple as the sun goes down. FIG. 42 illustrates, according to some embodiments, a graph of the OPN5/OPN4 ratio of the spectral transitions illustrated in FIG. 40 as well as lumens, e.g., where the OPN5/OPN4 ratio is inversely proportional to lumens.

Figure 43:
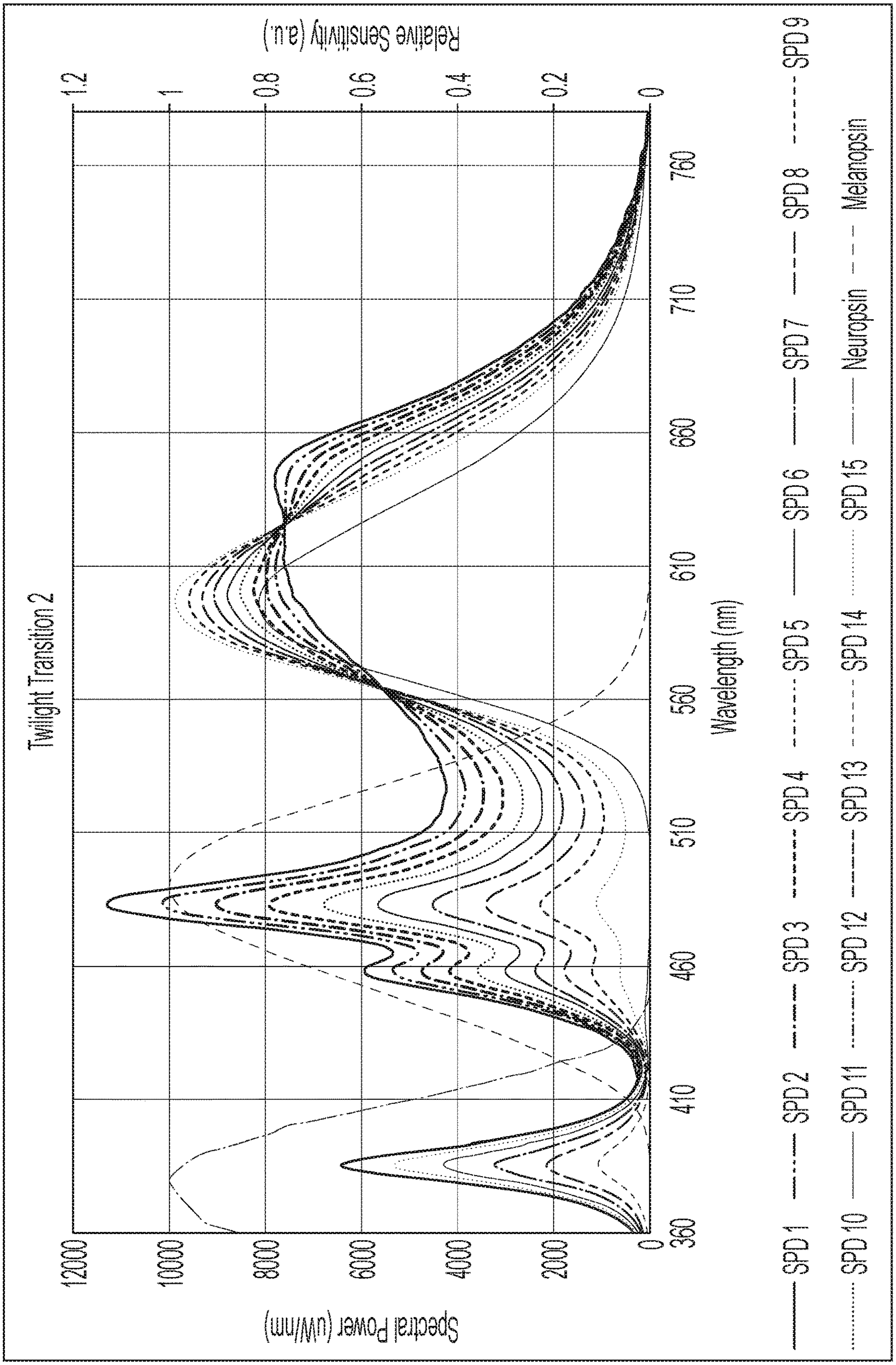
FIG. 43 illustrates, according to some embodiments, a graph of a second embodiment spectral power distribution that transitions its OPN5/OPN4 ratio similarly to a rising or setting sun.
Figure 44:
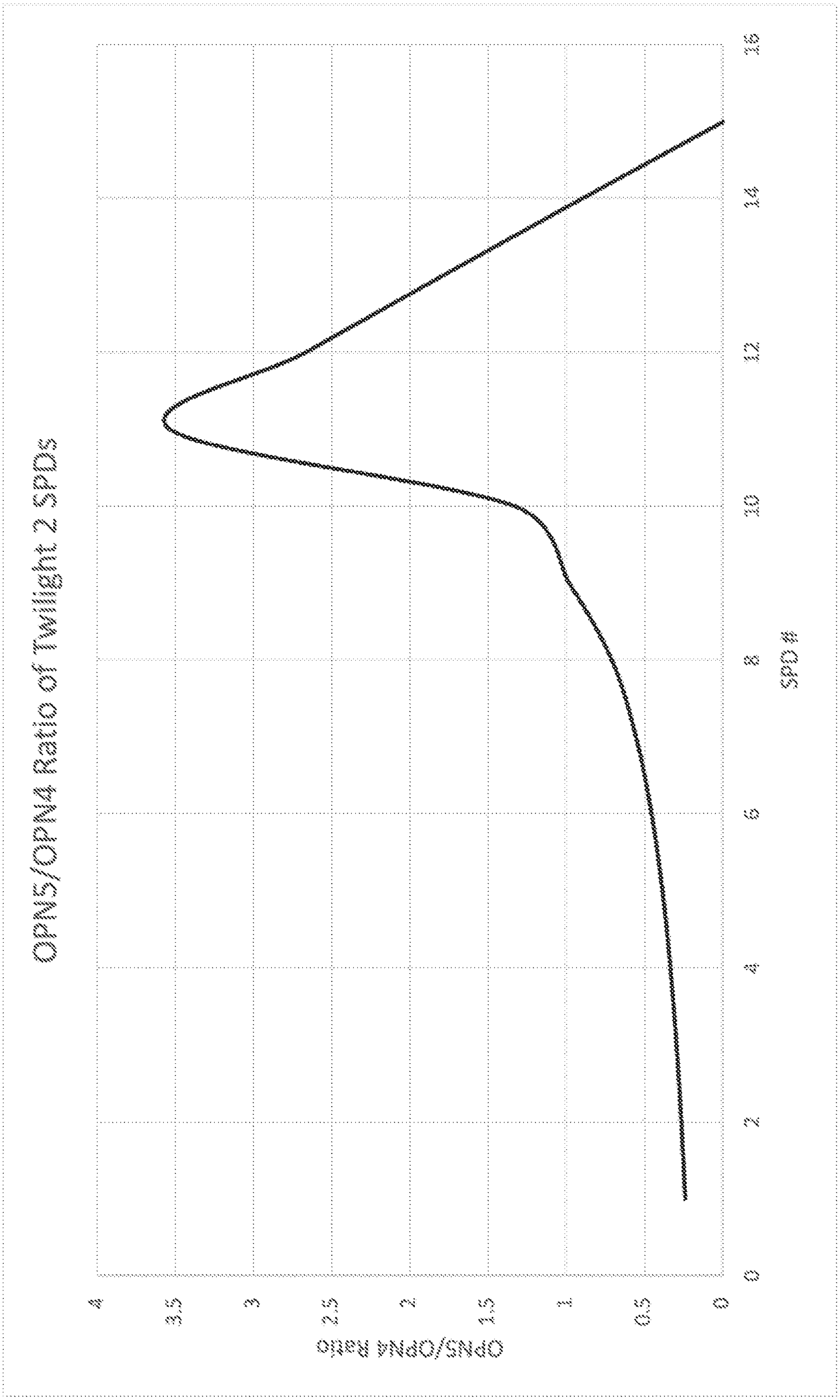
FIG. 44 illustrates, according to some embodiments, a graph of the OPN5/OPN4 ratio of the spectral transitions illustrated in FIG. 43.
Figure 45:
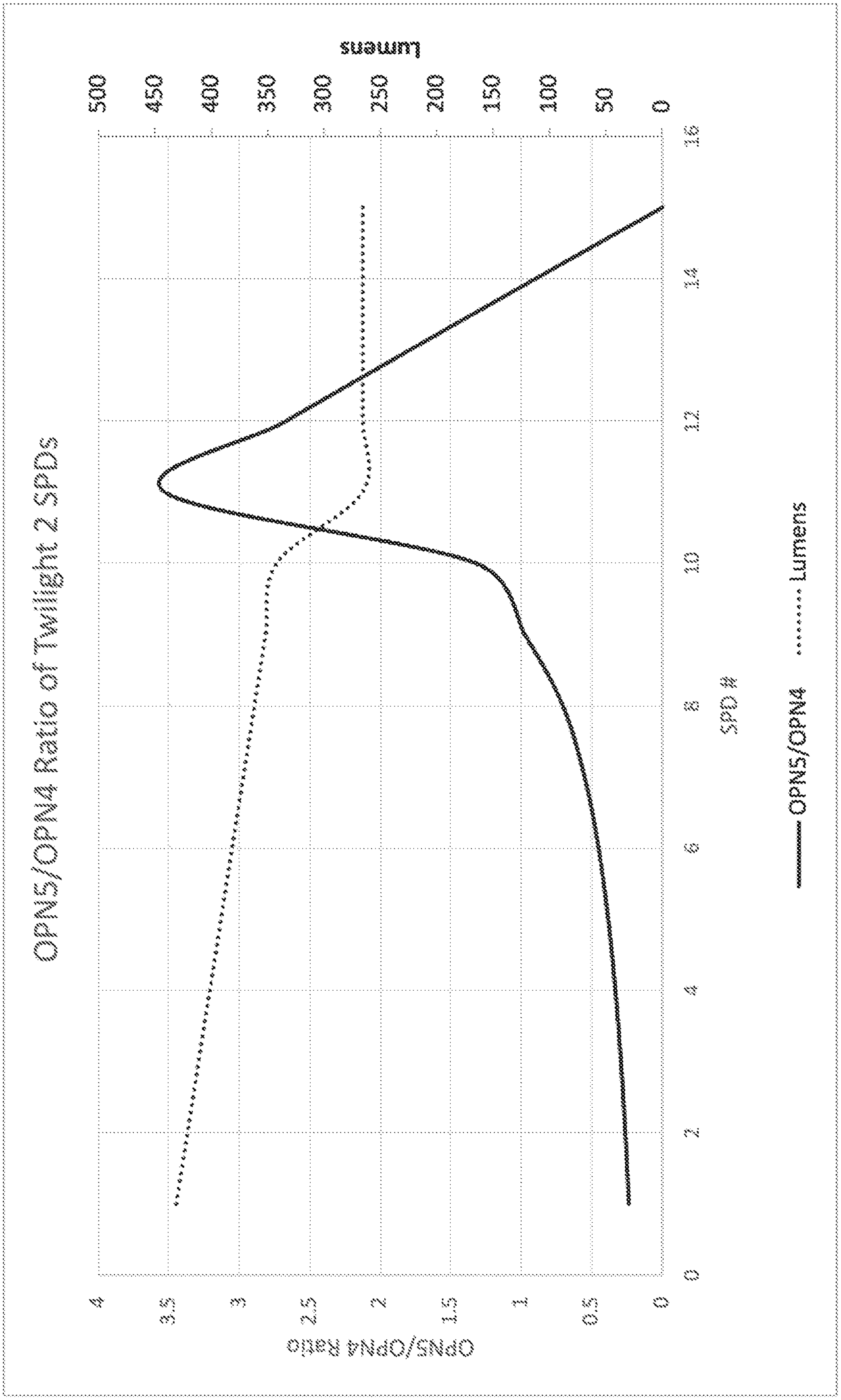
FIG. 45 illustrates, according to some embodiments, a graph of the OPN5/OPN4 ratio of the spectral transitions illustrated in FIG. 43 as well as lumens, e.g., where the OPN5/OPN4 ratio is modulated while intensity is only slightly modulated.

FIG. 43 illustrates a different type of spectral transition that also creates a transition in OPN5/OPN4 stimulation such that during the day the OPN5/OPN4 stimulation is less than 0.4 during the day and greater than 0.4 at night. However, this spectral embodiment is different in that its color becomes more yellow as the OPN5/OPN4 increases. This embodiment is similar to how the sunlight becomes more yellow as the sun goes down. Again, within this embodiment shown in FIG. 43, the "SPD" lines are illumination sources transmitting light in the wavelength and intensity ranges as illustrated by the graph. This OPN5/OPN4 transition is shown in FIG. 44. FIG. 45 illustrates, according to some embodiments, a graph of the OPN5/OPN4 ratio of the spectral transitions illustrated in FIG. 43 as well as lumens, e.g., where the OPN5/OPN4 ratio is modulated while intensity is only slightly modulated.

Figure 46:
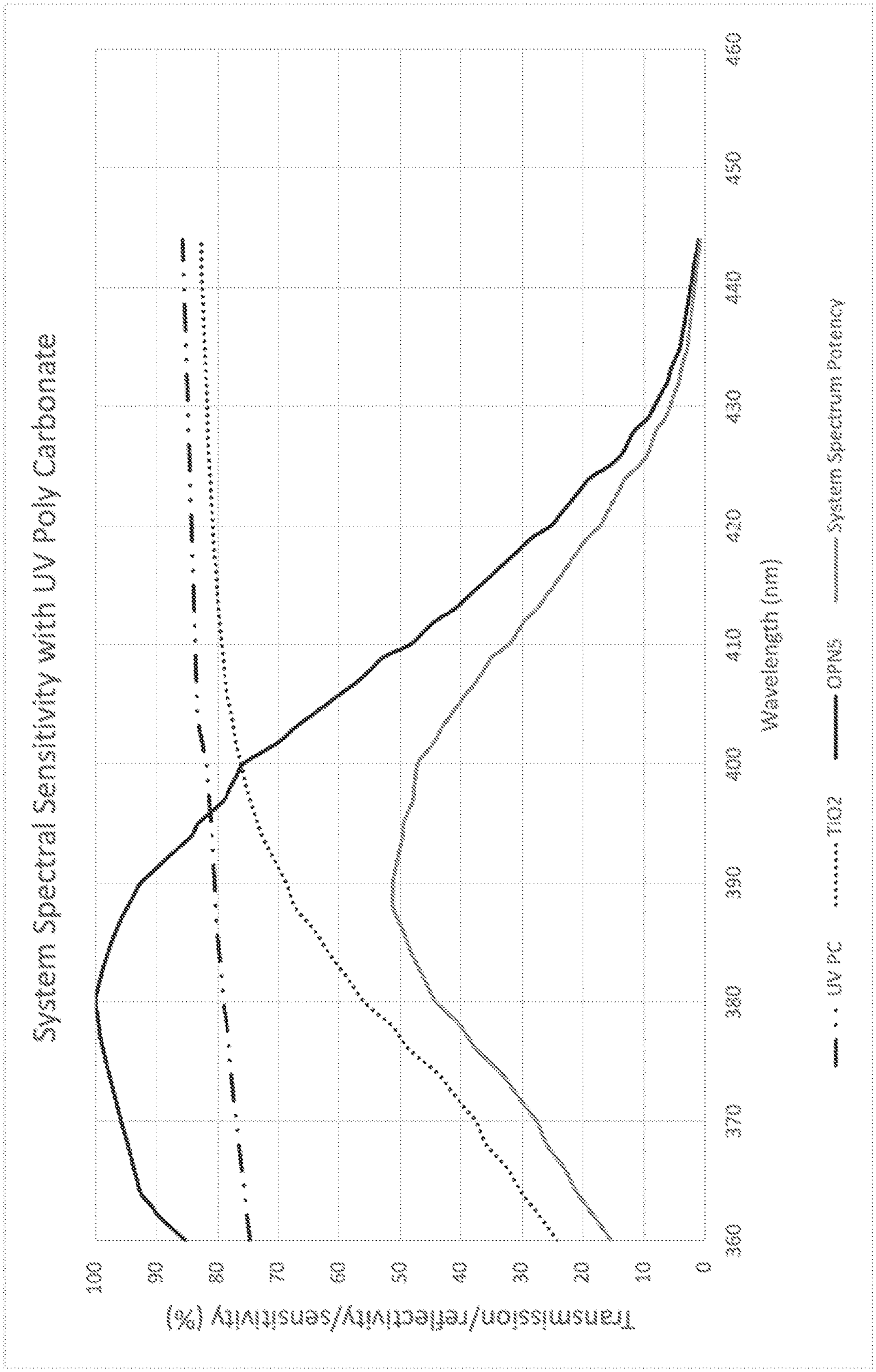
FIG. 46 illustrates, according to some embodiments, a graph of the spectral sensitivity of OPN5, the spectral transmission of a UV polycarbonate optical material, the spectral reflectance of titanium dioxide (TiO2) and the resulting system spectral potency of a device taking into account the light travelling through the polycarbonate optical device and taking a single bounce off a TiO2 based paint.
Figure 47:
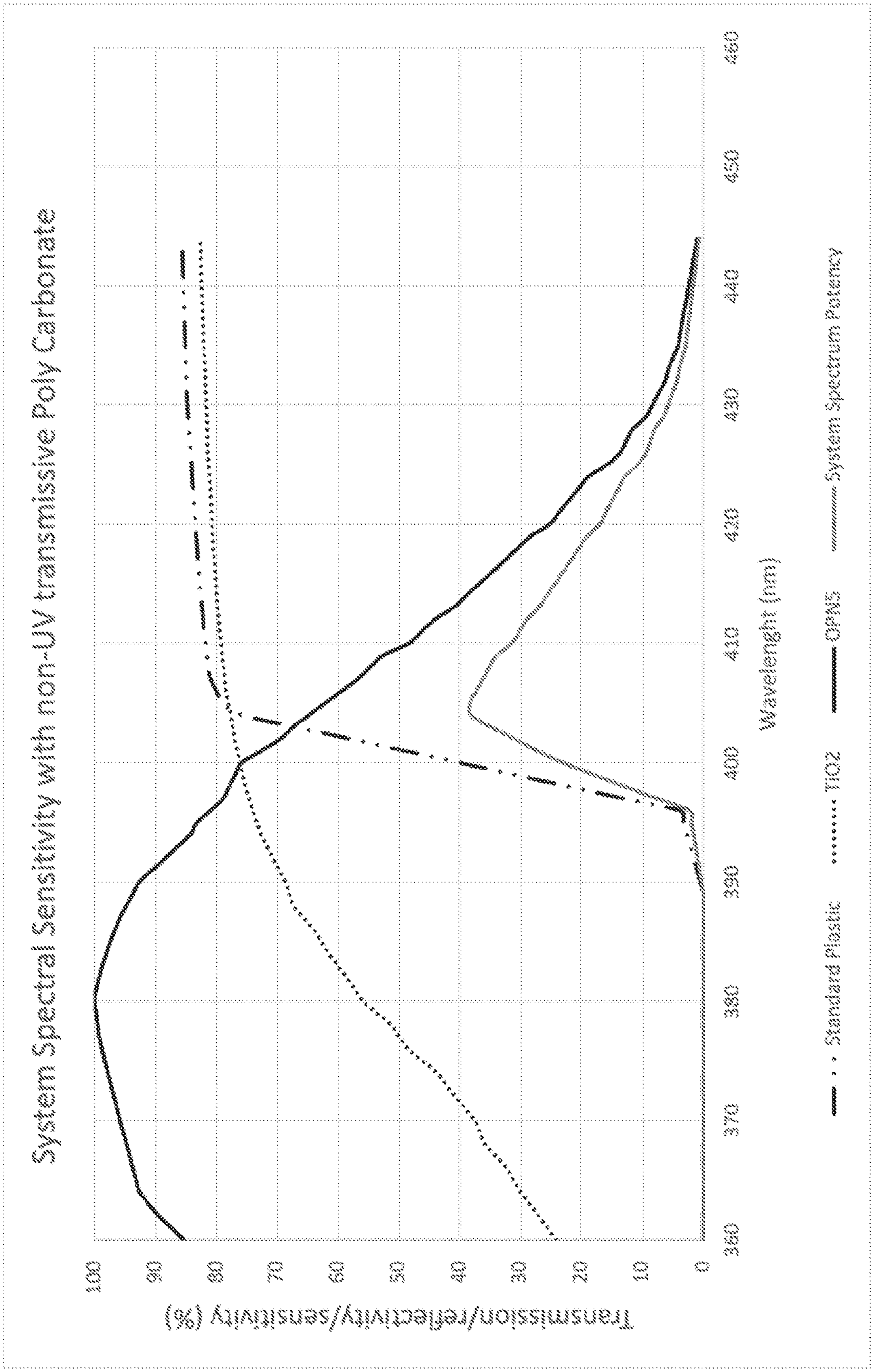
FIG. 47 illustrates, according to some embodiments, a graph of the spectral sensitivity of OPN5, the spectral transmission of a standard polycarbonate optical material, the spectral reflectance of titanium dioxide (TiO2) and the resulting system spectral potency of a device taking into account the light travelling through the polycarbonate optical device and taking a single bounce off a TiO2 based paint.

When considering these types of novel spectra, the material selection is of particular importance. Most optical materials such as polycarbonates and acrylics (PMMA) are spectrally characterized with a sharp cutoff at around 400 nm, not allowing any wavelengths below 400 nm through. Additionally, surface pigments may not reflect violet wavelength the same as longer wavelengths. Titanium dioxide ($TiO_2$) is a common pigment for creating a white color. Thus its spectral reflectance serves as a baseline for white paint or surface coatings. Considering the combination of UV plastics and $TiO_2$ based surfaces shifts the spectrum needed to generate the highest biological stimulation of OPN5 from its peak sensitivity of 380 nm to a longer wavelength of 388 nm. Moreover, when utilizing standard plastics this combination moves much longer to 405 nm, with a significant reduction in overall biological potency of 405 nm. These interactions are shown in FIGS. 46 and 47. For example, FIG. 46 illustrates a graph of the spectral sensitivity of OPN5, the spectral transmission of a UV polycarbonate optical material, the spectral reflectance of titanium dioxide ($TiO_2$) and the resulting system spectral potency of a device taking into account the light travelling through the polycarbonate optical device and taking a single bounce off a $TiO_2$ based paint. FIG. 47 illustrates a graph of the spectral sensitivity of OPN5, the spectral transmission of a standard polycarbonate optical material, the spectral reflectance of titanium dioxide ($TiO_2$) and the resulting system spectral potency of a device taking into account the light travelling through the polycarbonate optical device and taking a single bounce off a $TiO_2$ based paint.

Figure 48:
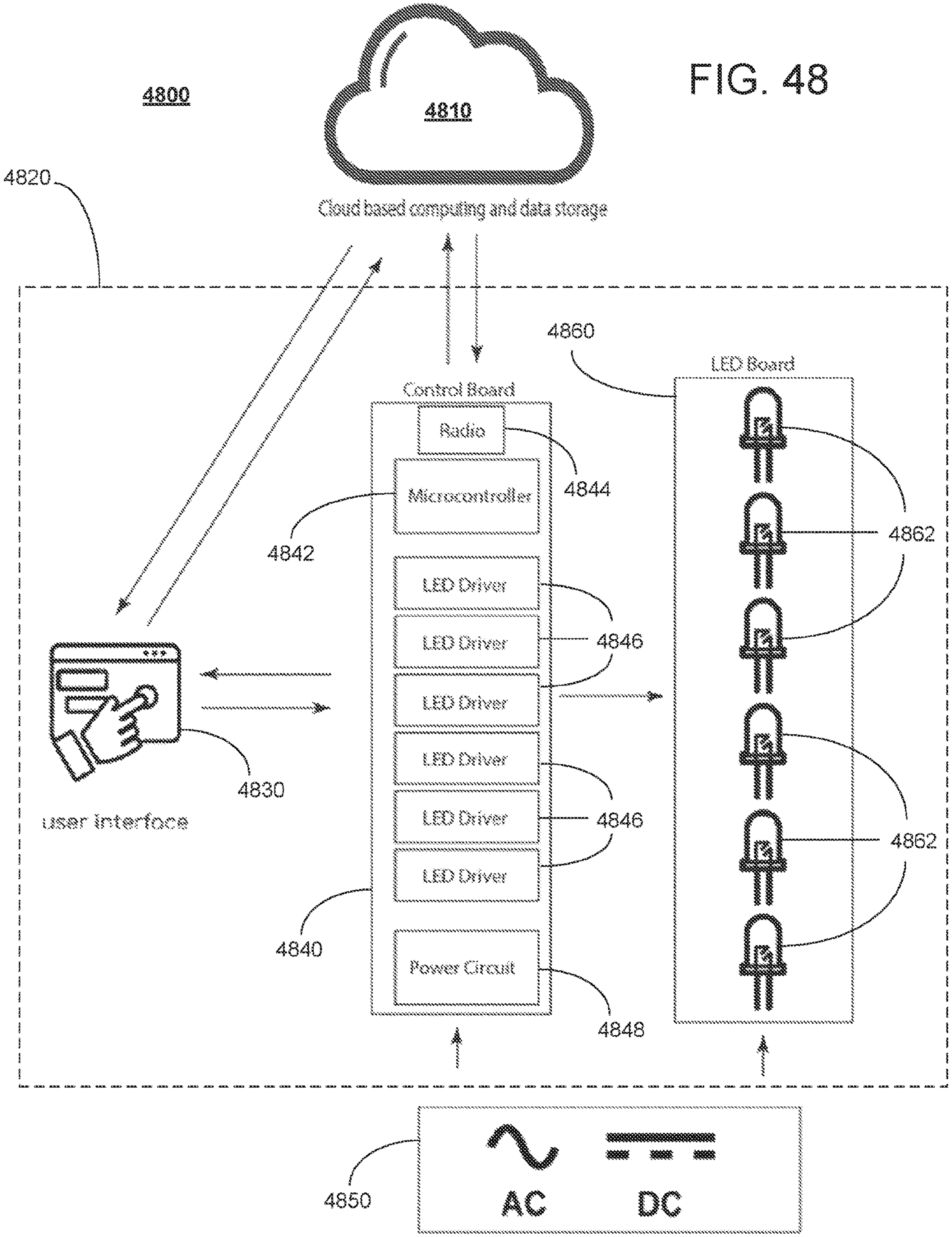
FIG. 48 illustrates, according to some embodiments, a block diagram of a device consisting of a user interface, a control means, and a plurality of light emitting diode types.

FIG. 48 illustrates, according to some embodiments, a block diagram of a system 4800. The system 4800 includes cloud based computing and data storage 4810 and device 4820. Device 4820 includes a user interface 4830, a controller 4840, a power supply 4850, and a plurality of light emitting diode types (e.g., LED Board 4860 including LEDs 4862). For example, a user interface 4830 may select twilight timing and duration based on a plurality of variables such as latitude, longitude, atmospheric conditions, weather conditions, genetic factors, age, and health conditions. Additionally, perinatal lighting schemes can be devised to provide children with a lighting thumbprint unique to their genetic makeup, conception location, birth location, birth time, gestational age, and sex.

The controller 4840 may be disposed on a control board and may include a radio 4844, one or more microcontrollers 4842, and one or more LED drivers 4846. The user interface 4830 may interact with the controller 4840 via wired or wireless communications (e.g., communication through cloud based computing and data storage 4810 with radio 4844). In some aspects, the controller 4840 may store and populate timing, spectrum and duration data locally or via external data computation or storage, such as a computer, smart phone, or cloud interface. For example, the controller may program the output and timing to LED devices 4862 on an LED board 4860. Moreover, the LED board 4860 may be protected behind an optical system including a UV transmitting polycarbonate or glass.

Additionally, some embodiments may include other violet transmitting materials (e.g., glass) and applications may utilize a device that suspends in space to limit interactions with materials such as $TiO_2$ based paints or other surface finishes. Accordingly, some embodiments, the device 4820 may include an optical element (e.g., a lens, window, enclosure or cover for the device) associated with the illumination source (e.g., LEDs) that is ultraviolet transmissive.

Referring again to FIG. 48, the device 4820 may include light emitting diodes (LEDs) 4862 emitting violet light within a range of 360-420 nm (e.g., 380-410 nm), memory storing computer instructions (e.g., microcontroller 4862), and one or more processors coupled with the memory and configured to execute the computer instructions stored in the memory (e.g., microcontroller 4862). In some embodiments, the computer instructions may include steps for controlling a selective activation of the illumination source to stimulate neuropsin (OPN5) in a human based at least in part upon a circadian clock of the human. For example, the selective activation of LEDs 4862 may include controlling a rhythmic intensity of the violet light emitted by the LEDs (e.g., based on a first transition associated with dawn and a second transition associated with dusk). In another example, the selective activation of the LEDs 4862 may be based on one or more spectral composition changes associated with one or more seasons.

In some embodiments, the device 4820 of FIG. 48 may include LEDs 4862 emitting blue light within a range of 400-525 nm (e.g., 450-500 nm). In some embodiments, the computer instructions may include steps for controlling the selective activation of the LEDs 4862 to stimulate melanopsin (OPN4) in the human based at least in part upon the circadian clock of the human. In some embodiments, the computer instructions may include steps for controlling the selective activation of the LEDs 4862 to stimulate melanopsin (OPN3) in the human based at least in part upon the circadian clock of the human.

In some embodiments, the computer instructions may include steps for controlling the selective activation of the LEDs 4862 to stimulate an OPN5/OPN4 ratio in the human. For example, the computer instructions may include steps for controlling the selective activation of the LEDs 4862 to stimulate an OPN5/OPN4 ratio less than 0.4 in the human at a midpoint in a daytime schedule and to stimulate an OPN5/OPN4 ratio greater than 0.4 at a beginning and an end of the daytime schedule. According to some embodiments, the computer instructions may include steps for controlling the selective activation of the LEDs 4862 to stimulate an OPN5/OPN3 ratio in the human.

According to some embodiments, the device 4820 of FIG. 48 may be incorporated into a display device (such as a video screen, computer display, appliance display and the like), where the LEDs 4862 are embodied as micro-LEDs incorporated as display pixels (or display elements).

Referring again to FIG. 48, the user interface 4830 may be configured to receive information pertaining to a geographical location. For example, the selective activation of the LEDs 4862 may be based on transitions associated with the geographical location. According to some embodiments, the selective activation of the LEDs 4862 may be further based upon one or more additional conditions, including time of year, atmospheric conditions, weather conditions, genetic factors, age and health conditions, etc. According to some embodiments, the user interface 4830 may be configured to receive information pertaining to two or more factors associated with a child (e.g., genetic makeup, conception location, birth location, birth time, gestational age, and sex) and the selective activation of the illumination source (e.g., LEDs 4862) may be based on transitions associated with the received factors associated with the child. For example, the device 4820 may include one or more interior lighting devices disposed in a child-care facility.

The user interface 4830 of FIG. 48 may be embodied as a graphical user interface. In some embodiments, other forms of interfaces may be utilized such as transceivers (examples of which are discussed herein) receiving information from a source (such as from a database, the Internet, the Cloud, etc.) other than directly from a user.

While embodiments disclosed herein may utilize LEDs and/or micro-LEDs, the disclosure is not intended to be limited to any particular illumination source. Other illumination sources are available that may be used to create the effects described herein. For example, illumination sources may be utilized such as quantum dot base systems, solid state laser systems, broad spectrum illumination (such as xenon) combined with dynamic optical filters, such as those used in projection based systems (such as color wheels, digital mirror devices, etc.). Further, when the LEDs are described as being activated to emit light within a particular wavelength range, it is contemplated that the LEDs may be specifically designed or provided to emit light within that particular wavelength range or may be incorporated with other components or materials (e.g., specific components or materials with band-pass characteristics for the selected ranges) so that the LED in combination with that component/material transmits light within a particular wavelength.

Figure 49:
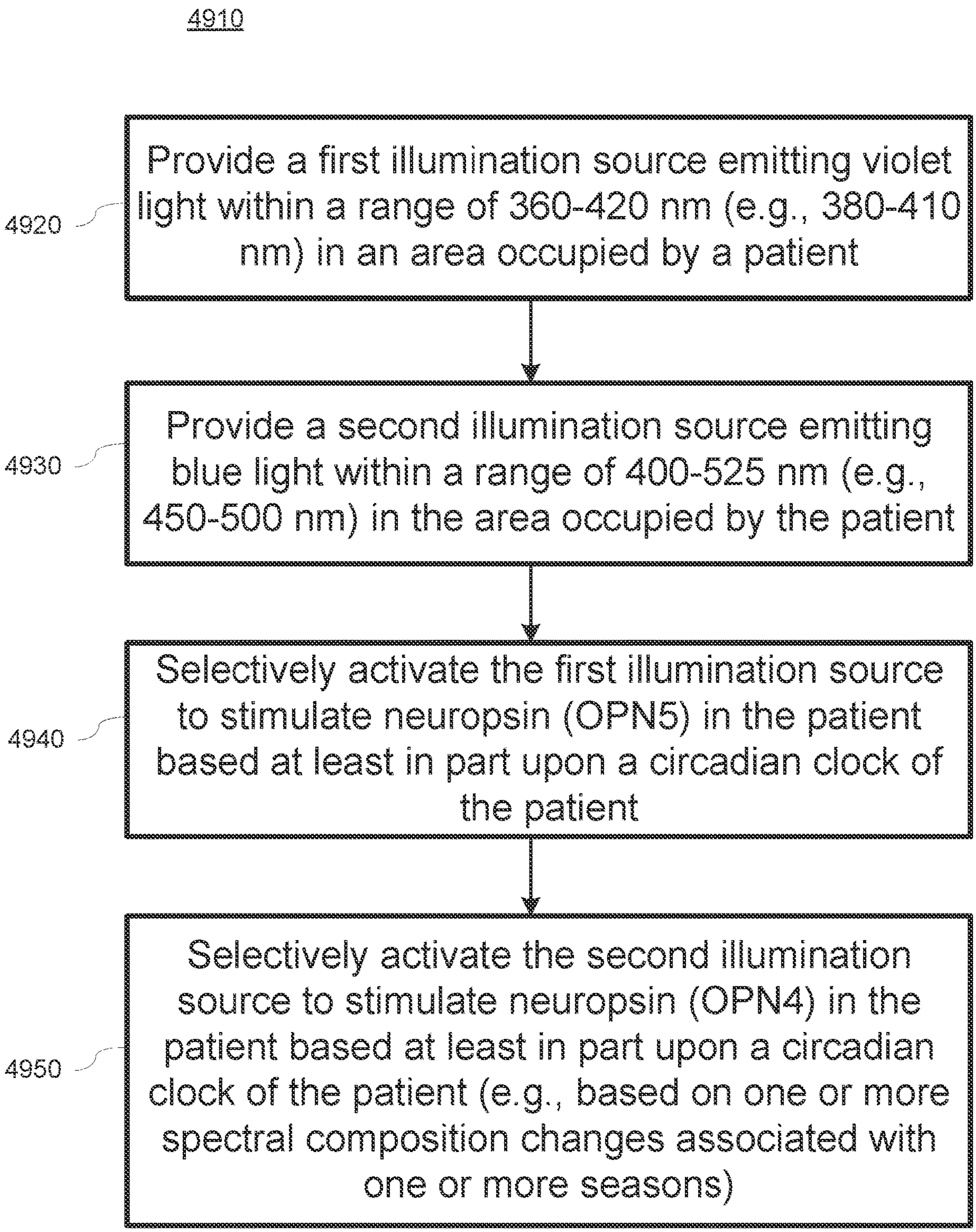
FIG. 49 illustrates an exemplary method of using artificial lighting to treat disease in patients, among other things.

As shown in FIG. 49, according to some embodiments, a method 4910 for treating disease (such as myopia or metabolic syndrome) in patients (e.g., children) may include providing a first illumination source emitting violet light within a range of 360-420 nm (e.g., 380-410 nm) in an area occupied by a patient (step 4920), providing a second illumination source emitting blue light within a range of 400-525 nm (e.g., 450-500 nm) in the area (step 4930), and selectively activating the first illumination source to stimulate neuropsin (OPN5) in the patient based at least in part upon a circadian clock of the patient (step 4940) and selectively activating the second illumination source to stimulate neuropsin (OPN4) in the patient based at least in part upon a circadian clock of the patient (e.g., based on one or more spectral composition changes associated with one or more seasons) (step 4950).

According to some embodiments, the above method may control a rhythmic intensity of the violet light emitted by the first illumination source, e.g., based on a first transition associated with dawn and a second transition associated with dusk. For example, the selective activation steps may selectively activate the first and second illumination sources to stimulate an OPN5/OPN4 ratio less than 0.4 in the patient at a midpoint in a daytime schedule and to stimulate an OPN5/OPN4 ratio greater than 0.4 at a beginning or an end of the daytime schedule.

According to some embodiments, selectively activating the first illumination source may be based on transitions associated information pertaining to a geographical location of the area. According to some embodiments, selectively activating the first illumination source may be based upon one or more additional condition, including time of year, atmospheric conditions, weather conditions, genetic factors, age and health conditions, etc. According to some embodiments, selectively activating the first illumination source may be based upon transitions associated with one or more received factors associated with a patient (e.g., genetic makeup, conception location, birth location, birth time, gestational age, and sex).

While examples of a system for utilizing LEDs that emit wavelengths associated with human opsin absorption spectra have been described in connection with various computing devices/processors, the underlying concepts may be applied to any computing device, processor, or system capable of facilitating a telecommunications system. The various techniques described herein may be implemented in connection with hardware or software or, where appropriate, with a combination of both. Thus, the methods and devices may take the form of program code (i.e., instructions) embodied in concrete, tangible, storage media having a concrete, tangible, physical structure. Examples of tangible storage media include floppy diskettes, CD-ROMs, DVDs, hard drives, or any other tangible machine-readable storage medium (computer-readable storage medium). Thus, a computer-readable storage medium is not a signal. A computer-readable storage medium is not a transient signal. Further, a computer readable storage medium is not a propagating signal. A computer-readable storage medium as described herein is an article of manufacture. When the program code is loaded into and executed by a machine, such as a computer, the machine becomes a device for telecommunications. In the case of program code execution on programmable computers, the computing device will generally include a processor, a storage medium readable by the processor (including volatile or nonvolatile memory or storage elements), at least one input device, and at least one output device. The program(s) can be implemented in assembly or machine language, if desired. The language can be a compiled or interpreted language and may be combined with hardware implementations.

The methods and devices associated with a system as described herein also may be practiced via communications embodied in the form of program code that is transmitted over some transmission medium, such as over electrical wiring or cabling, through fiber optics, or via any other form of transmission, wherein, when the program code is received and loaded into and executed by a machine, such as an erasable programmable read-only memory (EPROM), a gate array, a programmable logic device (PLD), a client computer, or the like, the machine becomes a device for implementing telecommunications as described herein. When implemented on a general purpose processor, the program code combines with the processor to provide a unique device that operates to invoke the functionality of a lighting system.

While the disclosed systems have been described in connection with the various examples of the various figures, it is to be understood that other similar implementations may be used, or modifications and additions may be made to the described examples without deviating therefrom. Therefore, the disclosed systems as described herein should not be limited to any single example, but rather should be construed in breadth and scope in accordance with the appended claims.

In describing preferred methods, systems, or apparatuses of the subject matter of the present disclosure—using artificial lighting to promote circadian health of a patient—as illustrated in the Figures, specific terminology is employed for the sake of clarity. The claimed subject matter, however, is not intended to be limited to the specific terminology so selected. In addition, the use of the word “or” is generally used inclusively unless otherwise provided herein.

This written description uses examples to enable any person skilled in the art to practice the claimed subject matter, including making and using any devices or systems and performing any incorporated methods. Other variations of the examples are contemplated herein.

What is claimed:

1. A device comprising:

a first plurality of light emitting diodes (LEDs) emitting violet light within a range of 360-420 nm;

a second plurality of LEDs emitting blue light within a range of 400-525 nm;

memory storing computer instructions; and one or more processors coupled with the memory and configured to execute the computer instructions stored in the memory, wherein the computer instructions include steps for controlling a selective activation of the first plurality of LEDs to stimulate neuropsin (OPN5) in a human based at least in part upon a circadian clock of the human and for controlling a selective activation of the second plurality of LEDs to stimulate melanopsin (OPN4) in the human based at least in part upon the circadian clock of the human; and wherein the computer instructions include steps for controlling selective activation of the first and second plurality of LEDs to simulate transition of twilight at a beginning or end of a daytime schedule, the simulated transition of twilight including controlling spectral power distribution of violet light within a range of 360-420 nm and controlling spectral power distribution of blue light within a range of 400-525 nm to simulate a transition of a position of the sun between (a) a position below the horizon by controlling the spectral power distribution of violet light emitted by the first plurality of LEDs to be higher than the spectral power distribution of the blue light emitted by the second plurality of LEDs and (b) a position above the horizon in by controlling the spectral power distribution of the blue light emitted by the second plurality of LEDs to be higher than the spectral power distribution of the violet light emitted by the first plurality of LEDs.

2. The device of claim 1, wherein the second plurality of LEDs emit blue light within a range of 450-500 nm.

3. The device of claim 2, wherein the first plurality of LEDs emit violet light within a range of the 380-410 nm.

4. The device of claim 1, wherein the first plurality of LEDs emit violet light within a range of 380-410 nm.

5. The device of claim 1, wherein the selective activation of the first plurality of LEDs comprises controlling a rhythmic intensity of the violet light emitted by the plurality of LEDs.

6. The device of claim 1 further comprising:
an interface configured to receive information pertaining to a geographical location;
wherein the selective activation of the first plurality of LEDs is based on transitions associated with the geographical location.

7. The device of claim 6,
wherein the interface is further configured to receive information pertaining to one or more additional conditions taken from a group consisting of: time of year, atmospheric conditions, weather conditions, genetic factors, age and health conditions; and the selective activation of the first plurality of LEDs is based further upon the one or more additional conditions.

8. The device of claim 6, wherein the interface includes a graphical user interface.

9. The device of claim 1, wherein the selective activation of the first plurality of LEDs is based on one or more spectral composition changes associated with one or more seasons.

10. The device of claim 1, wherein the device is one or more interior lighting devices disposed in a child-care facility.

11. The device of claim 1, further comprising an optical element associated with the first plurality of LEDs that is ultraviolet transmissive.

12. The device of claim 11, wherein the optical element is one or more of a lens, window, enclosure or cover for the device.

13. The device of claim 1, wherein the computer instructions include steps for controlling the selective activation of the second plurality of LEDs to stimulate encephalopsin (OPN3) in the human based at least in part upon the circadian clock of the human.

14. The device of claim 13, wherein the computer instructions include steps for controlling the selective activation of the first and second plurality of LEDs to stimulate an OPN5/OPN3 ratio in the human.

15. A device comprising:
a first illumination source emitting violet light within a range of 360-420 nm;
a second illumination source emitting blue light within a range of 400-525 nm;
memory storing computer instructions; and
one or more processors coupled with the memory and configured to execute the computer instructions stored in the memory,
wherein the computer instructions include steps for controlling a selective activation of the first illumination source to stimulate neuropsin (OPN5) in a human based at least in part upon a circadian rhythm and for controlling a selective activation of the second illumination source to stimulate melanopsin (OPN4) in the human based at least in part upon the circadian clock of the human; and
wherein the computer instructions include steps for controlling selective activation of the first and second illumination sources to simulate transition of twilight at a beginning or end of a daytime schedule, the simulated transition of twilight including controlling spectral power distribution of violet light within a range of 360-420 nm and controlling spectral power distribution of blue light within a range of 400-525 nm to simulate a transition of a position of the sun between (a) a position below the horizon by controlling the spectral power distribution of violet light emitted by the first illumination source to be higher than the spectral power distribution of the blue light emitted by the second illumination source and (b) a position above the horizon in by controlling the spectral power distribution of the blue light emitted by the second illumination source to be higher than the spectral power distribution of the violet light emitted by the first illumination source.

16. The device of claim 15, wherein the second illumination source emits blue light within a range of 450-500 nm.

17. The device of claim 16, wherein the first illumination source emits violet light within a range of 380-410 nm.

18. The device of claim 15, wherein the first illumination source emits violet light within a range of 380-410 nm.

19. The device of claim 15, wherein the selective activation of the first illumination source comprises controlling a rhythmic intensity of the violet light emitted by the first illumination source.

20. The device of claim 15 further comprising:
an interface configured to receive information pertaining to a geographical location;
wherein the selective activation of the first illumination source is based on transitions associated with the geographical location.

21. A device comprising:
a first plurality of light emitting diodes (LEDs) emitting violet light within a range of 360-420 nm;
an interface configured to receive information pertaining to two or more of the following factors associated with a child: genetic makeup, conception location, birth location, birth time, gestational age, and sex;
memory storing computer instructions; and
one or more processors coupled with the memory and configured to execute the computer instructions stored in the memory,
wherein the computer instructions include steps for controlling a selective activation of the first plurality of LEDs to stimulate neuropsin (OPN5) in a human based at least in part upon a circadian clock of the human; and
wherein the selective activation of the first plurality of LEDs is based on transitions associated with the received information pertaining to the two or more factors associated with the child.

22. A device comprising:
a display device taken from a group consisting of: a video screen, a computer display or an appliance display, the display device including a display and a first plurality micro-LEDs incorporated into the display emitting violet light within a range of 360-420 nm;
memory storing computer instructions; and
one or more processors coupled with the memory and configured to execute the computer instructions stored in the memory,
wherein the computer instructions include steps for controlling a selective activation of the first plurality of micro-LEDs to stimulate neuropsin (OPN5) in a human based at least in part upon a circadian clock of the human.

* * * * *

SEQUENCE LISTING

```
<160> NUMBER OF SEQ ID NOS: 51

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

cagtgtggtg cacgtctcca atc                                              23


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

tgaaccaaag ttgaccacca g                                                21


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

cagcacggtg aagccattc                                                   19


<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gcgtgcatcc gcttgtg                                                     17


<210> SEQ ID NO 5
```

<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
ccctgccatt gttaagacc 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6
tgctgctgtt cctgttttc 19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
tgctcttctg tatcgcccag t 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
gccgtgttaa ggaatctgct g 21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
actgccacac ctccagtcat t 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
ctttgcctca ctcaggattg g 21

<210> SEQ ID NO 11
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gtgccagttt cgatccgtag a                                              21


<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

ggccagcatc gtgtagatga                                                20


<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

tcagtcaacg ggggacataa a                                              21


<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

ggggctgtac tgcttaacca g                                              21


<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

gaagctgcgg tacaattcca g                                              21


<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

ccccttgtac ccttcaccaa t                                              21


<210> SEQ ID NO 17
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 17

taccgtggac tggagatcca                                              20


<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

tagcaacgaa tgcaaaggta ggg                                          23


<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

atccacatgt tctgcccagg agg                                          23


<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

gcgctatgtt ggtaaggtgt ggg                                          23


<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

tgtggtttta atcagcacag ggg                                          23


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

acccaggctt cttttggtct                                              20


<210> SEQ ID NO 23
<211> LENGTH: 20
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 23
agagtcgttg gcatccttgg 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
actatcccga ccgccttact 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gaactgatgg cgagctcaga 20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tgctggccta tgaacgttat atcc 24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tcagttctgg gtgactaact gatc 24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cactcgttgc atcgaccggt aatgc 25

<210> SEQ ID NO 29
<211> LENGTH: 30
<212> TYPE: DNA
<213> ORGANISM: Artificial Sequence
<220> FEATURE:

<223> OTHER INFORMATION: Description of Artificial Sequence: Synthetic
primer

<400> SEQUENCE: 29
gcattaccgg tcgatgcaac gagtgatgag 30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
gagtgaacga acctggtcga aatcagtgcg 30

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
ctcagaaccc acaaagtgct gg 22

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
gtggactgca atgtcccatc tatc 24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
gtgggcatca tagcccattg ctac 24

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
aggagtgtat agagccggaa gtctg 25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ccagtccaga agcctagggc atgcc 25

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
tgctcctgcc gagtatccat catggc 26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
cgccaagctc ttcatatcac gggtag 26

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
aggctggatg gatgagagc 19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
gttgtgaagc tgggatcctg 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
cgaccaggtt cgttcactca 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
cagcgttttc gttctgccaa 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
cccctgctgt ccattcctta 20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tgaccatgat tacgcaagc 19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
tggagtccta ctcgcggacg 20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tggaaagaga tgcatttgtg ag 22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
acagcctatg aattctctca atgc 24

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 47

cactgcattc tagttgtggt ttgtcc                                          26


<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

cacagtatgt gtgacaacct                                                 20


<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

gtggacagat taactgaagc                                                 20


<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

gacagaacaa agccaga                                                    17


<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

caccgccttg gcttgtcac                                                  19
```